(12) United States Patent
Viet et al.

(10) Patent No.: US 10,316,035 B2
(45) Date of Patent: Jun. 11, 2019

(54) TRIAZOLOPYRIDINE INHIBITORS OF MYELOPEROXIDASE

(71) Applicant: BRISTOL-MYERS SQUIBB COMPANY, Princeton, NJ (US)

(72) Inventors: Andrew Quoc Viet, Schwenksville, PA (US); Nicholas Ronald Wurtz, Pennington, NJ (US); Scott A. Shaw, Lawrence Township, NJ (US); Ellen K. Kick, Ewing, NJ (US); Andrew K. Dilger, Ewing, NJ (US); Kumar Balashanmuga Pabbisetty, Piscataway, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/756,373

(22) PCT Filed: Aug. 30, 2016

(86) PCT No.: PCT/US2016/049353
§ 371 (c)(1),
(2) Date: Feb. 28, 2018

(87) PCT Pub. No.: WO2017/040450
PCT Pub. Date: Mar. 9, 2017

(65) Prior Publication Data
US 2018/0244671 A1    Aug. 30, 2018

Related U.S. Application Data

(60) Provisional application No. 62/213,664, filed on Sep. 3, 2015.

(51) Int. Cl.
*C07D 471/04*    (2006.01)

(52) U.S. Cl.
CPC .................. *C07D 471/04* (2013.01)

(58) Field of Classification Search
None
See application file for complete search history.

(56) References Cited

FOREIGN PATENT DOCUMENTS

WO    WO 2007/120098 A1    10/2007

*Primary Examiner* — Alicia L Otton
(74) *Attorney, Agent, or Firm* — Elliott Korsen; Jing Sun

(57) ABSTRACT

The present invention provides compounds of Formula (I): wherein A, Y and $R^1$ are each as defined in the specification, and compositions comprising any of such novel compounds. These compounds are myeloperoxidase (MPO) inhibitors and/or eosinophil peroxidase (EPX) inhibitors, which may be used as medicaments.

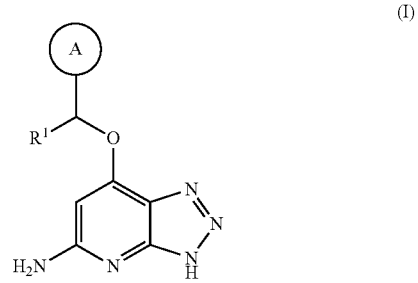

(I)

9 Claims, No Drawings

TRIAZOLOPYRIDINE INHIBITORS OF MYELOPEROXIDASE

CROSS-REFERENCE TO RELATED APPLICATIONS

This application claims priority from U.S. Provisional Application No. 62/213,664 filed Sep. 3, 2015, the disclosures of which are incorporated herein by reference in their entirety.

FIELD OF THE INVENTION

The present invention relates to novel triazolopyridine compounds, which are myeloperoxidase (MPO) inhibitors and/or eosinophil peroxidase (EPX) inhibitors, compositions containing them, and methods of using them, for example, for the treatment and/or prophylaxis of atherosclerosis, heart failure, chronic obstructive pulmonary disease (COPD), and related diseases.

BACKGROUND OF THE INVENTION

Cardiovascular disease is a major health risk throughout the industrialized world. Atherosclerosis, the most prevalent of cardiovascular diseases, is the principal cause of heart attack and stroke, and thereby the principal cause of death in the United States. Atherosclerosis is a complex disease involving many cell types and molecular factors (for a detailed review, see Weber et al., Nature Med., 17(11):1410-1422 (2011)).

MPO inhibitors have been suggested to reduce the atherosclerotic burden and/or the vulnerability of existing atherosclerotic lesions and thereby decrease the risk of acute myocardial infarction, unstable angina or stroke, and reduce ischemia-reperfusion injury during acute coronary syndrome and ischemic cerebrovascular events. Several lines of data support a role for MPO in atherosclerosis. MPO is expressed in the shoulder regions and necrotic core of human atherosclerotic lesions and active enzyme has been isolated from autopsy specimens of human lesions (Daugherty, A. et al., J. Clin. Invest., 94(1):437-444 (1994)). Moreover, HOCl-modified lipoproteins have been detected in advanced human atherosclerotic lesions (Hazell, L. J. et al., J. Clin. Invest., 97:1535-1544 (1996)). In eroded and ruptured human lesions, as compared to fatty streaks, an increased number of MPO expressing macrophages have been demonstrated, suggesting a particular role for MPO in acute coronary syndromes (Sugiyama, S. et al., Am. J. Pathol., 158(3):879-891 (2001), Tavora, F. R., BMC Cardiovasc. Disord., 9:27 (Jun. 23, 2009).

Data accumulated during the last fifteen years indicate that the pro-atherogenic actions of MPO include oxidation of lipoproteins, induction of endothelial dysfunction via consuming nitric oxide and destabilization of atherosclerotic lesions by activation of proteases (Nicholls, S. J. et al., Arterioscler. Thromb. Vasc. Biol., 25(6): 1102-1111 (2005), Nicholls, S. J. et al., JLR, S346-S351 (2009)). Several studies have focused on nitro- and chlorotyrosine modifications of LDL and HDL lipoproteins. Since chlorotyrosine modifications in vivo are generated by hypochlorous acid produced by MPO these modifications are regarded as specific markers of MPO activity (Hazen, S. et al., J. Clin. Invest., 99(9):2075-2081 (1997)).

ApoA-I isolated from atherosclerotic lesions is modified by reactive chlorine and nitrogen species as well as by reactive carbonyls (Pennathur, S. et al., J. Biol. Chem., 279:42977-42983 (2004); Shao, B. et al., J. Biol. Chem., 279:7856-7866 (2004); Zheng, L. et al., J. Clin. Invest., 114(4):529-541 (2004); Shao, B. et al. JBC in press (2012)). Chlorotyrosine modification of apoA1, the main apolipoprotein of HDL cholesterol, was associated with impaired cholesterol acceptor function (Bergt, C. S. et al., Proc. Natl. Acad. Sci. USA, 101(35):13032-13037 (2004); Zheng, L. et al., J. Clin. Invest., 114(4):529-541 (2004)). Thus, oxidation of apoA-I amino acid residues by the MPO-$H_2O_2$—Cl$^-$ system is one mechanism for loss of its biological activities.

The lipid and protein content of LDL are also targets for MPO oxidation and presence of chlorotyrosine in LDL extracted from human atherosclerotic tissues has been shown (Hazen, S. et al., J. Clin. Invest., 2075-2081 (1997)). LDL particles exposed to MPO in vitro become aggregated, leading to facilitated uptake via macrophage scavenger receptors and foam cell formation (Hazell, L. J. et al., Biochem. J., 290(Pt. 1): 165-172 (1993); Podrez, E. A. et al., J. Clin. Invest., 105:1095-1108 (2000)). Thus, MPO appears to play a role in the generation of oxidized LDL, which contributes to atherosclerosis plaque development.

Further evidence implicating MPO in the pathophysiology of atherosclerosis comes from the study of hMPO transgenic mice crossed with LDL-R KO mice (Castelini, L. W. et al., J. Lipid Res., 47:1366-1377 (2006)). These mice expressed MPO in lesions and developed significantly larger aortic lesions than control LDL-R KO mice.

Many clinical studies have implicated MPO in cardiovascular disease in human patients. Patients with established coronary artery disease have higher plasma and leukocyte MPO levels than healthy controls (Zhang, R. et al., JAMA, 286(17):2136-2142 (2001)). Moreover, in three large prospective studies plasma levels of MPO predicted the risk of future coronary events or revascularization (Baldus, S. et al., Circulation, 108(12):1440-1445 (2003); Brennan, M. et al., N. Engl. J. Med., 349(17):1595-1604 (2003); Kohli, P. et al., Circulation, 122:A13175 (2010)). In two recent large nested case control prospective studies, the EPIC-Norfolk and MONICA-/KORA Augsburg studies, baseline MPO levels in these initially healthy populations turned out to be an excellent predictor of future risk of CAD and CHD respectively, showing that this inflammatory marker precedes the presentation of clinical symptoms of CVD (Meuwese, M. C. et al., J. Am. Coll. Cardiol., 50:159-165 (2007); Karakas et al., J. Int. Med., 271:43-50 (2011)). Interestingly, MPO deficient humans are less affected by cardiovascular disease than controls with normal MPO levels (Kutter, D. et al., Acta Haematol., 104:10-15 (2000)). A polymorphism in the MPO promoter affects expression leading to high and low MPO expressing individuals. In three different studies the high expression genotype has been associated with an increased risk of cardiovascular disease (Nikpoor, B. et al., Am. Heart J., 142(2):336-339 (2001); Makela, R. et al., Lab. Invest., 83(7):919-925 (2003); Asselbergs, F. W. et al., Am. J. Med., 116(6):429-430 (2004)).

MPO inhibitors are expected to preserve heart function and reduce heart failure burden in patients. In MPO null mice, preservation of left ventricular (LV) function has been observed in both a coronary artery ligation model (Askari, A. T. et al., J. Exp. Med., 197:615-624 (2003)) and an ischemia reperfusion model (Vasilyev, N. et al., Circulation, 112:2812-2820 (2005)), suggesting that MPO may provide a mechanistic link between inflammation, oxidant stress, and impaired cardiac remodeling. High circulating levels of MPO have also been linked to chronic heart failure in patients. Systemic MPO was increased in patients with established chronic systolic HF and correlated with diastolic dysfunction independent of age and plasma B-type natriuretic peptide (Tang, W. H. et al., *Am. J. Cardiol.*, 98:796-799 (2006)). Studies also showed that systemic MPO in subjects with myocardial infarction (MI) (Mocatta, T. J. et al., *J. Am. Coll. Cardiol.*, 49:1993-2000 (2007)) or chronic systolic HF (Tang, W. H. et al., *J. Am. Coll. Cardiol.*, 49:2364-2370 (2007)) may predict long-term adverse clinical events.

Inhibitors of MPO or EPX may be used to treat other neuroinflammatory diseases, including multiple sclerosis, Alzheimer's disease, Parkinson's disease, multiple system atrophy, and stroke as well as other inflammatory diseases or conditions like asthma, COPD, cystic fibrosis, inflammatory bowel disease, chronic kidney disease, renal glomerular damage and rheumatoid arthritis.

In these chronic inflammatory diseases, a role of MPO in the development of tissue injury has been suggested. In lesional tissues of patients with Alzheimer's disease, MPO protein was detected along with elevated levels of chlorotyrosine (Green, P. S. et al., *J. Neurochem.*, 90:724-733 (2004)). In an animal model of Parkinson's disease, increased levels of chlorotyrosine and HOCl-modified proteins in brain tissues have been reported (Choi, D. K. et al., *J. Neuroscience*, 25(28):6394-6600 (2005)). In asthmatic patients the level of bromotyrosine, a molecular fingerprint of eosinophil-catalyzed oxidation was associated with symptom severity (Wedes, S. H. et al., *J Pediatr.*, 248-255 (2011)). Upon allergen challenge, a model that elicits primarily a strong eosinophilic response, lung segments of asthmatic subjects exhibit a >10 fold increase in bronchioalveolar lavage 3-bromotyrosine an indicator of eosinophil activity vs. a 3-fold increase in 3-chlorotyrosine characteristic of MPO activity (Wu, W. et al., *JCI*, 105:1455-1463 (2000)). The presence of HOCl-modified protein was also detected in patients with membranous glomerulonephritis (Grone et al., *Lab. Invest.*, 82:5-14 (2002)). High MPO circulating levels have been implicated in the development of cardiovascular and chronic kidney disease in patients on hemodialysis (Honda, H. et al., *Clin. J. Am. Soc., Nephrol.*, 142-151 (2009). In addition MPO activity and 3-chlorotyrosine levels were also increased during hemodyalisis in patients with end-stage renal disease (Delporte, C et al., *Talanta*, 99:603-609 (2012)). Similarly, there is accumulation of neutrophils and eosinophils in conjunction with MPO and EPX seen in intestinal mucosa of patients with inflammatory bowel disease (Kruidenier, L. et al., *J. Pathol.*, 201:17-27 (2003); Carlson, M. et al., *Am. J. Gastrol.*, 94(7):1876-1883 (1999)) and in synovial fluids of rheumatoid arthritis patients (Edwards, S. W. et al., *Biochem. J.*, 250:81-85 (1988); Nucombe, H. L. et al., *Ann. Rheum. Dis.*, 50:237-242 (1991)).

Thus, there is considerable evidence that MPO and/or EPX derived oxidants contribute to tissue injury in chronic inflammatory disorders. MPO and/or EPX inhibitors are anticipated to reduce the levels of oxidants and tissue injury associated with the progression of these diseases.

SUMMARY OF THE INVENTION

The present disclosure provides novel triazolopyridine compounds, including stereoisomers, tautomers, pharmaceutically acceptable salts, or solvates thereof, which are useful as MPO inhibitors and/or EPX inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of diseases or disorders associated with the activity of MPO and/or EPX.

The compounds of the invention may be used in therapy.

The compounds of the invention may be used for the manufacture of a medicament for the treatment and/or prophylaxis of diseases or disorders associated with the activity of MPO and/or EPX.

Examples of diseases or disorders associated with the activity of MPO and/or EPX include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

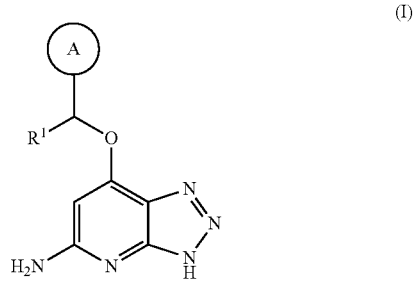

or a stereoisomer, a tautomer, a pharmaceutically acceptable salt, or a solvate thereof, wherein:
  ring A is independently $C_{5-10}$ carbocycle substituted with 0-1 $R^2$ and 0-4 $R^3$;
  $R^1$ is independently selected from: H, CN, $C_{1-6}$ alkyl, and $C_{1-6}$ haloalkyl;
  $R^2$ is independently selected from: $SF_5$, —$(CH_2)_tOH$, —$(CH_2)_nR^4$, —$(CH_2)_n(X_1)_n(CH_2)_nR^5$, and —$(CH_2)_nO(CH_2)_sCONH(CH_2)_m$—$C_{3-6}$ cycloalkyl;
  $X_1$ is independently selected from: O, S, CO and $SO_2$;
  $R^3$ is, at each occurrence, independently selected from: halogen, CN, $C_{1-4}$ alkyl, $C_{1-4}$ alkoxy, $C_{1-4}$ haloalkyl, $C_{1-4}$ haloalkoxy, $NO_2$, $CONH_2$, and $SO_2(C_{1-4}$ alkyl);
  $R^4$ is independently selected from: halogen, $C_{1-4}$ alkyl, $C_{1-4}$ alkoxy, $C_{1-4}$ alkylthio, $C_{1-4}$ haloalkyl, $C_{1-4}$ haloalkoxy, $C_{1-4}$ haloalkylthio, CN, $CO_2(C_{1-4}$ alkyl), NO$_2$, NR$^6$R$^7$, CONR$^6$R$^7$, NHCOR$^8$, NHCO$_2$R$^8$, COR$^{10}$, —CONHCH$_2$CONR$^9$R$^{10}$, SO$_2$NR$^9$R$^{10}$, and S(O)$_p$R$^8$;

R$^5$ is independently selected from: C$_{3-10}$ carbocycle substituted with 0-2 R$^{11}$, phenyl substituted with 0-3 R$^{11}$ and 0-1 R$^{12}$, and 5- to 10-membered heterocycle comprising carbon atoms and 1-4 heteroatoms selected from N, NR$^a$, O, and S(O)$_p$; wherein said heterocycle is substituted with 0-2 R$^{11}$ and 0-1 R$^{13}$;

R$^6$ is, at each occurrence, independently selected from: H, C$_{1-4}$ haloalkyl, C$_{1-6}$ alkyl substituted with 0-2 R$^{15}$, —(CH$_2$)$_t$—(C$_{3-6}$ cycloalkyl substituted with 0-1 R$^{14}$), —(CHR$^b$)$_n$-(phenyl substituted with 0-1 R$^{16}$), —(CH$_2$)$_t$-(phenyl substituted with 0-1 R$^{16}$), —(CH$_2$)$_t$-(a 5- to 10-membered heterocycle comprising carbon atoms and 1-4 heteroatoms selected from N, NR$^a$, O, and S(O)$_p$, wherein said heterocycle is substituted with 0-1 R$^{17}$);

R$^7$ is, at each occurrence, independently selected from: H and C$_{1-4}$ alkyl substituted with R$^{11}$;

alternatively, R$^6$ and R$^7$, together with the nitrogen atom to which they are attached, combine to form a 4- to 10-membered heterocyclic ring comprising carbon atoms and 1-4 heteroatoms selected from N, NR$^a$, O, and S(O)$_p$; wherein said heterocycle is substituted with 0-1 R$^{17}$;

R$^8$ is, at each occurrence, independently selected from: C$_{1-4}$ alkyl, —(CH$_2$)$_t$—C$_{3-6}$ cycloalkyl, and —(CH$_2$)$_t$-phenyl;

R$^9$ is, at each occurrence, independently selected from: H and C$_{1-4}$ alkyl; R$^{10}$ is, at each occurrence, independently selected from: R$^8$ and H;

R$^{11}$ is, at each occurrence, independently selected from: OH, halogen, C$_{1-4}$ alkoxy, C$_{1-4}$ haloalkyl, and C$_{1-4}$ haloalkoxy;

R$^{12}$ is independently selected from: halogen, CN, C$_{1-4}$ alkyl, C$_{1-4}$ alkoxy, C$_{1-4}$ haloalkyl, C$_{1-4}$ haloalkoxy, C$_{1-4}$ alkylthio, OH, CH$_2$OH, CO$_2$H, CO$_2$(C$_{1-4}$ alkyl), NH$_2$, CH$_2$NH$_2$, N(C$_{1-4}$ alkyl)$_2$, CH$_2$N(C$_{1-4}$ alkyl)$_2$, CONH$_2$, CON(C$_{1-4}$ alkyl)$_2$, SO$_2$NH$_2$, SO$_2$NH(C$_{1-4}$ alkyl), SO$_2$N(C$_{1-4}$ alkyl)$_2$, CONHPh, NHCOPh, —(CH$_2$)$_n$—(C$_{3-6}$ carbocycle substituted with 0-2 R$^c$), and a 5- to 6-membered heterocycle comprising carbon atoms and 1-4 heteroatoms selected from N, NR$^a$, O, and S(O)$_p$, wherein said heterocycle is substituted with 0-2 R$^c$);

R$^{13}$ is independently selected from: R$^{12}$ and =O;

R$^{14}$ and R$^{16}$ are, at each occurrence, independently selected from: halogen, C$_{1-4}$ alkyl, C$_{1-4}$ alkoxy, C$_{1-4}$ haloalkyl, C$_{1-4}$ haloalkoxy, OH, CH$_2$OH, N(C$_{1-4}$ alkyl)$_2$, CONH$_2$, CONH(C$_{1-4}$ alkyl), CON(C$_{1-4}$ alkyl)$_2$, OCH$_2$CONH$_2$, NHCO(C$_{1-4}$ alkyl), NHCO$_2$(C$_{1-4}$ alkyl), SO$_2$(C$_{1-4}$ alkyl), —(CH$_2$)$_n$-phenyl, —O—(CH$_2$)$_n$-phenyl, and pyridylmethyl;

R$^{15}$ is, at each occurrence, independently selected from: OH, C$_{1-4}$ alkoxy, C$_{1-4}$ haloalkyl, C$_{1-4}$ haloalkoxy, N(C$_{1-4}$ alkyl)$_2$, CONH$_2$, CONH(C$_{1-4}$ alkyl), and CON(C$_{1-4}$ alkyl)$_2$;

R$^{17}$ is independently selected from: R$^{14}$ and =O;

R$^a$ is, at each occurrence, independently selected from the group consisting of H, C$_{1-4}$ alkyl, CO(C$_{1-4}$ alkyl), CO$_2$(C$_{1-4}$ alkyl), SO$_2$(C$_{1-4}$ alkyl), —(CH$_2$)$_n$-phenyl, and —CO(—(CH$_2$)$_n$-phenyl);

R$^b$ is, at each occurrence, independently selected from: H and C$_{1-4}$ alkyl;

R$^c$ is, at each occurrence, independently selected from: OH, C$_{1-4}$ alkyl, halogen, C$_{1-4}$ alkoxy, C$_{1-4}$ haloalkyl, and C$_{1-4}$ haloalkoxy;

n is, at each occurrence, independently selected from: 0 and 1;

p is, at each occurrence, independently selected from: 0, 1 and 2;

s is, at each occurrence, independently selected from: 1 and 2; and t is, at each occurrence, independently selected from: 0, 1, 2, 3 and 4;

provided that

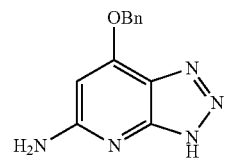 [SMILES: Nc1cc(OCc2ccccc2)c2nn[nH]c2n1]

is excluded.

In a second aspect, the present invention includes a compound of Formula (I), or a stereoisomer, a tautomer, a pharmaceutically acceptable salt, or a solvate thereof, within the scope of the first aspect; wherein:

ring A is substituted with 0-1 R$^2$ and 0-3 R$^3$ and selected from: cyclohexyl, bicyclo[2.2.1]heptanyl, phenyl, 1,2,3,4-tetrahydronaphthalenyl, and naphthalenyl;

provided that

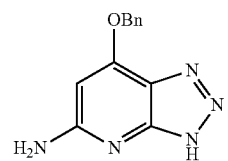 [SMILES: Nc1cc(OCc2ccccc2)c2nn[nH]c2n1]

is excluded.

In a third aspect, the present invention includes a compound of Formula (I), or a stereoisomer, a tautomer, a pharmaceutically acceptable salt, or a solvate thereof, within the scope of the first or second aspect, wherein:

ring A is phenyl substituted with 1 R$^2$ and 0-3 R$^3$.

In a fourth aspect, the present invention includes a compound of Formula (I), or a stereoisomer, a tautomer, a pharmaceutically acceptable salt, or a solvate thereof, within the scope of any of the above aspects, wherein:

R$^2$ is independently selected from: halogen, CN, CH$_2$OH, C$_{1-4}$ alkyl, —CH$_2$—C$_{1-4}$ alkoxy, C$_{1-4}$ alkoxy, C$_{1-4}$ haloalkyl, C$_{1-4}$ haloalkoxy, C$_{1-4}$ haloalkylthio, SF$_5$, CO$_2$(C$_{1-4}$ alkyl), NR$^6$R$^7$, CONR$^6$R$^7$, —NHCO(C$_{1-4}$ alkyl), NO$_2$, SO$_2$NR$^8$R$^9$, SO$_2$R$^8$, C$_{3-6}$ cycloalkyl, —O—C$_{3-6}$ cycloalkyl, phenoxy, benzoxy, —(CH$_2$)$_{0-1}$-(phenyl substituted with 0-2 R$^{11}$ and 0-1 R$^{12}$), (a heterocycle substituted with 0-1 R$^{11}$ and 0-1 R$^{13}$, wherein said heterocycle is a 5- to 10-membered heterocycle comprising carbon atoms and 1-4 heteroatoms selected from N, NR$^a$, O, and S),

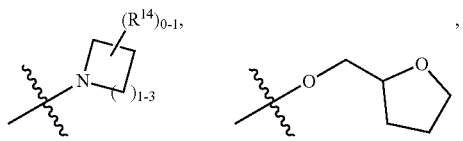

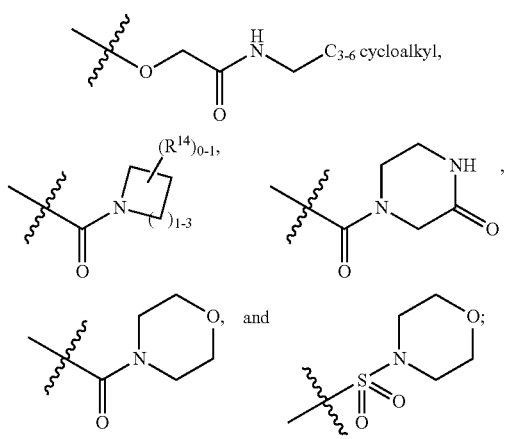

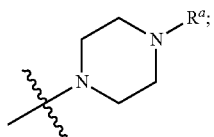

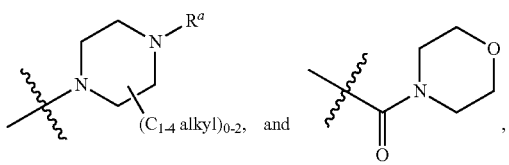

$R^6$ is independently selected from: H, $C_{1-4}$ haloalkyl, $C_{1-6}$ alkyl substituted with 0-2 $R^{15}$, —$(CH_2)_n$—($C_{3-6}$ cycloalkyl substituted with 0-1 $R^{14}$), —$(CHR^b)_n$-(phenyl substituted with 0-1 $R^{16}$), —$(CH_2)_r$-(a 5- to 10-membered heterocycle comprising carbon atoms and 1-4 heteroatoms selected from N, $NR^a$, O, and $S(O)_p$, wherein said heterocycle is substituted with 0-1 $R^{17}$);

$R^{12}$ is, at each occurrence, independently selected from: halogen, CN, $C_{1-4}$ alkoxy, $C_{1-4}$ haloalkyl, $C_{1-4}$ haloalkoxy, $CON(C_{1-4}$ alkyl$)_2$, $SO_2NH_2$, $SO_2NH(C_4$ alkyl), $SO_2N(C_{1-4}$ alkyl$)_2$, Ph, CONHPh, NHCOPh, pyrazolyl, and

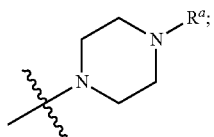

$R^{13}$ is, at each occurrence, independently selected from: =O, halogen, $C_{1-4}$ alkyl, $C_{1-4}$ alkoxy, $C_{1-4}$ haloalkyl, $C_{1-4}$ alkylthio, OH, $CH_2OH$, $CO_2(C_{1-4}$ alkyl), CN, $NH_2$, $CH_2NH_2$, $N(C_{1-4}$ alkyl$)_2$, $CH_2N(C_{1-4}$ alkyl$)_2$, $CONH_2$, $C_{3-6}$ cycloalkyl, Ph, Bn, pyrrolidinyl, piperidinyl, morpholinyl, piperazinyl,

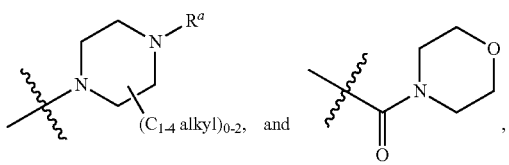

$R^{15}$ is, at each occurrence, independently selected from: OH, $C_{1-4}$ alkyl, $C_{1-4}$ alkoxy, $C_{1-4}$ haloalkyl, $N(C_{1-4}$ alkyl$)_2$, $CONH_2$, $CONH(C_{1-4}$ alkyl), and $CON(C_{1-4}$ alkyl$)_2$; and $R^{16}$ is independently selected from: halogen, $C_{1-4}$ alkoxy, and $SO_2(C_{1-4}$ alkyl).

In a fifth aspect, the present disclosure provides a compound of Formula (II),

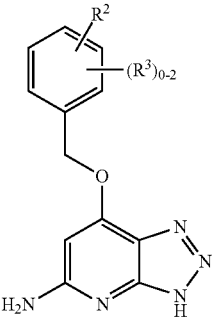

(II)

or a stereoisomer, a tautomer, a pharmaceutically acceptable salt, or a solvate thereof, within the scope of any of the above aspects; wherein:

$R^2$ is independently selected from: halogen, CN, $CH_2OH$, $C_{1-4}$ alkoxy, $C_{1-4}$ haloalkyl, $C_{1-4}$ haloalkoxy, $C_{1-4}$ haloalkylthio, $SF_5$, $CO_2(C_{1-4}$ alkyl), NHBn, $CONR^6R^7$, —NHCO($C_{1-4}$ alkyl), $NO_2$, $SO_2(C_{1-4}$ alkyl), $SO_2Bn$, $SO_2NH_2$, $SO_2NH(C_{1-4}$ alkyl), $C_{3-6}$ cycloalkyl, —O—$C_{3-6}$ cycloalkyl, phenoxy, benzoxy, —$(CH_2)_{0-1}$-(phenyl substituted with 0-2 $R^{11}$ and 0-1 $R^{12}$), (a heterocycle substituted with 0-1 $R^{11}$ and 0-1 $R^{13}$, wherein said heterocycle is selected from: pyrazolyl, 1-$C_{1-4}$ alkyl-pyrazolyl, 1-(4-halo-Ph)-pyrazolyl 1-Bn-pyrazolyl, imidazolyl, oxadiazolyl, triazolyl, pyridyl, pyrimidinyl,

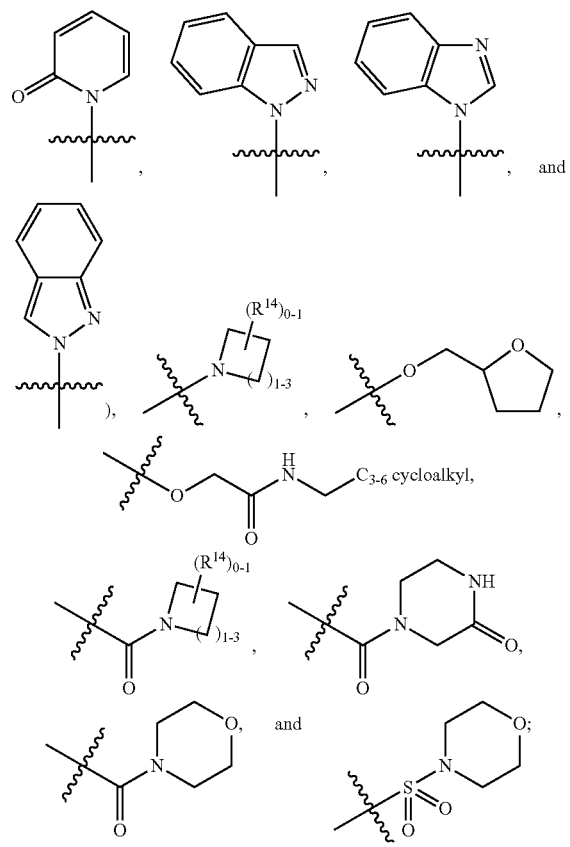

$R^3$ is, at each occurrence, independently selected from: halogen, CN, $C_{1-4}$ alkyl, $C_{1-4}$ alkoxy, $C_{1-4}$ haloalkyl, $C_{1-4}$ haloalkoxy, $NO_2$, $CONH_2$, and $SO_2(C_{1-4}$ alkyl);

$R^6$ is independently selected from: H, $C_{1-4}$ haloalkyl, $C_{1-6}$ alkyl substituted with 0-2 $R^{15}$, —$(CH_2)_{0-1}$—$C_{3-6}$ cycloalkyl, —$CH(C_{1-4}$ alkyl)(Ph), —$(CH_2)_{0-1}$-(phenyl substituted with 0-1 $R^{16}$);

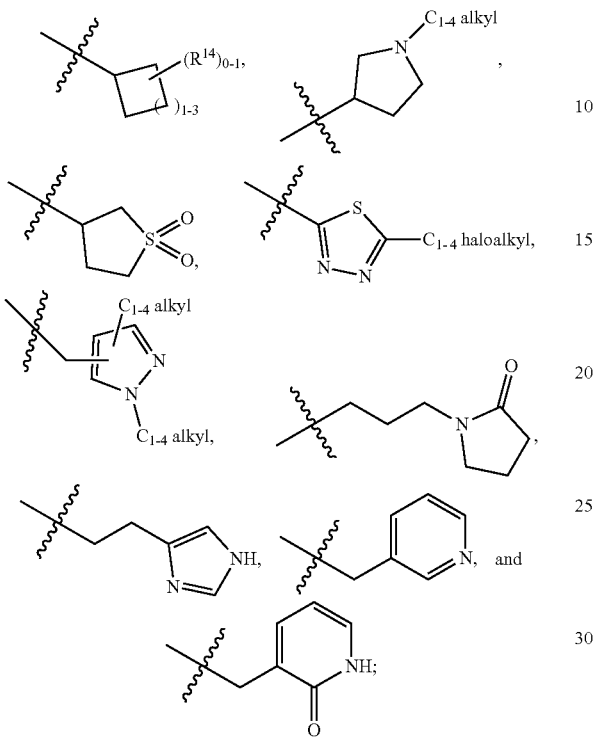

$R^7$ is independently selected from: H and $C_{1-4}$ alkyl substituted with 0-1 OH;

$R^{11}$ is, at each occurrence, independently selected from: halogen, $C_{1-4}$ alkoxy, $C_{1-4}$ haloalkyl, and $C_{1-4}$ haloalkoxy;

$R^{12}$ is independently selected from: halogen, CN, $C_{1-4}$ alkoxy, $C_{1-4}$ haloalkyl, $C_{1-4}$ haloalkoxy, $CO_2(C_{1-4}$ alkyl), $CON(C_{1-4}$ alkyl)$_2$, $SO_2NH_2$, $SO_2NH(C_{1-4}$ alkyl), $SO_2N(C_{1-4}$ alkyl)$_2$, Ph, CONHPh, NHCOPh, pyrazolyl, and

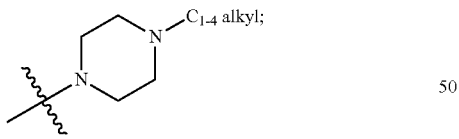

$R^{13}$ is independently selected from: halogen, $C_{1-4}$ alkyl, $C_{1-4}$ alkoxy, $C_{1-4}$ haloalkyl, $C_{1-4}$ alkylthio, OH, $CH_2OH$, $CO_2(C_{1-4}$ alkyl), CN, $NH_2$, $CH_2NH_2$, $N(C_{1-4}$ alkyl)$_2$, $CH_2N(C_{1-4}$ alkyl)$_2$, $CONH_2$, $C_{3-6}$ cycloalkyl, Ph, Bn, pyrrolidinyl, piperidinyl, morpholinyl, piperazinyl,

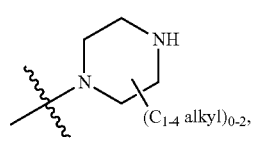

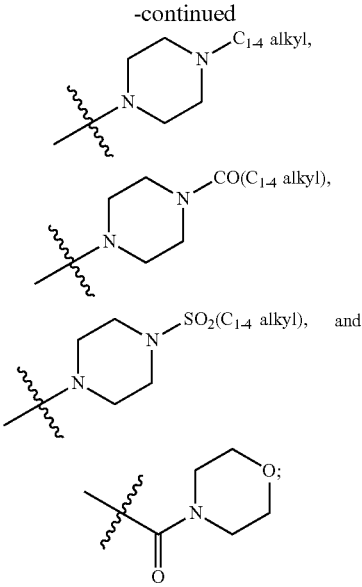

$R^{14}$ is independently selected from: $C_{1-4}$ alkyl, $C_{1-4}$ alkoxy, OH, $CH_2OH$, $CONH_2$, $NHCO(C_{1-4}$ alkyl), Ph, Bn, phenoxy, benzoxy, and pyridylmethyl;

$R^{15}$ is, at each occurrence, independently selected from: OH, $C_{1-4}$ alkyl, $C_{1-4}$ alkoxy, $C_{1-4}$ haloalkyl, $N(C_{1-4}$ alkyl)$_2$, $CONH_2$, $CONH(C_{1-4}$ alkyl), and $CON(C_{1-4}$ alkyl)$_2$; and $R^{16}$ is independently selected from: halogen, $C_{1-4}$ alkoxy, and $SO_2(C_{1-4}$ alkyl).

In a sixth aspect, the present disclosure provides a compound of Formula (IIa) or (IIb):

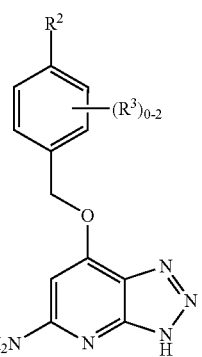

(IIa)

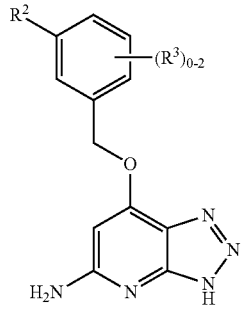

(IIb)

or a stereoisomer, a tautomer, a pharmaceutically acceptable salt, or a solvate thereof, within the scope of any of the above aspects.

In a seventh aspect, the present disclosure provides a compound of Formula (II), (IIa) or (IIb), or a stereoisomer, a tautomer, a pharmaceutically acceptable salt, or a solvate thereof, within the scope of any of the above aspects wherein:

$R^2$ is independently selected from: halogen, CN, CH$_2$OH, C$_{1-4}$ alkoxy, C$_{1-4}$ haloalkyl, C$_{1-4}$ haloalkoxy, C$_{1-4}$ haloalkylthio, SF$_5$, CO$_2$(C$_{1-4}$ alkyl), NHBn, CONH$_2$, —CONH(CH$_2$)$_{1-2}$O(C$_{1-4}$ alkyl), —CONHCH$_2$CH(OH)(C$_{1-4}$ alkyl), —CONH(CH$_2$)$_2$N(C$_{1-4}$ alkyl)$_2$, —CONH(CH$_2$)$_{1-2}$CONH$_2$, —CONHCH(C$_{1-4}$ alkyl)CONH$_2$, —CONH(CH$_2$)$_{1-2}$CONH(C$_{1-4}$ alkyl), —CONH(C$_{1-4}$ haloalkyl), —CON(C$_{1-4}$ alkyl)CH$_2$CONH$_2$, CON(C$_{1-4}$ alkyl)$_2$, —CON(C$_{1-4}$ alkyl)(CH$_2$)$_2$OH, —CON(C$_{1-4}$ alkyl)(CH$_2$)$_2$N(C$_{1-4}$ alkyl)$_2$, —CONH(C$_{3-6}$ cycloalkyl), —CONHPh, —CONH(3-halo-Ph), —CONHBn, —CONH(2-C$_{1-4}$ alkoxy-Bn), —CONH(2-halo-Bn), —CONH(3-SO$_2$(C$_{1-4}$ alkyl)-Bn), —CONHCH(C$_{1-4}$ alkyl)(Ph), —CON(C$_{1-4}$ alkyl)(C$_{3-6}$ cycloalkyl), —CON(C$_{1-4}$ alkyl)Ph, —CON(C$_{1-4}$ alkyl)Bn, —CON(Bn)(CH$_2$)$_2$OH, —NHCO(C$_{1-4}$ alkyl), NO$_2$, SO$_2$(C$_{1-4}$ alkyl), SO$_2$Bn, SO$_2$NH$_2$, SO$_2$NH(C$_{1-4}$ alkyl), Ph, Bn, 2-C$_{1-4}$ alkoxy-Ph, 3-C$_{1-4}$ alkoxy-Ph, 4-C$_{1-4}$ alkoxy-Ph, 2-halo-Ph, 3-halo-Ph, 4-halo-Ph, 3-CN-Ph, 4-CN-Ph, 3-C$_{1-4}$ haloalkyl-Ph, 4-C$_{1-4}$ haloalkoxy-Ph, 3-SO$_2$NH$_2$-Ph, 4-SO$_2$NH(C$_{1-4}$ alkyl)-Ph, 2-SO$_2$N(C$_{1-4}$ alkyl)$_2$-Ph, 4-(CONHPh)-Ph, 4-(NHCOPh)-Ph, 4-(1H-pyrazol-5-yl)-Ph, 2-C$_{1-4}$ alkoxy-3-halo-Ph, 2-halo-4-C$_{1-4}$ alkoxy-Ph, 3-halo-4-C$_{1-4}$ alkoxy-Ph, 2-C$_{1-4}$ alkoxy-6-halo-Ph, 3-halo-4-(CON(C$_{1-4}$ alkyl)$_2$)-Ph, 2-C$_{1-4}$ alkoxy-3-halo-5-halo-Ph, —O—C$_{3-6}$ cycloalkyl, phenoxy, benzoxy, 4-biphenyl, pyrazolyl, 3-C$_{1-4}$ alkyl-pyrazol-1-yl, 1-C$_{1-4}$ alkyl-pyrazolyl, 4-CN-pyrazol-1-yl, 4-C$_{1-4}$ haloalkyl-pyrazol-1-yl, 1-(4-halo-Ph)-pyrazolyl, 1-Bn-pyrazolyl, 1-C$_{1-4}$ alkyl-3-C$_{1-4}$ alkyl-pyrazol-5-yl, 1-C$_{1-4}$ alkyl-3-C$_{1-4}$ haloalkyl-pyrazol-5-yl, 1-C$_{1-4}$ alkyl-5-C$_{1-4}$ haloalkyl-pyrazol-3-yl, 1-C$_{1-4}$ alkyl-5-C$_{3-6}$ cycloalkyl-pyrazol-3-yl, imidazolyl, 2-C$_{1-4}$ alkyl-imidazol-1-yl, 3-C$_{1-4}$ alkyl-imidazol-1-yl, 4-C$_{1-4}$ alkyl-imidazol-1-yl, 4-CH$_2$OH-imidazol-1-yl, 4-C$_{1-4}$ haloalkyl-imidazol-1-yl, 4-CO$_2$(C$_{1-4}$ alkyl)-imidazol-1-yl, 4-CH$_2$N(C$_{1-4}$ alkyl)$_2$-imidazol-1-yl, 4-Ph-imidazol-1-yl, 5-C$_{1-4}$ alkyl-1,2,4-oxadiazol-3-yl, 1,2,4-triazol-1-yl, 3-C$_{1-4}$ alkyl-1,2,4-triazol-1-yl, 3-C$_{1-4}$ haloalkyl-1,2,4-triazol-1-yl, pyridyl, 5-halo-pyrid-3-yl, 6-halo-pyrid-3-yl, 6-OH-pyrid-3-yl, 2-OH-pyrid-4-yl, 6-CH$_2$OH-pyrid-3-yl, 6-C$_{1-4}$ alkoxy-pyrid-3-yl, 6-C$_{1-4}$ alkylthio-pyrid-3-yl, 5-SO$_2$(C$_{1-4}$ alkyl)-pyrid-3-yl, 6-CN-pyrid-3-yl, 6-C$_{1-4}$ haloalkyl-pyrid-2-yl, 6-C$_{1-4}$ haloalkyl-pyrid-3-yl, 5-NH$_2$-pyrid-3-yl, 6-NH$_2$-pyrid-3-yl, 6-CH$_2$NH$_2$-pyrid-3-yl, 6-CONH$_2$-pyrid-3-yl, 6-OBn-pyrid-3-yl, 2-halo-6-halo-pyrid-3-yl, 2-C$_{1-4}$ alkoxy-5-halo-pyrid-4-yl, 5-halo-6-C$_{1-4}$ alkoxy-pyrid-3-yl, pyrimidinyl, 2-C$_{1-4}$ alkoxy-pyrimidin-5-yl, 2-N(C$_{1-4}$ alkyl)$_2$-pyrimidin-5-yl,

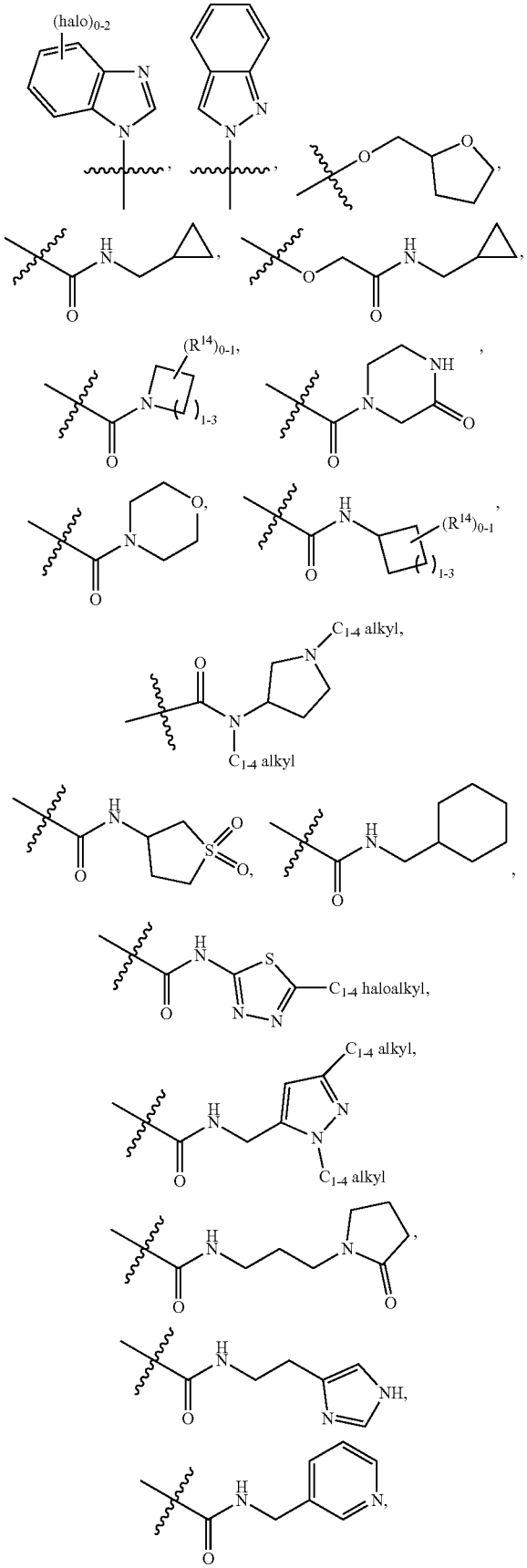

-continued

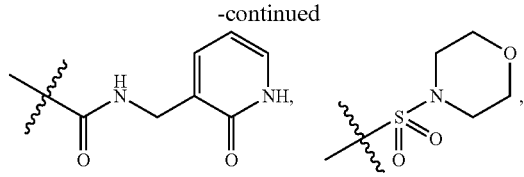

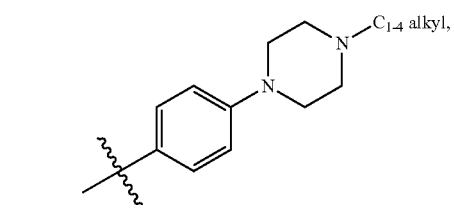

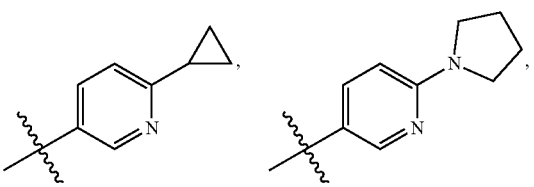

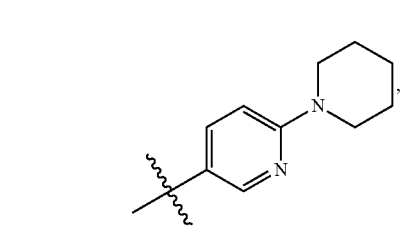

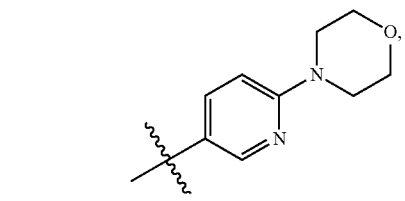

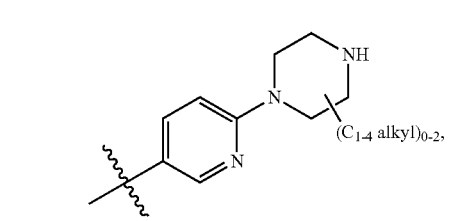

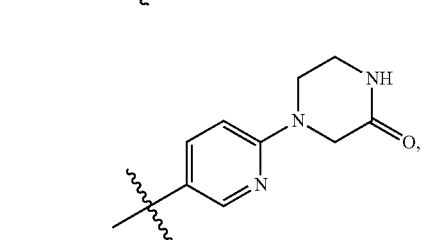

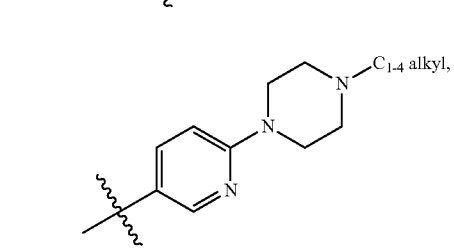

-continued

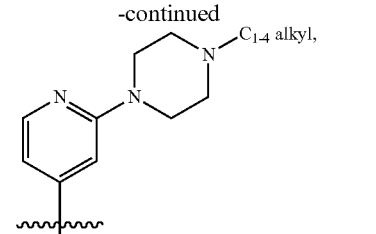

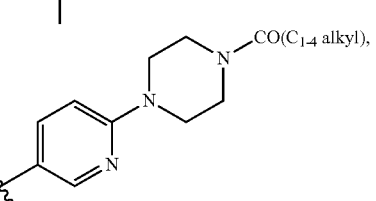

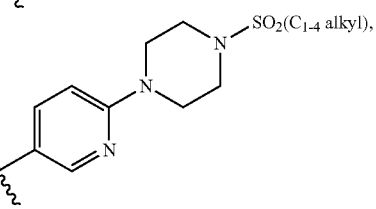

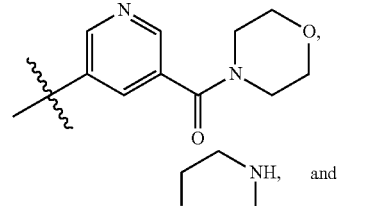

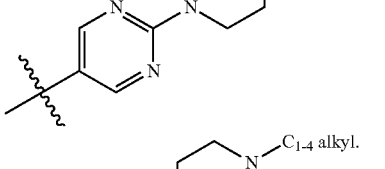

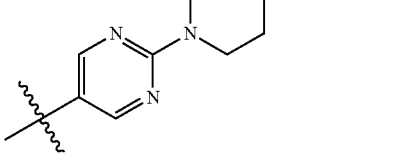

In an eighth aspect, the present disclosure includes a compound of Formula (II), (IIa) or (IIb), or a stereoisomer, a tautomer, a pharmaceutically acceptable salt, or a solvate thereof, within the scope of any of the above aspects wherein:

$R^2$ is independently selected from: F, Cl, Br, OMe, OEt, CN, CH$_2$OH, CF$_3$, OCHF$_2$, OCF$_3$, SCF$_3$, SF$_5$, CO$_2$Me, NHBn, CONH$_2$, —CONH(CH$_2$)$_2$OMe, —CONHCH$_2$CH(OH)Me, —CONH(CH$_2$)$_2$N(Me)$_2$, —CONH(CH$_2$)$_{1-2}$CONH$_2$, —CONHCH$_2$CONHMe, —CONHCH$_2$CF$_3$, —CON(Me)CH$_2$CONH$_2$, CON(Me)$_2$, —CON(Me)(CH$_2$)$_2$OH, —CON(Me)(CH$_2$)$_2$N(Me)$_2$, —CON(Et)(CH$_2$)$_2$OH, —CONH(cyclopropyl), —CONH(cyclobutyl), —CONH(cyclohexyl), —CONHPh, —CONH(3-Cl-Ph), —CONHBn, —CONH(2-OMe-Bn), —CONH(2-Cl-Bn), —CONH(3-SO$_2$Me-Bn), —CONHCH(Me)(Ph), —CON(Me)(cyclohexyl), —CON(Me)Ph, —CON(Me)Bn, —CON(Bn)(CH$_2$)$_2$OH, —NHCOMe, NO$_2$, SO$_2$Me, SO$_2$Et, SO₂Bn, SO₂NH₂, SO₂NHMe, Ph, Bn, 2-OMe-Ph, 3-OMe-Ph, 4-OMe-Ph, 2-F-Ph, 3-F-Ph, 4-F-Ph, 2-Cl-Ph, 3-Cl-Ph, 4-Cl-Ph, 3-CF₃-Ph, 4-OCF₃-Ph, 3-CN-Ph, 4-CN-Ph, 3-SO₂NH₂-Ph, 4-SO₂NHMe-Ph, 2-SO₂N(Me)₂-Ph, 4-(CONHPh)-Ph, 4-(NHCOPh)-Ph, 4-(1H-pyrazol-5-yl)-Ph, 2-OMe-3-F-Ph, 2-F-4-OMe-Ph, 3-F-4-OMe-Ph, 2-OMe-6-Cl-Ph, 3-F-4-(CON(Me)(Et))-Ph, 2-OMe-3,5-diF-Ph, phenoxy, benzoxy, 4-biphenyl, pyrazol-1-yl, 3-Me-pyrazol-1-yl, 1-Me-pyrazol-3-yl, 1-Me-pyrazol-4-yl, 1-(i-Pr)-pyrazol-4-yl, 1-(i-Bu)-pyrazol-4-yl, 1-Me-pyrazol-5-yl, 4-CN-pyrazol-1-yl, 4-CF₃-pyrazol-1-yl, 1-Bn-pyrazol-3-yl, 1-Bn-pyrazol-4-yl, 1-Me-3-CF₃-pyrazol-5-yl, imidazol-1-yl, 2-Me-imidazol-1-yl, 4-Me-imidazol-1-yl, 4-CH₂OH-imidazol-1-yl, 4-CF₃-imidazol-1-yl, 4-CO₂Me-imidazol-1-yl, 4-CH₂N(Me)₂-imidazol-1-yl, 4-Ph-imidazol-1-yl, 5-Me-1,2,4-oxadiazol-3-yl, 1,2,4-triazol-1-yl, 3-Me-1,2,4-triazol-1-yl, 3-CHF₂-1,2,4-triazol-1-yl, pyrid-3-yl, 5-F-pyrid-3-yl, 6-F-pyrid-3-yl, 6-Cl-pyrid-3-yl, 6-OH-pyrid-3-yl, 2-OH-pyrid-4-yl, 6-CH₂OH-pyrid-3-yl, 6-OMe-pyrid-3-yl, 6-(O-i-Pr)-pyrid-3-yl, 6-SMe-pyrid-3-yl, 5-SO₂Me-pyrid-3-yl, 6-CN-pyrid-3-yl, 6-CF₃-pyrid-3-yl, 5-NH₂-pyrid-3-yl, 6-NH₂-pyrid-3-yl, 6-CH₂NH₂-pyrid-3-yl, 6-CONH₂-pyrid-3-yl, 6-OBn-pyrid-3-yl, 2,6-diF-pyrid-3-yl, 2-OMe-5-F-pyrid-4-yl, 5-F-6-OMe-pyrid-3-yl, pyrimidin-2-yl, 2-OMe-pyrimidin-5-yl, 2-N(Me)₂-pyrimidin-5-yl,

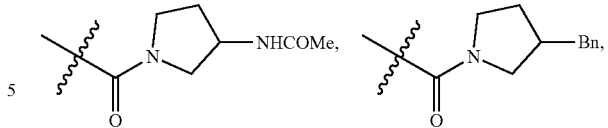
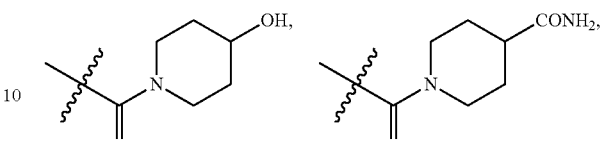
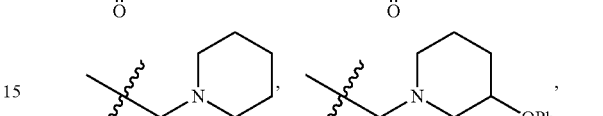
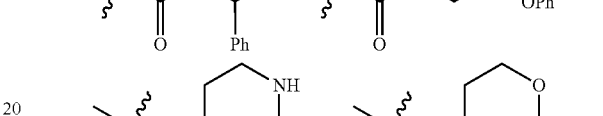
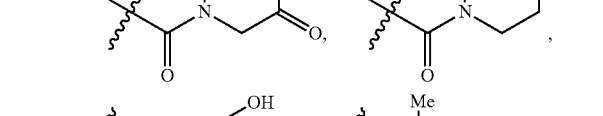
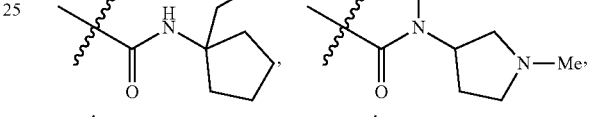
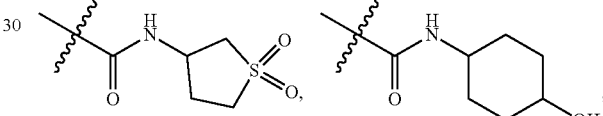
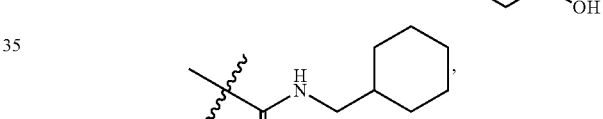
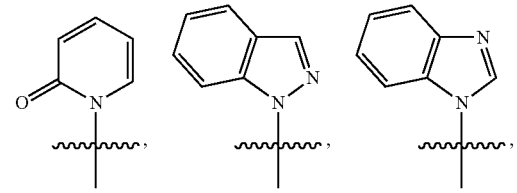
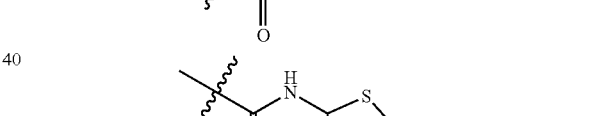
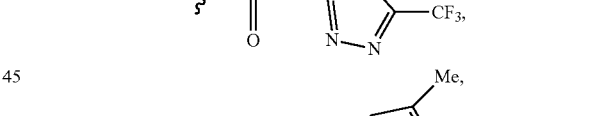
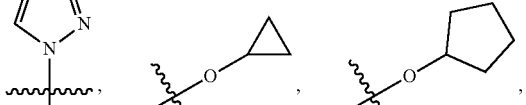
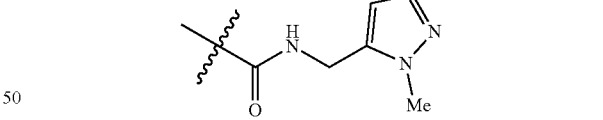
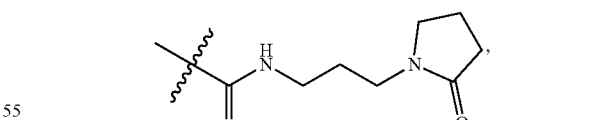
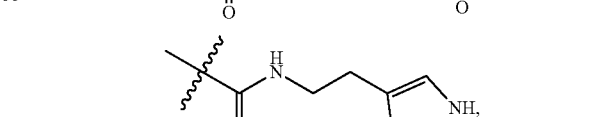
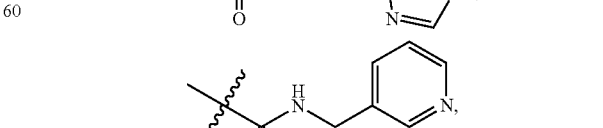
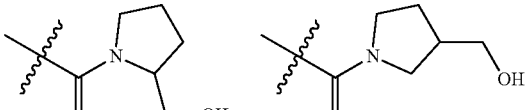

-continued

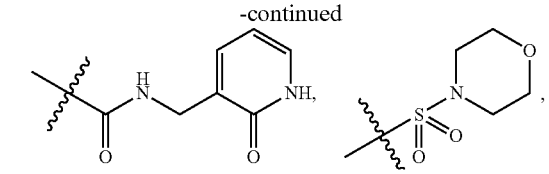

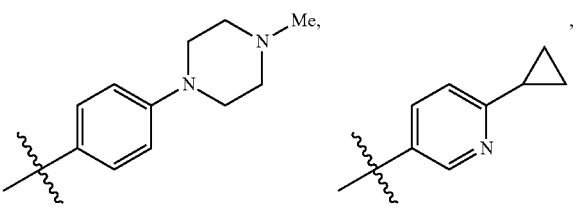

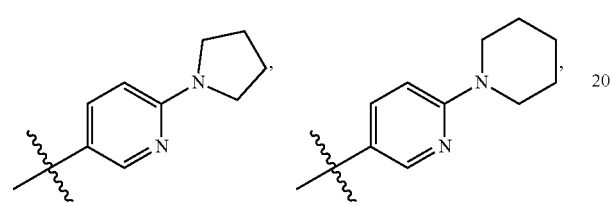

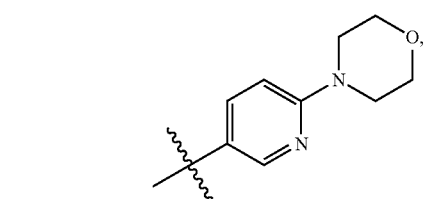

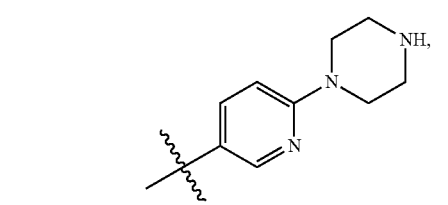

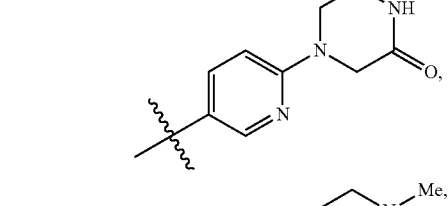

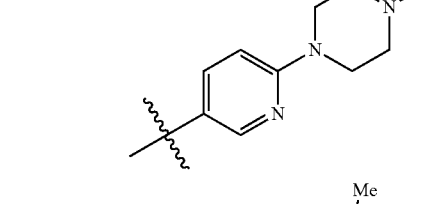

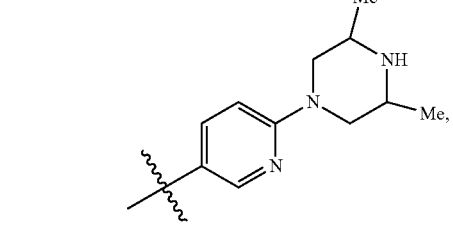

-continued

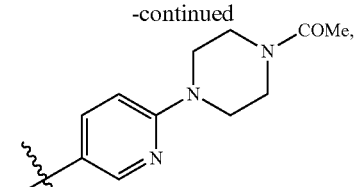

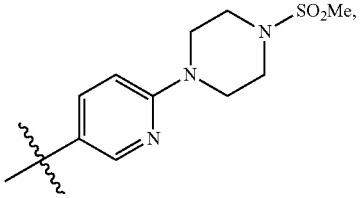

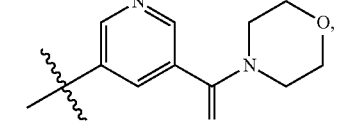

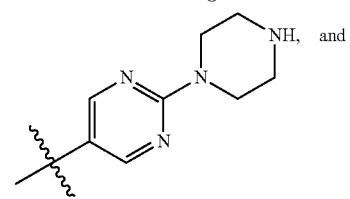

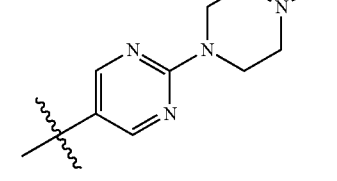

$R^3$ is, at each occurrence, independently selected from: F, Cl, Me, OMe, OEt, CN, $CF_3$, $OCHF_2$, $OCF_3$, $NO_2$, $CONH_2$, $SO_2Me$, and $SO_2Et$.

In a ninth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the ninth aspect.

In another embodiment, the compounds of the present invention have $IC_{50}$ values≤10 μM, using the MPO peroxidation assay disclosed herein, preferably, $IC_{50}$ values≤3 μM, more preferably, $IC_{50}$ values≤0.3 μM, even more preferably, $IC_{50}$ values≤0.1 μM.

In another embodiment, the compounds of the present invention have $IC_{50}$ values≤10 μM, using the MPO chlorination assay disclosed herein, preferably, $IC_{50}$ values≤3 μM, more preferably, $IC_{50}$ values≤0.3 μM, even more preferably, $IC_{50}$ values≤0.1 μM.

In another embodiment, the compounds of the present invention have $IC_{50}$ values≤10 μM, using the EPX bromination assay described herein, preferably, $IC_{50}$ values≤3 μM, more preferably, $IC_{50}$ values≤0.3 μM, even more preferably, $IC_{50}$ values≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a pharmaceutical composition as defined above further comprising additional therapeutic agent(s).

In another embodiment, the present invention provides a process for making a compound of the present invention.

In another embodiment, the present invention provides an intermediate for making a compound of the present invention.

In another embodiment, the present invention provides a compound of the present invention, for use in therapy, alone, or optionally in combination with another compound of the present invention and/or at least one other type of therapeutic agent.

In another embodiment, the present invention provides a compound of the present invention for use in therapy, for the treatment and/or prophylaxis of diseases or disorders associated with the activity of MPO and/or EPX, alone, or optionally in combination with another compound of the present invention and/or at least one other type of therapeutic agent.

In another embodiment, the present invention provides a method for the treatment and/or prophylaxis of diseases or disorders associated with the activity of MPO and/or EPX, comprising administering to a patient in need of such treatment and/or prophylaxis a therapeutically effective amount of at least one of the compounds of the present invention, alone, or optionally in combination with another compound of the present invention and/or at least one other type of therapeutic agent.

In another embodiment, the present invention provides a method for the treatment and/or prophylaxis of diseases or disorders associated with the activity of MPO and/or EPX, comprising administering to a patient in need thereof a therapeutically effective amount of a first and second therapeutic agent, wherein the first therapeutic agent is a compound of the present invention and the second therapeutic agent is one other type of therapeutic agent.

In another embodiment, the present invention also provides the use of a compound of the present invention for the manufacture of a medicament for the treatment and/or prophylaxis of diseases or disorders associated with the activity of MPO and/or EPX, alone, or optionally in combination with another compound of the present invention and/or at least one other type of therapeutic agent.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of diseases or disorders associated with the activity of MPO and/or EPX.

Examples of diseases or disorders associated with the activity of MPO and/or EPX that may be prevented, modulated, or treated according to the present invention include, but are not limited to, atherosclerosis, coronary heart disease, coronary artery disease, coronary vascular disease, cerebrovascular disorders, peripheral vascular disease, dyslipidemias and the sequelae thereof, cardiovascular disorders, angina, ischemia, cardiac ischemia, heart failure, stroke, myocardial infarction, reperfusion injury, angioplastic restenosis, hypertension, vascular complications of diabetes, obesity or endotoxemia.

In one embodiment, examples of diseases or disorders include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, transient ischemic attack and stroke. In one embodiment, examples of diseases or disorders include atherosclerosis, coronary heart disease, cerebrovascular disorders and dyslipidemias and the sequelae thereof. In one embodiment, examples of diseases or disorders include coronary artery disease and acute coronary syndrome. In one embodiment, examples of diseases or disorders include dyslipidemias and the sequelae thereof. In one embodiment, examples of diseases or disorders include heart failure. In one embodiment, examples of diseases or disorders include lung diseases including asthma, COPD and cystic fibrosis. In one embodiment, examples of diseases or disorders include neuroinflammatory diseases, including multiple sclerosis, Alzheimer's disease, Parkinson's disease, multiple system atrophy, and stroke.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, diurectics, mineralocorticoid receptor antagonists, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma high-density lipoprotein (HDL)-raising agents, anti-hypercholesterolemic agents, cholesterol biosynthesis inhibitors (such as HMG CoA reductase inhibitors), acyl-coenzyme A: cholesterol acyltransferase (ACAT) inhibitors, cholesterylester transfer protein (CETP) inhibitors, liver X receptor (LXR) agonists, anti-probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, diurectics, mineralocorticoid receptor antagonists, calcium channel blockers, anti-diabetes agents, angiotensin II receptor antagonists, angiotensin converting enzyme inhibitors, platelet aggregation inhibitors, factor Xa inhibitors, anti-thrombotic agents, renin inhibitors, fibrinogen receptor antagonists, aspirin and fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S- and ethyl-S-.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S-, and pentafluoroethyl-S-.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Hawley's Condensed Chemical Dictionary (15$^{th}$ ed.), R. J. Lewis, ed., J. Wiley & Sons, Inc., New York, 2007. "$C_6$ or $C_{10}$ aryl" or "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

When a dotted ring is used within a ring structure, this indicates that the ring structure may be saturated, partially saturated, or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

As a person of ordinary skill in the art would be able to understand, a ketone (—CH—C=O) group in a molecule may tautomerize to its enol form (—C=C—OH). Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of the present invention may have prodrug forms. Any compound that will be converted in vivo to provide the bioactive agent (i.e., a compound of Formula (I) or Formula (II)) is a prodrug within the scope and spirit of the invention. Various forms of prodrugs are well known in the art. For examples of such prodrug derivatives, see:
(a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988);
e) Kakeya, N. et al., *Chem. Pharm. Bull.*, 32:692 (1984); and
f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield Formula (I) or Formula (II) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) or Formula (II) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "wave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Ac: Acetic (AcOH: acetic acid, EtOAc: ethyl acetate)
ACN (or MeCN): acetonitrile
APF: aminophenyl fluorescein
BINAP: 2,2'-bis(diphenylphosphino)-1,1'-binaphthyl
Bn: benzyl
Boc: tert-butyl carbonyl
Boc$_2$O: Di-tert-butyl dicarbonate
Bu: butyl
dba (Pd$_2$(dba)$_3$): dibenzylideneacetone
DCM: dichloromethane
DEAD: diethyl azodicarboxylate
DIEA: diisopropylethylamine
DMAP: 4-dimethylaminopyridine
DME: Dimethoxyethane
DMF: dimethylformamide
DMSO: dimethyl sulfoxide
dppf (PdCl$_2$(dppf)): 1,1'-bis(diphenylphosphino)ferrocene
Et: ethyl (EtOH: ethanol, EtOAc: ethyl acetate)
HATU: 2-(7-Aza-1H-benzotriazole-1-yl)-1,1,3,3-tetramethyluronium hexafluorophosphate
hex: hexanes
HBTU: 2-1H-Benzotriazole-1-yl)-1,1,3,3-tetramethyluronium hexafluorophosphate
i-Bu: isobutyl
i-Pr: isopropyl
Me: methyl (MeOH: methanol, MeCN: acetonitrile)
NMP: N-Methylpyrrolidone
Ph: phenyl
Pr: propyl
t-Bu: tert-butyl
TCA: Trichloroacetic acid
TFA: Trifluoroacetic acid
THF: tetrahydrofuran
Ts: tosyl
Trt: trityl Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH Publishers, Inc., New York, N.Y. (1999). Preferred methods include, but are not limited to, those described below. All references cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts, P. G. M. and Greene, T. W. *Protecting Groups in Organic Synthesis*, 4th Edition, Wiley (2007)).

Compounds having the general Formula (I):

(I)

wherein A and R$^1$ are each defined above, can be prepared by the following one or more of the synthetic Schemes.

Scheme 1

1

2

X = Br or Cl

A mixture of chloro or bromotriazolopyridine 1 with a base such as sodium hydride or cesium carbonate and an alcohol can be heated in a suitable solvent such as DMSO to afford triazolopyridine 2. The synthesis of chloro or bromo-triazolopyridine 1 is provided in the methods below as Intermediate 2 and Intermediate 3, respectively. Many alcohols are commercially available and can also be prepared by methods known in the art.

Scheme 2

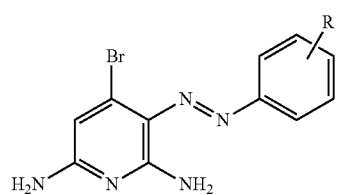

3

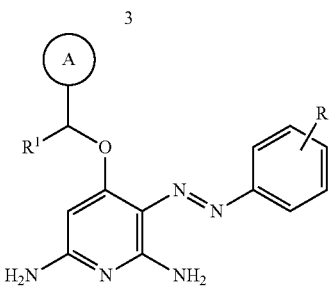

4

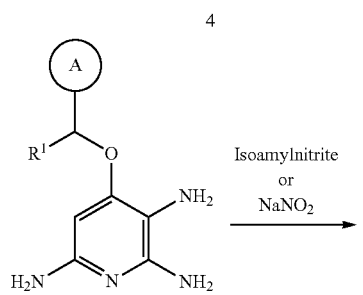

5    6

R is a variable

Alternatively to Scheme 1, diaza intermediate 3 can be heated with a base such as cesium carbonate and an alcohol in a solvent such as DMSO to yield ether 4. Intermediate 4 can be converted to triamine 5 by heating with hydrazine or with zinc in a mixture of acetic acid and ethanol or methanol. The triamine can be cyclized with isoamylnitrite or sodium nitrite or other reagent with similar reactivity to yield triazolopyridine 6. The synthesis of an example diaza intermediate 3 is described below in the synthesis methods as Intermediate 1.

Scheme 3

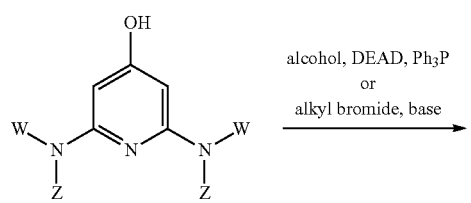

7

-continued

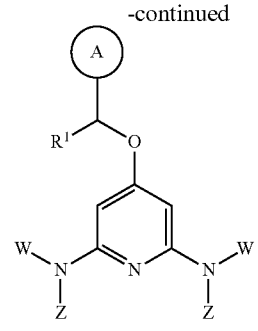

8

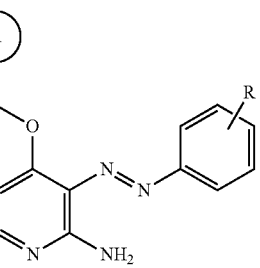

9

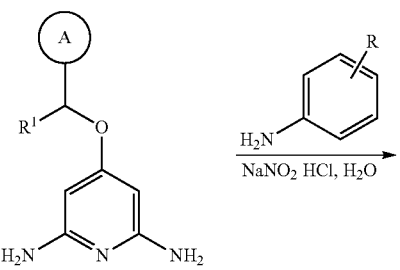

4

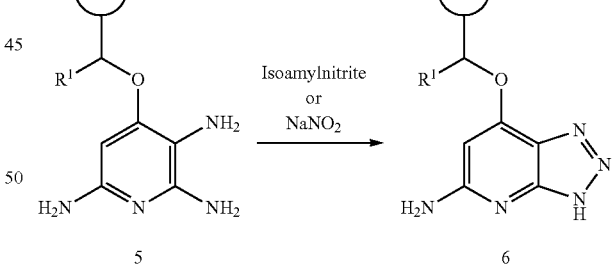

5    6

R is a variable

Pyridine ethers can also be prepared via Mitsunobu reaction or alkylation using Intermediate 7 where W is a suitable protecting group and Z is a protecting group or H. One example of a protecting group used in the invention is where W and Z are both equal to Boc. Once the protecting groups are removed, the subsequent pyridine diamine 9 can be diazatized with a diazonium salt prepared from anilines such as para-chloro aniline. The diaza species 4 can be converted into the desired triazolopyrine using the same synthetic sequence as shown in Scheme 2.

Scheme 4

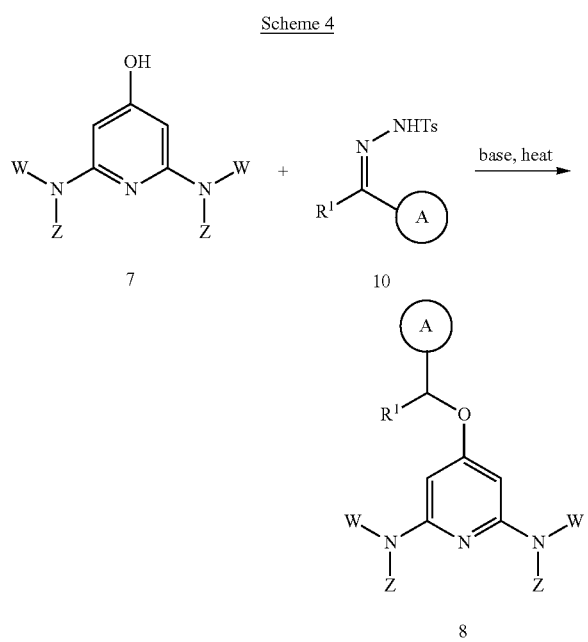

The ether linkage can also be formed using a reductive coupling of a tosylhydrazone (*Angew. Chem. Int. Ed.*, 49:4993-4996 (2010)) by heating hydrazone 10 with Intermediate 7 in the presence of base as depicted in Scheme 4. The resulting ether 8 can be converted into the corresponding triazolopyridine via the sequence shown in Scheme 3.

Scheme 5

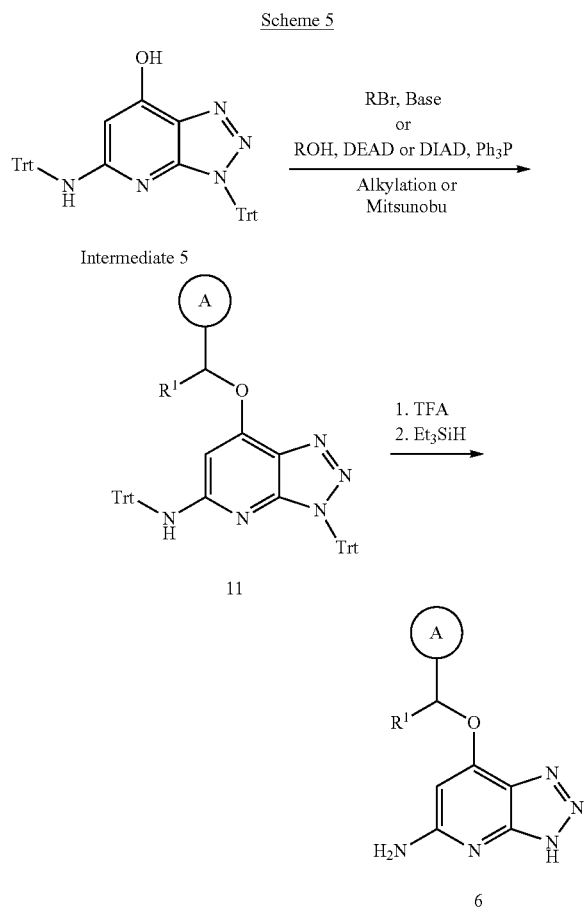

Pyridine ethers can also be prepared via Mitsunobu reaction or alkylation using trityl protected Intermediate 5. The resulting pyridyl ether 11 can be deprotected with an acid such as TFA and the trityl cation can be quenched by the addition of a scavenger such as triethyl silane followed by concentrated and purification to yield the desired compound.

The pyridyl ethers can also be formed by other methods known in the literature. For example, the appropriately protected pyridyl halide and an alcohol can be coupled using transition metal catalysis. (see *Angew. Chem. Int. Ed.*, 50:9943-9947 (2011); *Angew. Chem. Int. Ed.*, 48:6954-6971 (2009) and references therein).

The above compounds can be accessed through other starting materials such as 3-nitropyridines but these compounds should be handled with caution since derivatives can be highly energetic.

General Methods

The following methods were used in the exemplified Examples, except where noted otherwise.

Purification of intermediates and final products was carried out via either normal or reverse phase chromatography. Normal phase chromatography was carried out using pre-packed $SiO_2$ cartridges eluting with either gradients of hexanes and ethyl acetate or DCM and MeOH unless otherwise indicated. For highly polar amines, gradients of DCM and 1M $NH_3$ in MeOH were used. Reverse phase preparative HPLC was carried out using C18 columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (90% water, 10% ACN, 0.1% TFA) and Solvent B (10% water, 90% ACN, 0.1% TFA) or with gradients of Solvent A (95% water, 2% ACN, 0.1% HCOOH) and Solvent B (98% ACN, 2% water, 0.1% HCOOH) or with gradients of Solvent A (95% water, 5% ACN, 10 mM $NH_4OAc$) and Solvent B (98% ACN, 5% water, 10 mM $NH_4OAc$) or with gradients of Solvent A (95% water, 2% ACN, 0.1% $NH_4OH$) and Solvent B (98% ACN, 2% water, 0.1% $NH_4OH$). Compounds isolated as salts are reported in the experimental section.

Analytical HPLC: Methods Employed in Characterization of Examples

Products were analyzed by reverse phase analytical HPLC: carried out on a Shimadzu Analytical HPLC: system running Discovery VP software. RT=retention time.

Method A: Linear gradient of 0 to 100% B over 10 min, with 5 min hold at 100% B;
UV visualization at 254 nm
Column: SunFire C18; 3.5 m; 4.6×150 mm
Flow rate: 1 mL/min (Method A).
Solvent A: 10% acetonitrile, 90% water, 0.05% TFA
Solvent B: 10% water, 90% acetonitrile, 0.05% TFA Method B: Linear gradient of 0 to 100% B over 10 min, with 5 min hold at 100% B;
UV visualization at 254 nm
Column: XBridge Phenyl 3.5 µm; 4.6×150 mm
Flow rate: 1 mL/min (Method A).
Solvent A: 10% acetonitrile, 90% water, 0.05% TFA
Solvent B: 10% water, 90% acetonitrile, 0.05% TFA Method C: Linear gradient: 0-100% B over 3 min, then a 0.75-min hold at 100% B
Temperature: 50° C.
UV visualization at 220 nm
Column: Waters Acquity UPLC BEH C18, 1.7 m; 2.1×50 mm
Flow: 1.11 mL/min (Method A).
Solvent A: 5:95 acetonitrile:water with 0.1% TFA
Solvent B: 95:5 acetonitrile:water with 0.1% TFA Method D: Linear gradient: 0-100% B over 3 min, then a 0.75-min hold at 100% B
Temperature: 50° C.
UV visualization at 220 nm
Column: Waters Acquity UPLC BEH C18, 1.7 m; 2.1×50 mm
Flow: 1.11 mL/min (Method A).
Solvent A: 5:95 acetonitrile:water with 10 mM ammonium acetate
Solvent B: 95:5 acetonitrile:water with 10 mM ammonium acetate
Method E: Linear Gradient: 0.5 min hold at 0% B, 0-100% B over 4 minutes, then a 0.5-min hold at 100% B
Column: Waters BEH C18, 2.0×50 mm, 1.7-μm particles
Temperature: 40° C.;
Flow: 1 mL/min
Solvent A: 5:95 acetonitrile:water with 10 mM ammonium acetate
Solvent B: 95:5 acetonitrile:water with 10 mM ammonium acetate LC/MS Methods Employed in Characterization of Examples
Reverse phase analytical HPLC/MS was performed on Shimadzu LC10AS systems coupled with Waters ZMD Mass Spectrometers (Methods A-E) or Waters Acquity system coupled with a Waters MICROMASS® ZQ Mass Spectrometer (Method F).

Method A: Linear gradient of 0 to 100% B over 4 min, with 1 min hold at 100% B;
UV visualization at 220 nm
Column: PHENOMENEX® Luna C18 4.6×50 mm
Flow rate: 4 mL/min
Solvent A: 0.1% trifluoroacetic acid, 90% water, 10% acetonitrile
Solvent B: 0.1% trifluoroacetic acid, 90% acetonitrile, 10% water.

Method B: Linear gradient of 0 to 100% B over 4 min, with 1 min hold at 100% B;
UV visualization at 220 nm
Column: PHENOMENEX® Luna C18 2×50 mm
Flow rate: 4 mL/min
Solvent A: 98% water, 2% methanol, 0.1% formic acid
Solvent B: Methanol, 0.1% formic acid.

Method C: Linear gradient of 0 to 100% B over 4 min, with 1 min hold at 100% B;
UV visualization at 220 nm
Column: PHENOMENEX® Luna C18 4.6×50 mm
Flow rate: 4 mL/min
Solvent A: 0.1% trifluoroacetic acid, 90% water, 10% methanol
Solvent B: 0.1% trifluoroacetic acid, 90% methanol, 10% water.

Method D: Linear gradient of 0 to 100% B over 2 min, with 1 min hold at 100% B;
UV visualization at 220 nm
Column: PHENOMENEX® Luna C18 2.0×30 mm
Flow rate: 1 mL/min
Solvent A: 0.1% trifluoroacetic acid, 90% water, 10% methanol
Solvent B: 0.1% trifluoroacetic acid, 90% methanol, 10% water.

Method E: Linear gradient of 0 to 100% B over 2 min, with 1 min hold at 100% B;
UV visualization at 220 nm
Column: PHENOMENEX® Luna C18 2.0×30 mm
Flow rate: 1 mL/min
Solvent A: 98% water, 2% methanol, 0.1% formic acid
Solvent B: Methanol, 0.1% formic acid.

Method F: Linear gradient of 2 to 98% B over 1 min, with 0.5 min hold time at 98% B;
UV visualization at 220 nm
Column: Waters BEH C18 2.1×50 mm
Flow rate: 0.8 mL/min
Solvent A: 0.05% TFA, 100% water
Solvent B: 0.05% TFA, 100% acetonitrile Preparative HPLC Methods Employed in the Purification of Products Method G: Linear gradient of 20 to 100% B over 10 min, with 2 min hold time at 100% B
Shimadzu LC-8A binary pumps
Shimadzu SPD-10 A or 20A UV detector
UV visualization at 220 nm
Column: Waters SunFire 19×100 mm 5 m C18
Flow rate: 20 mL/min
Solvent A: 0.1% TFA, 10% MeOH, 90% water
Solvent B: 0.1% TFA, 90% MeOH, 10% water Method J: Linear gradient of 20 to 100% B over 10 min, with 2 min hold time at 100% B
Shimadzu LC-8A binary pumps
Shimadzu SPD-10A or 20A UV detector
UV visualization at 220 nm
Column: PHENOMENEX® Luna Axia 30×100 mm 5 m C18
Flow rate: 20 mL/min
Peak collection triggered by UV absorbance
Solvent A: 0.1% TFA, 10% MeOH, 90% water
Solvent B: 0.1% TFA, 90% MeOH, 10% water Method K: Linear gradient of 0 to 100% B over 10 min, with 2 min hold time at 100% B
Shimadzu LC-8A binary pumps
Shimadzu SPD-20A UV detector
UV visualization at 220 nm
Column: PHENOMENEX® Luna Axia 30×75 mm 5 m C18
Flow rate: 20 mL/min
Peak collection triggered by UV absorbance
Solvent A: 0.1% TFA, 10% ACN, 90% water
Solvent B: 0.1% TFA, 90% ACN, 10% water NMR Employed in Characterization of Examples $^1$H NMR spectra were obtained with Bruker or JEOL® Fourier transform spectrometers operating at frequencies as follows: $^1$H NMR: 400 MHz (Bruker or JEOL®) or 500 MHz (Bruker or JEOL®). $^{13}$C NMR: 100 MHz (Bruker or JEOL®). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

IV. Biology

Myeloperoxidase (MPO) and eosinophil peroxidase (EPX) are heme-containing enzymes and are members of the family of mammalian heme peroxidases that also includes salivary peroxidase, lactoperoxidase (LPO), thyroid peroxidase (TPO), prostaglandin H synthase and others. Both MPO and EPX use hydrogen peroxide to oxidize an array of substrates to either hypohalous acids or free radicals. Whereas both EPX and MPO are able to oxidize bromine (Br⁻), iodine (I⁻) and thiocyanate (⁻SCN), only MPO is able to oxidize chloride (Cl⁻) to hypochlorous acid (HOCl) efficiently.

MPO is present predominantly in neutrophils and to a lesser extent in monocytes and subtypes of tissue macrophages. The processed mature form of the enzyme is a glycosylated 146 kDa homodimer. Each subunit is made of a light and heavy polypeptide chain and contains a protoporphyrin IX group with a central iron. The three-fold linkage of the heme is unique compared to other heme proteins and provides specific spectral and catalytic properties to MPO. MPO uses hydrogen peroxide to oxidize an array of substrates to either hypohalous acids or free radicals. The main substrate for MPO is generally accepted to be chloride, which is oxidized to hypochlorous acid. This is one of the most reactive oxidants produced in vivo. Other substrates include thiocyanate, bromide, tyrosine, tryptophan, sulfhydryls, phenol and indole derivatives, ascorbate, nitrite, nitric oxide, and urate.

The physiological role of MPO is to participate in the killing of invading bacterial and fungal pathogens (Klebanoff, S. J., *J Exp Med.*, 126:1063-1078 (1967); Klebanoff, S. J., *J. Bacteriol.*, 95:2131-2138 (1968); Klebanoff, S. J., *Science*, 169:1095-1097 (1970)). However, excessive generation of oxidants by MPO and other peroxidases has been linked to tissue damage in many diseases, especially those characterized by acute or chronic inflammation. At sites of inflammation, PMNs or tissue macrophages can generate hydrogen peroxide and upon activation also produce myeloperoxidase. This is evidenced by the fact that, in many cases, enzymatically active MPO in conjunction with 3-chlorotyrosine, a tissue marker for HOCl-mediated damage, or HOCl-modified proteins can be detected in diseased tissues colocalized with neutrophils or macrophages (Daugherty, A. et al., *JCI*, 94:437-444 (1994); Bergt et al., *Proc. Natl. Acad. Sci.*, 101:13032-13037 (2004); Pennathur, S. et al., *JBC*, 279:42977-42983 (2004); Choi, D. K. et al., *J. Neurosci.*, 25(28):6394-6600 (2005)).

Eosinophil peroxidase (EPX) is a cationic heme-containing protein, and represents nearly 25% of the total mass of the secondary granule protein in eosinophils. It is an highly basic 77 kDa protein made up of two subunits containing a modified Fe-protoporphyrin-IX prosthetic group. EPX shares with MPO the ability to use $H_2O_2$ to oxidize thiocyanate, bromide, and nitrite in vivo to kill bacteria, and viruses (Jong, E. C. et al., *J. Immunol.*, 124:1949-1953 (1980)). Eosinophils play a unique role in host defense mechanisms but increased levels of circulating and tissue eosinophils are implicated in promoting cellular and tissue injury in particular in asthma, and during allergic inflammatory responses of lung diseases.

MPO Peroxidation Assay (Amplex Red Assay)

MPO peroxidation activity was measured in 100 mM KPi (pH 7.4) by utilizing the non-fluorescent reagent Amplex Red (Invitrogen catalog # A12222) which can be oxidized to the highly fluorescent resorufin. Amplex Red is oxidized by the peroxidase action of MPO to resorufin. Reactions were carried out in 50 µL total volume by adding a 25 µL mixture of 200 pM myeloperoxidase and 40 nM $H_2O_2$(Sigma #349887) to 100 nL inhibitor in 100% DMSO in a 384 well Perkin Elmer Optiplate. Enzyme and compound were preincubated for ten minutes at room temperature.

After the ten minute preincubation, 25 µL of an Amplex Red mixture containing 200 µM Amplex Red and 10 mM $H_2O_2$ was added to the plate. Kinetic determinations were carried out immediately on a Perkin Elmer Envision (15 minute kinetic read, Ex: 535 nm, Em: 590 nm).

$IC_{50}$ values were calculated by determining the slope of the linear portion of the kinetic trace (180-540 secs), and using that calculated slope to determine % inhibition occurring at each concentration of inhibitor using the following equation:

$$Y = A + \frac{B - A}{1 + (C/x)^D}$$

where A=minimal Y value (activity level of inhibited sample), B=maximal Y value (activity level of uninhibited sample), C=Log $IC_{50}$, D=Hill Slope, x=concentration of inhibitor.

MPO Chlorination Assay (APF Assay)

MPO chlorination activity was measured in 100 mM KPi (pH 7.4) by utilizing the non-fluorescent reagent Aminophenyl fluorescein (APF, Invitrogen catalog #A36003). APF is cleaved by (—OCl) to yield the fluorescent compound fluorescein. Reactions were carried out in 50 µL total volume by adding a 25 µL mixture of 200 pM myeloperoxidase and 120 mM NaCl to 100 nL inhibitor in 100% DMSO in a 384 well, non-binding surface clear bottom plate (CORNING® #3655). Enzyme, inhibitor, and chloride were preincubated for ten minutes at room temperature.

After the ten minute preincubation, 25 µL of an APF mixture containing 10 mM APF, 120 mM NaCl and 10 µM $H_2O_2$ was added to the plate using the internal dispensing system of a Hammatsu FDSS 6000. Kinetic determinations were carried out immediately on the FDSS 6000 (3 minute kinetic read, 1 read every second, ex: 485 nm, em: 535 nm). $IC_{50}$ values for inhibitors were calculated by taking the slope of the linear portion of the kinetic measurement (20 seconds to ~80-120 secs).

$IC_{50}$ values were calculated by determining the slope of the linear portion of the kinetic trace (180-540 secs), and using that calculated slope to determine % inhibition occurring at each concentration of inhibitor using the following equation:

$$Y = A + \frac{B - A}{1 + (C/x)^D}$$

where A=minimal Y value (activity level of inhibited sample), B=maximal Y value (activity level of uninhibited sample), C=Log $IC_{50}$, D=Hill Slope, x=concentration of inhibitor.

EPX Bromination Assay

EPX bromination activity was measured in 100 mM KPi (pH 7.4) by monitoring the $H_2O_2$ catalyzed formation of 3-bromo tyrosine from tyrosine and potassium bromide. A 50 µl mixture of 0.6 µM EPX (Lee Biosolutions Cat#342-60) was added to 100 nL inhibitor in 100% DMSO in a 384 well REMP plate. Enzyme and compound were preincubated for ten minutes at room temperature.

After the ten minute preincubation of enzyme and inhibitor, 25 µL of a mixture containing 400 µM tyrosine and 1200 µM potassium bromide was added to the plate containing enzyme and inhibitor, followed by the addition of 25 µl of 20 µM $H_2O_2$. The reaction was allowed to proceed for 15 minutes, at which time it was quenched with 10 µL of 20% TCA. The final concentrations of all components were 0.3 µM EPX, 100 µM tyrosine, 400 µM potassium bromide, 5 µM $H_2O_2$, 0.1% DMSO, 2.0% TCA.

IC$_{50}$ values were determined by determining the peak areas of 3-bromotyrosine present at the end of the 15 minute reaction and fitting the data to:

$$Y = A + \frac{B-A}{1+(C/x)^D}$$

where A=minimal Y value (activity level of inhibited sample), B=maximal Y value (activity level of uninhibited sample), C=Log IC$_{50}$, D=Hill Slope, x=concentration of inhibitor.

Reversed-phase analysis was performed on a Waters Acquity Ultra Performance LC system using an Acquity UPLC BEH C$_{18}$ 1.7 μM, 2.1×50 mm analytical column. The column was maintained at 60° C. Samples were eluted using a gradient of 0%-100% B over 2.5 minutes, followed by equilibration with 100% A for 1 minute where A consisted of 0.1% TFA and B consisted of 90% MeOH/0.1% TFA at a flow rate of 0.6 mL/min. The retention time of 3-bromo tyrosine was 1.22 min.

The exemplified Examples disclosed below were tested in the MPO peroxidation assay described above and found having MPO inhibitory activity. A range of IC$_{50}$ values of ≤10 μM (10000 nM) was observed.

Some of the exemplified Examples disclosed below were tested in the MPO chlorination assay described above and found having MPO inhibitory activity. A range of IC$_{50}$ values of ≤10 μM (10000 nM) was observed.

Some compounds of the invention were tested in the EPX bromination assay described above and were found to inhibit EPX with a range of IC$_{50}$ values of ≤10 μM (10000 nM), as demonstrated by Example 2 (EPX IC$_{50}$=0.08 μM), Example 6 (EPX IC$_{50}$=0.01 μM), Example 8 (EPX IC$_{50}$=0.04 μM) and Example 54 (EPX IC$_{50}$=0.01 μM).

Table 1 below lists IC$_{50}$ value range in the MPO peroxidation (Amplex Red) assay and MPO chlorination assay (APF) measured for the following Examples. Potency ranges A 1-100 nM; B=101-999 nM; C=1000-10000 nM.

TABLE 1

| Example No. | Amplex Red IC$_{50}$ (μM) | APF IC$_{50}$ (μM) |
| --- | --- | --- |
| 1 | A | |
| 2 | A | |
| 3 | A | |
| 4 | B | |
| 5 | A | |
| 6 | A | |
| 7 | B | |
| 8 | A | |
| 10 | A | |
| 11 | A | |
| 12 | A | |
| 13 | A | |
| 16 | B | |
| 17 | B | |
| 20 | A | |
| 21 | A | |
| 22 | A | |
| 24 | A | |
| 25 | B | |
| 26 | A | |
| 27 | A | |
| 28 | A | |
| 29 | A | |
| 30 | A | |
| 31 | A | |
| 32 | A | |
| 33 | B | |
| 35 | A | |
| 36 | A | A |
| 37 | B | |
| 38 | A | |
| 41 | A | |
| 43 | A | B |
| 44 | B | |
| 45 | A | |
| 46 | A | |
| 47 | A | |
| 48 | A | |
| 49 | A | |
| 50 | A | B |
| 51 | B | |
| 52 | B | C |
| 53 | B | |
| 54 | A | |
| 55 | A | |
| 56 | B | |
| 57 | A | A |
| 58 | A | |
| 59 | A | |
| 60 | A | |
| 61 | A | A |
| 62 | A | |
| 63 | A | |
| 64 | B | |
| 65 | A | |
| 66 | A | |
| 67 | B | |
| 68 | A | |
| 69 | A | |
| 70 | A | |
| 71 | A | |
| 72 | A | |
| 73 | A | |
| 74 | A | |
| 75 | B | |
| 77 | A | |
| 78 | A | |
| 79 | B | |
| 80 | B | |
| 81 | A | |
| 82 | A | |
| 83 | A | |
| 84 | B | |
| 85 | B | |
| 86 | A | |
| 87 | C | |
| 88 | A | |
| 89 | A | |
| 90 | A | |
| 91 | A | |
| 92 | A | |
| 93 | A | |
| 95 | A | |
| 96 | A | |
| 97 | B | |
| 98 | A | |
| 99 | B | |
| 100 | A | |
| 101 | A | |
| 102 | B | |
| 103 | A | |
| 104 | B | |
| 105 | A | |
| 106 | A | |
| 107 | B | |
| 108 | B | |
| 109 | B | |
| 110 | C | |
| 111 | C | |
| 112 | B | |
| 113 | A | |
| 114 | B | |
| 115 | A | |
| 116 | B | |
| 117 | B | |

TABLE 1-continued

| Example No. | Amplex Red IC$_{50}$ (μM) | APF IC$_{50}$ (μM) |
|---|---|---|
| 118 | A | |
| 119 | B | |
| 120 | B | |
| 121 | A | |
| 122 | A | |
| 123 | A | |
| 124 | B | |
| 125 | A | |
| 126 | B | |
| 127 | B | |
| 128 | A | |
| 129 | A | |
| 130 | A | |
| 131 | A | |
| 132 | B | |
| 133 | A | B |
| 135 | B | |
| 136 | B | |
| 137 | A | |
| 138 | B | |
| 139 | A | B |
| 140 | B | |
| 142 | C | |
| 143 | B | |
| 144 | B | |
| 145 | B | |
| 147 | B | |
| 148 | A | |
| 152 | B | |
| 153 | B | |
| 154 | B | |
| 155 | B | |
| 156 | B | |
| 157 | A | |
| 158 | A | |
| 159 | A | |
| 160 | B | |
| 161 | A | |
| 162 | A | |
| 163 | B | |
| 164 | B | |
| 166 | B | |
| 169 | B | |
| 170 | A | |
| 171 | A | |
| 173 | A | |
| 175 | A | |
| 176 | B | |
| 177 | B | C |
| 178 | B | |
| 179 | B | |
| 182 | B | |
| 183 | B | |
| 184 | B | |
| 185 | B | |
| 187 | B | |
| 188 | A | |
| 189 | B | |
| 190 | A | |
| 191 | A | |
| 192 | A | |
| 193 | B | |
| 194 | A | |
| 196 | A | |
| 197 | B | |
| 198 | B | |
| 199 | B | |
| 201 | A | |
| 202 | A | |
| 203 | A | |
| 204 | A | |
| 205 | A | |
| 206 | B | |
| 207 | A | |
| 209 | A | |
| 210 | B | |
| 212 | B | |
| 213 | A | |
| 214 | A | |
| 215 | A | |
| 216 | A | |
| 218 | B | |
| 219 | A | |
| 220 | B | |
| 221 | A | |
| 222 | B | |
| 223 | B | |
| 224 | A | |
| 225 | A | |
| 226 | A | B |
| 227 | B | |
| 228 | B | |
| 229 | B | |
| 230 | B | |
| 231 | A | |
| 232 | B | |
| 233 | A | |
| 234 | A | A |
| 235 | A | |
| 236 | A | |
| 237 | A | |
| 238 | A | |
| 239 | A | |
| 240 | A | |
| 241 | A | |
| 242 | A | A |
| 243 | A | |
| 244 | A | |
| 245 | A | |
| 246 | B | |
| 247 | A | |
| 248 | A | |
| 249 | A | |
| 250 | B | |
| 251 | A | |
| 252 | A | |
| 253 | B | |
| 254 | C | C |
| 255 | B | |
| 256 | B | |
| 257 | A | |
| 258 | A | |
| 259 | A | |
| 260 | A | |
| 261 | B | |
| 264 | B | |
| 265 | A | |
| 266 | B | |
| 267 | A | |
| 268 | A | |
| 270 | A | |
| 271 | A | C |
| 272 | B | |
| 273 | B | |
| 274 | B | |
| 276 | B | |
| 277 | B | C |
| 279 | B | |
| 280 | B | |
| 281 | A | |
| 282 | A | |
| 285 | A | |
| 286 | A | |
| 288 | B | |
| 289 | A | |
| 290 | A | |
| 291 | A | |
| 292 | A | |
| 293 | B | |
| 294 | B | |
| 295 | B | |
| 296 | A | |
| 297 | A | |
| 299 | A | |
| 300 | A | |
| 301 | A | |

TABLE 1-continued

| Example No. | Amplex Red IC$_{50}$ (µM) | APF IC$_{50}$ (µM) |
|---|---|---|
| 302 | A | |
| 303 | A | |
| 304 | A | |
| 305 | A | B |
| 307 | A | |
| 308 | A | |
| 309 | A | |
| 310 | A | |
| 311 | A | |
| 312 | A | |
| 313 | A | |
| 314 | A | |
| 315 | A | |
| 316 | A | |
| 317 | A | |
| 318 | A | |
| 319 | A | |
| 320 | B | |
| 321 | A | |
| 322 | A | |
| 323 | A | |
| 324 | A | |
| 325 | A | |
| 326 | A | |
| 327 | A | |
| 328 | A | |
| 329 | A | |
| 330 | A | |
| 331 | A | |
| 332 | A | |
| 333 | A | |
| 334 | A | B |
| 335 | A | |
| 336 | A | A |
| 337 | A | |
| 338 | A | |
| 339 | B | |
| 340 | B | |
| 341 | A | |
| 342 | A | |
| 343 | A | |
| 344 | A | |
| 345 | B | C |
| 346 | B | |
| 347 | A | |
| 348 | B | |
| 349 | B | |
| 350 | A | |
| 351 | A | |
| 352 | A | |

Accordingly, the compounds of the present invention may be administered to mammals, preferably humans, for the treatment of a variety of conditions and disorders, including, but not limited to, atherosclerosis, coronary artery disease, acute coronary syndrome, dyslipidemias and the sequelae thereof, angina, ischemia, cardiac ischemia, myocardial infarction, reperfusion injury, angioplastic restenosis, hypertension, vascular complications of diabetes, obesity or endotoxemia, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 Volumes), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors, antihypertensives or other pharmaceutically active material.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin and fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα ☐inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the myeloperoxidase. Such compounds may be provided in a commercial kit, for example, for use in pharmaceutical research involving myeloperoxidase activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving myeloperoxidase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

VI. Examples

The following Examples have been prepared, isolated and characterized using the methods disclosed herein. The following Examples demonstrate a partial scope of the invention and are not meant to be limiting of the scope of the invention.

General Synthesis Procedures

General Route 1:

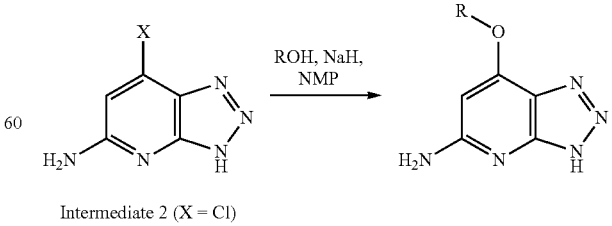

Intermediate 2 (X = Cl)
or Intermediate 3 (X = Br)

NaH (2.0-4.0 eq, 60% dispersion in oil) was added to a mixture of ROH (1.5-4.0 eq), 7-bromo-3H-[1,2,3]triazolo

[4,5-b]pyridin-5-amine or 7-chloro-3H-[1,2,3]triazolo[4,5-b]pyridin-5-amine (1.0 eq) in NMP (0.10-0.50 μM) and stirred at 100-130° C. for 1-3 days. The reaction was quenched with aqueous ammonium acetate, partially concentrated and purified by prep HPLC to yield the desired product.

General Route 2:

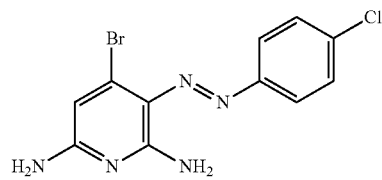 [SMILES: Nc1cc(Br)c(/N=N/c2ccc(Cl)cc2)c(N)n1]

Intermediate 1

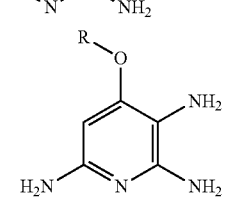

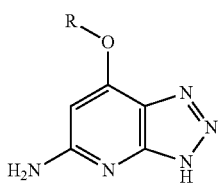

General Displacement

A mixture of (E)-4-bromo-3-((4-chlorophenyl)diazenyl)pyridine-2,6-diamine (1.0 eq), ROH (1.0-3.0 eq) and Cs₂CO₃ (2.0 eq) in DMSO (0.10-0.30 M) was heated for 2 days at 70-110° C. The reaction was diluted with water/brine and extracted with EtOAc. The combined organics were washed with brine, dried over Na₂SO₄ and concentrated in vacuo. The crude mixture was purified by column chromatography to yield the desired product.

General Reduction

A mixture of the diazo compound (1.0 eq) and zinc (3.0-5.0 eq) in EtOH (0.10-0.20 M) and acetic acid (5.0-10 eq) was stirred at 40-70° C. for 15 min-5 h. The mixture was filtered and concentrated. The crude material was optionally redissolved in 7.0 M NH₃ (0.50 M) in MeOH and concentrated. The crude product was purified by column chromatography to yield the desired product.

General Cyclization

Isoamyl nitrite (0.90-3.0 eq) was added to a mixture of the triamine (1.0 eq) in THF (0.10 M) and acetic acid (0.0-10 eq) and stirred at rt for 2 h-64 h. The reaction mixture was concentrated and purified by prep HPLC to yield the desired product.

General Route 3:

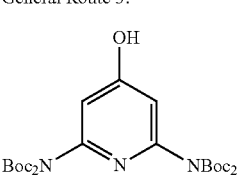

Intermediate 4

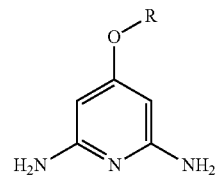

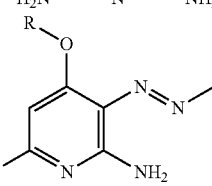

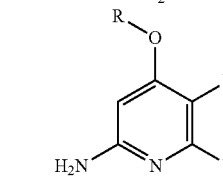

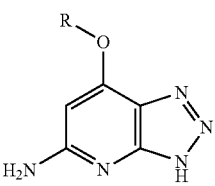

General Alkylation

An alkyl bromide (1.0-1.5 eq) was added to a mixture of Intermediate 4 (1.0 eq), Na₂CO₃ or K₂CO₃ (2 eq) and tetrabutylammoniumbromide (0.0-2.0 eq) in DMSO (0.10-0.30 M) and stirred 4-16 h. The mixture was diluted with EtOAc, washed with water and/or brine, dried over Na₂SO₄ and concentrated. The crude product was purified by flash chromatography to yield the desired product.

General Mitsunobu Procedure

DEAD or DIAD (2.0 eq) was added to a mixture of Intermediate 4 (1.0 eq), ROH (1.5 eq) and triphenylphosphine (2.0 eq) in THF (0.20 M) and stirred at rt 4-24 h. The reaction mixture was concentrated and the crude product was purified by flash chromatography to yield the desired product.

General Boc Deprotection

TFA (equal volume to DCM) was added to a solution of the pyridine ether in DCM (0.10-0.50 M) and stirred at rt for 1-8 h. The mixture was concentrated and the crude was used in the next reaction without purification.

General Diazatization

A solution of 6.0 N HCl (3.5 eq) was added to 4-chloroaniline (1.2 eq) with vigorous stirring at 0° C. A solution of sodium nitrite (1.0 eq) in water (1.0 M) was added to the flask. After stirring for 30 min, urea (0.10 eq) added to destroy excess $NaNO_2$.

The above solution was added to a suspension of diaminopyridine (1.0 eq) in water, ethyl acetate and methanol (0.10 M, 5:2:1 ratio). After 30 min, sodium acetate (4.0 eq) was added and the mixture was stirred overnight. The mixture was partially concentrated and partitioned between EtOAc and $NaHCO_3$. The combined organics were washed with brine, dried over $Na_2SO_4$ and concentrated in vacuo to yield a solid that was carried into the next step without purification. The resulting product can be converted into the desired triazolopyridine using the chemistry described in General Route 2.

General Route 4:

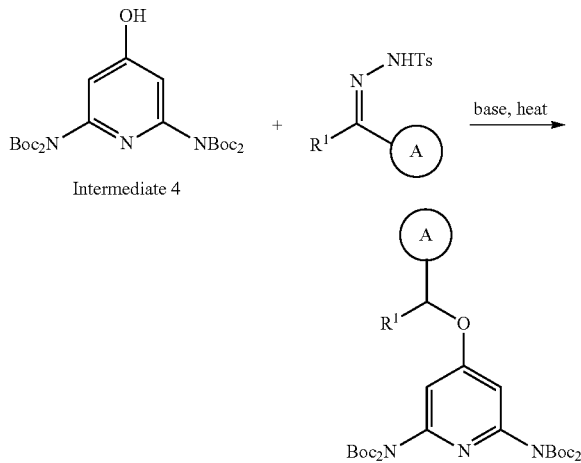

Intermediate 4

A mixture of Intermediate 4 (1.0 eq), a tosylhyrazone (1.0 eq), and potassium carbonate (3.0-5.0 eq) in dioxane was stirred at 110° C. The reaction mixture was cooled to room temperature, diluted with EtOAc and filtered. Upon concentration in vacuo, the reaction mixture was purified by flash column chromatography to yield the desired compound as a clear, colorless oil. The resulting product can be converted into the desired triazolopyridine using the chemistry described in General Routes 2 and 3.

General Route 5:

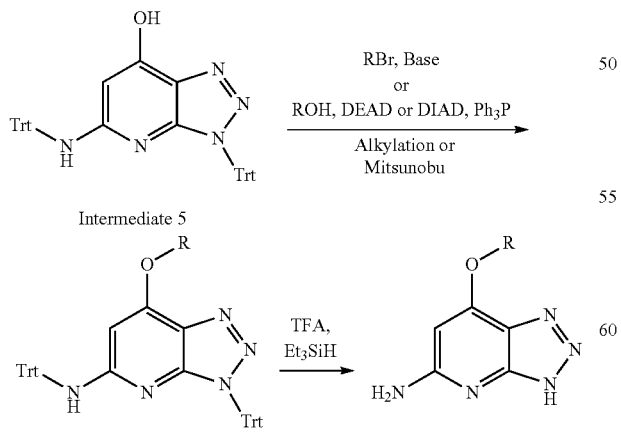

Intermediate 5

General Alkylation

An alkyl bromide (1.0-1.5 eq) was added to a mixture of Intermediate 5 (1.0-2.0 eq), $Na_2CO_3$ or $K_2CO_3$ (2 eq) in DMSO (0.10-0.30 M) and stirred 4-16 h. The mixture was diluted with EtOAc, washed with water and/or brine, dried over $Na_2SO_4$ or $MgSO_4$ and concentrated.

General Mitsunobu Procedure

DEAD or DIAD (2.0 eq) was added to a mixture of Intermediate 4 (1.0 eq), ROH (1-2 eq) and triphenylphosphine (2.0 eq) in THF (0.05-0.50 M) and stirred at rt 4-24 h. The reaction mixture was concentrated.

General Trt Deprotection

TFA was added to a solution of the pyridine ether in DCM or THF (0.10-0.50 M) and stirred at rt for 1-8 h. Triethylsilane (2-10 eq) was added and the mixture was concentrated in vacuo. The crude produce was purified by preparatory HPLC.

Common Intermediates:

Intermediate 1: (E)-4-Bromo-3-((4-chlorophenyl)diazenyl)pyridine-2,6-diamine

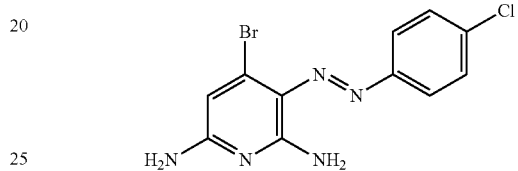

A solution of HCl (34 mL, 200 mmol) was added to 4-chloroaniline (7.5 g, 59 mmol) with vigorous stirring at 0° C. A solution of sodium nitrite (3.7 g, 53 mmol) in water (20 mL) was added to the flask. After stirring for 30 mins, urea (0.32 g, 5.3 mmol) was added to destroy excess $NaNO_2$.

The above solution was poured into a heterogeneous mixture of 4-bromopyridine-2,6-diamine (10 g, 53 mmol) in water (300 mL) and was stirred for 1.5 h. Sodium acetate (15 g, 190 mmol) in 300 mL of water was added and the mixture was stirred overnight. The precipitate was collected by filtration and washed thoroughly with water (5×) and dried in vacuo. The remaining water was removed by azeotroping the solid with DCM/acetonitrile to provide Intermediate 1 (17 g, 53 mmol, 99% yield) as a yellow solid. $^1$H NMR (500 MHz, DMSO-$d_6$) δ 9.65 (br. s., 1H), 7.78-7.70 (m, 2H), 7.65 (br. s., 1H), 7.56-7.47 (m, 2H), 7.04 (br. s., 2H), 6.43 (s, 1H).

Intermediate 2: 7-Chloro-3H-[1,2,3]triazolo[4,5-b]pyridin-5-amine

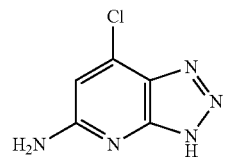 [SMILES: Nc1cc(Cl)c2nn[nH]c2n1]

Intermediate 2A: (E)-4-Chloro-3-((4-chlorophenyl)diazenyl)pyridine-2,6-diamine

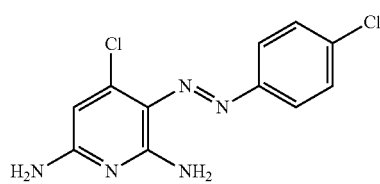 [SMILES: Nc1cc(Cl)c(/N=N/c2ccc(Cl)cc2)c(N)n1]

Intermediate 2A was synthesized using procedure similar to the Intermediate 1 synthesis procedure starting from 4-chloropyridine-2,6-diamine. MS(ESI) m/z 282.0 (M+H).

Intermediate 2B: 4-Chloropyridine-2,3,6-triamine

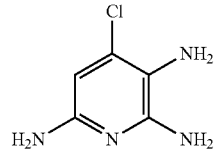

A mixture of (E)-4-chloro-3-((4-chlorophenyl)diazenyl)pyridine-2,6-diamine (7.0 g, 25 mmol) and zinc (4.9 g, 74 mmol) in EtOH (120 mL)/acetic acid (7.1 mL) was stirred at 70° C. for 2 h. The mixture was filtered and concentrated. The crude product was purified by column chromatography (2.0 M $NH_3$ in MeOH/DCM, 0-20% gradient) to yield Intermediate 2B (2.3 g, 14 mmol, 57% yield) as a brown solid.

Intermediate 2

Isoamyl nitrite (1.1 mL, 8.0 mmol) was added to a mixture of 4-chloropyridine-2,3,6-triamine (1.4 g, 8.8 mmol) in THF (50 mL) and acetic acid (2.5 mL) and was stirred at rt overnight. The reaction mixture was concentrated and purified by column chromatography (0% to 20% gradient, MeOH/DCM with 0.5% AcOH) to yield Intermediate 2 (600 mg, 3.5 mmol, 40% yield) as a brown solid. MS(ESI) m/z 170.1 (M+H).

Intermediate 3: 7-Bromo-3H-[1,2,3]triazolo[4,5-b]pyridin-5-amine

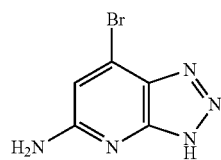 [SMILES: Nc1cc(Br)c2nn[nH]c2n1]

Intermediate 3 was synthesized from Intermediate 1 using the procedures described in the synthesis of Intermediate 2.

Intermediate 4: 2-[6-[Bis[(1,1-dimethylethoxy)carbonyl]amino]-1,4-dihydro-4-oxo-2-pyridinyl]-1,3-bis(1,1-dimethylethyl)ester

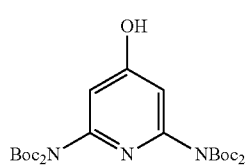

Intermediate 4A:
4-(Benzyloxy)pyridine-2,6-diamine

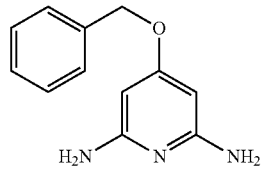 [SMILES: Nc1cc(OCc2ccccc2)cc(N)n1]

4-Benzyloxy-2,6-pyridine was synthesized from chelidamic acid as described in the literature (*Chem. Eur. J.*, 7(9):1889-1898 (2001)).

Intermediate 4B: Di-tert-butyl(4-(benzyloxy)pyridine-2,6-diyl)bis(tert-butoxy carbonylcarbamate)

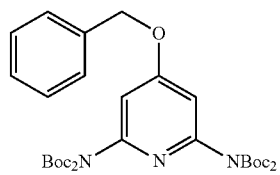

$Boc_2O$ (13 mL, 56 mmol) and DMAP (0.55 g, 4.5 mmol) were added as solids to a solution of 4-(benzyloxy)pyridine-2,6-diamine (2.4 g, 11 mmol) in acetonitrile (50 mL)/DCM (25 mL) and the mixture was stirred overnight at rt. An additional of 5.0 eq $Boc_2O$ and 0.25 eq DMAP were added and the mixture was stirred overnight. The reaction was concentrated in vacuo. The crude product was purified by flash chromatography (loading in 10:1 hexanes/EtOAC, 0% to 50% ethyl acetate in hexane over 30 min using a 120 g silica gel cartridge) to yield Intermediate 4B (5.7 g, 9.3 mmol, 83% yield) as a white solid.

Intermediate 4

A mixture of Intermediate 4B (5.7 g, 9.3 mmol) and Pd/C (500 mg, 0.47 mmol) in MeOH (100 mL) was stirred under $H_2$ (1.0 atm) overnight. The mixture was filtered and concentrated to yield Intermediate 4 (4.7 g, 8.9 mmol, 97% yield) as a clear foam. MS(ESI) m/z 526.2 (M+H).

Intermediate 5: 3-Trityl-5-(tritylamino)-3H-[1,2,3]triazolo[4,5-b]pyridin-7-ol

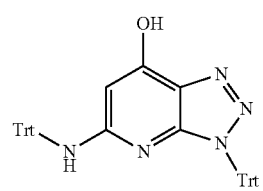

Intermediate 5A: (E)-4-(Benzyloxy)-3-((4-chlorophenyl)diazenyl)pyridine-2,6-diamine

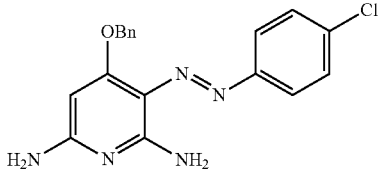 [SMILES: Nc1cc(OCc2ccccc2)c(/N=N/c2ccc(Cl)cc2)c(N)n1]

A solution of sodium nitrite (3.0 g, 44 mmol) in water (2 mL) was added to a slurry of 4-chloroaniline (5.6 g, 44 mmol) in 6 M HCl (15 mL, 88 mmol), and the reaction mixture was allowed to stir at room temperature for 30 minutes. The solution was added to a suspension of 4-(benzyloxy)pyridine-2,6-diamine (Intermediate 4a) (9.5 g, 44 mmol) in MeOH (440 mL). The resultant slurry was stirred at room temperature for 18 hours. The reaction mixture was filtered to isolate (E)-4-(benzyloxy)-3-((4-chlorophenyl)diazenyl)pyridine-2,6-diamine (13 g, 37 mmol, 84% yield) as an orange solid.

Intermediate 5B: 4-(Benzyloxy)pyridine-2,3,6-triamine

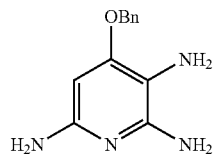

Zinc (4.5 g, 69 mmol) was added portionwise to a solution of (E)-4-(benzyloxy)-3-((4-chlorophenyl)diazenyl)pyridine-2,6-diamine (12 g, 35 mmol) and acetic acid (7.9 mL) at 60° C. The reaction mixture was stirred until the color had disappeared, and TLC/LCMS analysis indicated starting material consumption. The reaction was filtered through CELITE®, concentrated, and purified by column chromatography (eluting with a linear gradient of 0% to 40% MeOH in DCM over 28 minutes). 4-(Benzyloxy)pyridine-2,3,6-triamine (5.7 g, 25 mmol, 71% yield) was isolated as a brown solid.

Intermediate 5C: 7-(Benzyloxy)-3H-[1,2,3]triazolo[4,5-b]pyridin-5-amine

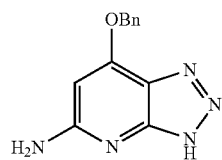 [SMILES: Nc1cc(OCc2ccccc2)c2nn[nH]c2n1]

Isoamyl nitrite (2.8 mL, 21 mmol) was added to a solution of 4-(benzyloxy)pyridine-2,3,6-triamine (4.7 g, 21 mmol) and acetic acid (5.9 mL) in THF (100 ml), and the reaction was stirred for 1.5 hours at room temperature. The reaction mixture was partially concentrated and diluted with hexane to precipitate product. The solid was filtered and dried in vacuo to yield 7-(benzyloxy)-3H-[1,2,3]triazolo[4,5-b]pyridin-5-amine (4.1 g, 17 mmol, 83% yield) as a brown powder. MS(ESI) m/z 242.2 (M+H).

Intermediate 5D: 7-(Benzyloxy)-N,3-ditrityl-3H-[1,2,3]triazolo[4,5-b]pyridin-5-amine

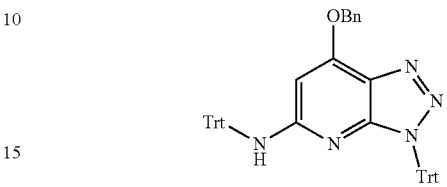

Triethylamine (3.6 mL, 26 mmol) was added to a suspension of 7-(benzyloxy)-3H-[1,2,3]triazolo[4,5-b]pyridin-5-amine (1.3 g, 5.2 mmol) and (chloromethanetriyl)tribenzene (2.9 g, 10 mmol) in dichloromethane (52 ml), and the reaction mixture was stirred at room temperature for 18 hours. The reaction mixture was concentrated and purified by column chromatography (EtOAc/hex) to yield 7-(benzyloxy)-N,3-ditrityl-3H-[1,2,3]triazolo[4,5-b]pyridin-5-amine (3.6 g, 5.0 mmol, 96% yield) as a tan solid.

Intermediate 5

Triethylsilane (0.90 mL, 5.6 mmol) and triethylamine (0.63 mL, 4.5 mmol) were added to a solution of palladium (II) acetate (0.042 g, 0.19 mmol) in dichloromethane (5 mL), and the reaction mixture was stirred for 10 minutes. A solution of 7-(benzyloxy)-N,3-ditrityl-3H-[1,2,3]triazolo[4,5-b]pyridin-5-amine (2.7 g, 3.8 mmol) in dichloromethane (7 mL) was added and stirring was continued overnight. MeOH (10 mL) was added and the reaction mixture was stirred at rt for 2 h. The reaction mixture was concentrated in vacuo, diluted with EtOAc and washed with saturated aqueous ammonium chloride solution. The combined organics were dried over sodium sulfate and concentrated in vacuo. 3-Trityl-5-(tritylamino)-3H-[1,2,3]triazolo[4,5-b]pyridin-7-ol (2.3 g, 3.4 mmol, 89% yield) was isolated as a grayish solid. MS(ESI) m/z 636.2 (M+H).

Example 1: 7-(4-(Trifluoromethoxy)benzyloxy)-3H-[1,2,3]triazolo[4,5-b]pyridin-5-amine

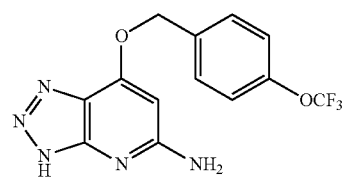 [SMILES: Nc1cc(OCc2ccc(OC(F)(F)F)cc2)c2nn[nH]c2n1]

A mixture of (4-(trifluoromethoxy)phenyl)methanol (36 mg, 0.19 mmol), Intermediate 3 (20 mg, 0.093 mmol) and $Cs_2CO_3$ (61 mg, 0.19 mmol) in DMSO (400 µL) was stirred at 120° C. overnight and then an additional 24 h at 135° C. Sodium acetate (100 µL, saturated aqueous solution) was added, and the product was purified by preparatory HPLC to yield Example 1 (3.0 mg, 8.9 µmol, 9.5% yield) as a white solid. MS(ESI) m/z 326.3 (M+H). $^1$H NMR (500 MHz, $CD_3OD$) δ 7.65 (d, J=8.3 Hz, 2H), 7.34 (d, J=8.3 Hz, 2H), 6.22 (s, 1H), 5.44 (s, 2H). Analytical HPLC Method A: 5.84 min, 96%; Method B: 6.42 min, 97%.

Example 2: 7-(3-(Benzyloxy)benzyloxy)-3H-[1,2,3]triazolo[4,5-b]pyridin-5-amine

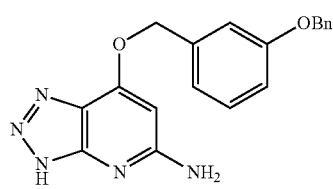 [SMILES: Nc1cc(OCc2cccc(OCc3ccccc3)c2)c2nn[nH]c2n1]

Example 2 was synthesized from (3-(benzyloxy)phenyl)methanol and Intermediate 2 using General Route 1. MS(ESI) m/z 348.3 (M+H). $^1$H NMR (500 MHz, CD$_3$OD) δ 7.43-7.38 (m, 2H), 7.38-7.30 (m, 3H), 7.29-7.23 (m, 1H), 7.16-7.12 (m, 1H), 7.10 (d, J=7.4 Hz, 1H), 7.03 (dd, J=8.0, 2.2 Hz, 1H), 6.30 (s, 1H), 5.45 (s, 2H), 5.12 (s, 2H). Analytical HPLC Method A: 6.47 min, 94%; Method B: 7.14 min, 97%.

Example 3: 7-(3-(1H-1,2,4-Triazol-1-yl)benzyloxy)-3H-[1,2,3]triazolo[4,5-b]pyridin-5-amine

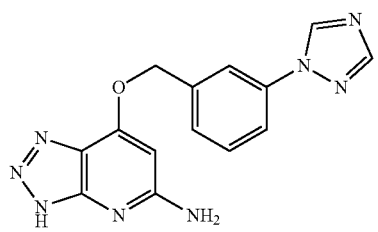 [SMILES: Nc1cc(OCc2cccc(-n3cncn3)c2)c2nn[nH]c2n1]

Example 3 was synthesized from (3-(1H-1,2,4-triazol-1-yl)phenyl)methanol and Intermediate 2 using General Route 1. MS(ESI) m/z 309.3 (M+H). $^1$H NMR (500 MHz, CD$_3$OD) δ 9.15 (s, 1H), 8.19 (s, 1H), 8.05 (s, 1H), 7.89 (dt, J=7.2, 1.9 Hz, 1H), 7.69-7.60 (m, 2H), 6.43 (s, 1H), 5.61 (s, 2H). Analytical HPLC Method A: 3.34 min, 97%; Method B: 3.66 min, 98%.

Example 4: 7-(3-(Morpholinosulfonyl)benzyloxy)-3H-[1,2,3]triazolo[4,5-b]pyridin-5-amine

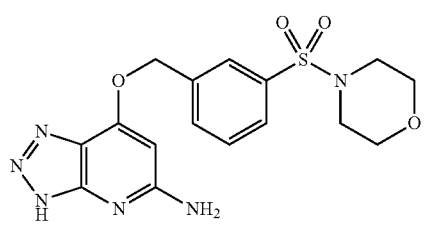 [SMILES: Nc1cc(OCc2cccc(S(=O)(=O)N3CCOCC3)c2)c2nn[nH]c2n1]

Example 4 was synthesized from (3-(morpholinosulfonyl)phenyl)methanol and Intermediate 2 using General Route 1. MS(ESI) m/z 391.2 (M+H). $^1$H NMR (500 MHz, CD$_3$OD) δ 7.78 (d, J=0.6 Hz, 1H), 7.69-7.65 (m, 2H), 7.63-7.57 (m, 1H), 4.71 (s, 2H), 3.73-3.68 (m, 4H), 3.00-2.94 (m, 4H). Analytical HPLC Method A: 4.24 min, 93%; Method B: 4.85 min, 96%.

Example 5: 7-(3-(1-Methyl-1H-pyrazol-3-yl)benzyloxy)-3H-[1,2,3]triazolo[4,5-b]pyridin-5-amine

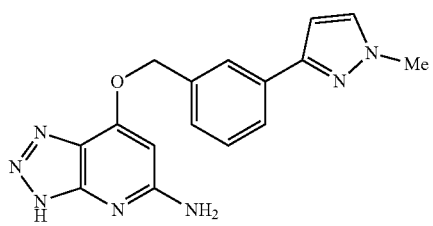 [SMILES: Cn1ccc(-c2cccc(COc3cc(N)nc4[nH]nnc34)c2)n1]

Example 5 was synthesized from (3-(1-methyl-1H-pyrazol-3-yl)phenyl)methanol and Intermediate 2 using General Route 1. MS(ESI) m/z 322.3 (M+H). $^1$H NMR (500 MHz, CD$_3$OD) δ 7.92 (s, 1H), 7.75 (dt, J=7.2, 1.8 Hz, 1H), 7.59 (d, J=2.5 Hz, 1H), 7.49-7.40 (m, 2H), 6.64 (d, J=2.2 Hz, 1H), 6.22 (s, 1H), 5.40 (s, 2H), 3.92 (s, 3H). Analytical HPLC Method A: 4.47 min, 94%; Method B: 5.02 min, 92%.

Example 6: 7-(3-Cyclopropoxybenzyloxy)-3H-[1,2,3]triazolo[4,5-b]pyridin-5-amine

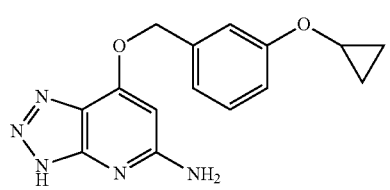 [SMILES: Nc1cc(OCc2cccc(OC3CC3)c2)c2nn[nH]c2n1]

Example 6 was synthesized from (3-cyclopropoxyphenyl)methanol and Intermediate 2 using General Route 1. MS(ESI) m/z 298.1 (M+H). $^1$H NMR (500 MHz, CD$_3$OD) δ 7.34 (t, J=8.0 Hz, 1H), 7.25-7.16 (m, 1H), 7.16-7.03 (m, 2H), 6.36 (s, 1H), 5.45 (s, 2H), 3.80 (tt, J=6.0, 3.0 Hz, 1H), 0.84-0.76 (m, 2H), 0.72-0.64 (m, 2H). Analytical HPLC Method A: 6.26 min, 98%; Method B: 7.57 min, 99%.

Example 7: 7-(3-(2-Methyl-1H-imidazol-1-yl)benzyloxy)-3H-[1,2,3]triazolo[4,5-b]pyridin-5-amine

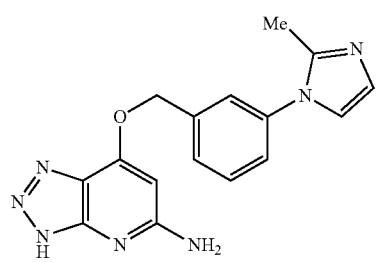 [SMILES: Cc1nccn1-c1cccc(COc2cc(N)nc3[nH]nnc23)c1]

Example 7 was synthesized from (3-(2-methyl-1H-imidazol-1-yl)phenyl)methanol and Intermediate 2 using General Route 1. MS(ESI) m/z 322.0 (M+H). $^1$H NMR (500 MHz, CD$_3$OD) δ 7.85 (d, J=7.7 Hz, 1H), 7.82-7.80 (m, 1H), 7.76 (t, J=7.8 Hz, 1H), 7.72 (d, J=2.2 Hz, 1H), 7.67-7.62 (m, 2H), 6.47 (s, 1H), 5.62 (s, 2H), 2.61 (s, 3H). Analytical HPLC Method B: 2.78 min, 94%.

Example 8: 7-(3-(Pyrimidin-2-yl)benzyloxy)-3H-[1, 2,3]triazolo[4,5-b]pyridin-5-amine

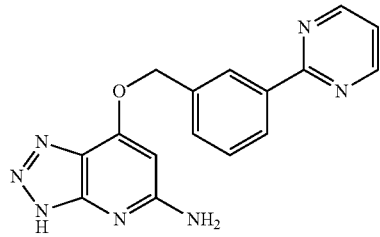 [SMILES: Nc1cc(OCc2cccc(-c3ncccn3)c2)c2nn[nH]c2n1]

Example 8 was synthesized from (3-(pyrimidin-2-yl)phenyl)methanol and Intermediate 2 using General Route 1. MS(ESI) m/z 320.1 (M+H). $^1$H NMR (500 MHz, CD$_3$OD) δ 8.89-8.83 (m, 2H), 8.57 (s, 1H), 8.45 (dt, J=7.9, 1.4 Hz, 1H), 7.70 (d, J=7.7 Hz, 1H), 7.59 (t, J=7.7 Hz, 1H), 7.42-7.36 (m, 1H), 6.44 (s, 1H), 5.59 (s, 2H). Analytical HPLC Method A: 4.30 min, 94%; Method B: 4.68 min, 90%.

Example 10: 7-(3-Chlorobenzyloxy)-3H-[1,2,3]triazolo[4,5-b]pyridin-5-amine

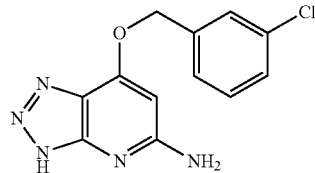 [SMILES: Nc1cc(OCc2cccc(Cl)c2)c2nn[nH]c2n1]

Example 10 was synthesized from (3-chlorophenyl)methanol and Intermediate 2 using General Route 1. MS(ESI) m/z 276.0 (M+H). $^1$H NMR (500 MHz, CD$_3$OD) δ 7.58 (s, 1H), 7.50-7.38 (m, 3H), 6.36 (s, 1H), 5.48 (s, 2H). Analytical HPLC Method A: 5.86 min, 97%; Method B: 7.25 min, 99%.

Example 11: 7-(4-Chlorobenzyloxy)-3H-[1,2,3]triazolo[4,5-b]pyridin-5-amine

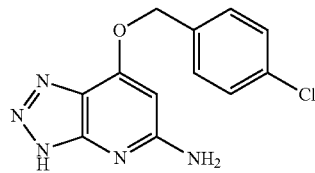 [SMILES: Nc1cc(OCc2ccc(Cl)cc2)c2nn[nH]c2n1]

Example 11 was synthesized from (4-chlorophenyl)methanol and Intermediate 2 using General Route 1. MS(ESI) m/z 276.0 (M+H). MS(ESI) m/z 276.2 (M+H). $^1$H NMR (500 MHz, CD$_3$OD) δ 7.57 (d, J=8.4 Hz, 2H), 7.49 (d, J=8.4 Hz, 2H), 6.36 (s, 1H), 5.50 (s, 2H). Analytical HPLC Method A: 6.07 min, 95%; Method B: 7.45 min, 97%.

Example 12: 7-(2-Chlorobenzyloxy)-3H-[1,2,3]triazolo[4,5-b]pyridin-5-amine

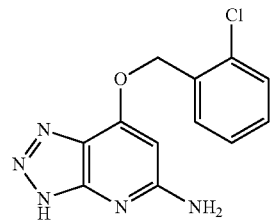 [SMILES: Nc1cc(OCc2ccccc2Cl)c2nn[nH]c2n1]

12A: (E)-4-(2-Chlorobenzyloxy)-3-((4-chlorophenyl)diazenyl)pyridine-2,6-diamine

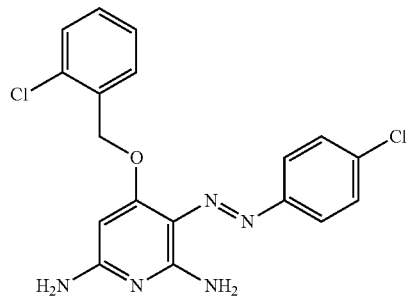 [SMILES: Nc1cc(OCc2ccccc2Cl)c(/N=N/c2ccc(Cl)cc2)c(N)n1]

A mixture of Intermediate 1 (400 mg, 1.2 mmol), (2-chlorophenyl)methanol (350 mg, 2.5 mmol) and Cs$_2$CO$_3$ (800 mg, 2.5 mmol) in DMSO (5.0 mL) was heated for 2 days at 110° C. The mixture was diluted with water/brine (1:1) and extracted with EtOAc. The combined organics were washed with brine, dried over Na$_2$SO$_4$ and concentrated in vacuo. The crude was purified by column chromatography to yield 12A as an impure brown oil. MS(ESI) m/z 388.1/390.1.

12B: 4-(2-Chlorobenzyloxy)pyridine-2,3,6-triamine

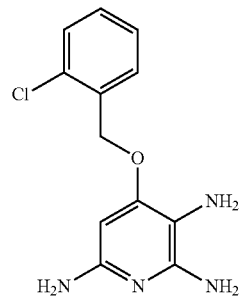 [SMILES: Nc1cc(OCc2ccccc2Cl)c(N)c(N)n1]

A mixture of 12A (400 mg, 1.0 mmol) and zinc (200 mg, 3.1 mmol) in ethanol (5.0 mL)/acetic acid (0.30 mL, 5.2 mmol) was stirred at 70° C. for 1 h. The mixture was filtered and concentrated. The crude product was dissolved in 5.0 mL 7.0 M NH$_3$ in MeOH and concentrated. The crude product was purified by column chromatography (2.0 M NH$_3$ in MeOH/CH$_2$Cl$_2$, 0-20% gradient) to yield 12B (60 mg, 0.23 mmol, 22% yield). MS(ESI) m/z 265.2.

Example 12

Isoamyl nitrite (0.027 mL, 0.20 mmol) was added to 12B (0.060 g, 0.23 mmol) in THF (2.0 mL) and acetic acid (0.065 mL, 1.1 mmol) and the mixture was stirred at rt overnight. The mixture was concentrated and purified by preparatory HPLC to yield Example 12 (22 mg, 0.079 mmol, 35% yield) as a brown solid. MS(ESI) m/z 276.2 (M+H). ¹H NMR (500 MHz, CD₃OD) δ 7.71-7.64 (m, 1H), 7.57-7.49 (m, 1H), 7.46-7.37 (m, 2H), 6.40 (s, 1H), 5.58 (s, 2H). Analytical HPLC Method A: 6.62 min, 99%; Method B: 7.65 min, 99%.

Example 13: 7-(3-(Trifluoromethoxy)benzyloxy)-3H-[1,2,3]triazolo[4,5-b]pyridin-5-amine

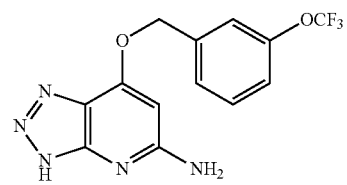 [SMILES: Nc1cc(OCc2cccc(OC(F)(F)F)c2)c2nn[nH]c2n1]

Example 13 was synthesized from (3-(trifluoromethoxy)phenyl)methanol and Intermediate 2 using General Route 1. MS(ESI) m/z 324.0 (M+H). ¹H NMR (500 MHz, CD₃OD) δ 7.57-7.54 (m, 2H), 7.49 (s, 1H), 7.36-7.28 (m, 1H), 6.40 (s, 1H), 5.53 (s, 2H). Analytical HPLC Method A: 5.78 min, 96%; Method B: 6.31 min, 97%.

Example 16: 7-(3-Phenoxybenzyloxy)-3H-[1,2,3]triazolo[4,5-b]pyridin-5-amine

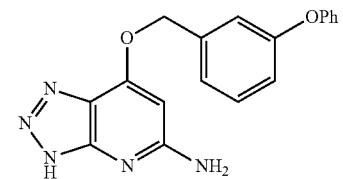 [SMILES: Nc1cc(OCc2cccc(Oc3ccccc3)c2)c2nn[nH]c2n1]

Example 16 was synthesized from (3-phenoxyphenyl)methanol and Intermediate 2 using General Route 1. MS(ESI) m/z 333.9 (M+H). ¹H NMR (500 MHz, CD₃OD) δ 7.44-7.39 (m, 1H), 7.37-7.31 (m, 2H), 7.27 (d, J=8.0 Hz, 1H), 7.17-7.09 (m, 2H), 7.03-6.96 (m, 3H), 6.34 (s, 1H), 5.46 (s, 2H). Analytical HPLC Method A: 6.12 min, 98%; Method B: 6.88 min, 98%.

Example 17: 7-(4-(Difluoromethoxy)benzyloxy)-3H-[1,2,3]triazolo[4,5-b]pyridin-5-amine

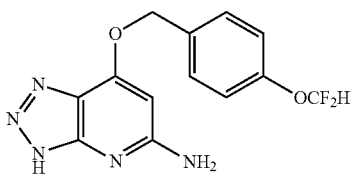

Example 17 was synthesized from (4-(difluoromethoxy)phenyl)methanol and Intermediate 1 using General Route 2. MS(ESI) m/z 308.3 (M+H). ¹H NMR (500 MHz, CD₃OD) δ 7.59 (d, J=8.6 Hz, 2H), 7.22 (d, J=8.6 Hz, 2H), 6.94 (t, J=74.0 Hz, 1H), 6.37 (s, 1H), 5.48 (s, 2H). Analytical HPLC Method A: 5.75 min, 83%; Method B: 6.43 min, 88%.

Example 20: 7-(2-(Benzyloxy)benzyloxy)-3H-[1,2,3]triazolo[4,5-b]pyridin-5-amine

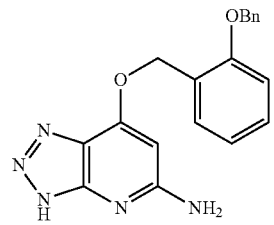 [SMILES: Nc1cc(OCc2ccccc2OCc2ccccc2)c2nn[nH]c2n1]

Example 20 was synthesized from (2-(benzyloxy)phenyl)methanol and Intermediate 1 using General Route 2. MS(ESI) m/z 348.3 (M+H). ¹H NMR (500 MHz, CD₃OD) δ 7.50 (dd, J=7.6, 1.5 Hz, 1H), 7.41 (td, J=8.0, 1.7 Hz, 1H), 7.33 (dd, J=6.6, 3.0 Hz, 2H), 7.28-7.20 (m, 3H), 7.15 (d, J=8.0 Hz, 1H), 7.07-7.00 (m, 1H), 6.37 (s, 1H), 5.53 (s, 2H), 5.12 (s, 2H). Analytical HPLC Method A: 6.76 min, 88%; Method B: 7.74 min, 78%.

Example 21: 7-(2-(Trifluoromethoxy)benzyloxy)-3H-[1,2,3]triazolo[4,5-b]pyridin-5-amine

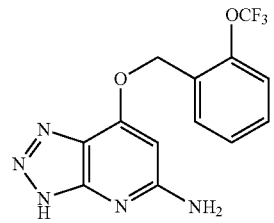 [SMILES: Nc1cc(OCc2ccccc2OC(F)(F)F)c2nn[nH]c2n1]

21A: Di-tert-butyl(4-((2-(trifluoromethoxy)benzyl)oxy)pyridine-2,6-diyl)bis(tert-butoxy carbonylcarbamate)

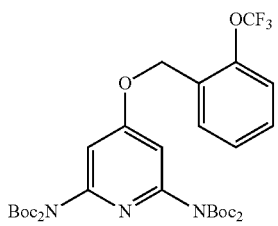

1-(Bromomethyl)-2-(trifluoromethoxy)benzene (260 mg, 1.0 mmol) was added to a mixture of Intermediate 4 (440 mg, 0.84 mmol), K₂CO₃ (410 mg, 2.9 mmol) and tetrabutylammonium bromide (270 mg, 0.84 mmol) in DMSO (4.0 mL) and the mixture was stirred overnight. The mixture was diluted with EtOAc and washed with brine, dried over Na₂SO₄ and concentrated in vacuo. The crude product was purified by flash chromatography (loading in hexanes/EtOAc, 0% to 50% ethyl acetate in hexane over 15 min using a 40 g silica gel cartridge) to yield 21A (730 mg) as a yellow solid with impurities. MS(ESI) m/z 700.5 (M+H).

21B: 4-(2-(Trifluoromethoxy)benzyloxy)pyridine-2,6-diamine 2,2,2-trifluoroacetate

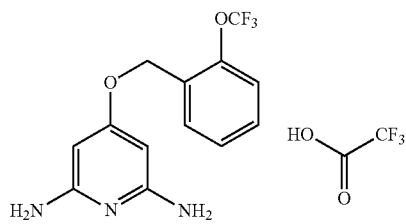

TFA (5.0 mL) was added to a solution of 21A (730 mg, 1.0 mmol) in DCM (5.0 mL). The solution was stirred for 4 h at rt and concentrated to yield 21B (500 mg) as an impure yellow solid.

21C: (E)-3-((4-Chlorophenyl)diazenyl)-4-(2-(trifluoromethoxy)benzyloxy)pyridine-2,6-diamine

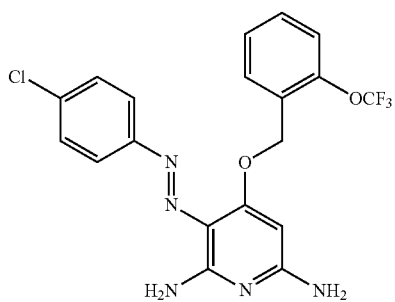 [SMILES: Nc1cc(OCc2ccccc2OC(F)(F)F)c(/N=N/c2ccc(Cl)cc2)c(N)n1]

A solution of 6.0 N HCl (0.76 mL, 4.6 mmol) was added to 4-chloroaniline (170 mg, 1.3 mmol) with vigorous stirring at 0° C. A solution of sodium nitrite (83 mg, 1.2 mmol) in water (0.50 mL) was added to the above flask. After stirring for 30 minutes, urea (7.2 mg, 0.12 mmol) was added to destroy excess $NaNO_2$. The above solution was added to a suspension of 21B (500 mg, 1.2 mmol) in water (6.0 mL). After 30 min, sodium acetate (340 mg, 4.2 mmol) was added and the mixture was stirred for 3 days. The mixture was filtered and the collected solid was washed with water to yield 21C (0.50 g, 1.1 mmol, 95% yield) as an orange solid. MS(ESI) m/z 438.1 (M+H).

21D: 4-(2-(Trifluoromethoxy)benzyloxy)pyridine-2,3,6-triamine

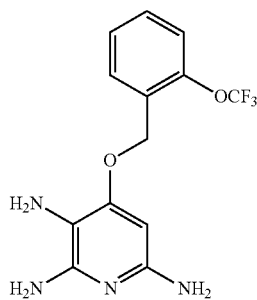 [SMILES: Nc1cc(OCc2ccccc2OC(F)(F)F)c(N)c(N)n1]

A mixture of 21C (0.50 g, 1.1 mmol) and zinc (0.22 g, 3.4 mmol) in EtOH (5.7 mL)/acetic acid (0.33 mL, 5.7 mmol) was stirred at 70° C. for 2 h. The mixture was filtered and concentrated. The crude product was dissolved in 4.0 mL 7.0 M $NH_3$ in MeOH and concentrated. The crude product was purified by column chromatography (2.0 M $NH_3$ in MeOH/ $CH_2Cl_2$ 0-20% gradient) to yield 21D (0.18 g, 0.57 mmol, 50% yield). MS(ESI) m/z 315.1 (M+H).

Example 21

Isoamyl nitrite (0.069 mL, 0.52 mmol) was added to a mixture of 21D (0.18 g, 0.57 mmol) in THF (5.0 mL) and acetic acid (0.16 mL) and the mixture was stirred at rt overnight. The mixture was concentrated and purified by column chromatography to yield Example 21 (0.048 g, 0.14 mmol, 24% yield) as a brown solid. MS(ESI) m/z 325.9 (M+H). $^1$H NMR (500 MHz, $CD_3OD$) δ 7.74 (dd, J=7.6, 1.5 Hz, 1H), 7.60-7.52 (m, 1H), 7.49-7.40 (m, 2H), 6.41 (s, 1H), 5.57 (s, 2H). Analytical HPLC Method A: 5.94 min, 82%; Method B: 6.72 min, 85%.

Example 22: Methyl 3-((5-amino-3H-[1,2,3]triazolo[4,5-b]pyridin-7-yloxy)methyl)benzoate

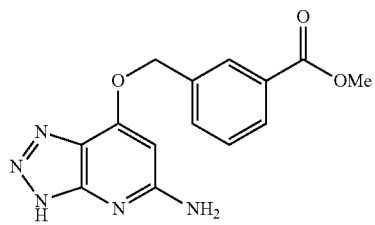 [SMILES: COC(=O)c1cccc(COc2cc(N)nc3[nH]nnc23)c1]

Example 22 was synthesized from methyl 3-(bromomethyl)benzoate and Intermediate 4 using General Route 3. MS(ESI) m/z 300.2 (M+H). $^1$H NMR (500 MHz, $CD_3OD$) δ 8.19 (s, 1H), 8.05 (d, J=7.7 Hz, 1H), 7.79 (d, J=7.7 Hz, 1H), 7.58 (t, J=7.7 Hz, 1H), 6.38 (s, 1H), 5.55 (s, 2H), 3.92 (s, 3H). Analytical HPLC Method A: 4.39 min, 97%; Method B: 5.06 min, 97%.

Example 24: Methyl 3-((5-amino-3H-[1,2,3]triazolo[4,5-b]pyridin-7-yloxy)methyl)-2-chlorobenzoate

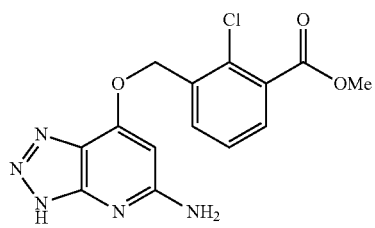 [SMILES: COC(=O)c1cccc(COc2cc(N)nc3[nH]nnc23)c1Cl]

Example 24 was synthesized from methyl 3-(bromomethyl)-2-chlorobenzoate and Intermediate 4 using General Route 3. MS(ESI) m/z 334.1 (M+H). $^1$H NMR (500 MHz, $CD_3OD$) δ 7.89-7.80 (m, 2H), 7.50 (t, J=7.7 Hz, 1H), 6.40 (s, 1H), 5.64 (s, 2H), 3.94 (s, 3H). Analytical HPLC Method A: 4.84 min, 93%; Method B: 5.44 min, 91%.

Example 25: (3-((5-Amino-3H-[1,2,3]triazolo[4,5-b]pyridin-7-yloxy)methyl)phenyl)(morpholino)methanone

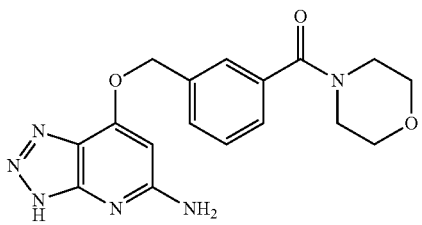 [SMILES: Nc1cc(OCc2cccc(C(=O)N3CCOCC3)c2)c2nn[nH]c2n1]

25A: 3-((5-Amino-3H-[1,2,3]triazolo[4,5-b]pyridin-7-yloxy)methyl)benzoic acid

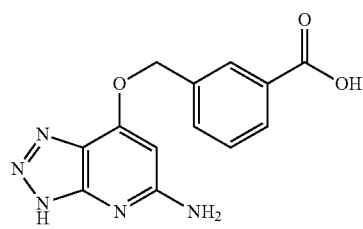 [SMILES: Nc1cc(OCc2cccc(C(=O)O)c2)c2nn[nH]c2n1]

LiOH (0.30 mL, 2.0 M aqueous) was added to a solution of Example 22 (28 mg, 0.094 mmol) in THF (1.0 mL) and the mixture was stirred at rt for 2 h. HCl (0.30 mL, 1.0 M aqueous) was added and the mixture was concentrated. The product was purified by prep HPLC (Method G) to yield 25A (20 mg, 0.068 mmol, 72% yield) as a white solid. MS(ESI) m/z 286.2 (M+H). $^1$H NMR (500 MHz, CD$_3$OD) δ 8.20 (s, 1H), 8.12-8.03 (m, 1H), 7.79 (d, J=7.7 Hz, 1H), 7.57 (t, J=7.7 Hz, 1H), 6.38 (s, 1H), 5.55 (s, 2H). Analytical HPLC Method A: 3.63 min, 96%; Method B: 4.00 min, 99%.

Example 25

HBTU (6.7 mg, 0.018 mmol) was added to a mixture of 25A (5.0 mg, 0.018 mmol) and morpholine (7.6 µl, 0.088 mmol) in DMF (180 µl) and the mixture was stirred overnight at rt. The mixture was diluted with water and MeOH and purified by prep HPLC (Method G) to yield Example 25 (2.0 mg, 4.8 µmol, 27% yield) as a white solid. MS(ESI) m/z 355.3 (M+H). $^1$H NMR (500 MHz, CD$_3$OD) δ 7.67 (d, J=7.7 Hz, 1H), 7.62 (s, 1H), 7.56 (t, J=7.4 Hz, 1H), 7.48 (d, J=7.7 Hz, 1H), 6.38 (s, 1H), 5.55 (s, 2H), 3.77 (br. s., 4H), 3.63 (br. s., 2H), 3.47 (br. s., 2H). Analytical HPLC Method A: 3.47 min, 85%; Method B: 3.99 min, 99%.

Example 26: 7-(2-Methoxy-3-(trifluoromethyl)benzyloxy-3H-[1,2,3]triazolo[4,5-b]pyridin-5-amine

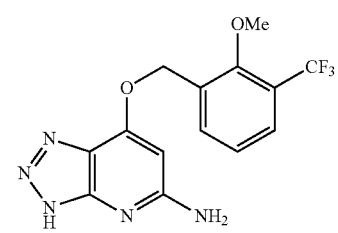 [SMILES: COc1c(COc2cc(N)nc3[nH]nnc23)cccc1C(F)(F)F]

Example 26 was synthesized from 1-(bromomethyl)-2-methoxy-3-(trifluoromethyl)benzene and Intermediate 4 using General Route 3. MS(ESI) m/z 340.2 (M+H). $^1$H NMR (500 MHz, CD$_3$OD) δ 7.91-7.83 (m, 1H), 7.72 (dd, J=7.8, 1.2 Hz, 1H), 7.45-7.32 (m, 1H), 6.46 (s, 1H), 5.58 (s, 2H), 3.93 (s, 3H). Analytical HPLC Method A: 5.84 min, 93%; Method B: 6.58 min, 94%.

Example 27: 7-(2-Fluoro-5-(trifluoromethoxy)benzyloxy)-3H-[1,2,3]triazolo[4,5-b]pyridin-5-amine

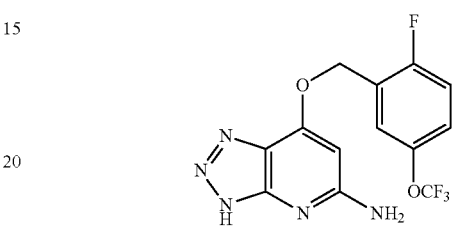

Example 27 was synthesized from 2-(bromomethyl)-1-fluoro-4-(trifluoromethoxy)benzene and Intermediate 4 using General Route 3. MS(ESI) m/z 344.2 (M+H). $^1$H NMR (500 MHz, CD$_3$OD) δ 8.03 (s, 1H), 7.77-7.70 (m, 2H), 6.48 (s, 1H), 5.63 (s, 2H). Analytical HPLC Method A: 5.94 min, 94%; Method B: 6.61 min, 95%. The compound was isolated as a TFA salt.

Example 28: 7-(2-Chloro-5-(trifluoromethyl)benzyloxy)-3H-[1,2,3]triazolo[4,5-b]pyridin-5-amine

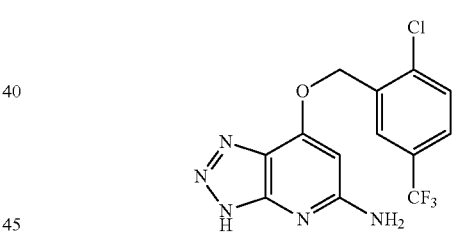

Example 28 was synthesized from 2-(bromomethyl)-1-chloro-4-(trifluoromethyl)benzene and Intermediate 4 using General Route 3. MS(ESI) m/z 344.1 (M+H). $^1$H NMR (500 MHz, CD$_3$OD) δ 8.03 (s, 1H), 7.77-7.70 (m, 2H), 6.48 (s, 1H), 5.63 (s, 2H). Analytical HPLC Method A: 5.80 min, 95%; Method B: 6.49 min, 96%. The compound was isolated as a TFA salt.

Example 29: 7-(3,5-Bis(trifluoromethyl)benzyloxy)-3H-[1,2,3]triazolo[4,5-b]pyridin-5-amine

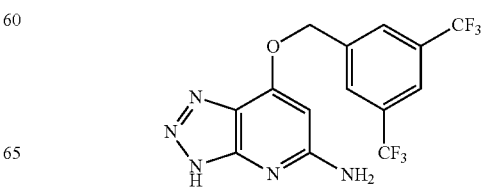

29A:
1-(Bromomethyl)-3,5-bis(trifluoromethyl)benzene

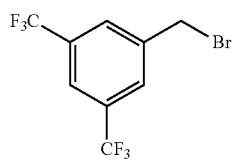

(3,5-Bis(trifluoromethyl)phenyl)methanol (1.0 g, 4.1 mmol) and phosphorus tribromide (0.39 mL, 4.1 mmol) in ether (10 mL) were stirred overnight at rt. The mixture was partitioned between water/brine and ether. The organic layer was filtered through silica and concentrated to furnish 29A (350 mg, 1.1 mmol, 28% yield) as a clear oil. $^1$H NMR (500 MHz, CD$_3$OD) δ 8.19 (s, 2H), 8.02 (s, 1H), 6.44 (s, 1H), 5.65 (s, 2H). The compound was isolated as a TFA salt.

Example 29

Example 29 was synthesized from Example 29A and Intermediate 4 using General Route 3. MS(ESI) m/z 378.2 (M+H). $^1$H NMR (500 MHz, CD$_3$OD) δ 8.19 (s, 2H), 8.02 (s, 1H), 6.44 (s, 1H), 5.65 (s, 2H). Analytical HPLC Method A: 6.57 min, 95%; Method B: 7.20 min, 96%.

Example 30: 7-(2-Methoxy-5-(trifluoromethyl)benzyloxy)-3H-[1,2,3]triazolo[4,5-b]pyridin-5-amine

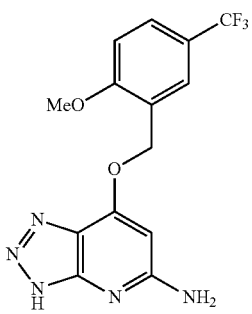 [SMILES: COc1ccc(C(F)(F)F)cc1COc1cc(N)nc2[nH]nnc12]

Example 30 was synthesized from Intermediate 4 and (2-methoxy-5-(trifluoromethyl)phenyl)methanol using General Route 3. MS(ESI) m/z 340 (M+H). $^1$H NMR (500 MHz, CD$_3$OD) δ 7.83 (d, J=1.9 Hz, 1H), 7.72 (dd, J=8.8, 1.9 Hz, 1H), 7.24 (d, J=8.8 Hz, 1H), 6.43 (s, 1H), 5.52 (s, 2H). Analytical HPLC Method A: 5.96 min, 99%; Method B: 6.50 min, 98%. The compound was isolated as a TFA salt.

Example 31: 7-(2-Chloro-6-(trifluoromethoxy)benzyloxy)-3H-[1,2,3]triazolo[4,5-b]pyridin-5-amine

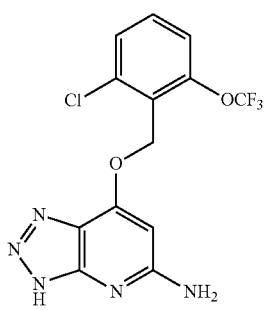 [SMILES: Nc1cc(OCc2c(Cl)cccc2OC(F)(F)F)c2nn[nH]c2n1]

Example 31 was synthesized from 2-(bromomethyl)-1-chloro-3-(trifluoromethoxy)benzene and Intermediate 4 using General Route 3. MS(ESI) m/z 360.2 (M+H). $^1$H NMR (500 MHz, DMSO-d$_6$) δ 7.84 (d, J=2.8 Hz, 1H), 7.66 (dd, J=8.8, 2.8 Hz, 1H), 7.58-7.51 (m, 1H), 6.25 (br. s., 1H). Analytical HPLC Method A: 6.12 min, 97%; Method B: 6.80 min, 98%. The compound was isolated as a TFA salt.

Example 32: 7-(5-(Difluoromethoxy)-2-fluorobenzyloxy)-3H-[1,2,3]triazolo[4,5-b]pyridin-5-amine

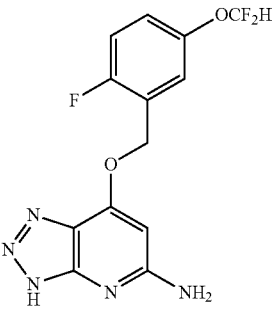

Example 32 was synthesized from 2-(bromomethyl)-4-(difluoromethoxy)-1-fluorobenzene and Intermediate 4 using General Route 3. MS(ESI) m/z 326.2 (M+H). $^1$H NMR (500 MHz, CD$_3$OD) δ 7.44 (d, J=6.3 Hz, 1H), 7.29-7.20 (m, 2H), 6.81 (t, J=73.5 Hz, 1H), 6.44 (s, 1H), 5.53 (s, 2H). Analytical HPLC Method A: 5.27 min, 97%; Method B: 5.96 min, 98%. The compound was isolated as a TFA salt.

Example 33: 3-((5-Amino-3H-[1,2,3]triazolo[4,5-b]pyridin-7-yloxy)methyl)-2-chlorobenzamide

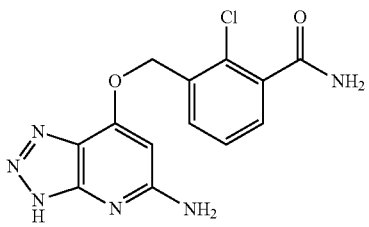 [SMILES: NC(=O)c1cccc(COc2cc(N)nc3[nH]nnc23)c1Cl]

A solution of Example 24 (10 mg, 0.030 mmol) in 7.0 M NH$_3$ in MeOH (1.0 mL) was stirred for 3 days at 100° C. in a sealed tube. The mixture was concentrated and purified by prep HPLC to yield Example 33 (4.0 mg, 0.0087 mmol, 29% yield) as a yellow solid. MS(ESI) m/z 319.1 (M+H). $^1$H NMR (500 MHz, CD$_3$OD) δ 7.79 (dd, J=7.7, 1.7 Hz, 1H), 7.62-7.55 (m, 1H), 7.54-7.46 (m, 1H), 6.40 (s, 1H), 5.64 (s, 2H). Analytical HPLC Method A: 2.82 min, 83%; Method B: 3.19 min, 96%. The compound was isolated as a TFA salt.

Example 35: 7-(2-Methoxy-5-(trifluoromethoxy)benzyloxy)-3H-[1,2,3]triazolo[4,5-b]pyridin-5-amine

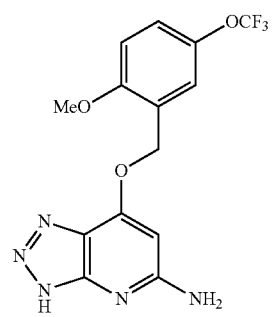 [SMILES: COc1ccc(OC(F)(F)F)cc1COc1cc(N)nc2[nH]nnc12]

Example 35 was synthesized from Intermediate 4 and 2-(bromomethyl)-1-methoxy-4-(trifluoromethoxy)benzene using General Route 3. MS(ESI) m/z 356 (M+H). $^1$H NMR (500 MHz, CD$_3$OD) δ 7.46 (d, J=2.5 Hz, 1H), 7.31 (dd, J=9.1, 2.2 Hz, 1H), 7.13 (d, J=9.1 Hz, 1H), 6.42 (s, 1H), 5.47 (s, 2H). Analytical HPLC Method A: 6.16 min, 99%; Method B: 6.64 min, 99%. The compound was isolated as a TFA salt.

Example 36: 7-(5-Chloro-2-(trifluoromethoxy)benzyloxy)-3H-[1,2,3]triazolo[4,5-b]pyridin-5-amine

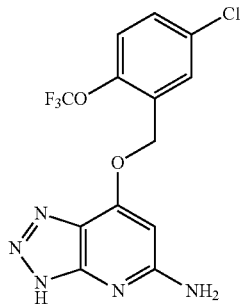 [SMILES: Nc1cc(OCc2cc(Cl)ccc2OC(F)(F)F)c2nn[nH]c2n1]

Example 36 was synthesized from Intermediate 4 and (5-chloro-2-(trifluoromethoxy)phenyl)methanol using General Route 3. MS(ESI) m/z 360 (M+H). $^1$H NMR (500 MHz, CD$_3$OD) δ 7.79 (m, 1H), 7.58-7.52 (m, 1H), 7.43 (m, 1H), 6.43 (s, 1H), 5.54 (s, 2H). Analytical HPLC Method A: 5.26 min, 90%; Method B: 5.87 min, 93%. The compound was isolated as a TFA salt.

Example 37: 2-(2-((5-Amino-3H-[1,2,3]triazolo[4,5-b]pyridin-7-yloxy)methyl)phenoxy)-N-(cyclopropylmethyl)acetamide

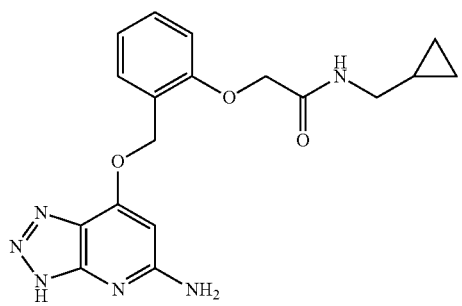 [SMILES: Nc1cc(OCc2ccccc2OCC(=O)NCC2CC2)c2nn[nH]c2n1]

Example 37 was synthesized from N-(cyclopropylmethyl)-2-(2-(hydroxymethyl)phenoxy)acetamide and Intermediate 4 using General Route 3. MS(ESI) m/z 369.0 (M+H). $^1$H NMR (500 MHz, CD$_3$OD) δ 7.53 (dd, J=7.4, 1.7 Hz, 1H), 7.44-7.36 (m, 1H), 7.07 (td, J=7.6, 0.8 Hz, 1H), 7.02 (d, J=8.3 Hz, 1H), 6.58 (s, 1H), 5.60 (s, 2H), 4.67 (s, 2H), 3.17-3.08 (m, 2H), 0.98-0.86 (m, 1H), 0.45-0.35 (m, 2H), 0.20-0.12 (m, 2H). Analytical HPLC Method A: 4.83 min, 95%; Method B: 5.12 min, 94%. The compound was isolated as a TFA salt.

Example 38: 7-(2-Phenoxybenzyloxy)-3H-[1,2,3]triazolo[4,5-b]pyridin-5-amine

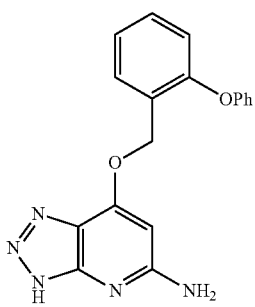 [SMILES: Nc1cc(OCc2ccccc2Oc2ccccc2)c2nn[nH]c2n1]

Example 38 was synthesized from 1-(bromomethyl)-2-phenoxybenzene and Intermediate 4 using General Route 3. MS(ESI) m/z 334.0 (M+H). $^1$H NMR (500 MHz, CD$_3$OD) δ 7.65 (dd, J=7.6, 1.5 Hz, 1H), 7.44-7.37 (m, 1H), 7.33-7.26 (m, 2H), 7.23 (td, J=7.6, 1.1 Hz, 1H), 7.09-7.01 (m, 1H), 6.99-6.90 (m, 3H), 6.38 (s, 1H), 5.54 (s, 2H). Analytical HPLC Method A: 6.15 min, 97%; Method B: 6.64 min, 96%. The compound was isolated as a TFA salt.

Example 41: Methyl 3-((5-amino-3H-[1,2,3]triazolo[4,5-b]pyridin-7-yloxy)methyl)-4-fluorobenzoate

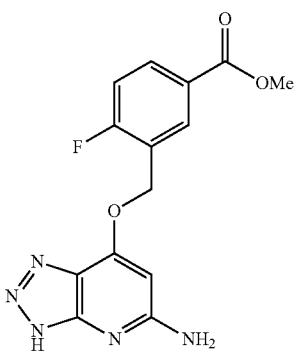 [SMILES: COC(=O)c1ccc(F)c(COc2cc(N)nc3[nH]nnc23)c1]

Example 41 was synthesized from methyl 3-(bromomethyl)-4-fluorobenzoate and Intermediate 4 using General Route 3. MS(ESI) m/z 318.1 (M+H). $^1$H NMR (500 MHz, acetonitrile-d$_3$) δ 8.24 (dd, J=6.9, 2.2 Hz, 1H), 8.10 (ddd, J=8.6, 5.2, 2.2 Hz, 1H), 7.41-7.24 (m, 1H), 6.27 (s, 1H), 5.50 (s, 2H), 3.88 (s, 3H). Analytical HPLC Method A: 5.39 min, 96%; Method B: 5.47 min, 98%. The compound was isolated as a TFA salt.

Example 43: 7-(5-Chloro-2-(cyclopentyloxy)benzyloxy)-3H-[1,2,3]triazolo[4,5-b]pyridin-5-amine

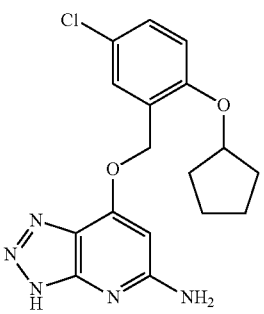 [SMILES: Nc1cc(OCc2cc(Cl)ccc2OC2CCCC2)c2nn[nH]c2n1]

Example 43 was synthesized from Intermediate 4 and (5-chloro-2-(cyclopentyloxy)phenyl)methanol using General Route 3. MS(ESI) m/z 360 (M+H). $^1$H NMR (500 MHz, CD$_3$OD) δ 7.52 (d, J=2.5 Hz, 1H), 7.36 (dd, J=8.8, 2.8 Hz, 1H), 7.05 (d, J=8.8 Hz, 1H), 6.43 (s, 1H), 5.43 (s, 2H), 1.99-1.87 (m, 2H), 1.87-1.76 (m, 2H), 1.75-1.56 (m, 4H). Analytical HPLC Method A: 6.67 min, 94%; Method B: 7.08 min, 93%. The compound was isolated as a TFA salt.

Example 44: 7-(3-Chloro-5-(methylsulfonyl)benzyloxy)-3H-[1,2,3]triazolo[4,5-b]pyridin-5-amine

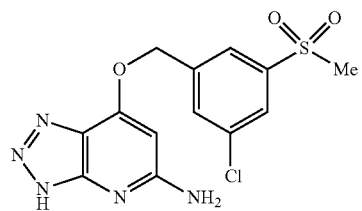 [SMILES: CS(=O)(=O)c1cc(Cl)cc(COc2cc(N)nc3[nH]nnc23)c1]

Example 44A: (3-Chloro-5-(methylsulfonyl)phenyl)methanol

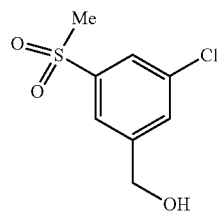 [SMILES: CS(=O)(=O)c1cc(Cl)cc(CO)c1]

Borane tetrahydofuran complex (6.4 mL, 6.4 mmol) was added to a solution of 3-chloro-5-(methylsulfonyl)benzoic acid (1.0 g, 4.3 mmol) in THF (21 mL) and the mixture was stirred overnight at rt. The reaction was incomplete by LC/MS so the mixture was heated at 50° C. for 5 h. The mixture was quenched with MeOH (10 mL) and concentrated. The crude product was purified by flash chromatography (loading in DCM, 0% to 20% MeOH in DCM over 15 min using a 40 g silica gel cartridge) to yield Example 44A (620 mg, 2.8 mmol, 66% yield) as an off white solid. The compound was isolated as a TFA salt.

Example 44

Example 44 was synthesized from Example 44a and Intermediate 4 using General Route 3. MS(ESI) m/z 353.9 (M+H). $^1$H NMR (500 MHz, CD$_3$OD) δ 8.10 (s, 1H), 8.03-7.97 (m, 2H), 6.37 (s, 1H), 5.67 (s, 2H), 3.19 (s, 3H). Analytical HPLC Method A: 5.19 min, 96%; Method B: 6.14 min, 95%.

Example 45: 7-(3-(3-(Difluoromethyl)-1H-1,2,4-triazol-1-yl)benzyloxy)-3H-[1,2,3]triazolo[4,5-b]pyridin-5-amine

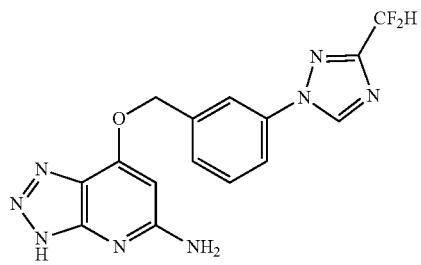 [SMILES: Nc1cc(OCc2cccc(-n3cnc(C(F)F)n3)c2)c2nn[nH]c2n1]

45A: (3-(3-(Difluoromethyl)-1H-1,2,4-triazol-1-yl)phenyl)methanol

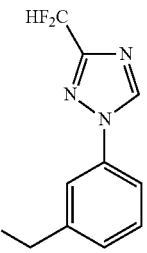

A mixture of (3-iodophenyl)methanol (1.0 g, 4.3 mmol), 3-(difluoromethyl)-1H-1,2,4-triazole (1.0 g, 8.6 mmol), copper (I) iodide (0.41 g, 2.1 mmol) and potassium carbonate (1.8 g, 12 mmol) in DMF (10 mL) was stirred at 120° C. overnight. The mixture was partitioned between EtOAc and brine. The organics were separated and washed with brine, dried over Na$_2$SO$_4$ and concentrated in vacuo. The crude product was purified by flash chromatography (loading in chloroform, 0% to 100% ethyl acetate in hexane over 15 min using a 40 g silica gel cartridge) to yield 45A (500 mg, 2.2 mmol, 52% yield) as a yellow solid.

45B: 1-(3-(Bromomethyl)phenyl)-3-(difluoromethyl)-1H-1,2,4-triazole

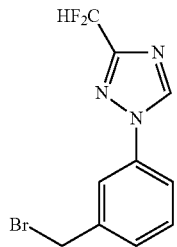

45B was synthesized using a method analogous to that used to make 29A.

Example 45

Example 45 was synthesized from 45B and Intermediate 4 using General Route 3. m/z 359.2 (M+H). $^1$H NMR (500 MHz, CD$_3$OD) δ 9.26 (s, 1H), 8.10 (s, 1H), 7.92 (m, 1H), 7.68 (m, 2H), 7.10-6.83 (m, 1H), 6.39 (s, 1H), 5.60 (s, 2H). Analytical HPLC Method A: 4.61 min, 88%; Method B: 5.17 min, 93%. The compound was isolated as a TFA salt.

Example 46: 4'-((5-Amino-3H-[1,2,3]triazolo[4,5-b]pyridin-7-yloxy)methyl)-3'-chloro-N,N-dimethylbiphenyl-2-sulfonamide

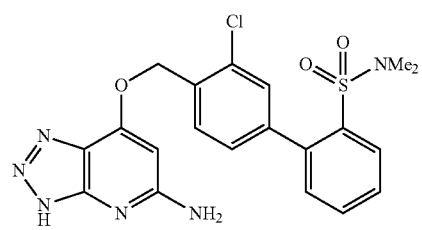 [SMILES: CN(C)S(=O)(=O)c1ccccc1-c1ccc(COc2cc(N)nc3[nH]nnc23)c(Cl)c1]

46A: 3'-Chloro-4'-(hydroxymethyl)-N,N-dimethylbiphenyl-2-sulfonamide

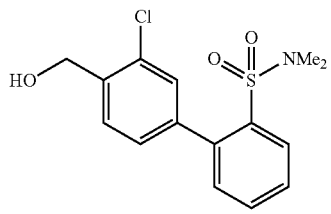 [SMILES: CN(C)S(=O)(=O)c1ccccc1-c1ccc(CO)c(Cl)c1]

46A was synthesized using a similar method to that was used to synthesize 44A using 3-chloro-2'-(N,N-dimethylsulfamoyl)-[1,1'-biphenyl]-4-carboxylic acid. MS(ESI) m/z 326.0 (M+H).

Example 46

Example 46 was synthesized from 46B and Intermediate 4 using General Route 3. MS(ESI) m/z 459.4 (M+H). $^1$H NMR (500 MHz, CD$_3$OD) δ 8.03 (dd, J=8.0, 1.1 Hz, 1H), 7.73-7.67 (m, 2H), 7.63 (dd, J=7.8, 1.5 Hz, 1H), 7.54 (d, J=1.7 Hz, 1H), 7.39 (dt, J=7.7, 1.7 Hz, 2H), 6.42 (s, 1H), 5.64 (s, 2H), 2.49 (s, 6H). Analytical HPLC Method A: 6.56 min, 99%; Method B: 6.91 min, 99%. The compound was isolated as a TFA salt.

Example 47: 3-((5-Amino-3H-[1,2,3]triazolo[4,5-b]pyridin-7-yloxy)methyl)-N-benzyl-4-fluorobenzamide

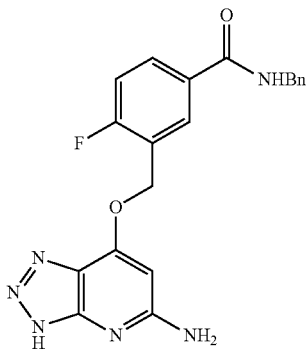

47A: 3-(((5-Amino-3H-[1,2,3]triazolo[4,5-b]pyridin-7-yl)oxy)methyl)-4-fluorobenzoic Acid

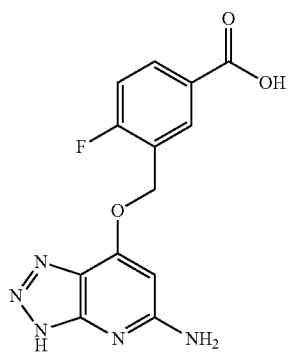 [SMILES: Nc1cc(OCc2cc(C(=O)O)ccc2F)c2nn[nH]c2n1]

LiOH (2.9 mL, 1.0 M aq solution) was added to a suspension of Example 41 (620 mg, 1.4 mmol) in THF (12 mL) and the mixture was stirred overnight. An additional 1.4 mL LiOH solution was added and the mixture was stirred for 8 h. HCl (4.4 mL, 1 M aq) was added and the mixture was concentrated in vacuo to yield 47A as a gray solid containing THF and other salts. MS(ESI) m/z 304.3 (M+H).

Example 47

DIEA (52 μL, 0.30 mmol) was added to a solution of 47A (10 mg, 0.033 mmol) and HATU (13 mg, 0.033 mmol) in DMF (330 μL) and stirred for 5 min. Benzylamine (11 μL, 0.099 mmol) was added and the mixture was stirred at rt overnight. The mixture was diluted with water and MeOH and purified by preparatory HPLC to yield Example 47 (5.5 mg, 11 μmol, 33% yield) as a white solid. MS(ESI) m/z: 393.0 (M+H)$^+$. $^1$H NMR (500 MHz, CD$_3$OD) δ 8.16 (dd, J=6.9, 2.2 Hz, 1H), 7.98 (ddd, J=8.5, 5.0, 2.5 Hz, 1H), 7.39-7.28 (m, 5H), 7.25 (d, J=7.2 Hz, 1H), 6.41 (s, 1H), 5.59 (s, 2H), 4.58 (s, 2H). Analytical HPLC Method A: 5.65 min, 99%; Method B: 5.81 min, 99%. The compound was isolated as a TFA salt.

Example 48: 3-((5-Amino-3H-[1,2,3]triazolo[4,5-b]pyridin-7-yloxy)methyl)-N-cyclopropyl-4-fluorobenzamide

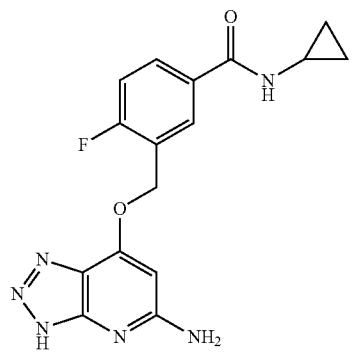 [SMILES: Nc1cc(OCc2cc(C(=O)NC3CC3)ccc2F)c2nn[nH]c2n1]

Example 48 was synthesized from 47A and cyclopropylamine using a similar method to that was used to synthesize Example 47. MS(ESI) m/z: 343.1 (M+H)$^+$. $^1$H NMR (500 MHz, CD$_3$OD) δ 8.13 (dd, J=6.9, 2.2 Hz, 1H), 7.94 (ddd, J=8.7, 4.9, 2.3 Hz, 1H), 7.32 (dd, J=9.4, 8.8 Hz, 1H), 6.44 (s, 1H), 5.60 (s, 2H), 2.87 (dt, J=7.4, 3.4 Hz, 1H), 0.92-0.77 (m, 2H), 0.76-0.56 (m, 2H). Analytical HPLC Method A: 4.31 min, 99%; Method B: 4.29 min, 99%. The compound was isolated as a TFA salt.

Example 49: 3-((5-Amino-3H-[1,2,3]triazolo[4,5-b]pyridin-7-yloxy)methyl)-N-(3-chlorophenyl)-4-fluorobenzamide

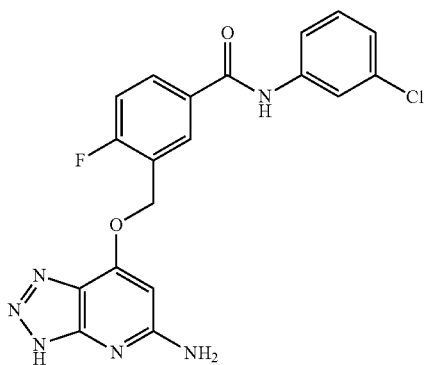 [SMILES: Nc1cc(OCc2cc(C(=O)Nc3cccc(Cl)c3)ccc2F)c2nn[nH]c2n1]

Example 49 was synthesized from 47A and 3-chloroaniline using a similar method to that was used to synthesize Example 47. MS(ESI) m/z: 412.9 (M+H)⁺. ¹H NMR (500 MHz, CD₃OD) δ 8.29 (dd, J=6.9, 2.2 Hz, 1H), 8.09 (ddd, J=8.7, 4.9, 2.3 Hz, 1H), 7.89 (t, J=1.9 Hz, 1H), 7.66-7.56 (m, 1H), 7.40-7.35 (m, 1H), 7.32 (t, J=8.1 Hz, 1H), 7.17-7.09 (m, 1H), 6.56 (s, 1H), 5.62 (s, 2H). Analytical HPLC Method A: 6.57 min, 99%; Method B: 6.93 min, 99%. The compound was isolated as a TFA salt.

Example 50: 7-(5-Chloro-2-(methylsulfonyl)benzyloxy)-3H-[1,2,3]triazolo[4,5-b]pyridin-5-amine

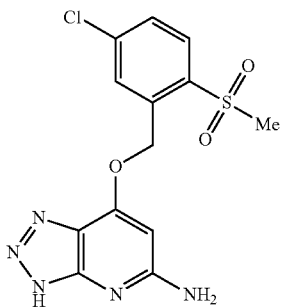 [SMILES: CS(=O)(=O)c1ccc(Cl)cc1COc1cc(N)nc2[nH]nnc12]

50A:
2-(Bromomethyl)-4-chloro-1-(methylsulfonyl)benzene

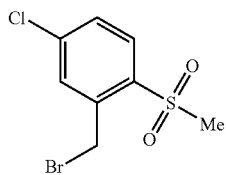 [SMILES: CS(=O)(=O)c1ccc(Cl)cc1CBr]

A mixture of 4-chloro-2-methyl-1-(methylsulfonyl)benzene (600 mg, 2.93 mmol), NBS (650 mg, 3.7 mmol) and AIBN (96 mg, 0.59 mmol) in CCl₄ (25 mL) was stirred at 80° C. for 16 h. The mixture was partitioned between DCM and water. The layers were separated and the aqueous phase was extracted with DCM (2×). The combined organic layers were dried over MgSO₄ and concentrated in vacuo to give the crude product which was purified by column chromatography (EtOAc/hexanes: 0-30% gradient) to yield the desired product as a 1:1 mixture with starting material (280 mg). MS(ESI) m/z 283/285 (M+H).

Example 50

Example 50 was synthesized from Intermediate 4 and Example 50A using General Route 3. MS(ESI) m/z 354 (M+H). ¹H NMR (500 MHz, CD₃OD) δ 8.11 (d, J=8.3 Hz, 1H), 7.94 (d, J=2.2 Hz, 1H), 7.74 (dd, J=8.3, 2.2 Hz, 1H), 6.41 (s, 1H), 5.85 (s, 2H), 3.28 (s, 3H). Analytical HPLC Method A: 4.64 min, 98%; Method B: 4.98 min, 99%. The compound was isolated as a TFA salt.

Example 51: 7-((1,2,3,4-Tetrahydronaphthalen-2-yl)methoxy)-3H-[1,2,3]triazolo[4,5-b]pyridin-5-amine

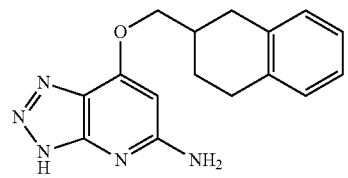 [SMILES: Nc1cc(OCC2CCc3ccccc3C2)c2nn[nH]c2n1]

51A: (1,2,3,4-Tetrahydronaphthalen-2-yl)methanol

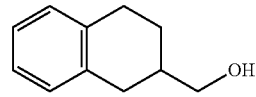 [SMILES: OCC1CCc2ccccc2C1]

BH₃-THF in THF (10 mL, 10 mmol) was added to a solution of 1,2,3,4-tetrahydronaphthalene-2-carboxylic acid (0.60 g, 3.40 mmol) in THF (25 mL) dropwise at 0° C. The cooling bath was removed and the reaction mixture was stirred for 3 days at rt. The reaction mixture was cooled to 0° C. and water (50 mL) followed by 10 N HCl (10 mL) were added. After stirring for 1 h, the mixture was extracted with EtOAc (2×50 mL). The organics were combined, washed with 0.1 N HCl, water and brine (50 mL each), dried over Na₂SO₄ and concentrated. The crude product was purified by column chromatography (0 to 60% EtOAc in hexanes) to yield (1,2,3,4-tetrahydronaphthalen-2-yl)methanol (500 mg, 3.1 mmol, 91% yield) as a clear oil. ¹H NMR (500 MHz, CD₃OD) δ 7.03 (s, 4H), 3.56-3.48 (m, 2H), 2.89-2.74 (m, 3H), 2.45 (m, 1H), 2.00 (m, 1H), 1.94-1.80 (m, 1H), 1.40 (m, 1H). The compound was isolated as a TFA salt.

Example 51

Example 51 was synthesized from Intermediate 4 and (1,2,3,4-tetrahydronaphthalen-2-yl)methanol using General Route 4. MS(ESI) m/z 294 (M+H). ¹H NMR (500 MHz, CD₃OD) δ 7.13-7.07 (m, 4H), 6.20 (s, 1H), 4.32 (d, J=6.3 Hz, 2H), 3.08 (dd, J=16.4, 4.0 Hz, 1H), 2.96-2.87 (m, 2H), 2.72 (dd, J=16.5, 10.5 Hz, 1H), 2.52-2.41 (m, 1H), 2.24-2.15 (m, 1H), 1.72-1.66 (m, 1H).

Example 52: 7-((1,2,3,4-Tetrahydronaphthalen-1-yl)methoxy)-3H-[1,2,3]triazolo[4,5-b]pyridin-5-amine

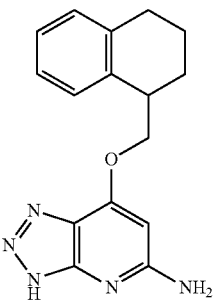 [SMILES: Nc1cc(OCC2CCCc3ccccc32)c2nn[nH]c2n1]

52A: (1,2,3,4-Tetrahydronaphthalen-1-yl)methanol

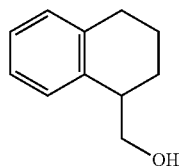 [SMILES: OCC1CCCc2ccccc21]

52A was synthesized from 1,2,3,4-tetrahydronaphthalene-1-carboxylic acid using a procedure analogous to that used in 51A to yield 52A. $^1$H NMR (500 MHz, CD$_3$OD) 7.20-7.13 (m, 1H), 7.12-6.99 (m, 3H), 3.72 (dd, J=11.0, 5.0 Hz, 1H), 3.59 (dd, J=11.0, 9.1 Hz, 1H), 2.89 (dd, J=9.4, 4.7 Hz, 1H), 2.80-2.65 (m, 2H), 2.07-1.94 (m, 1H), 1.92-1.77 (m, 2H), 1.77-1.64 (m, 1H).

Example 52

Example 52 was synthesized from Intermediate 4 and 52A using General Route 3. MS(ESI) m/z 296 (M+H). $^1$H NMR (500 MHz, DMSO-d$_6$) δ 7.50-7.35 (m, 1H), 7.21-7.09 (m, 3H), 6.17 (br. s., 1H), 4.50 (dd, J=9.8, 5.1 Hz, 1H), 4.35 (t, J=9.6 Hz, 1H), 2.85-2.68 (m, 3H), 2.02-1.80 (m, 3H), 1.79-1.66 (m, 1H). The compound was isolated as a TFA salt.

Example 53: 7-((2-Methyl-4-phenylcyclohexyl)methoxy)-3H-[1,2,3]triazolo[4,5-b]pyridin-5-amine

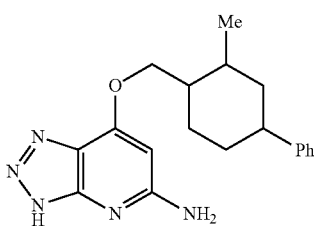 [SMILES: CC1CC(c2ccccc2)CCC1COc1cc(N)nc2[nH]nnc12]

53A: 2-Methyl-4-phenylcyclohexanone

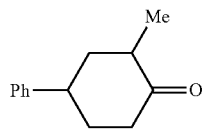

Lithium bis(trimethylsilyl)amide in THF (11.5 mL, 11.5 mmol) was added dropwise to a solution of 4-phenylcyclohexanone (2 g, 11.5 mmol) in THF (46 mL) at −78° C. and stirred for 30 min at −78° C. Methyl iodide (6.3 mL, 13 mmol) was added and the cooling bath was removed. The mixture was stirred over night. Water was added to the reaction and the mixture was extracted with EtOAc (2×). The combined organics were washed with brine, dried over Na$_2$SO$_4$ and concentrated in vacuo. The crude product was purified by flash chromatography (loading in chloroform, 0% to 20% ethyl acetate in hexane over 30 min using a 80 g silica gel cartridge) to yield 53A (1.1 g, 5.6 mmol, 48.6% yield) as a clear oil. A 2.5:1 mixture of diastereomers is observed by NMR. $^1$H NMR (500 MHz, CD$_3$OD) δ 7.36-7.24 (m, 4H), 7.22-7.15 (m, 1H), 3.27-3.13 (m, 1H), 2.78-2.55 (m, 2H), 2.44-2.31 (m, 1H), 2.30-2.16 (m, 2H), 2.16-2.08 (m, 1H), 1.96-1.86 (m, 1H), 1.65 (m, 1H), 1.13 (m, 3H),

53B: (4-(Methoxymethylene)-3-methylcyclohexyl)benzene

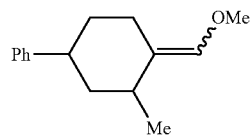 [SMILES: COC=C1CCC(c2ccccc2)CC1C]

To a suspension of (methoxymethyl)triphenylphosphonium chloride (3.2 g, 9.2 mmol) in THF (20 mL) was added potassium tert-butoxide (1.0 g, 9.2 mmol) at rt under argon. The red suspension was stirred at rt for 30 min, then a solution of 2-methyl-4-phenylcyclohexanone (1.1 g, 5.6 mmol) in THF (10 mL) was added. The resulting suspension allowed to stir overnight at rt. THF was removed under reduced pressure, and hexanes (100 mL) was added to the residue. The resulting suspension was sonicated and then stirred for 30 minutes, and then filtered. The filtrate was concentrated. To remove the excess Ph$_3$P, the residue was dissolved in acetone (10 mL), and methyl iodide (0.52 ml, 8.4 mmol) was added to the residue. The reaction mixture was stirred at rt for 1 h. The volatiles were removed under reduced pressure. The crude was purified by column chromatography (0 to 50% EtOAc in hexanes) to yield 53B (770 mg, 3.6 mmol, 64% yield) (mixture of E- and Z-isomers) as a yellowish oil.

53C: (2-Methyl-4-phenylcyclohexyl)methanol

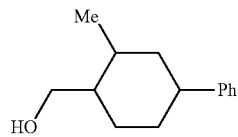 [SMILES: CC1CC(c2ccccc2)CCC1CO]

A mixture containing (4-(methoxymethylene)-3-methylcyclohexyl)benzene (0.77 g, 3.6 mmol), dioxane (10 mL) and HCl (conc.) (5 mL) was heated at 60° C. for 1 h. The mixture was partially concentrated and the residue was partitioned between EtOAc (50 mL) and water (20 mL). The EtOAc phase was washed with water (2×) and brine (1×) and dried over Na$_2$SO$_4$. The solvent was removed under reduced pressure. The crude aldehyde was dissolved in MeOH (12 mL) and cooled to 0° C. To this solution sodium borohydride (0.27 g, 7.1 mmol) was added portionwise over 1 h and the reaction mixture was stirred at 0° C. for 15 min and at rt overnight. The reaction mixture was concentrated, dissolved in EtOAc (50 mL), washed with HCl (1.0 M), NaHCO$_3$ (1×) and brine (1×) and dried over Na$_2$SO$_4$. The volatiles were removed and the crude mixture was purified by column chromatography (0 to 50% EtOAc in hexanes) to yield 53C (360 mg, 1.8 mmol, 50% yield) as a clear oil. $^1$H NMR (500 MHz, CD$_3$OD) δ 7.27-7.21 (m, 2H), 7.21-7.16 (m, 2H), 7.15-7.10 (m, 1H), 3.71 (dd, J=10.7, 3.3 Hz, 1H), 3.49 (dd, J=11.0, 6.6 Hz, 1H), 2.01 (s, 1H), 1.46 (s, 2H), 1.38-1.19 (m, 3H), 0.98 (d, J=6.6 Hz, 3H).

Example 53

Example 53 was synthesized from Intermediate 4 and 53C using General Route 3. MS(ESI) m/z 338 (M+H).

Example 54: 7-(2,6-Difluorobenzyloxy)-3H-[1,2,3]triazolo[4,5-b]pyridin-5-amine

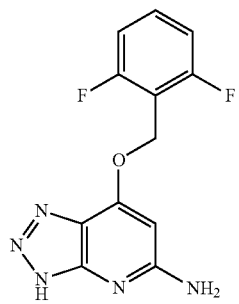 [SMILES: Nc1cc(OCc2c(F)cccc2F)c2nn[nH]c2n1]

Example 54 was synthesized from Intermediate 1 and (2,6-difluorophenyl)methanol using General Route 2. MS(ESI) m/z 338.2 (M+H). $^1$H NMR (400 MHz, CD$_3$OD) δ 7.61-7.50 (m, 1H), 7.18-7.06 (m, 2H), 6.41 (s, 1H), 5.53 (s, 2H). Analytical HPLC Method A: 5.24 min, 94%; Method B: 6.56 min, 94%. The compound was isolated as a TFA salt.

Example 55: 7-(2-Fluorobenzyloxy)-3H-[1,2,3]triazolo[4,5-b]pyridin-5-amine

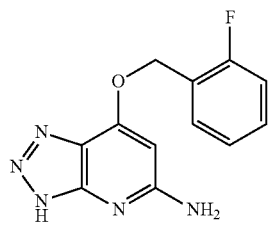 [SMILES: Nc1cc(OCc2ccccc2F)c2nn[nH]c2n1]

Example 55 was synthesized from Intermediate 1 and (2-fluorophenyl)methanol using General Route 2. MS(ESI) m/z 260.2 (M+H). $^1$H NMR (400 MHz, DMSO-d$_6$) δ 7.71-7.57 (m, 1H), 7.57-7.39 (m, 1H), 7.30 (d, J=7.7 Hz, 2H), 6.35 (br. s., 1H), 5.45 (s, 2H). Analytical HPLC Method A: 4.55 min, 97%; Method B: 4.97 min, 97%. The compound was isolated as a TFA salt.

Example 56: 3-((5-Amino-3H-[1,2,3]triazolo[4,5-b]pyridin-7-yloxy)methyl)benzamide

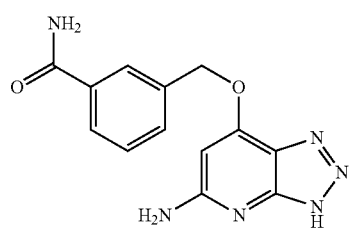 [SMILES: NC(=O)c1cccc(COc2cc(N)nc3[nH]nnc23)c1]

Example 56 was synthesized from Intermediate 1 and 3-(hydroxymethyl)benzonitrile using General Route 2. The nitrile hydrolyzed during the first synthetic step in this sequence. MS(ESI) m/z 285.1 (M+H). $^1$H NMR (400 MHz, CD$_3$OD) δ ppm 8.07 (1H, s), 7.98 (1H, s), 7.92 (1H, d, J=7.7 Hz), 7.74 (1H, d, J=7.7 Hz), 7.57 (1H, t, J=7.7 Hz), 6.41 (1H, s), 5.57 (2H, s), 3.00 (2H, s), 2.87 (2H, s). Analytical HPLC Method A: 3.10 min, 91%; Method B: 3.27 min, 90%.

Example 57: 7-(5-Chloro-2-methoxybenzyloxy)-3H-[1,2,3]triazolo[4,5-b]pyridin-5-amine

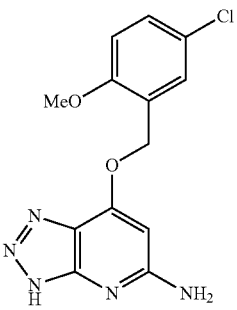 [SMILES: COc1ccc(Cl)cc1COc1cc(N)nc2[nH]nnc12]

57A: (5-Chloro-2-methoxyphenyl)methanol

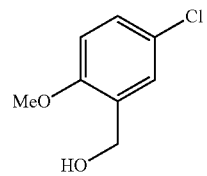

57A was synthesized using a similar method to that was used to synthesize 44A using 5-chloro-2-methoxybenzoic acid. MS(ESI) m/z 155.1 (M+H).

57B: 2-(Bromomethyl)-4-chloro-1-methoxybenzene

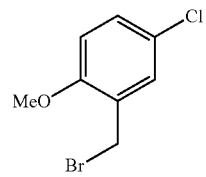 [SMILES: COc1ccc(Cl)cc1CBr]

57B was synthesized using a method analogous to that used to make 29A using 57A.

Example 57

Example 57 was synthesized from Intermediate 4 and 57B using General Route 3. MS(ESI) m/z 306.3 (M+H). $^1$H NMR (400 MHz, CD$_3$OD) δ 7.57-7.46 (m, 1H), 7.38 (dd, J=8.8, 2.7 Hz, 1H), 7.07 (d, J=8.8 Hz, 1H), 6.39 (s, 1H), 5.45 (s, 2H), 3.89 (s, 3H). Analytical HPLC Method A: 5.40 min, 98%; Method B: 6.07 min, 97%. The compound was isolated as a TFA salt.

Example 58: 7-(5-Bromo-2-methoxybenzyloxy)-3H-[1,2,3]triazolo[4,5-b]pyridin-5-amine

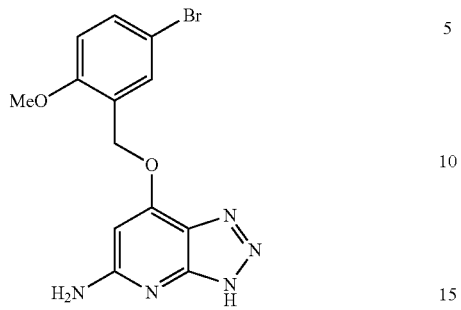

Example 58 was synthesized from Intermediate 1 and (5-bromo-2-methoxyphenyl)methanol using General Route 2. MS(ESI) m/z 350.2 (M+H). $^1$H NMR (400 MHz, CD$_3$OD) δ 7.69 (d, J=2.7 Hz, 1H), 7.48 (dd, J=8.8, 2.2 Hz, 1H), 6.99 (d, J=8.8 Hz, 1H), 6.17 (s, 1H), 5.33 (s, 2H), 3.88 (s, 3H). Analytical HPLC Method A: 6.14 min, 98%; Method B: 7.82 min, 97%.

Example 59: 7-(3-Bromo-2-methoxybenzyloxy)-3H-[1,2,3]triazolo[4,5-b]pyridin-5-amine

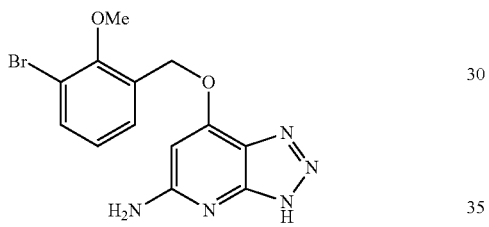

Example 59 was synthesized from Intermediate 1 and (3-bromo-2-methoxyphenyl)methanol using General Route 2. MS(ESI) m/z 350.1 (M+H). $^1$H NMR (400 MHz, CD$_3$OD) δ 7.68 (dd, J=8.1, 1.5 Hz, 1H), 7.56 (dd, J=7.6, 1.5 Hz, 1H), 7.14 (m, 1H), 6.41 (s, 1H), 5.53 (s, 2H), 3.93 (s, 3H). Analytical HPLC Method A: 5.96 min, 95%; Method B: 6.97 min, 95%. The compound was isolated as a TFA salt.

Example 60: 7-(3-Bromo-2-methylbenzyloxy)-3H-[1,2,3]triazolo[4,5-b]pyridin-5-amine

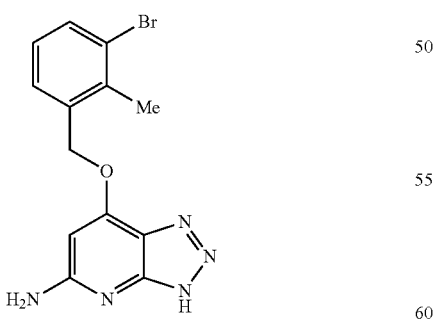

Example 60 was synthesized from Intermediate 1 and (3-bromo-2-methylphenyl)methanol using General Route 2. MS(ESI) m/z 334.1 (M+H). $^1$H NMR (400 MHz, CD$_3$OD) δ 7.64 (d, J=7.3 Hz, 1H), 7.49 (d, J=7.6 Hz, 1H), 7.17 (t, J=7.8 Hz, 1H), 6.42 (s, 1H), 5.54 (s, 2H), 2.50 (s, 3H). Analytical HPLC Method A: 6.38 min, 99%; Method B: 7.96 min, 99%. The compound was isolated as a TFA salt.

Example 61: 7-(5-Bromo-2-fluorobenzyloxy)-3H-[1,2,3]triazolo[4,5-b]pyridin-5-amine

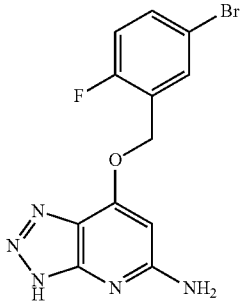 [SMILES: Nc1cc(OCc2cc(Br)ccc2F)c2nn[nH]c2n1]

61A: (5-Bromo-2-fluorophenyl)methanol

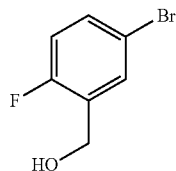

61A was synthesized using a similar method to that was used to synthesize 44A using 5-bromo-2-fluorobenzoic acid. MS(ESI) m/z 187 (M+H).

61B: 4-Bromo-2-(bromomethyl)-1-fluorobenzene

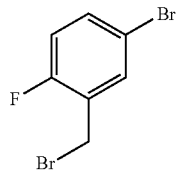

61B was synthesized using a method analogous to that used to make 29A using 61A.

Example 61

Example 61 was synthesized from Intermediate 4 and 61B using General Route 3. MS(ESI) m/z 338.2 (M+H). $^1$H NMR (400 MHz, CD$_3$OD) δ 7.82 (dd, J=6.3, 2.5 Hz, 1H), 7.65-7.57 (m, 1H), 7.18 (t, J=9.1 Hz, 1H), 6.38 (s, 1H), 5.51 (s, 2H). Analytical HPLC Method A: 6.17 min, 97%; Method B: 7.54 min, 98%. The compound was isolated as a TFA salt.

Example 62: 7-(3-Bromo-2-fluorobenzyloxy)-3H-[1,2,3]triazolo[4,5-b]pyridin-5-amine

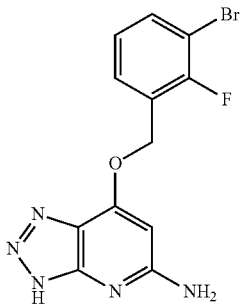 [SMILES: Nc1cc(OCc2cccc(Br)c2F)c2nn[nH]c2n1]

62A: (3-Bromo-2-fluorophenyl)methanol

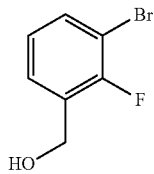

62A was synthesized using a similar method to that was used to synthesize 44A using 3-bromo-2-fluorobenzoic acid. MS(ESI) m/z 187.1 (M+H).

62B: 1-Bromo-3-(bromomethyl)-2-fluorobenzene

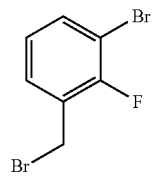

62B was synthesized using a method analogous to that used to make 29A using 62A.

Example 62

Example 62 was synthesized from Intermediate 4 and 62B using General Route 3. MS(ESI) m/z 338.2 (M+H). $^1$H NMR (400 MHz, CD$_3$OD) δ 7.76-7.67 (m, 1H), 7.63 (t, J=7.1 Hz, 1H), 7.21 (t, J=8.2 Hz, 1H), 6.39 (s, 1H), 5.57 (s, 2H). Analytical HPLC Method A: 5.41 min, 95%; Method B: 6.02 min, 95%. The compound was isolated as a TFA salt.

Example 63: 7-(3-(5-Fluoropyridin-3-yl)-2-methylbenzyloxy)-3H-[1,2,3]triazolo[4,5-b]pyridin-5-amine

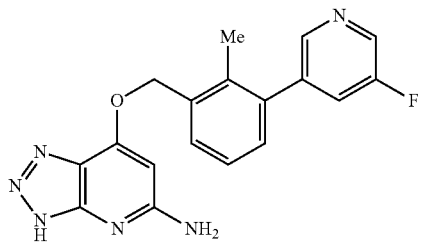 [SMILES: Cc1c(COc2cc(N)nc3[nH]nnc23)cccc1-c1cncc(F)c1]

In a microwave vial, (5-fluoropyridin-3-yl)boronic acid (21 mg, 0.15 mmol), Example 60 (50 mg, 0.15 mmol), K$_2$CO$_3$ (62 mg, 0.45 mmol), and PdCl$_2$(dppf)-CH$_2$Cl$_2$ adduct (11 mg, 0.015 mmol) were brought up in DME (1.4 mL) and water (0.14 mL). The solution was flushed with argon before it was sealed and heated in microwave at 150° C. for 30 minutes. The reaction solution was filtered over CELITE® and concentrated in vacuo to give the crude product, which was purified by preparative HPLC (Method J). The product fractions containing the product were filtered over a NaHCO$_3$ resin frit, and concentrated in vacuo to give Example 63 as a white solid (17 mg, 0.035 mmol, 23% yield). MS(ESI) m/z 351.3 (M+H). $^1$H NMR (400 MHz, CD$_3$OD) δ 8.51 (d, J=1.6 Hz, 1H), 8.39 (s, 1H), 7.75-7.58 (m, 2H), 7.44-7.29 (m, 2H), 6.46 (s, 1H), 5.58 (s, 2H), 2.32 (s, 3H). Analytical HPLC Method A: 5.15 min, 97%; Method B: 5.66 min, 96%. The compound was isolated as a TFA salt.

Example 64: 7-((2'-Fluoro-4'-methoxybiphenyl-3-yl)methoxy)-3H-[1,2,3]triazolo[4,5-b]pyridin-5-amine

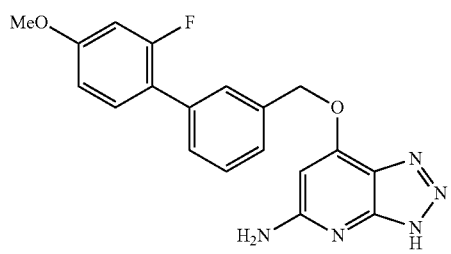 [SMILES: COc1ccc(-c2cccc(COc3cc(N)nc4[nH]nnc34)c2)c(F)c1]

Example 64 was synthesized using a method analogous to that used to make Example 63 from Example 148 and (2-fluoro-4-methoxyphenyl)boronic acid. MS(ESI) m/z 366.4 (M+H). $^1$H NMR (400 MHz, CD$_3$OD) δ ppm 7.66 (br. s., 1H), 7.54-7.46 (m, 3H), 7.42 (t, J=8.8 Hz, 1H), 6.84 (dd, J=8.8, 2.7 Hz, 1H), 6.80 (d, J=2.7 Hz, 1H), 6.26 (s, 1H), 5.45 (s, 2H), 3.83 (s, 3H). Analytical HPLC Method A: 6.64 min, 88%; Method B: 8.31 min, 90%. The compound was isolated as a TFA salt.

Example 65: 7-((3'-Fluoro-4-methylbiphenyl-3-yl)methoxy)-3H-[1,2,3]triazolo[4,5-b]pyridin-5-amine

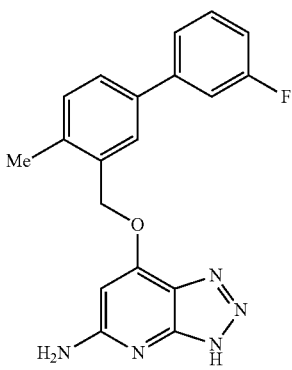 [SMILES: Cc1ccc(-c2cccc(F)c2)cc1COc1cc(N)nc2[nH]nnc12]

65A: (5-Bromo-2-methylphenyl)methanol

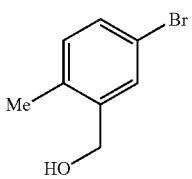

65A was synthesized using a similar method to that was used to synthesize 44A using 5-bromo-2-methylbenzoic acid.

65B: 7-(5-Bromo-2-methylbenzyloxy)-3H-[1,2,3]triazolo[4,5-b]pyridin-5-amine

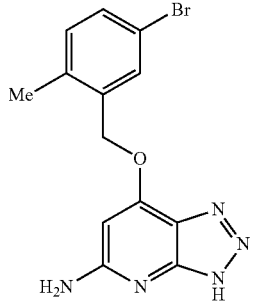 [SMILES: Cc1ccc(Br)cc1COc1cc(N)nc2[nH]nnc12]

65B was synthesized from Intermediate 1 and 65A using General Route 2. MS(ESI) m/z 334.2 (M+H).

Example 65

Example 65 was synthesized using a method analogous to that used to make Example 63 from 65B and (3-fluorophenyl)boronic acid. MS(ESI) m/z 350.0 (M+H). $^1$H NMR (400 MHz, CD$_3$OD) δ 7.76 (d, J=2.2 Hz, 1H), 7.60 (dd, J=8.0, 1.9 Hz, 1H), 7.46-7.42 (m, 2H), 7.41-7.34 (m, 2H), 7.09-7.03 (m, 1H), 6.43 (s, 1H), 5.55 (s, 2H), 2.47 (s, 3H). Analytical HPLC Method A: 7.21 min, 94%; Method B: 8.21 min, 90%. The compound was isolated as a TFA salt.

Example 66: 7-((3'-Fluoro-4-methoxybiphenyl-3-yl)methoxy)-3H-[1,2,3]triazolo[4,5-b]pyridin-5-amine

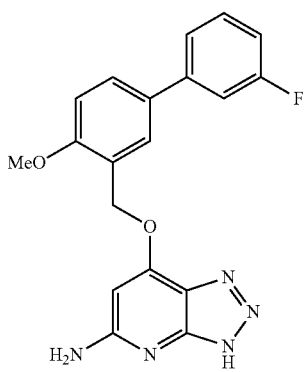 [SMILES: COc1ccc(-c2cccc(F)c2)cc1COc1cc(N)nc2[nH]nnc12]

Example 66 was synthesized using a method analogous to that used to make Example 63 from Example 58 and (3-fluorophenyl)boronic acid. MS(ESI) m/z 366.0 (M+H). $^1$H NMR (400 MHz, CD$_3$OD) δ 7.78 (d, J=2.2 Hz, 1H), 7.69 (dd, J=8.8, 2.2 Hz, 1H), 7.41 (tt, J=3.2, 1.7 Hz, 2H), 7.36-7.31 (m, 1H), 7.17 (d, J=8.8 Hz, 1H), 7.06-6.98 (m, 1H), 6.42 (s, 1H), 5.52 (s, 2H), 3.93 (s, 3H). Analytical HPLC Method A: 6.95 min, 99%; Method B: 8.61 min, 100%. The compound was isolated as a TFA salt.

Example 67: 7-((3'-Fluoro-2-methoxybiphenyl-3-yl)methoxy)-3H-[1,2,3]triazolo[4,5-b]pyridin-5-amine

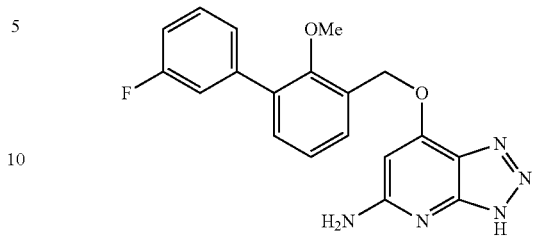

Example 67 was synthesized using a method analogous to that used to make Example 63 from Example 59 and (3-fluorophenyl)boronic acid. MS(ESI) m/z 366.3 (M+H). $^1$H NMR (400 MHz, CD$_3$OD) δ 7.51-7.48 (m, 1H), 7.40-7.36 (m, 2H), 7.35-7.31 (m, 1H), 7.29-7.25 (m, 1H), 7.21 (t, J=7.7 Hz, 1H), 7.07-7.01 (m, 1H), 6.43 (s, 1H), 5.50 (s, 2H), 3.45-3.43 (m, 3H), 3.36 (s, 3H). Analytical HPLC Method A: 7.26 min, 95%; Method B: 8.95 min, 95%. The compound was isolated as a TFA salt.

Example 68: 7-((3'-Fluoro-2-methylbiphenyl-3-yl)methoxy)-3H-[1,2,3]triazolo[4,5-b]pyridin-5-amine

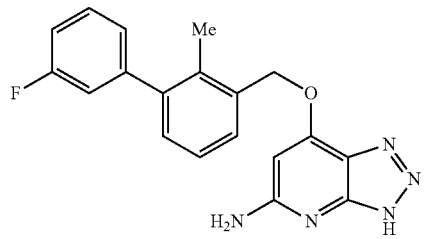 [SMILES: Cc1c(COc2cc(N)nc3[nH]nnc23)cccc1-c1cccc(F)c1]

Example 68 was synthesized using a method analogous to that used to make Example 63 from Example 60 and (3-fluorophenyl)boronic acid. MS(ESI) m/z 350.2 (M+H). $^1$H NMR (400 MHz, CD$_3$OD) δ 7.65 (dd, J=12.9, 7.4 Hz, 1H), 7.57-7.52 (m, 1H), 7.46 (td, J=8.0, 6.0 Hz, 1H), 7.36-7.27 (m, 2H), 7.13 (dd, J=8.0, 1.9 Hz, 1H), 7.08 (td, J=9.6, 2.2 Hz, 1H), 6.45 (s, 1H), 5.57 (s, 2H), 2.34-2.25 (m, 3H). Analytical HPLC Method A: 6.82 min, 97%; Method B: 7.52 min, 95%. The compound was isolated as a TFA salt.

Example 69: 7-((2-Methylbiphenyl-3-yl)methoxy)-3H-[1,2,3]triazolo[4,5-b]pyridin-5-amine

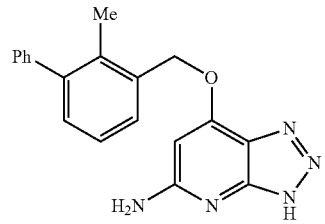 [SMILES: Cc1c(COc2cc(N)nc3[nH]nnc23)cccc1-c1ccccc1]

Example 69 was synthesized from Intermediate 1 and (2-methyl-[1,1'-biphenyl]-3-yl)methanol using General Route 2. MS(ESI) m/z 322.1 (M+H). $^1$H NMR (400 MHz, CD$_3$OD) δ 7.54 (d, J=6.3 Hz, 1H), 7.50-7.44 (m, 2H), 7.41 (d, J=7.6 Hz, 1H), 7.39-7.27 (m, 4H), 6.45 (s, 1H), 5.58 (s, 2H), 2.32 (s, 3H). Analytical HPLC Method A: 6.77 min, 95%; Method B: 7.49 min, 95%. The compound was isolated as a TFA salt.

Example 70: 7-((4-Chloro-3'-fluorobiphenyl-3-yl)methoxy)-3H-[1,2,3]triazolo[4,5-b]pyridin-5-amine

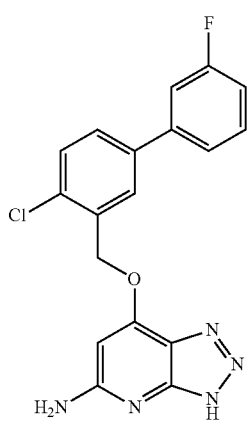 [SMILES: Nc1cc(OCc2cc(-c3cccc(F)c3)ccc2Cl)c2nn[nH]c2n1]

70A: (4-Chloro-3'-fluorobiphenyl-3-yl)methanol

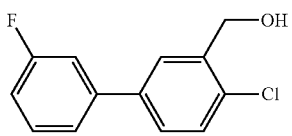 [SMILES: OCc1cc(-c2cccc(F)c2)ccc1Cl]

70A was synthesized using a method analogous to that used to make 19A from (5-bromo-2-chlorophenyl)methanol and (3-fluorophenyl)boronic acid. $^1$H NMR (400 MHz, CDCl$_3$) δ 7.72 (s, 1H), 7.44 (s, 2H), 7.43-7.34 (m, 2H), 7.31-7.28 (m, 1H), 7.10-7.02 (m, 1H), 4.86 (d, J=6.0 Hz, 2H).

Example 70

Example 70 was synthesized from Intermediate 1 and 70A using General Route 2. MS(ESI) m/z 370.0 (M+H). $^1$H NMR (400 MHz, CD$_3$OD) δ ppm 7.97 (d, J=2.2 Hz, 1H), 7.69 (dd, J=8.5, 2.5 Hz, 1H), 7.59 (d, J=8.2 Hz, 1H), 7.50-7.45 (m, 2H), 7.44-7.39 (m, 1H), 7.15-7.08 (m, 1H), 6.40-6.37 (m, 1H), 5.59 (s, 2H). Analytical HPLC Method A: 7.04 min, 94%; Method B: 7.65 min, 94%. The compound was isolated as a TFA salt.

Example 71: 7-((3',4-Difluorobiphenyl-3-yl)methoxy)-3H-[1,2,3]triazolo[4,5-b]pyridin-5-amine

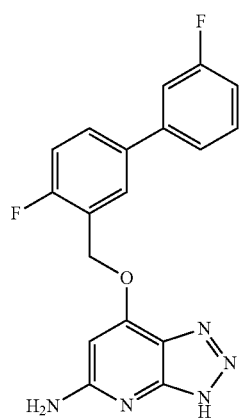 [SMILES: Nc1cc(OCc2cc(-c3cccc(F)c3)ccc2F)c2nn[nH]c2n1]

71A: (3',4-Difluoro-[1,1'-biphenyl]-3-yl)methanol

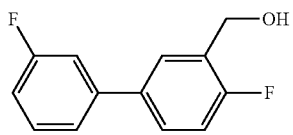

71A was synthesized using a method analogous to that used to make 19A from 61A and (3-fluorophenyl)boronic acid.

Example 71

Example 71 was synthesized from Intermediate 1 and 71A using General Route 2. MS(ESI) m/z 354.3 (M+H). $^1$H NMR (400 MHz, CD$_3$OD) δ ppm 7.93-7.87 (m, 1H), 7.77-7.70 (m, 1H), 7.50-7.43 (m, 2H), 7.41-7.36 (m, 1H), 7.35-7.27 (m, 1H), 7.13-7.07 (m, 1H), 6.43-6.40 (m, 1H), 5.58 (s, 2H). Analytical HPLC Method A: 6.72 min, 100%; Method B: 7.33 min, 96%. The compound was isolated as a TFA salt.

Example 72: 7-((2,3'-Difluorobiphenyl-3-yl)methoxy)-3H-[1,2,3]triazolo[4,5-b]pyridin-5-amine

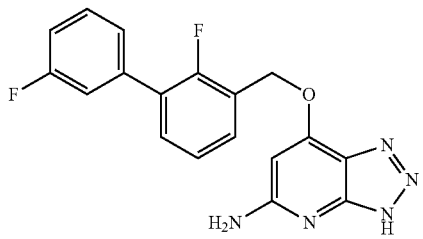 [SMILES: Nc1cc(OCc2cccc(-c3cccc(F)c3)c2F)c2nn[nH]c2n1]

72A: (2,3'-Difluoro-[1,1'-biphenyl]-3-yl)methanol

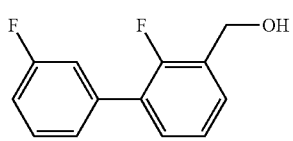 [SMILES: OCc1cccc(-c2cccc(F)c2)c1F]

72A was synthesized using a method analogous to that used to make 19A from 62A and (3-fluorophenyl)boronic acid.

Example 72

Example 72 was synthesized from Intermediate 1 and 72A using General Route 2. MS(ESI) m/z 354.0 (M+H). $^1$H NMR (400 MHz, CD$_3$OD) δ 7.68-7.61 (m, 1H), 7.57 (td, J=7.6, 1.9 Hz, 1H), 7.48 (td, J=8.0, 6.0 Hz, 1H), 7.41-7.29 (m, 3H), 7.18-7.11 (m, 1H), 6.41 (s, 1H), 5.59 (s, 2H). Analytical HPLC Method A: 6.69 min, 91%; Method B: 7.33 min, 92%.

Example 73: 7-((2,4-Difluoro-2'-methoxybiphenyl-3-yl)methoxy)-3H-[1,2,3]triazolo[4,5-b]pyridin-5-amine

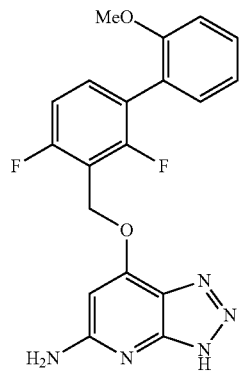 [SMILES: COc1ccccc1-c1ccc(F)c(COc2cc(N)nc3[nH]nnc23)c1F]

73A: (3-Bromo-2,6-difluorophenyl)methanol

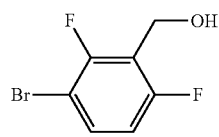 [SMILES: OCc1c(F)ccc(Br)c1F]

73A was synthesized using a similar method to that was used to make 44A using 3-bromo-2,6-difluorobenzoic acid.

73B: (2,4-Difluoro-2'-methoxy-[1,1'-biphenyl]-3-yl)methanol

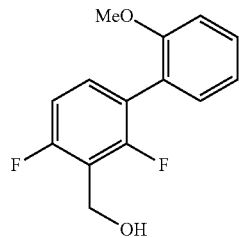 [SMILES: COc1ccccc1-c1ccc(F)c(CO)c1F]

73B was synthesized using a method analogous to that used to make 19A from 73A and (2-methoxyphenyl)boronic acid. MS(ESI) m/z 233.1 (M+H).

Example 73

Example 73 was synthesized from Intermediate 1 and 73B using General Route 2. MS(ESI) m/z 384.3 (M+H). $^1$H NMR (400 MHz, CD$_3$OD) δ 7.48-7.40 (m, 1H), 7.36 (s, 1H), 7.19 (dd, J=7.5, 1.4 Hz, 1H), 7.14-7.07 (m, 1H), 7.05 (d, J=8.3 Hz, 1H), 7.02-6.96 (m, J=7.5, 0.9 Hz, 1H), 6.49 (s, 1H), 5.59 (s, 2H), 3.74 (s, 3H). Analytical HPLC Method A: 6.98 min, 95%; Method B: 8.71 min, 95%. The compound was isolated as a TFA salt.

Example 74: 7-(3-(1-Benzyl-1H-pyrazol-4-yl)benzyloxy)-3H-[1,2,3]triazolo[4,5-b]pyridin-5-amine

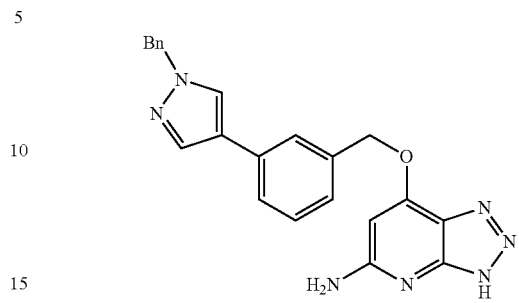

Example 74 was synthesized using a method analogous to that used to make Example 63 from Example 148 and 1-benzyl-4-(4,4,5,5-tetramethyl-1,3,2-dioxaborolan-2-yl)-1H-pyrazole. MS(ESI) m/z 398.3 (M+H). $^1$H NMR (400 MHz, CD$_3$OD) δ ppm 8.09 (s, 1H), 7.90 (s, 1H), 7.71 (s, 1H), 7.61-7.55 (m, 1H), 7.48-7.23 (m, 7H), 6.41 (s, 1H), 5.47 (s, 2H), 5.36 (s, 2H). Analytical HPLC Method A: 5.04 min, 97%; Method B: 5.72 min, 92%.

Example 75: 7-(3-(1-Benzyl-1H-pyrazol-3-yl)benzyloxy)-3H-[1,2,3]triazolo[4,5-b]pyridin-5-amine

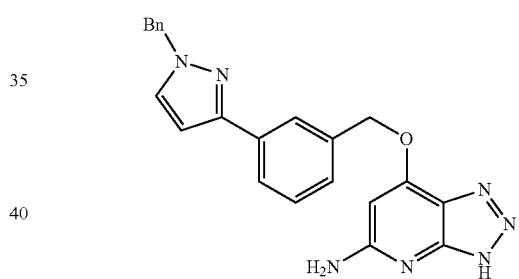

In a sealed vial, (1H-pyrazol-3-yl)boronic acid (39 mg, 0.35 mmol) and (bromomethyl)benzene (89 mg, 0.52 mmol) were brought up in DMF (1.0 mL) and stirred at room temperature overnight. LCMS showed the formation of (1-benzyl-1H-pyrazol-3-yl)boronic acid, MS(ESI) m/z 203.1 (M+H). To the reaction solution was added Example 148 (110 mg, 0.35 mmol) and PdCl$_2$(dppf)-CH$_2$Cl$_2$ adduct (47 mg, 0.058 mmol), Cs$_2$CO$_3$ (250 mg, 0.77 mmol) and DMF (2.0 mL). Argon was bubbled through the solution for 1 minute, and the reaction mixture was heated to 110° C. for 18 hours. The reaction solution was filtered over CELITE® and concentrated in vacuo to give the crude product, which was purified by preparative HPLC (Method J). The product was repurified by preparative HPLC (10% MeCN—90% H$_2$O—0.1% TFA to 90% MeCN—10% H$_2$O—0.1% TFA, 20-100% Solvent B PHENOMENEX® Luna Axia 30×100A C18 5 u, 10 minutes) to yield Example 75. MS(ESI) m/z 398.3 (M+H). $^1$H NMR (400 MHz, CD$_3$OD) δ ppm 7.97 (s, 1H), 7.83-7.78 (m, 1H), 7.73-7.68 (m, 1H), 7.50-7.45 (m, 2H), 7.37-7.29 (m, 2H), 7.29-7.23 (m, 3H), 6.72 (d, J=2.2 Hz, 1H), 6.41 (s, 1H), 5.53 (s, 2H), 5.39 (s, 2H). Analytical HPLC Method A: 6.44 min, 90%; Method B: 8.14 min, 93%.

Example 77: 7-(3-(1-Methyl-1H-pyrazol-4-yl)benzyloxy)-3H-[1,2,3]triazolo[4,5-b]pyridin-5-amine

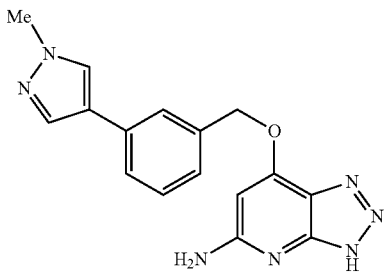 [SMILES: Cn1cc(-c2cccc(COc3cc(N)nc4[nH]nnc34)c2)cn1]

Example 77 was synthesized using a method analogous to that used to make Example 63 from Example 148 and 1-methyl-4-(4,4,5,5-tetramethyl-1,3,2-dioxaborolan-2-yl)-1H-pyrazole. MS(ESI) m/z 322.1 (M+H). $^1$H NMR (400 MHz, CD$_3$OD) δ ppm 8.01 (s, 1H), 7.86 (s, 1H), 7.73 (s, 1H), 7.60 (dt, J=7.7, 1.4 Hz, 1H), 7.47-7.36 (m, 2H), 6.42 (s, 1H), 5.51 (s, 2H), 3.93 (s, 3H). Analytical HPLC Method A: 4.53 min, 97%; Method B: 5.03 min, 97%.

Example 78: 7-(3-(1-Methyl-1H-pyrazol-5-yl)benzyloxy)-3H-[1,2,3]triazolo[4,5-b]pyridin-5-amine

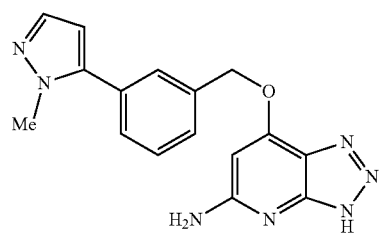 [SMILES: Cn1nccc1-c1cccc(COc2cc(N)nc3[nH]nnc23)c1]

Example 78 was synthesized using a method analogous to that used to make Example 63 from Example 148 and (1-methyl-1H-pyrazol-5-yl)boronic acid. MS(ESI) m/z 322.2 (M+H). $^1$H NMR (400 MHz, CD$_3$OD) δ ppm 7.69 (s, 1H), 7.66-7.54 (m, 3H), 7.52 (d, J=1.6 Hz, 1H), 6.44 (s, 1H), 6.43 (d, J=2.2 Hz, 1H), 5.57 (s, 2H), 3.89 (s, 3H). Analytical HPLC Method A: 4.61 min, 87%; Method B: 5.06 min, 88%.

Example 79: 7-(3-(1-Methyl-3-(trifluoromethyl)-1H-pyrazol-5-yl)benzyloxy)-3H-[1,2,3]triazolo[4,5-b]pyridin-5-amine

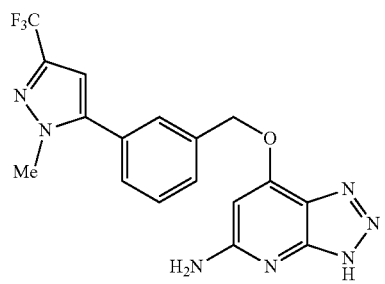 [SMILES: Cn1nc(C(F)(F)F)cc1-c1cccc(COc2cc(N)nc3[nH]nnc23)c1]

Example 79 was synthesized using a method analogous to that used to make Example 63 from Example 148 and (1-methyl-3-(trifluoromethyl)-1H-pyrazol-5-yl)boronic acid. MS(ESI) m/z 390.3 (M+H). $^1$H NMR (400 MHz, CD$_3$OD) δ ppm 7.78-7.59 (m, 4H), 6.75 (s, 1H), 6.45 (s, 1H), 5.60 (s, 2H), 3.96 (s, 3H). Analytical HPLC Method A: 6.80 min, 90%; Method B: 8.17 min, 90%. The compound was isolated as a TFA salt.

Example 80: 7-(2-Methoxy-3-(1-methyl-1H-pyrazol-3-yl)benzyloxy)-3H-[1,2,3]triazolo[4,5-b]pyridin-5-amine

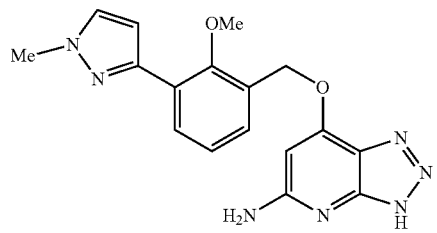 [SMILES: COc1c(COc2cc(N)nc3[nH]nnc23)cccc1-c1ccn(C)n1]

Example 80 was synthesized using a method analogous to that used to make Example 63 from Example 59 and 1-methyl-3-(4,4,5,5-tetramethyl-1,3,2-dioxaborolan-2-yl)-1H-pyrazole. MS(ESI) m/z 352.3 (M+H). $^1$H NMR (400 MHz, CD$_3$OD) δ 7.80 (dd, J=8.0, 1.9 Hz, 1H), 7.66 (d, J=2.7 Hz, 1H), 7.53 (dd, J=7.7, 1.6 Hz, 1H), 7.25 (t, J=7.4 Hz, 1H), 6.73 (d, J=2.2 Hz, 1H), 6.48 (s, 1H), 5.57 (s, 2H), 3.96 (s, 3H), 3.64 (s, 3H). Analytical HPLC Method A: 5.46 min, 97%; Method B: 6.69 min, 98%. The compound was isolated as a TFA salt.

Example 81: 7-(2-Methyl-3-(1-methyl-1H-pyrazol-3-yl)benzyloxy)-3H-[1,2,3]triazolo[4,5-b]pyridin-5-amine

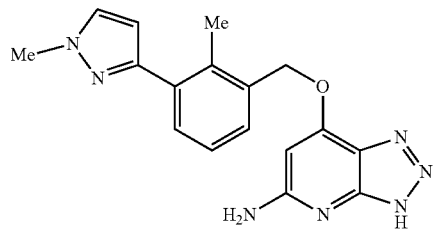 [SMILES: Cc1c(COc2cc(N)nc3[nH]nnc23)cccc1-c1ccn(C)n1]

Example 81 was synthesized using a method analogous to that used to make Example 63 from Example 60 and 1-methyl-3-(4,4,5,5-tetramethyl-1,3,2-dioxaborolan-2-yl)-1H-pyrazole. MS(ESI) m/z 336.1 (M+H). $^1$H NMR (400 MHz, CD$_3$OD) δ 7.66 (d, J=2.2 Hz, 1H), 7.51 (d, J=7.1 Hz, 1H), 7.47 (d, J=7.7 Hz, 1H), 7.33-7.27 (m, 1H), 6.42 (s, 1H), 6.38 (d, J=2.2 Hz, 1H), 5.56 (s, 2H), 3.95 (s, 3H), 2.44 (s, 3H). Analytical HPLC Method A: 5.24 min, 99%; Method B: 6.43 min, 99%. The compound was isolated as a TFA salt.

Example 82: 7-(2-Fluoro-5-(1-isobutyl-1H-pyrazol-4-yl)benzyloxy)-3H-[1,2,3]triazolo[4,5-b]pyridin-5-amine

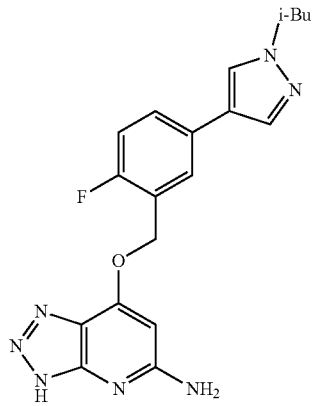

Example 82 was synthesized using a method analogous to that used to make Example 63 from Example 61 and 1-isobutyl-4-(4,4,5,5-tetramethyl-1,3,2-dioxaborolan-2-yl)-1H-pyrazole. MS(ESI) m/z 382.3 (M+H). $^1$H NMR (400 MHz, CD$_3$OD) δ 8.02 (s, 1H), 7.85 (s, 1H), 7.83-7.79 (m, 1H), 7.69-7.63 (m, 1H), 7.22 (dd, J=9.6, 8.5 Hz, 1H), 6.47 (s, 1H), 5.56 (s, 2H), 3.98 (d, J=7.1 Hz, 2H), 2.28-2.13 (m, 1H), 0.94 (s, 6H). Analytical HPLC Method A: 6.45 min, 98%; Method B: 7.81 min, 99%. The compound was isolated as a TFA salt.

Example 83: 7-(2-Methoxy-5-(1H-1,2,4-triazol-1-yl)benzyloxy)-3H-[1,2,3]triazolo[4,5-b]pyridin-5-amine

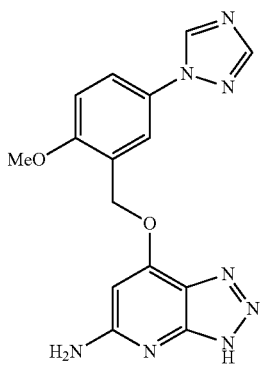 [SMILES: COc1ccc(-n2cncn2)cc1COc1cc(N)nc2[nH]nnc12]

In a 1 dram high pressure vial, 1H-1,2,4-triazole (30 mg, 0.43 mmol), Example 58 (50 mg, 0.14 mmol), N,N'-dimethyl-1,2-ethanediamine (25 mg, 0.29 mmol), Cs$_2$CO$_3$ (140 mg, 0.43 mmol), and copper (I) iodide (27 mg, 0.14 mmol) were brought up in DMF (0.50 mL) and heated to 110° C. for 18 hours. The crude mixture was purified by preparative HPLC (Method J) to give the title compound as a yellow solid (5.0 mg, 0.010 mmol, 7.1% yield). MS(ESI) m/z 339.3 (M+H). $^1$H NMR (400 MHz, CD$_3$OD) δ 9.06 (br. s., 1H), 8.18 (br. s., 1H), 7.99 (d, J=2.7 Hz, 1H), 7.86 (dd, J=8.8, 2.7 Hz, 1H), 7.28 (d, J=9.3 Hz, 1H), 6.45 (s, 1H), 5.57 (s, 2H), 3.98 (s, 3H). Analytical HPLC Method A: 4.00 min, 97%; Method B: 4.36 min, 97%. The compound was isolated as a TFA salt.

Example 84: 7-(3-(4-Methyl-1H-imidazol-1-yl)benzyloxy)-3H-[1,2,3]triazolo[4,5-b]pyridin-5-amine

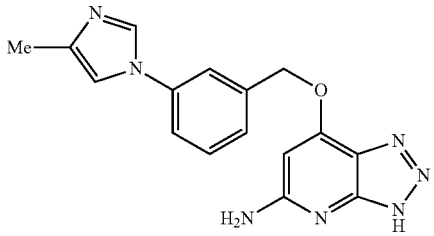 [SMILES: Cc1cn(-c2cccc(COc3cc(N)nc4[nH]nnc34)c2)cn1]

Example 84 was synthesized using a method analogous to that used to make Example 83 from Example 148 and 4-methyl-1H-imidazole. MS(ESI) m/z 322.2 (M+H). $^1$H NMR (400 MHz, CD$_3$OD) δ ppm 9.38 (s, 1H), 7.93 (s, 1H), 7.84 (br. s., 1H), 7.77-7.72 (m, 2H), 7.51-7.26 (m, 1H), 6.44 (s, 1H), 5.60 (s, 2H), 2.44 (s, 3H). Analytical HPLC Method A: 4.25 min, 95%; Method B: 5.71 min, 97%. The compound was isolated as a TFA salt.

Example 85: 7-(3-(3-Methyl-1H-pyrazol-1-yl)benzyloxy)-3H-[1,2,3]triazolo[4,5-b]pyridin-5-amine

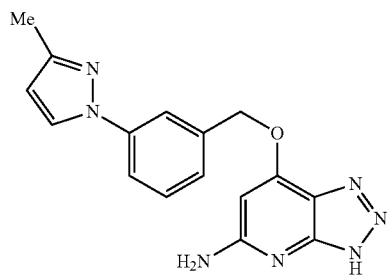 [SMILES: Cc1ccn(-c2cccc(COc3cc(N)nc4[nH]nnc34)c2)n1]

Example 85 was synthesized using a method analogous to that used to make Example 83 from Example 148 and 3-methyl-1H-pyrazole. MS(ESI) m/z 322.2 (M+H). $^1$H NMR (400 MHz, CD$_3$OD) δ ppm 8.14 (d, J=2.5 Hz, 1H), 7.92 (br. s., 1H), 7.74 (d, J=7.6 Hz, 1H), 7.57 (t, J=7.8 Hz, 1H), 7.49 (br. s., 1H), 6.45 (s, 1H), 6.36 (d, J=2.3 Hz, 1H), 5.60 (s, 2H), 2.36 (s, 3H). Analytical HPLC Method A: 5.40 min, 95%; Method B: 6.70 min, 95%.

Example 86: 7-(2-Methyl-3-(1H-1,2,4-triazol-1-yl)benzyloxy)-3H-[1,2,3]triazolo[4,5-b]pyridin-5-amine

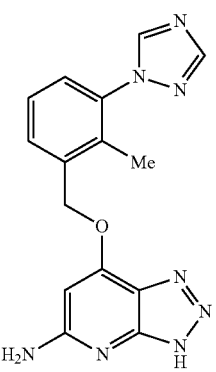 [SMILES: Cc1c(COc2cc(N)nc3[nH]nnc23)cccc1-n1cncn1]

Example 86 was synthesized using a method analogous to that used to make Example 83 from Example 60 and 1H-1,2,4-triazole. MS(ESI) m/z 323.2 (M+H). ¹H NMR (400 MHz, CD₃OD) δ 8.83-8.70 (m, 1H), 8.26 (br. s., 1H), 7.76 (dd, J=6.0, 3.3 Hz, 1H), 7.52-7.44 (m, 2H), 6.48 (s, 1H), 5.64 (s, 2H), 2.22 (s, 3H). Analytical HPLC Method A: 3.67 min, 93%; Method B: 4.03 min, 99%. The compound was isolated as a TFA salt.

Example 87: 7-(2-Methoxy-5-(3-methyl-1H-1,2,4-triazol-1-yl)benzyloxy)-3H-[1,2,3]triazolo[4,5-b]pyridin-5-amine

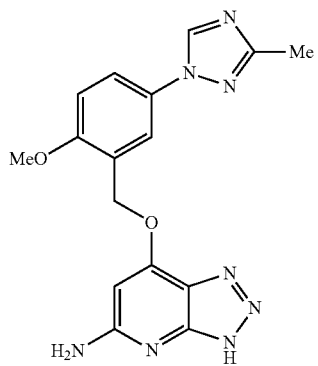 [SMILES: COc1ccc(-n2cnc(C)n2)cc1COc1cc(N)nc2[nH]nnc12]

Example 87 was synthesized using a method analogous to that used to make Example 83 from Example 58 and 3-methyl-1H-1,2,4-triazole. MS(ESI) m/z 353.3 (M+H). ¹H NMR (400 MHz, CD₃OD) δ 8.86 (s, 1H), 7.89 (d, J=2.7 Hz, 1H), 7.75 (dd, J=8.8, 2.7 Hz, 1H), 7.21 (d, J=8.8 Hz, 1H), 6.37 (s, 1H), 5.50 (s, 2H), 3.93 (s, 3H), 2.40 (s, 3H) Analytical HPLC Method A: 4.78 min, 94%; Method B: 5.59 min, 94%. The compound was isolated as a TFA salt.

Example 88: 7-(5-Chloro-2-ethoxybenzyloxy)-3H-[1,2,3]triazolo[4,5-b]pyridin-5-amine

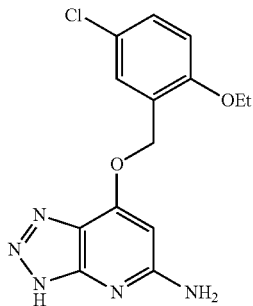 [SMILES: CCOc1ccc(Cl)cc1COc1cc(N)nc2[nH]nnc12]

Example 88 was synthesized from Intermediate 4 and (5-chloro-2-cyclopentyloxy)phenyl)methanol using General Route 3. MS(ESI) m/z 320 (M+H). ¹H NMR (500 MHz, CD₃OD) δ 7.54 (d, J=2.5 Hz, 1H), 7.37 (dd, J=8.8, 2.8 Hz, 1H), 7.06 (d, J=8.8 Hz, 1H), 6.42 (s, 1H), 5.48 (s, 2H), 4.14 (q, J=7.1 Hz, 2H), 1.39 (t, J=7.0 Hz, 3H). Analytical HPLC Method A: 5.66 min, 98%; Method B: 6.05 min, 98%. The compound was isolated as a TFA salt.

Example 89: 7-(5-Chloro-2-(((tetrahydrofuran-2-yl)methoxy)benzyloxy)-3H-[1,2,3]triazolo[4,5-b]pyridin-5-amine

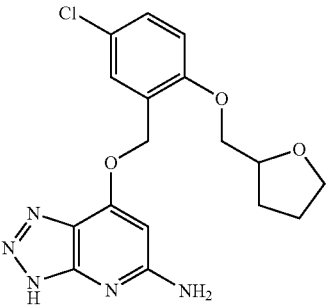 [SMILES: Nc1cc(OCc2cc(Cl)ccc2OCC2CCCO2)c2nn[nH]c2n1]

Example 89 was synthesized from Intermediate 4 and (5-chloro-2-((tetrahydrofuran-2-yl)methoxy)phenyl)methanol using General Route 3. MS(ESI) m/z 376 (M+H). ¹H NMR (500 MHz, CD₃OD) δ 7.55 (d, J=2.5 Hz, 1H), 7.38 (dd, J=8.8, 2.5 Hz, 1H), 7.09 (d, J=8.8 Hz, 1H), 6.47 (s, 1H), 5.50 (s, 2H), 4.32-4.23 (m, 1H), 4.14 (dd, J=10.2, 3.3 Hz, 1H), 4.06 (dd, J=10.2, 6.3 Hz, 1H), 3.87 (m, 1H), 3.83-3.76 (m, 1H), 2.12-2.01 (m, 1H), 1.99-1.88 (m, 2H), 1.87-1.75 (m, 1H). Analytical HPLC Method A: 5.51 min, 98%; Method B: 5.98 min, 98%. The compound was isolated as a TFA salt.

Example 90: 7-((4-Phenylcyclohexyl)methoxy)-3H-[1,2,3]triazolo[4,5-b]pyridin-5-amine

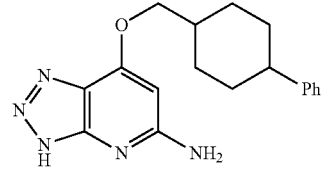 [SMILES: Nc1cc(OCC2CCC(c3ccccc3)CC2)c2nn[nH]c2n1]

Example 90 was synthesized from Intermediate 4 and (4-phenylcyclohexyl)methanol using General Route 3. MS(ESI) m/z 324 (M+H). ¹H NMR (500 MHz, CD₃OD) δ ¹H NMR (500 MHz, CD₃OD) δ 7.34-7.12 (m, 5H), 6.31 (s, 1H), 4.28 (d, J=6.3 Hz, 2H), 2.64-2.53 (m, 1H), 2.17-1.94 (m, 5H), 1.70-1.33 (m, 4H). Analytical HPLC Method A: 6.56 min, 99%; Method B: 6.97 min, 99%. The compound was isolated as a TFA salt.

Example 91: 7-((3'-Fluorobiphenyl-3-yl)methoxy)-3H-[1,2,3]triazolo[4,5-b]pyridin-5-amine

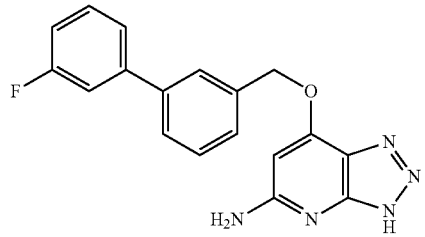 [SMILES: Nc1cc(OCc2cccc(-c3cccc(F)c3)c2)c2nn[nH]c2n1]

A mixture of Example 148 (20 mg, 0.062 mmol), 3-fluorophenylboronic acid (17 mg, 0.13 mmol), PdCl$_2$(dppf) (14 mg, 0.019 mmol) and tripotassium phosphate (40 mg, 0.19 mmol) in DME (2.0 mL) and water (0.20 mL) was purged with argon and subjected to μwave irradiation for 30 min at 110° C. The reaction mixture was filtered and the residue was washed with methanol several times. The filtrate was concentrated and purified by preparatory HPLC to yield Example 91 (2.5 mg, 6.9 μmol, 11% yield) as a white solid. MS(ESI) m/z 336 (M+H). $^1$H NMR (500 MHz, CD$_3$OD) δ 7.85-7.78 (m, 1H), 7.72-7.63 (m, 1H), 7.55 (s, 4H), 7.43-7.37 (m, 1H), 7.17-7.04 (m, 1H), 6.42-6.28 (m, 1H), 5.54 (s, 2H). Analytical HPLC Method A: 6.28 min, 93%; Method B: 7.04 min, 94%.

Example 92: 3'-((5-Amino-3H-[1,2,3]triazolo[4,5-b]pyridin-7-yloxy)methyl)biphenyl-3-carbonitrile

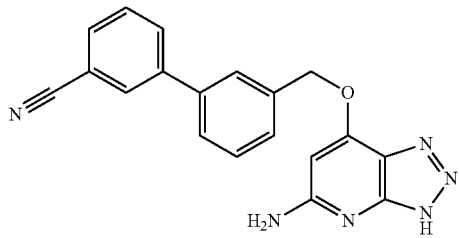 [SMILES: N#Cc1cccc(-c2cccc(COc3cc(N)nc4[nH]nnc34)c2)c1]

Example 92 was synthesized from Example 148 and 3-cyanophenylboronic acid using an analogous route to the procedures used in Example 91. MS(ESI) m/z 343 (M+H). $^1$H NMR (500 MHz, CD$_3$OD) δ 8.09-7.94 (m, 2H), 7.85 (s, 1H), 7.77-7.70 (m, 2H), 7.69-7.52 (m, 3H), 6.40 (s, 1H), 5.57 (s, 2H). Analytical HPLC Method A: 5.85 min, 96%; Method B: 6.54 min, 96%.

Example 93: 7-((2'-Chlorobiphenyl-3-yl)methoxy)-3H-[1,2,3]triazolo[4,5-b]pyridin-5-amine

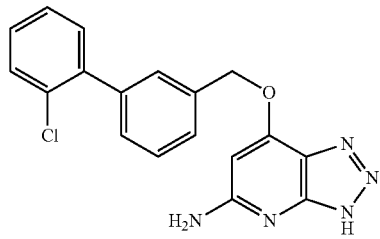 [SMILES: Nc1cc(OCc2cccc(-c3ccccc3Cl)c2)c2nn[nH]c2n1]

Example 93 was synthesized from Example 148 and 2-chlorophenylboronic acid using an analogous route to the procedures used in Example 91. MS(ESI) m/z 352 (M+H). $^1$H NMR (500 MHz, CD$_3$OD) δ 7.65-7.43 (m, 5H), 7.42-7.31 (m, 3H), 6.37 (s, 1H), 5.54 (s, 2H). Analytical HPLC Method A: 6.52 min, 96%; Method B: 7.35 min, 96%.

Example 95: 7-((4'-Fluorobiphenyl-3-yl)methoxy)-3H-[1,2,3]triazolo[4,5-b]pyridin-5-amine

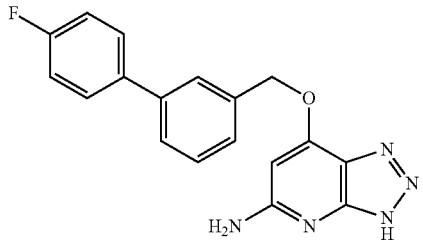 [SMILES: Nc1cc(OCc2cccc(-c3ccc(F)cc3)c2)c2nn[nH]c2n1]

Example 95 was synthesized from Example 148 and 4-fluorophenylboronic acid using an analogous route to the procedures used in Example 91. MS(ESI) m/z 336 (M+H). $^1$H NMR (500 MHz, CD$_3$OD) δ 7.77 (s, 1H), 7.71-7.61 (m, 3H), 7.52 (d, J=5.2 Hz, 2H), 7.23-7.15 (m, 2H), 6.38 (s, 1H), 5.54 (s, 2H). Analytical HPLC Method A: 6.36 min, 97%; Method B: 7.12 min, 94%.

Example 96: 7-((2'-Fluorobiphenyl-3-yl)methoxy)-3H-[1,2,3]triazolo[4,5-b]pyridin-5-amine

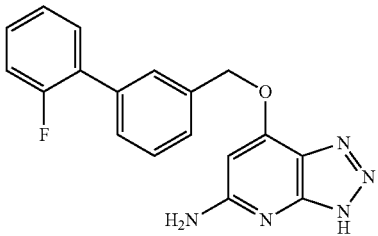 [SMILES: Nc1cc(OCc2cccc(-c3ccccc3F)c2)c2nn[nH]c2n1]

Example 96 was synthesized from Example 148 and 2-fluorophenylboronic acid using an analogous route to the procedures used in Example 91. MS(ESI) m/z 336 (M+H). $^1$H NMR (500 MHz, CD$_3$OD) δ 7.77-7.68 (m, 1H), 7.64-7.47 (m, 4H), 7.43-7.33 (m, 1H), 7.31-7.24 (m, 1H), 7.23-7.14 (m, 1H), 6.38 (s, 1H), 5.54 (s, 2H). Analytical HPLC Method A: 6.21 min, 95%; Method B: 6.98 min, 93%.

Example 97: 7-((4'-Chlorobiphenyl-3-yl)methoxy)-3H-[1,2,3]triazolo[4,5-b]pyridin-5-amine

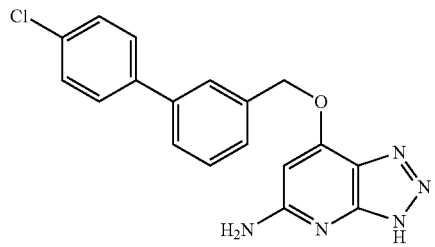 [SMILES: Nc1cc(OCc2cccc(-c3ccc(Cl)cc3)c2)c2nn[nH]c2n1]

Example 97 was synthesized from Example 148 and 4-chlorophenylboronic acid using an analogous route to the procedures used in Example 91. MS(ESI) m/z 352 (M+H). $^1$H NMR (500 MHz, CD$_3$OD) δ 7.84-7.77 (m, 1H), 7.71-7.62 (m, 3H), 7.58-7.51 (m, 2H), 7.49-7.41 (m, 2H), 6.37 (s, 1H), 5.54 (s, 2H). Analytical HPLC Method A: 6.87 min, 95%; Method B: 7.69 min, 92%.

Example 98: 7-((4'-(1H-Pyrazol-5-yl)biphenyl-3-yl)methoxy)-3H-[1,2,3]triazolo[4,5-b]pyridin-5-amine

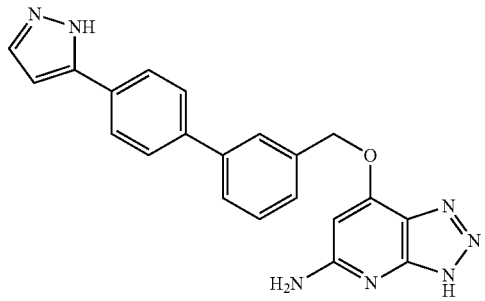 [SMILES: Nc1cc(OCc2cccc(-c3ccc(-c4ccn[nH]4)cc3)c2)c2nn[nH]c2n1]

Example 98 was synthesized from Example 148 and 4-(1H-pyrazol-5-yl)phenylboronic acid using an analogous route to the procedures used in Example 91. MS(ESI) m/z 384 (M+H). $^1$H NMR (500 MHz, CD$_3$OD) δ 8.26 (dd, J=2.5, 0.6 Hz, 1H), 7.91-7.67 (m, 6H), 7.63-7.48 (m, 2H), 6.55 (dd, J=2.5, 1.9 Hz, 1H), 6.40 (s, 1H), 5.56 (s, 2H). Analytical HPLC Method A: 6.05 min, 96%; Method B: 6.73 min, 94%.

Example 99: 7-((4'-(4-Methylpiperazin-1-yl)biphenyl-3-yl)methoxy)-3H-[1,2,3]triazolo[4,5-b]pyridin-5-amine

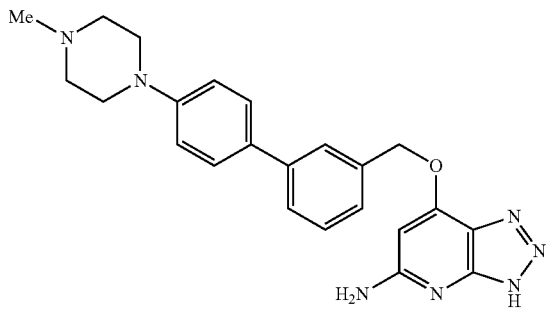 [SMILES: CN1CCN(c2ccc(-c3cccc(COc4cc(N)nc5[nH]nnc45)c3)cc2)CC1]

Example 99 was synthesized from Example 148 and 1-methyl-4-(4-(4,4,5,5-tetramethyl-1,3,2-dioxaborolan-2-yl)phenyl)piperazine using an analogous route to the procedures used in Example 91. MS(ESI) m/z 416 (M+H). $^1$H NMR (500 MHz, CD$_3$OD) δ 7.76 (s, 1H), 7.69-7.57 (m, 3H), 7.55-7.43 (m, 2H), 7.12 (d, J=8.8 Hz, 2H), 6.37 (s, 1H), 5.52 (s, 2H), 4.06-3.81 (m, 2H), 3.75-3.56 (m, 2H), 3.38-3.23 (m, 2H), 3.23-3.04 (m, 2H), 3.00-2.89 (m, 3H). Analytical HPLC Method A: 3.81 min, 85%; Method B: 4.49 min, 82%.

Example 100: N-(3'-((5-Amino-3H-[1,2,3]triazolo[4,5-b]pyridin-7-yloxy)methyl)biphenyl-4-yl)benzamide

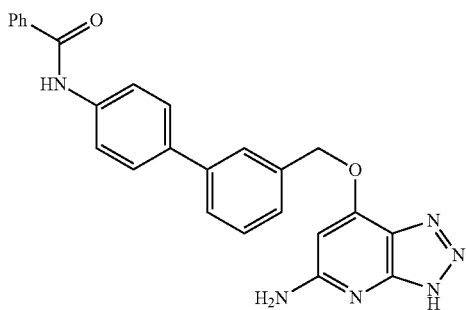 [SMILES: Nc1cc(OCc2cccc(-c3ccc(NC(=O)c4ccccc4)cc3)c2)c2nn[nH]c2n1]

Example 100 was synthesized from Example 148 and 4-benzamidophenylboronic acid using an analogous route to the procedures used in Example 91. MS(ESI) m/z 437 (M+H). $^1$H NMR (500 MHz, CD$_3$OD) δ 7.95 (d, J=7.7 Hz, 2H), 7.87-7.78 (m, 3H), 7.68 (d, J=8.5 Hz, 3H), 7.62-7.43 (m, 5H), 6.40 (s, 1H), 5.56 (s, 2H). Analytical HPLC Method A: 6.39 min, 93%; Method B: 7.14 min, 90%.

Example 101: 3'-((5-Amino-3H-[1,2,3]triazolo[4,5-b]pyridin-7-yloxy)methyl)biphenyl-4-carbonitrile

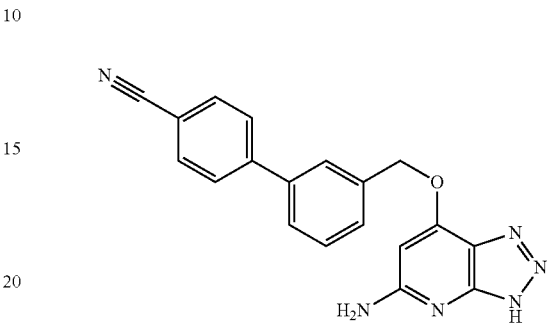

Example 101 was synthesized from Example 148 and 4-cyanophenylboronic acid using an analogous route to the procedures used in Example 91. MS(ESI) m/z 342 (M+H). $^1$H NMR (500 MHz, CD$_3$OD) δ 7.91-7.79 (m, 5H), 7.78-7.70 (m, 1H), 7.65-7.55 (m, 2H), 6.39 (s, 1H), 5.56 (s, 2H). Analytical HPLC Method A: 5.88 min, 92%; Method B: 6.56 min, 84%.

Example 102: 7-((4'-Phenylbiphenyl-3-yl)methoxy)-3H-[1,2,3]triazolo[4,5-b]pyridin-5-amine

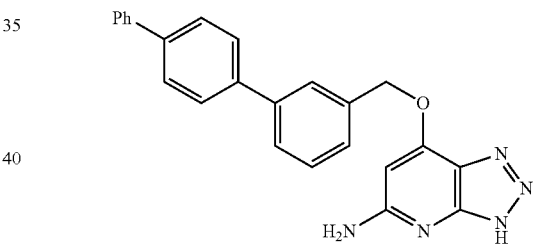

Example 102 was synthesized from Example 148 and biphenyl-4-ylmethylboronic acid using an analogous route to the procedures used in Example 91. MS(ESI) m/z 394 (M+H). $^1$H NMR (500 MHz, CD$_3$OD) δ 7.90-7.84 (m, 1H), 7.74 (d, J=6.3 Hz, 5H), 7.69-7.62 (m, 2H), 7.59-7.50 (m, 2H), 7.49-7.40 (m, 2H), 7.38-7.26 (m, 1H), 6.38 (s, 1H), 5.55 (s, 2H). Analytical HPLC Method A: 7.71 min, 88%; Method B: 8.51 min, 86%.

Example 103: 7-(3-(Pyridin-3-yl)benzyloxy)-3H-[1,2,3]triazolo[4,5-b]pyridin-5-amine

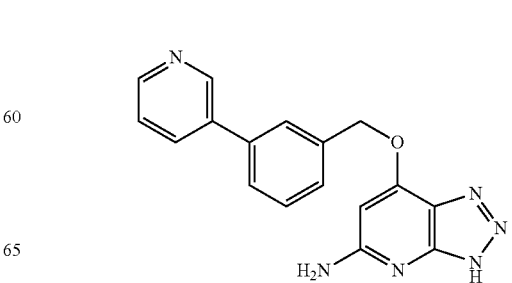

Example 103 was synthesized from Example 148 and pyridin-3-ylboronic acid using an analogous route to the procedures used in Example 91. MS(ESI) m/z 319 (M+H). $^1$H NMR (500 MHz, CD$_3$OD) δ 9.06-8.97 (m, 1H), 8.77-8.66 (m, 1H), 8.60-8.47 (m, 1H), 7.95 (s, 1H), 7.89-7.76 (m, 2H), 7.65 (s, 2H), 6.41 (s, 1H), 5.59 (s, 2H). Analytical HPLC Method A: 2.75 min, 72%; Method B: 3.17 min, 92%.

Example 104: 3'-((5-Amino-3H-[1,2,3]triazolo[4,5-b]pyridin-7-yloxy)methyl)-N-phenylbiphenyl-4-carboxamide

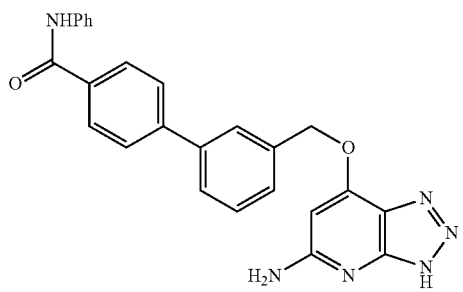

Example 104 was synthesized from Example 148 and 4-(phenylcarbamoyl)phenylboronic acid using an analogous route to the procedures used in Example 91. MS(ESI) m/z 437 (M+H). $^1$H NMR (500 MHz, CD$_3$OD) δ 8.05 (d, J=8.5 Hz, 2H), 7.89 (s, 1H), 7.86-7.66 (m, 5H), 7.62-7.52 (m, 2H), 7.37 (dd, J=8.4, 7.6 Hz, 2H), 7.23-7.11 (m, 1H), 6.41 (s, 1H), 5.58 (s, 2H). Analytical HPLC Method A: 6.51 min, 96%; Method B: 7.23 min, 93%.

Example 105: 7-((3'-Fluoro-4'-methoxybiphenyl-3-yl)methoxy)-3H-[1,2,3]triazolo[4,5-b]pyridin-5-amine

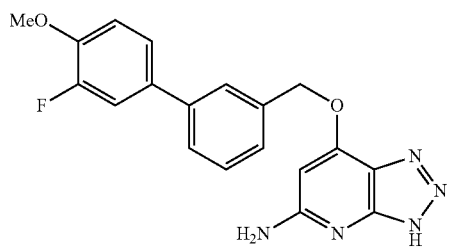 [SMILES: COc1ccc(-c2cccc(COc3cc(N)nc4[nH]nnc34)c2)cc1F]

Example 105 was synthesized from Example 148 and 2-(3-fluoro-4-methoxyphenyl)-4,4,5,5-tetramethyl-1,3,2-dioxaborolane using an analogous route to the procedures used in Example 91. MS(ESI) m/z 366 (M+H). $^1$H NMR (500 MHz, CD$_3$OD) δ 7.75 (s, 1H), 7.68-7.59 (m, 1H), 7.56-7.34 (m, 4H), 7.23-7.06 (m, 1H), 6.39 (s, 1H), 5.53 (s, 2H), 3.91 (s, 3H). Analytical HPLC Method A: 6.41 min, 92%; Method B: 7.03 min, 84%.

Example 106: 7-(4-Bromobenzyloxy)-3H-[1,2,3]triazolo[4,5-b]pyridin-5-amine

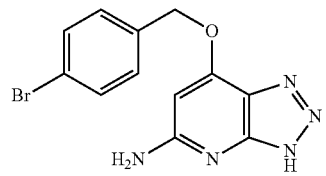 [SMILES: Nc1cc(OCc2ccc(Br)cc2)c2nn[nH]c2n1]

Example 106 was synthesized from (4-bromophenyl)methanol and Intermediate 1 using General Route 2. MS(ESI) m/z 320/322 (M+H). $^1$H NMR (500 MHz, CD$_3$OD) δ 7.63 (d, J=8.4 Hz, 2H), 7.49 (d, J=8.4 Hz, 2H), 6.36 (s, 1H), 5.47 (s, 2H). Analytical HPLC Method A: 5.48 min, 89%; Method B: 6.03 min, 92%.

Example 107: 4'-((5-Amino-3H-[1,2,3]triazolo[4,5-b]pyridin-7-yloxy)methyl)-N-ethyl-3-fluoro-N-methylbiphenyl-4-carboxamide

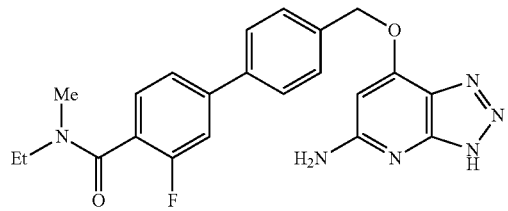 [SMILES: CCN(C)C(=O)c1ccc(-c2ccc(COc3cc(N)nc4[nH]nnc34)cc2)cc1F]

Example 107 was synthesized from Example 106 and 4-(ethyl(methyl)carbamoyl)-3-fluorophenylboronic acid using an analogous route to the procedures used in Example 91. MS(ESI) m/z 421 (M+H). $^1$H NMR (500 MHz, CD$_3$OD) δ 7.80 (m, 2H), 7.69 (m, 5H), 6.45 (s, 1H), 5.59 (s, 2H), 3.76-3.57 (m, 1H), 3.19-2.95 (m, 4H), 1.49-1.05 (m, 3H). Analytical HPLC Method A: 5.53 min, 90%; Method B: 6.0 min, 93%.

Example 108: 7-((3'-Fluoro-4'-methoxybiphenyl-4-yl)methoxy)-3H-[1,2,3]triazolo[4,5-b]pyridin-5-amine

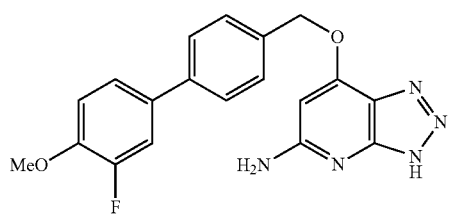 [SMILES: COc1ccc(-c2ccc(COc3cc(N)nc4[nH]nnc34)cc2)cc1F]

Example 108 was synthesized from Example 106 and 3-fluoro-4-methoxyphenylboronic acid using an analogous route to the procedures used in Example 91. MS(ESI) m/z 366 (M+H). $^1$H NMR (500 MHz, CD$_3$OD) δ 7.72-7.67 (m, 2H), 7.65-7.58 (m, 2H), 7.49-7.33 (m, 2H), 7.27-7.12 (m, 1H), 6.36 (s, 1H), 5.51 (s, 2H), 3.94 (s, 3H). Analytical HPLC Method A: 6.38 min, 82%; Method B: 7.0 min, 87%.

Example 109: 7-((2'-Chlorobiphenyl-4-yl)methoxy)-3H-[1,2,3]triazolo[4,5-b]pyridin-5-amine

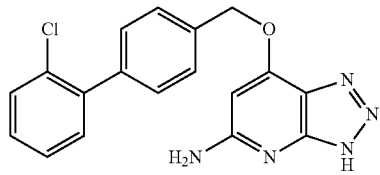 [SMILES: Nc1cc(OCc2ccc(-c3ccccc3Cl)cc2)c2nn[nH]c2n1]

Example 109 was synthesized from Example 106 and 2-chlorophenylboronic acid using an analogous route to the procedures used in Example 91. MS(ESI) m/z 352 (M+H). $^1$H NMR (500 MHz, CD$_3$OD) δ 7.65 (d, J=8.5 Hz, 2H), 7.53-7.48 (m, 3H), 7.46-7.31 (m, 3H), 6.42 (s, 1H), 5.57 (s, 2H). Analytical HPLC Method A: 6.59 min, 93%; Method B: 7.38 min, 94%.

Example 110: 4'-((5-Amino-3H-[1,2,3]triazolo[4,5-b]pyridin-7-yloxy)methyl)biphenyl-3-carbonitrile

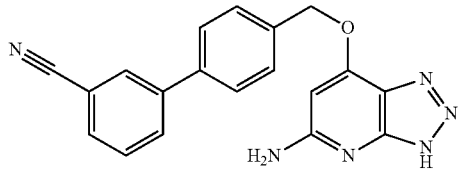 [SMILES: N#Cc1cccc(-c2ccc(COc3cc(N)nc4[nH]nnc34)cc2)c1]

Example 110 was synthesized from Example 106 and 3-cyanophenylboronic acid using an analogous route to the procedures used in Example 91. MS(ESI) m/z 343 (M+H). $^1$H NMR (500 MHz, CD$_3$OD) δ 8.08-8.04 (m, 1H), 8.01-7.97 (m, 1H), 7.84-7.73 (m, 3H), 7.70 (d, J=7.7 Hz, 3H), 6.40 (s, 1H), 5.57 (s, 2H). Analytical HPLC Method A: 5.88 min, 93%; Method B: 6.52 min, 92%.

Example 111: 7-((3'-Chlorobiphenyl-4-yl)methoxy)-3H-[1,2,3]triazolo[4,5-b]pyridin-5-amine

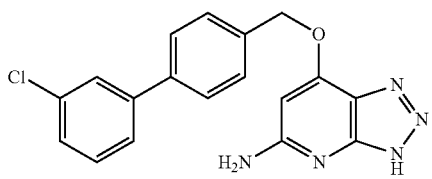 [SMILES: Nc1cc(OCc2ccc(-c3cccc(Cl)c3)cc2)c2nn[nH]c2n1]

Example 111 was synthesized from Example 106 and 3-chlorophenylboronic acid using an analogous route to the procedures used in Example 91. MS(ESI) m/z 351 (M+H). $^1$H NMR (500 MHz, CD$_3$OD) δ 7.76-7.71 (m, 2H), 7.70-7.56 (m, 4H), 7.51-7.34 (m, 2H), 6.41 (s, 1H), 5.56 (s, 2H). Analytical HPLC Method A: 6.88 min, 93%; Method B: 7.63 min, 95%.

Example 112: 7-((3'-Methoxybiphenyl-4-yl)methoxy)-3H-[1,2,3]triazolo[4,5-b]pyridin-5-amine

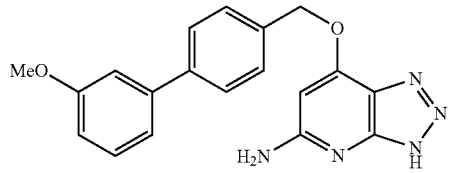 [SMILES: COc1cccc(-c2ccc(COc3cc(N)nc4[nH]nnc34)cc2)c1]

Example 112 was synthesized from Example 106 and 3-methoxyphenylboronic acid using an analogous route to the procedures used in Example 91. MS(ESI) m/z 348 (M+H). $^1$H NMR (500 MHz, CD$_3$OD) δ 7.69 (d, J=8.3 Hz, 2H), 7.65-7.54 (m, 2H), 7.36 (s, 1H), 7.25-7.11 (m, 2H), 6.99-6.89 (m, 1H), 6.38 (s, 1H), 5.52 (s, 2H), 3.85 (s, 3H). Analytical HPLC Method A: 6.25 min, 91%; Method B: 6.95 min, 91%.

Example 113: 7-((3'-Methoxybiphenyl-3-yl)methoxy)-3H-[1,2,3]triazolo[4,5-b]pyridin-5-amine

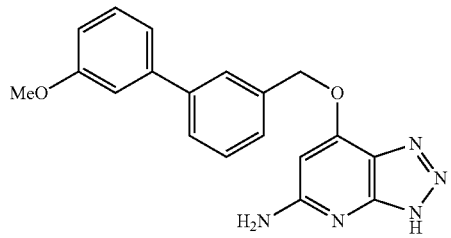 [SMILES: COc1cccc(-c2cccc(COc3cc(N)nc4[nH]nnc34)c2)c1]

Example 113 was synthesized from Example 148 and 3-methoxyphenylboronic acid using an analogous route to the procedures used in Example 91. MS(ESI) m/z 348 (M+H). $^1$H NMR (500 MHz, CD$_3$OD) δ 7.78 (s, 1H), 7.70-7.63 (m, 1H), 7.58-7.48 (m, 2H), 7.35 (d, J=8.0 Hz, 1H), 7.17 (d, J=2.2 Hz, 2H), 6.98-6.82 (m, 1H), 6.39 (s, 1H), 5.55 (s, 2H), 3.85 (s, 3H). Analytical HPLC Method A: 6.17 min, 95%; Method B: 6.89 min, 94%.

Example 114: 7-((2'-Fluorobiphenyl-4-yl)methoxy)-3H-[1,2,3]triazolo[4,5-b]pyridin-5-amine

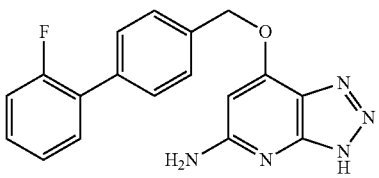 [SMILES: Nc1cc(OCc2ccc(-c3ccccc3F)cc2)c2nn[nH]c2n1]

Example 114 was synthesized from Example 106 and 2-fluorophenylboronic acid using an analogous route to the procedures used in Example 91. MS(ESI) m/z 336 (M+H). $^1$H NMR (500 MHz, CD$_3$OD) δ 7.63 (m, 4H), 7.50 (d, J=1.9 Hz, 1H), 7.43-7.35 (m, 1H), 7.26 (d, J=1.1 Hz, 1H), 7.23-7.17 (m, 1H), 6.39 (s, 1H), 5.54 (s, 2H). Analytical HPLC Method A: 6.18 min, 95%; Method B: 6.98 min, 96%.

Example 115: 7-((3'-Fluoro-2'-methoxybiphenyl-3-yl)methoxy)-3H-[1,2,3]triazolo[4,5-b]pyridin-5-amine

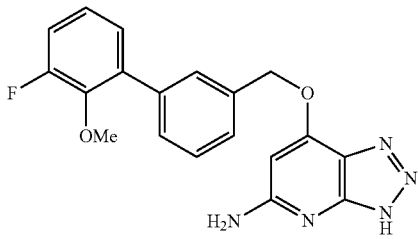 [SMILES: COc1c(F)cccc1-c1cccc(COc2cc(N)nc3[nH]nnc23)c1]

Example 115 was synthesized from Example 148 and 3-fluoro-2-methoxyphenylboronic acid using an analogous route to the procedures used in Example 91. MS(ESI) m/z 366 (M+H). $^1$H NMR (500 MHz, CD$_3$OD) δ 7.78-7.66 (m, 1H), 7.62-7.46 (m, 3H), 7.27-6.99 (m, 3H), 6.38 (s, 1H), 5.55 (s, 2H), 3.67 (d, J=1.4 Hz, 3H). Analytical HPLC Method A: 6.27 min, 94%; Method B: 7.13 min, 94%.

Example 116: 3'-((5-Amino-3H-[1,2,3]triazolo[4,5-b]pyridin-7-yloxy)methyl)-N-ethyl-3-fluoro-N-methylbiphenyl-4-carboxamide

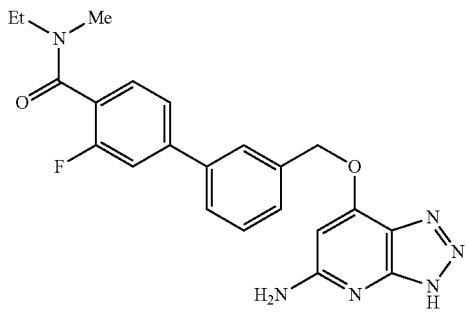 [SMILES: CCN(C)C(=O)c1ccc(-c2cccc(COc3cc(N)nc4[nH]nnc34)c2)cc1F]

Example 116 was synthesized from Example 148 and 4-(ethyl(methyl)carbamoyl)-3-fluorophenylboronic acid using an analogous route to the procedures used in Example 91. MS(ESI) m/z 421 (M+H). Analytical HPLC Method A: 5.35 min, 96%; Method B: 6.04 min, 95%.

Example 117: 7-((3',5'-Difluoro-2'-methoxybiphenyl-4-yl)methoxy)-3H-[1,2,3]triazolo[4,5-b]pyridin-5-amine

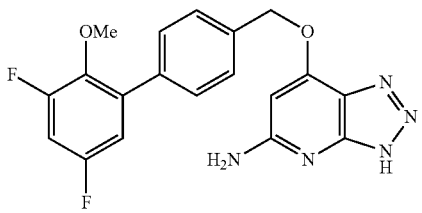 [SMILES: COc1c(F)cc(F)cc1-c1ccc(COc2cc(N)nc3[nH]nnc23)cc1]

Example 117 was synthesized from Example 106 and 3,5-difluoro-2-methoxyphenylboronic acid using an analogous route to the procedures used in Example 91. MS(ESI) m/z 384 (M+H). $^1$H NMR (500 MHz, CD$_3$OD) δ 7.66-7.59 (m, 4H), 7.04 (ddd, J=11.2, 8.3, 3.0 Hz, 1H), 6.98 (ddd, J=9.0, 3.1, 1.9 Hz, 1H), 6.38 (s, 1H), 5.54 (s, 2H), 3.65 (d, J=1.1 Hz, 3H). Analytical HPLC Method A: 6.59 min, 95%; Method B: 7.36 min, 96%.

Example 118: 7-((2'-Chloro-6'-methoxybiphenyl-4-yl)methoxy)-3H-[1,2,3]triazolo[4,5-b]pyridin-5-amine

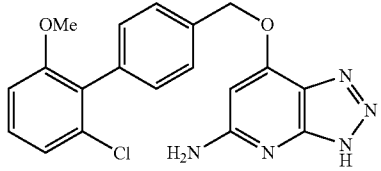 [SMILES: COc1cccc(Cl)c1-c1ccc(COc2cc(N)nc3[nH]nnc23)cc1]

Example 118 was synthesized from Example 106 and 2-chloro-6-methoxyphenylboronic acid using an analogous route to the procedures used in Example 91. MS(ESI) m/z 384 (M+H). Analytical HPLC Method A: 6.44 min, 95%; Method B: 7.34 min, 94%.

Example 119: 7-((4'-(Trifluoromethoxy)biphenyl-4-yl)methoxy)-3H-[1,2,3]triazolo[4,5-b]pyridin-5-amine

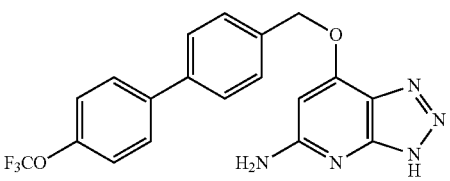 [SMILES: Nc1cc(OCc2ccc(-c3ccc(OC(F)(F)F)cc3)cc2)c2nn[nH]c2n1]

Example 119 was synthesized from Example 106 and 4-(trifluoromethoxy)phenylboronic acid using an analogous route to the procedures used in Example 91. MS(ESI) m/z 402 (M+H). $^1$H NMR (500 MHz, CD$_3$OD) δ 7.72 (d, J=10.7 Hz, 4H), 7.67-7.58 (m, 2H), 7.41-7.33 (m, 2H), 6.37 (s, 1H), 5.53 (s, 2H). Analytical HPLC Method A: 7.32 min, 94%; Method B: 7.94 min, 95%.

Example 120: 7-((3'-(Trifluoromethyl)biphenyl-4-yl)methoxy)-3H-[1,2,3]triazolo[4,5-b]pyridin-5-amine

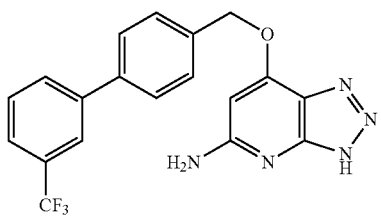 [SMILES: Nc1cc(OCc2ccc(-c3cccc(C(F)(F)F)c3)cc2)c2nn[nH]c2n1]

Example 120 was synthesized from Example 106 and 3-(trifluoromethyl)phenylboronic acid using an analogous route to the procedures used in Example 91. MS(ESI) m/z 386 (M+H). $^1$H NMR (500 MHz, CD$_3$OD) δ 7.97-7.88 (m, 2H), 7.75 (d, J=8.3 Hz, 2H), 7.71-7.62 (m, 4H), 6.37 (s, 1H), 5.55 (s, 2H). Analytical HPLC Method A: 7.05 min, 96%; Method B: 7.68 min, 98%.

Example 121: 7-(3-(5-Fluoropyridin-3-yl)benzyloxy)-3H-[1,2,3]triazolo[4,5-b]pyridin-5-amine

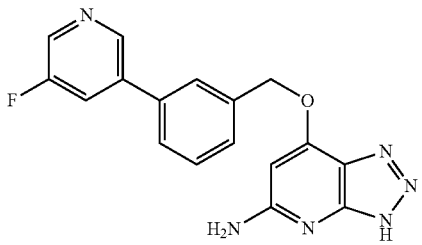 [SMILES: Nc1cc(OCc2cccc(-c3cncc(F)c3)c2)c2nn[nH]c2n1]

Example 121 was synthesized from Example 148 and 5-fluoropyridin-3-ylboronic acid using an analogous route to the procedures used in Example 91. MS(ESI) m/z 337 (M+H). $^1$H NMR (500 MHz, CD$_3$OD) δ 8.73 (s, 1H), 8.49 (s, 1H), 8.02-7.94 (m, 1H), 7.90 (s, 1H), 7.79-7.72 (m, 1H), 7.67-7.56 (m, 2H), 6.42 (s, 1H), 5.59 (s, 2H). Analytical HPLC Method A: 4.55 min, 95%; Method B: 5.12 min, 89%.

Example 122: 7-((4'-Methoxybiphenyl-4-yl)methoxy)-3H-[1,2,3]triazolo[4,5-b]pyridin-5-amine

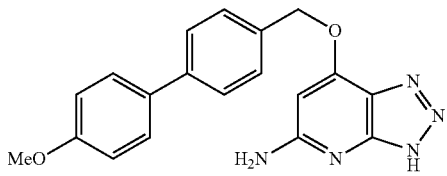 [SMILES: COc1ccc(-c2ccc(COc3cc(N)nc4[nH]nnc34)cc2)cc1]

Example 122 was synthesized from Example 106 and 4-methoxyphenylboronic acid using an analogous route to the procedures used in Example 91. MS(ESI) m/z 348 (M+H). $^1$H NMR (500 MHz, CD$_3$OD) δ 7.70-7.63 (m, 2H), 7.61-7.51 (m, 4H), 7.06-6.94 (m, 2H), 6.34 (s, 1H), 5.49 (s, 2H), 3.83 (s, 4H). Analytical HPLC Method A: 6.05 min, 96%; Method B: 6.85 min, 92%.

Example 123: 7-((2'-Methoxybiphenyl-4-yl)methoxy)-3H-[1,2,3]triazolo[4,5-b]pyridin-5-amine

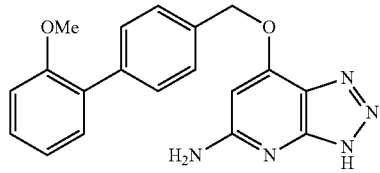 [SMILES: COc1ccccc1-c1ccc(COc2cc(N)nc3[nH]nnc23)cc1]

Example 123 was synthesized from Example 106 and 2-methoxyphenylboronic acid using an analogous route to the procedures used in Example 91. MS(ESI) m/z 348 (M+H). $^1$H NMR (500 MHz, CD$_3$OD) δ 7.58-7.53 (m, 4H), 7.41-7.24 (m, 2H), 7.15-6.91 (m, 2H), 6.39 (s, 1H), 5.52 (s, 2H), 3.79 (s, 3H). Analytical HPLC Method A: 6.15 min, 98%; Method B: 6.98 min, 98%.

Example 124: 7-((2'-Chloro-6'-methoxybiphenyl-3-yl)methoxy)-3H-[1,2,3]triazolo[4,5-b]pyridin-5-amine

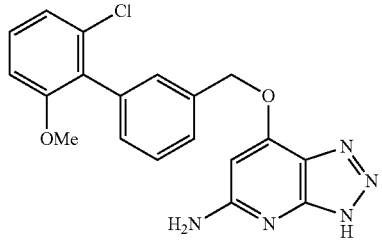 [SMILES: COc1cccc(Cl)c1-c1cccc(COc2cc(N)nc3[nH]nnc23)c1]

Example 124 was synthesized from Example 148 and 2-chloro-6-methoxyphenylboronic acid using an analogous route to the procedures used in Example 91. MS(ESI) m/z 382 (M+H). $^1$H NMR (500 MHz, CD$_3$OD) δ 7.62-7.47 (m, 2H), 7.43-7.40 (m, 1H), 7.33 (s, 2H), 7.12 (s, 1H), 7.08-7.02 (m, 1H), 6.44 (s, 1H), 5.57 (s, 2H), 3.73 (s, 3H). Analytical HPLC Method A: 6.41 min, 92%; Method B: 7.17 min, 95%.

Example 125: 7-(2,2,2-Trifluoro-1-phenylethoxy)-3H-[1,2,3]triazolo[4,5-d]pyrimidin-5-amine

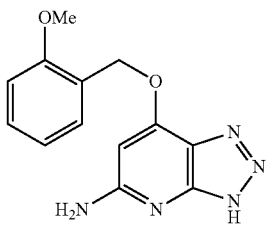 [SMILES: COc1ccccc1COc1cc(N)nc2[nH]nnc12]

Example 125 was synthesized from (2-methoxyphenyl)methanol and Intermediate 1 using General Route 2. MS(ESI) m/z 272 (M+H). $^1$H NMR (500 MHz, CD$_3$OD) δ 7.55-7.35 (m, 2H), 7.12-7.05 (m, 1H), 7.02-6.97 (m, 1H), 6.40 (s, 1H), 5.48 (s, 2H), 3.88 (s, 3H). Analytical HPLC Method A: 4.90 min, 83%; Method B: 5.42 min, 78%.

Example 126: 7-(2,2,2-Trifluoro-1-phenylethoxy)-3H-[1,2,3]triazolo[4,5-b]pyridin-5-amine

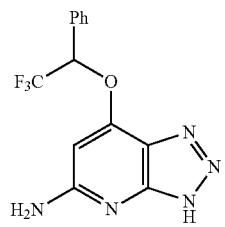 [SMILES: Nc1cc(OC(c2ccccc2)C(F)(F)F)c2nn[nH]c2n1]

126A: (E)-3-((4-Chlorophenyl)diazenyl)-4-(2,2,2-trifluoro-1-phenylethoxy)pyridine-2,6-diamine

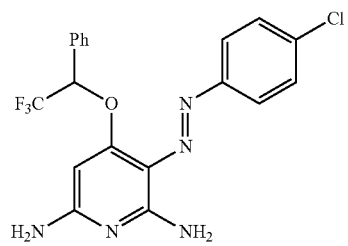 [SMILES: Nc1cc(OC(c2ccccc2)C(F)(F)F)c(/N=N/c2ccc(Cl)cc2)c(N)n1]

Reference: *J. Org. Chem.*, 73:9326-9333 (2008). A mixture of Intermediate 1 (500 mg, 1.5 mmol), 2,2,2-trifluoro-1-phenylethanol (810 mg, 4.6 mmol), Pd$_2$(dba)$_3$ (280 mg, 0.31 mmol) BINAP (380 mg, 0.61 mmol) and potassium tert-butoxide (520 mg, 4.6 mmol) in toluene (20 mL) was purged with argon for 10 min, then heated at 70° C. for 3 days. The reaction mixture was extracted with EtOAc, washed with brine, dried over MgSO$_4$ and concentrated. The residue was purified by column chromatography (MeOH/DCM: 0-20%) to yield 126A as a reddish solid. MS(ESI) m/z 422.0 (M+H).

Example 126

Example 126 was synthesized from 126A using the procedures from Example 12. MS(ESI) m/z 272 (M+H). $^1$H NMR (500 MHz, CD$_3$OD) δ 7.68-7.57 (m, 2H), 7.47 (m, 3H), 6.57-6.45 (m, 1H), 6.22-6.11 (m, 1H). Analytical HPLC Method A: 6.14 min, 86%; Method B: 6.48 min, 88%.

Example 127: 7-((3-Methoxybenzyl)oxy)-3H-[1,2,3]triazolo[4,5-b]pyridin-5-amine

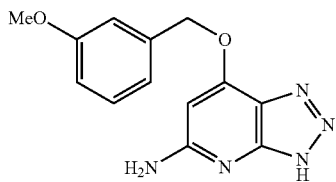 [SMILES: COc1cccc(COc2cc(N)nc3[nH]nnc23)c1]

Example 127 was synthesized from (3-methoxyphenyl)methanol and Intermediate 1 using General Route 2. MS(ESI) m/z 272 (M+H). $^1$H NMR (500 MHz, CD$_3$OD) δ 7.35 (s, 1H), 7.09 (m, 2H), 7.02-6.92 (m, 1H), 6.36 (s, 1H), 5.45 (s, 2H), 3.82 (s, 3H). Analytical HPLC Method A: 4.82 min, 94%; Method B: 5.62 min, 91%.

Example 128: 7-((2-Ethoxybenzyl)oxy)-3H-[1,2,3]triazolo[4,5-b]pyridin-5-amine

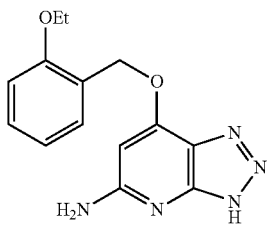 [SMILES: CCOc1ccccc1COc1cc(N)nc2[nH]nnc12]

Example 128 was synthesized from (2-ethoxyphenyl)methanol and Intermediate 1 using General Route 2. MS(ESI) m/z 286 (M+H). $^1$H NMR (500 MHz, CD$_3$OD) δ 7.57-7.36 (m, 2H), 7.15-6.97 (m, 2H), 6.42 (s, 1H), 5.51 (s, 2H), 4.14 (q, J=7.1 Hz, 2H), 1.38 (t, J=7.1 Hz, 3H). Analytical HPLC Method A: 5.72 min, 88%; Method B: 6.59 min, 88%.

Example 129: 7-((2,3-Difluorobenzyl)oxy)-3H-[1,2,3]triazolo[4,5-b]pyridin-5-amine

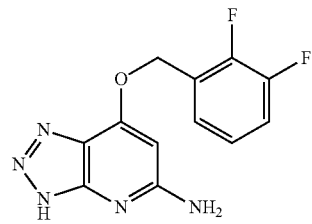 [SMILES: Nc1cc(OCc2cccc(F)c2F)c2nn[nH]c2n1]

Example 129 was synthesized from (2,3-difluorophenyl)methanol and Intermediate 1 using General Route 2. MS(ESI) m/z 278 (M+H). $^1$H NMR (500 MHz, CD$_3$OD) δ 7.48-7.43 (m, 1H), 7.42-7.35 (m, 1H), 7.31-7.25 (m, 1H), 6.43 (s, 1H), 5.61 (s, 2H). Analytical HPLC Method A: 5.32 min, 94%.

Example 130: 7-((2,4-Difluorobenzyl)oxy)-3H-[1,2,3]triazolo[4,5-b]pyridin-5-amine

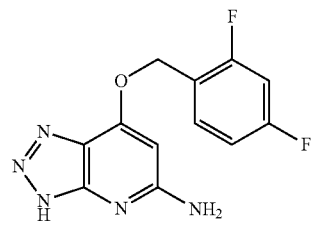 [SMILES: Nc1cc(OCc2ccc(F)cc2F)c2nn[nH]c2n1]

Example 130 was synthesized from (2,4-difluorophenyl)methanol and Intermediate 1 using General Route 2. MS(ESI) m/z 278 (M+H). $^1$H NMR (500 MHz, CD$_3$OD) δ 7.62-7.52 (m, 1H), 7.04-6.92 (m, 2H), 6.29 (s, 1H), 5.40 (s, 2H). Analytical HPLC Method A: 5.33 min, 92%.

Example 131: 7-(4-Chloro-2-(methylsulfonyl)benzyloxy)-3H-[1,2,3]triazolo[4,5-b]pyridin-5-amine

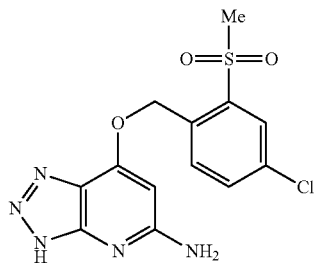 [SMILES: CS(=O)(=O)c1cc(Cl)ccc1COc1cc(N)nc2[nH]nnc12]

Example 131 was synthesized from Intermediate 4 and 1-(bromomethyl)-4-chloro-2-(methylsulfonyl)benzene using General Route 3. MS(ESI) m/z 354 (M+H). $^1$H NMR (500 MHz, CD$_3$OD) δ 8.15 (d, J=2.2 Hz, 1H), 7.93-7.82 (m, 3H), 6.48 (s, 1H), 5.87 (s, 3H), 3.32 (s, 3H) Analytical HPLC Method A: 4.32 min, 98%; Method B: 4.70 min, 93%.

Example 132: 7-(Cyclohexylmethoxy)-3H-[1,2,3]triazolo[4,5-b]pyridin-5-amine

Example 132 was synthesized from Intermediate 4 and cyclohexylmethanol using General Route 3. MS(ESI) m/z 248 (M+H). $^1$H NMR (500 MHz, CD$_3$OD) δ 6.30 (s, 1H), 4.20 (d, J=6.1 Hz, 2H), 2.05-1.90 (m, 3H), 1.84 (dt, J=13.0, 3.0 Hz, 2H), 1.79-1.72 (m, 1H), 1.47-1.27 (m, 3H), 1.26-1.12 (m, 2H). Analytical HPLC Method A: 4.22 min, 98%; Method B: 5.15 min, 99%. The compound was isolated as a TFA salt.

Example 133: 7-((2,6-Dimethylcyclohexyl)methoxy)-3H-[1,2,3]triazolo[4,5-b]pyridin-5-amine

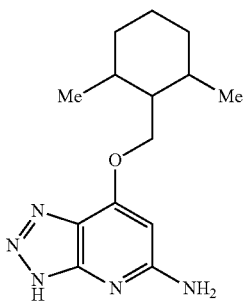 [SMILES: CC1CCCC(C)C1COc1cc(N)nc2[nH]nnc12]

Example 133 was synthesized from (2,6-dimethylcyclohexyl)methanol and Intermediate 4 using General Route 3. MS(ESI) m/z 276.3 (M+H). Analytical HPLC Method A: 6.02 min, 94%; Method B: 6.33 min, 93%. The compound was isolated as a TFA salt.

Example 135: 7-(2,2-Difluoro-1-phenylbutoxy)-3H-[1,2,3]triazolo[4,5-b]pyridin-5-amine (Racemic)

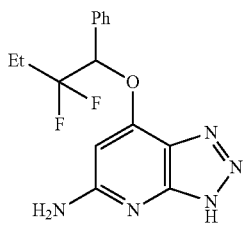 [SMILES: CCC(F)(F)C(Oc1cc(N)nc2[nH]nnc12)c1ccccc1]

135A: 2,2-Difluoro-1-phenylbutan-1-one

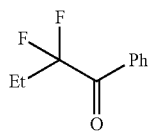

To a solution of ethyl 2,2-difluorobutanoate (2.1 g, 14 mmol) in anhydrous toluene (30 mL) at −78° C. was added a solution of 1.8 M phenyllithium in di-n-butylether (8.1 mL, 14 mmol). The reaction mixture was gradually warmed to room temperature over a period of 4 h. The reaction was quenched with 1.0 N HCl and extracted with EtOAc. The combined organics were washed with 1N HCl, brine, dried over MgSO$_4$ and concentrated.

135B: 2,2-Difluoro-1-phenylbutan-1-ol

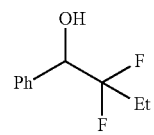

To a solution of 135A (2.5 g, 14 mmol) in MeOH (25 mL) was added sodium borohydride (0.77 g, 20 mmol). The reaction mixture was stirred at rt for 3 h. The mixture was quenched with 1.0 N HCl and extracted with EtOAc, washed with brine, dried over MgSO$_4$ and then concentrated to obtain the colorless oil. The crude product was purified via column chromatography (0-100% EtOAc/hexanes on 80 g column) to yield 135B (1.9 g, 10 mmol, 75% yield). $^1$H NMR (500 MHz, CDCl$_3$) δ 7.62-7.28 (m, 5H), 4.88 (td, J=10.2, 4.0 Hz, 1H), 2.00-1.83 (m, 1H), 1.80-1.63 (m, 1H), 1.09-0.87 (m, 3H).

Example 135

Example 135 was synthesized from 135B and Intermediate 4 using General Route 3. MS(ESI) m/z 320 (M+H). $^1$H NMR (500 MHz, CD$_3$OD) δ 7.64-7.54 (m, 2H), 7.47-7.40 (m, 3H), 6.16 (s, 1H), 6.10-5.99 (m, 1H), 2.32-1.96 (m, 2H), 1.11 (t, J=7.6 Hz, 3H). Analytical HPLC Method A: 6.12 min, 95%; Method B: 6.33 min, 97%.

Example 136: 7-(2,2-Difluoro-1-(2-methoxyphenyl)butoxy)-3H-[1,2,3]triazolo[4,5-b]pyridin-5-amine (Racemic)

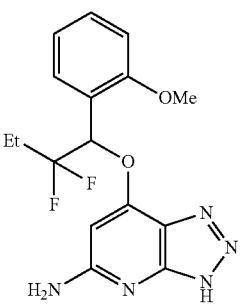 [SMILES: CCC(F)(F)C(Oc1cc(N)nc2[nH]nnc12)c1ccccc1OC]

Example 136 was synthesized using (2-methoxyphenyl)magnesium bromide using procedures similar to those used in Example 135. MS(ESI) m/z 350 (M+H). $^1$H NMR (500 MHz, CD$_3$OD) δ 7.45-7.38 (m, 1H), 7.34-7.26 (m, 1H), 7.01-6.89 (m, 2H), 6.26 (s, 1H), 5.14-5.01 (m, 1H), 3.81 (s, 3H), 2.19-1.66 (m, 2H), 0.96 (t, J=7.4 Hz, 3H). Analytical HPLC Method A: 6.36 min, 84%; Method B: 6.24 min, 83%.

Example 137: 7-(2,2-Difluoro-1-phenylbutoxy)-3H-
[1,2,3]triazolo[4,5-b]pyridin-5-amine (Enantiomer 2)

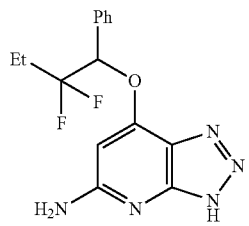

Example 135 was separated into individual enantiomers using a Berger Prep SFC equipped with a CHIRALPAK® AD-H, 21×250 mm ID, 5 m column (Flow rate: 45 mL/min, 150 bar BP, 40 C, 10% methanol/90% CO$_2$). The second eluting peak is Example 137. Chiral analytical retention: 15.32 min (Berger Analytical SFC, CHIRALPAK® AD-H, 4.6×250 mm, 5 micron, 3.0 mL/min, 150 bar BP, 10% MeOH/90% CO$_2$, 35° C.). MS(ESI) m/z 320 (M+H). $^1$H NMR (500 MHz, CD$_3$OD) δ 7.64-7.54 (m, 2H), 7.47-7.40 (m, 3H), 6.16 (s, 1H), 6.10-5.99 (m, 1H), 2.32-1.96 (m, 2H), 1.11 (t, J=7.6 Hz, 3H). Analytical HPLC Method A: 5.91 min, 98%; Method B: 6.16 min, 99%.

Example 138: 7-(2,2-Difluoro-1-phenylethoxy)-3H-
[1,2,3]triazolo[4,5-b]pyridin-5-amine (Racemic)

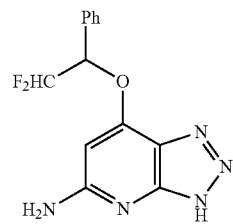 [SMILES: Nc1cc(OC(c2ccccc2)C(F)F)c2nn[nH]c2n1]

138A: 2,2-Difluoro-1-phenylethanol

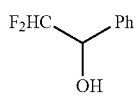

To a solution of 2,2-difluoro-1-phenylethanone (500 mg, 3.2 mmol) in MeOH (25 mL) was added lithium borohydride (210 mg, 9.6 mmol). The reaction was stirred at room temperature for 3 h. The mixture quenched with 1.0 N HCl and extracted with EtOAc. The combined organics were washed with brine, dried over MgSO$_4$ and concentrated to obtain the colorless oil. The crude product was purified by column chromatography (0-40% EtOAc/hexanes) to yield 138A (130 mg, 0.79 mmol, 25% yield). $^1$H NMR (500 MHz, CDCl$_3$) δ 7.52-7.30 (m, 5H), 5.99-5.59 (m, 1H), 4.95-4.78 (m, 1H)

Example 138

Example 138 was synthesized from 138A and Intermediate 4 using General Route 3. MS(ESI) m/z 292 (M+H). $^1$H NMR (500 MHz, CD$_3$OD) δ 7.56 (s, 2H), 7.45 (dd, J=7.2, 0.5 Hz, 3H), 6.47-6.21 (m, 1H), 6.20-6.16 (m, 1H), 6.09-5.93 (m, 1H). Analytical HPLC Method A: 5.64 min, 99%; Method B: 5.52 min, 99%.

Example 139: 7-(1-(3-Fluorophenyl)ethoxy)-3H-[1,2,3]triazolo[4,5-b]pyridin-5-amine

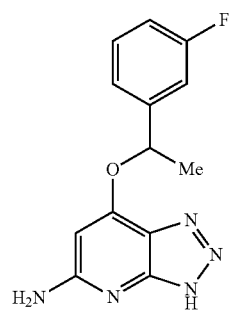 [SMILES: CC(Oc1cc(N)nc2[nH]nnc12)c1cccc(F)c1]

139A: (E)-N'-(1-(3-Fluorophenyl)ethylidene)-4-methylbenzenesulfonohydrazide

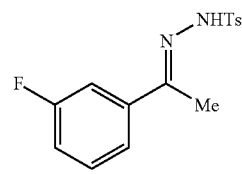

1-(3-Fluorophenyl)ethanone (1.0 g, 7.2 mmol) and 4-methylbenzenesulfonohydrazide (1.3 g, 7.2 mmol) were combined in EtOH (7.2 mL) and stirred overnight at rt. After the solvent was removed, the residue was recrystallized in ~7.0 mL of EtOH, filtered, washed with cold EtOH to yield 139A (1.5 g, 4.9 mmol, 68% yield). MS(ESI) m/z 307.0 (M+H).

139B: Di-tert-butyl(4-(1-(3-fluorophenyl)ethoxy)pyridine-2,6-diyl)bis(tert-butoxycarbonylcarbamate)

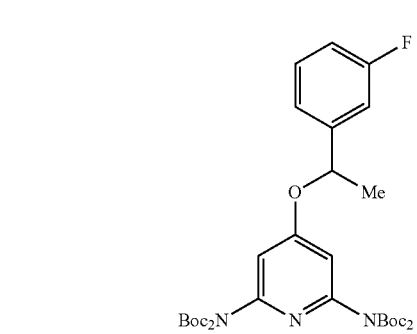

Dioxane (1.0 mL) was added to a mixture of Intermediate 4 (0.22 g, 0.41 mmol), 139A (0.13 g, 0.41 mmol), and potassium carbonate (0.20 g, 1.4 mmol). The resulting suspension was stirred at 110° C. After 1 hour, the starting hydrazone had been consumed (by TLC and LCMS). The reaction was cooled to rt, diluted with EtOAc (5.0 mL) and filtered. Upon concentration in vacuo, the reaction mixture was purified by flash column chromatography (0% EtOAc in hexanes to 40% EtOAc in hexanes) to yield 139B (150 mg, 0.23 mmol, 57%) as a clear, colorless oil.

Example 139

Example 139 was synthesized from 139B using procedures found in General Route 3. MS(ESI) m/z 274.4 (M+H). $^1$H NMR (500 MHz, acetonitrile-d$_3$) δ 7.44 (td, J=8.0, 5.8 Hz, 1H), 7.30 (d, J=7.7 Hz, 1H), 7.24 (dt, J=9.9, 2.1 Hz, 1H), 7.15-7.05 (m, 1H), 6.06 (s, 1H), 5.85 (q, J=6.5 Hz, 1H), 1.77 (d, J=6.6 Hz, 3H). Analytical HPLC Method A: 5.28 min, 99%; Method B: 5.64 min, 99%. The compound was isolated as a TFA salt.

Example 140: 7-(1-(2-Fluorophenyl)ethoxy)-3H-[1,2,3]triazolo[4,5-b]pyridin-5-amine

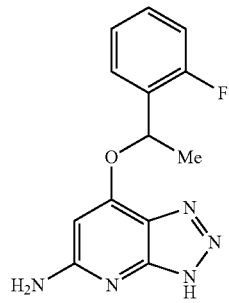 [SMILES: CC(Oc1cc(N)nc2[nH]nnc12)c1ccccc1F]

Example 140 was synthesized from 1-(2-fluorophenyl)ethanone and Intermediate 4 using General Route 4. MS(ESI) m/z 274.4 (M+H). $^1$H NMR (500 MHz, acetonitrile-d$_3$) δ 7.50 (d, J=1.9 Hz, 1H), 7.43-7.35 (m, 1H), 7.25-7.15 (m, 2H), 6.10 (q, J=6.3 Hz, 1H), 6.02 (s, 1H), 1.78 (d, J=6.3 Hz, 3H). Analytical HPLC Method A: 5.10 min, 99%; Method B: 5.29 min, 96%. The compound was isolated as a TFA salt.

Example 142: 7-(1-(4-(Trifluoromethoxy)phenyl)ethoxy)-3H-[1,2,3]triazolo[4,5-b]pyridin-5-amine

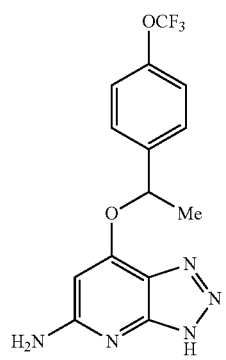 [SMILES: CC(Oc1cc(N)nc2[nH]nnc12)c1ccc(OC(F)(F)F)cc1]

Example 142 was synthesized from 1-(4-trifluoromethoxyphenyl)ethanone and Intermediate 4 using General Route 4. MS(ESI) m/z 340.3 (M+H). $^1$H NMR (500 MHz, acetonitrile-d$_3$) δ 7.60 (d, J=8.5 Hz, 2H), 7.36 (d, J=8.0 Hz, 2H), 6.08 (s, 1H), 5.91 (q, J=6.4 Hz, 1H), 1.78 (d, J=6.4 Hz, 3H). Analytical HPLC Method A: 6.30 min, 99%; Method B: 6.51 min, 97%. The compound was isolated as a TFA salt.

Example 143: 7-(1-(3-(Trifluoromethoxy)phenyl)ethoxy)-3H-[1,2,3]triazolo[4,5-b]pyridin-5-amine

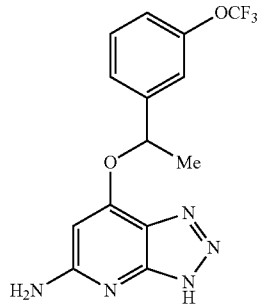 [SMILES: CC(Oc1cc(N)nc2[nH]nnc12)c1cccc(OC(F)(F)F)c1]

Example 143 was synthesized from 1-(3-trifluoromethoxyphenyl)ethanone and Intermediate 4 using General Route 4. MS(ESI) m/z 340.3 (M+H). $^1$H NMR (500 MHz, acetonitrile-d$_3$) δ 7.59-7.48 (m, 2H), 7.43 (s, 1H), 7.31 (dt, J=7.7, 1.2 Hz, 1H), 6.06 (s, 1H), 5.92 (q, J=6.3 Hz, 1H), 1.78 (d, J=6.3 Hz, 3H). Analytical HPLC Method A: 6.25 min, 99%; Method B: 6.40 min, 99%. The compound was isolated as a TFA salt.

Example 144: N-(3-(1-(5-Amino-3H-[1,2,3]triazolo[4,5-b]pyridin-7-yloxy)ethyl)phenyl)acetamide

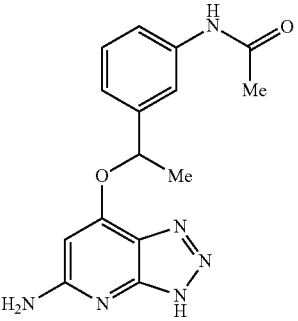 [SMILES: CC(=O)Nc1cccc(C(C)Oc2cc(N)nc3[nH]nnc23)c1]

Example 144 was synthesized from N-(3-acetylphenyl)acetamide and Intermediate 4 using General Route 4. MS(ESI) m/z 313.4 (M+H). $^1$H NMR (500 MHz, CD$_3$OD) δ 7.87-7.78 (m, 1H), 7.42 (dd, J=1.9, 1.4 Hz, 1H), 7.41-7.35 (m, 1H), 7.23 (d, J=7.4 Hz, 1H), 6.20 (s, 1H), 5.86 (q, J=6.3 Hz, 1H), 2.14 (s, 3H), 1.83 (d, J=6.3 Hz, 3H). Analytical HPLC: 3.16 min, 98%. The compound was isolated as a TFA salt.

Example 145: 7-(1-(3,4-Dichlorophenyl)propoxy)-3H-[1,2,3]triazolo[4,5-b]pyridin-5-amine

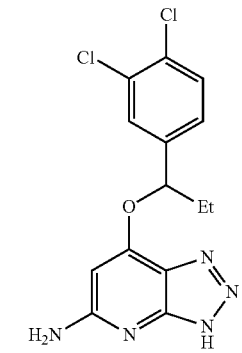 [SMILES: CCC(Oc1cc(N)nc2[nH]nnc12)c1ccc(Cl)c(Cl)c1]

Example 145 was synthesized from 1-(3,4-dichlorophenyl)propan-1-one and Intermediate 4 using General Route 4. MS(ESI) m/z 338.2 (M+H). ¹H NMR (500 MHz, CD₃OD) δ 7.67 (d, J=2.0 Hz, 1H), 7.59 (d, J=8.4 Hz, 1H), 7.42 (dd, J=8.4, 2.0 Hz, 1H), 6.14 (s, 1H), 5.68 (dd, J=7.2, 5.8 Hz, 1H), 2.27-2.16 (m, 1H), 2.13-2.01 (m, 1H), 1.10 (t, J=7.3 Hz, 3H). Analytical HPLC: 5.98 min, 99%. The compound was isolated as a TFA salt.

Example 147: 7-(Naphthalen-2-ylmethoxy)-3H-[1,2,3]triazolo[4,5-b]pyridin-5-amine

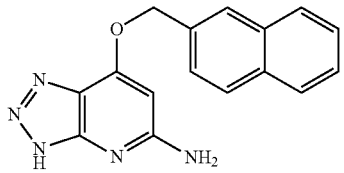 [SMILES: Nc1cc(OCc2ccc3ccccc3c2)c2nn[nH]c2n1]

To a slurry of methyl 7-chloro-3H-[1,2,3]triazolo[4,5-b]pyridin-5-ylcarbamate (0.030 g, 0.13 mmol, *JOC*, 43(26): 4910 (1978)) in DME (Volume: 1.3 mL) was added 60 wt % sodium hydride (0.053 g, 1.3 mmol) and naphthalen-2-ylmethanol (0.21 g, 1.3 mmol). The resulting material was heated to 150° C. overnight. The solution was then diluted with EtOAc and washed with sat. aq. ammonium chloride. The organic layer was then concentrated and the residue purified by preparative HPLC to yield Example 147 (0.016 g, 0.052 mmol, 39% yield). MS(ESI) m/z 292.1 (M+H). ¹H NMR (500 MHz, DMSO-d₆) δ 7.94-7.76 (m, 4H), 7.55-7.42 (m, 3H), 6.03 (br. s., 1H), 4.70 (br. s., 2H). Analytical HPLC Method A: 5.22 min, 99%; Method B: 5.66 min, 97.5%.

Example 148: 7-(3-Bromobenzyloxy)-3H-[1,2,3]triazolo[4,5-b]pyridin-5-amine

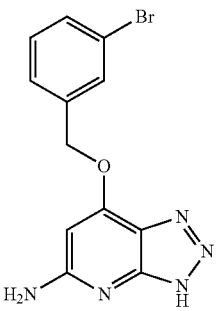 [SMILES: Nc1cc(OCc2cccc(Br)c2)c2nn[nH]c2n1]

Example 148 was synthesized from (3-bromophenyl)methanol and Intermediate 2 using General Route 1. MS(ESI) m/z 320/322 (M+H). ¹H NMR (500 MHz, CD₃OD) δ 7.74 (m, 1H), 7.54-7.48 (m, 2H), 7.38-7.30 (m, 1H), 6.15 (s, 1H), 5.38 (s, 2H). Analytical HPLC Method A: 5.17 min, 97%; Method B: 5.84 min, 99%.

The following compounds were prepared in a manner similar to experimental procedures that are described in Example 25 using 47A as starting material:

| Ex. No. | Structure | Name | MS(ESI) (M + H)⁺ |
|---|---|---|---|
| 152 | 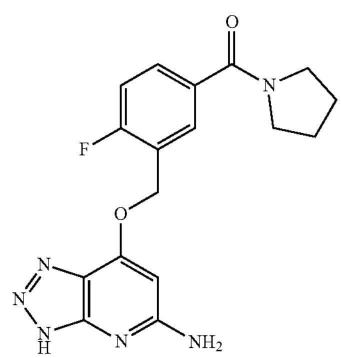 [SMILES: Nc1cc(OCc2cc(C(=O)N3CCCC3)ccc2F)c2nn[nH]c2n1] | (3-((5-amino-3H-[1,2,3]triazolo[4,5-b]pyridin-7-yloxy)methyl)-4-fluorophenyl)(pyrrolidin-1-yl)methanone | 357 |
| 153 | 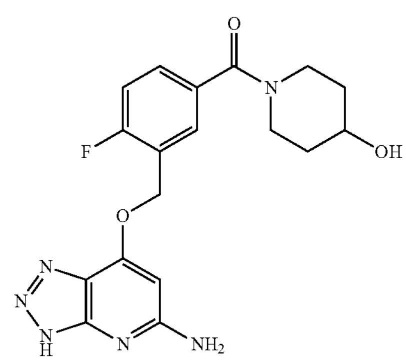 [SMILES: Nc1cc(OCc2cc(C(=O)N3CCC(O)CC3)ccc2F)c2nn[nH]c2n1] | (3-((5-amino-3H-[1,2,3]triazolo[4,5-b]pyridin-7-yloxy)methyl)-4-fluorophenyl)(4-hydroxypiperidin-1-yl)methanone | 387 |

| Ex. No. | Structure | Name | MS(ESI) (M + H)+ |
|---|---|---|---|
| 154 | 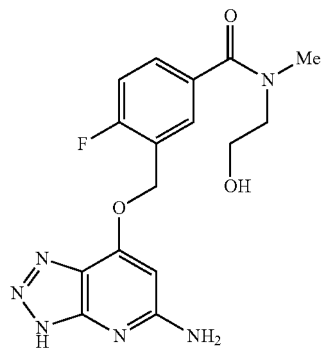 [SMILES: CN(CCO)C(=O)c1ccc(F)c(COc2cc(N)nc3[nH]nnc23)c1] | 3-((5-amino-3H-[1,2,3]triazolo[4,5-b]pyridin-7-yloxy)methyl)-4-fluoro-N-(2-hydroxyethyl)-N-methylbenzamide | 361 |
| 155 | 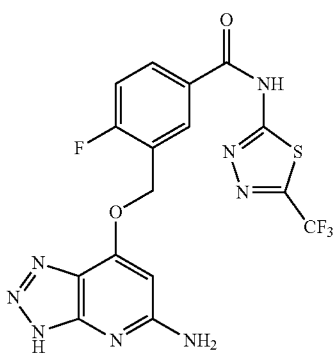 [SMILES: Nc1cc(OCc2cc(C(=O)Nc3nnc(C(F)(F)F)s3)ccc2F)c2nn[nH]c2n1] | 3-((5-amino-3H-[1,2,3]triazolo[4,5-b]pyridin-7-yloxy)methyl)-4-fluoro-N-(5-(trifluoromethyl)-1,3,4-thiadiazol-2-yl)benzamide | 455 |
| 156 | 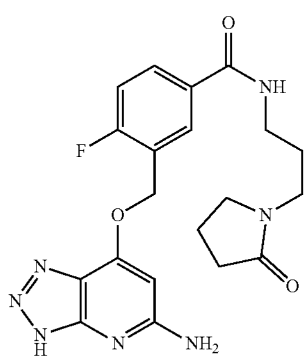 [SMILES: Nc1cc(OCc2cc(C(=O)NCCCN3CCCC3=O)ccc2F)c2nn[nH]c2n1] | 3-((5-amino-3H-[1,2,3]triazolo[4,5-b]pyridin-7-yloxy)methyl)-4-fluoro-N-(3-(2-oxopyrrolidin-1-yl)propyl)benzamide | 428 |
| 157 | 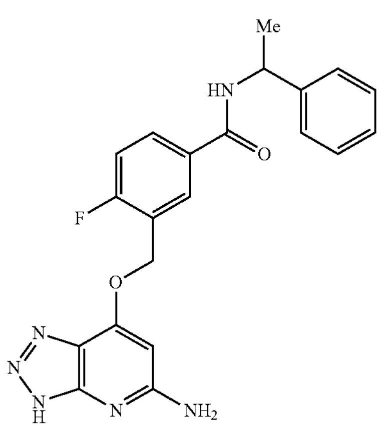 [SMILES: CC(NC(=O)c1ccc(F)c(COc2cc(N)nc3[nH]nnc23)c1)c1ccccc1] | 3-((5-amino-3H-[1,2,3]triazolo[4,5-b]pyridin-7-yloxy)methyl)-4-fluoro-N-(1-phenylethyl)benzamide | 407 |

-continued

| Ex. No. | Structure | Name | MS(ESI) (M + H)+ |
|---|---|---|---|
| 158 | 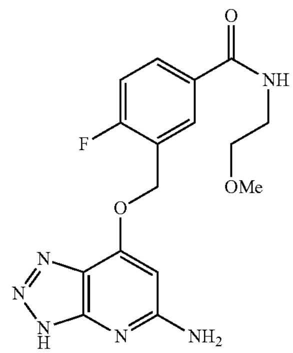 [SMILES: COCCNC(=O)c1ccc(F)c(COc2cc(N)nc3[nH]nnc23)c1] | 3-((5-amino-3H-[1,2,3]triazolo[4,5-b]pyridin-7-yloxy)methyl)-4-fluoro-N-(2-methoxyethyl)benzamide | 361 |
| 159 | 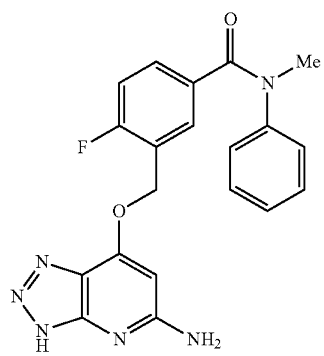 [SMILES: CN(C(=O)c1ccc(F)c(COc2cc(N)nc3[nH]nnc23)c1)c1ccccc1] | 3-((5-amino-3H-[1,2,3]triazolo[4,5-b]pyridin-7-yloxy)methyl)-4-fluoro-N-methyl-N-phenylbenzamide | 393 |
| 160 | 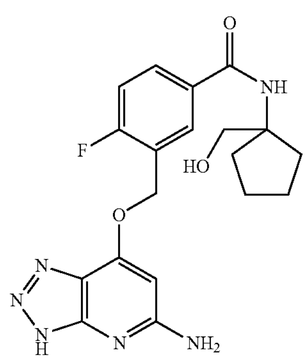 [SMILES: Nc1cc(OCc2cc(C(=O)NC3(CO)CCCC3)ccc2F)c2nn[nH]c2n1] | 3-((5-amino-3H-[1,2,3]triazolo[4,5-b]pyridin-7-yloxy)methyl)-4-fluoro-N-(1-(hydroxymethyl)cyclopentyl)benzamide | 401 |
| 161 | 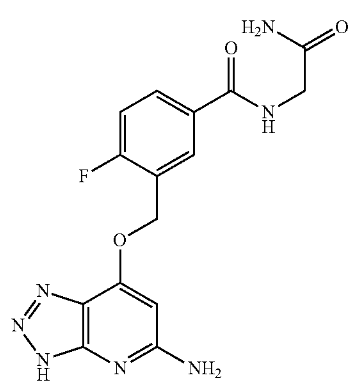 [SMILES: NC(=O)CNC(=O)c1ccc(F)c(COc2cc(N)nc3[nH]nnc23)c1] | N-(2-amino-2-oxoethyl)-3-((5-amino-3H-[1,2,3]triazolo[4,5-b]pyridin-7-yloxy)methyl)-4-fluorobenzamide | 360 |

-continued

| Ex. No. | Structure | Name | MS(ESI) (M + H)+ |
|---|---|---|---|
| 162 | 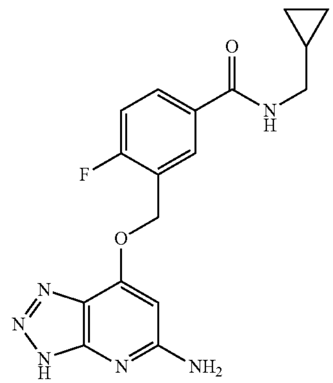 [SMILES: Nc1cc(OCc2cc(C(=O)NCC3CC3)ccc2F)c2nn[nH]c2n1] | 3-((5-amino-3H-[1,2,3]triazolo[4,5-b]pyridin-7-yloxy)methyl)-N-(cyclopropylmethyl)-4-fluorobenzamide | 357 |
| 163 | 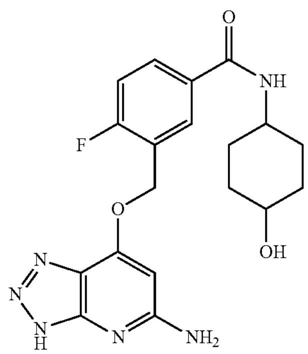 [SMILES: Nc1cc(OCc2cc(C(=O)NC3CCC(O)CC3)ccc2F)c2nn[nH]c2n1] | (3-((5-amino-3H-[1,2,3]triazolo[4,5-b]pyridin-7-yloxy)methyl)-4-fluoro-N-(4-hydroxycyclohexyl)benzamide | 401 |
| 164 | 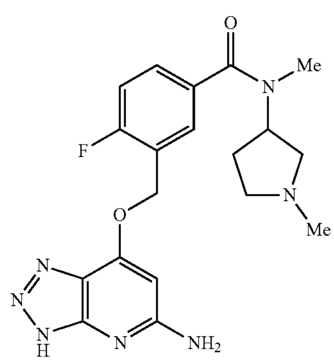 [SMILES: CN1CCC(N(C)C(=O)c2ccc(F)c(COc3cc(N)nc4[nH]nnc34)c2)C1] | (3-((5-amino-3H-[1,2,3]triazolo[4,5-b]pyridin-7-yloxy)methyl)-4-fluoro-N-methyl-N-(1-methylpyrrolidin-3-yl)benzamide | 400 |
| 166 | 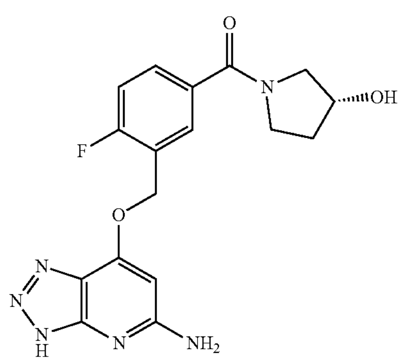 [SMILES: Nc1cc(OCc2cc(C(=O)N3CC[C@@H](O)C3)ccc2F)c2nn[nH]c2n1] | (R)-(3-((5-amino-3H-[1,2,3]triazolo[4,5-b]pyridin-7-yloxy)methyl)-4-fluorophenyl)(3-hydroxypyrrolidin-1-yl)methanone | 373 |

| Ex. No. | Structure | Name | MS(ESI) (M + H)+ |
|---|---|---|---|
| 169 | 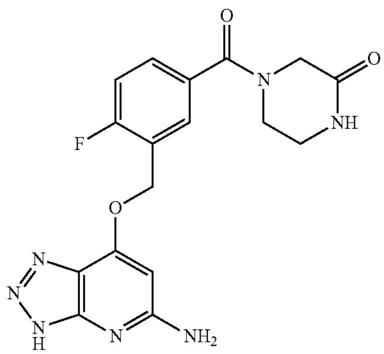 [SMILES: Nc1cc(OCc2cc(C(=O)N3CCNC(=O)C3)ccc2F)c2nn[nH]c2n1] | 4-(3-((5-amino-3H-[1,2,3]triazolo[4,5-b]pyridin-7-yloxy)methyl)-4-fluorobenzoyl)piperazin-2-one | 386 |
| 170 | 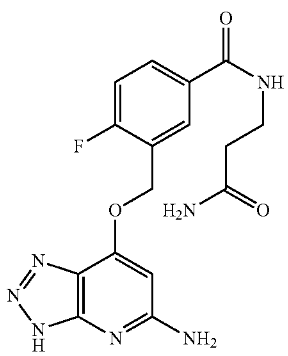 [SMILES: NC(=O)CCNC(=O)c1ccc(F)c(COc2cc(N)nc3[nH]nnc23)c1] | N-(3-amino-3-oxopropyl)-3-((5-amino-3H-[1,2,3]triazolo[4,5-b]pyridin-7-yloxy)methyl)-4-fluorobenzamide | 374 |

Example 171: Methyl 3-((5-amino-3H-[1,2,3]triazolo[4,5-b]pyridin-7-yloxy)methyl)-4-chlorobenzoate

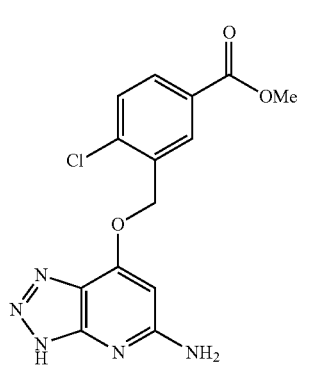

Example 171 was synthesized from Intermediate 4 and methyl 3-(bromomethyl)-4-chlorobenzoate using General Route 3. MS(ESI) m/z 334 (M+H). $^1$H NMR (500 MHz, DMSO-$d_6$) δ 8.26 (d, J=2.2 Hz, 1H), 8.01 (dd, J=8.4, 2.1 Hz, 1H), 7.75 (d, J=8.3 Hz, 1H), 6.24 (br. s., 1H), 5.55 (s, 2H), 3.88 (s, 3H) Analytical HPLC Method A: 5.38 min, 99%; Method B: 5.71 min, 99%. The compound was isolated as a TFA salt.

Intermediate 6: 3-((5-Amino-3H-[1,2,3]triazolo[4,5-b]pyridin-7-yloxy)methyl)-4-chlorobenzoic Acid

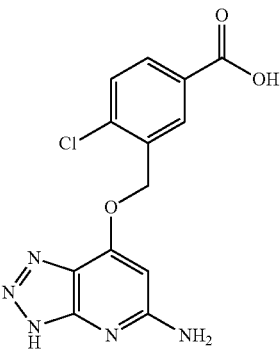 [SMILES: Nc1cc(OCc2cc(C(=O)O)ccc2Cl)c2nn[nH]c2n1]

Intermediate 6 was synthesized from Example 171 using an analogous procedure to Example 25A. MS(ESI) m/z 320 (M+H). $^1$H NMR (500 MHz, CD$_3$OD) δ 8.31 (d, J=1.9 Hz, 1H), 8.06 (dd, J=8.3, 2.2 Hz, 1H), 7.64 (d, J=8.3 Hz, 1H), 6.40 (s, 1H), 5.63 (s, 2H). Analytical HPLC Method A: 4.58 min, 99%; Method B: 4.80 min, 98%.

The following compounds were prepared in a manner similar to experimental procedures that are described in Example 25 using Intermediate 6 as starting material. Example 173 was isolated as a TFA salt.

| Ex. No. | Structure | Name | MS(ESI) (M + H)+ |
|---|---|---|---|
| 173 | 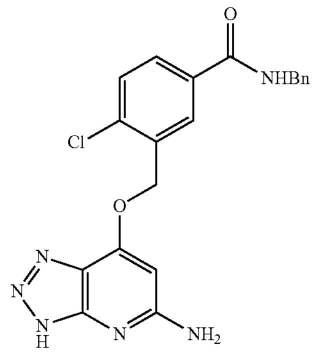 | 3-((5-amino-3H-[1,2,3]triazolo[4,5-b]pyridin-7-yloxy)methyl)-N-benzyl-4-chlorobenzamide | 409 |
| 174 | 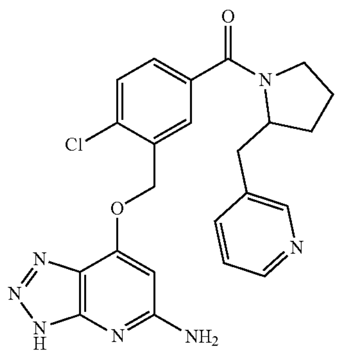 [SMILES: Nc1cc(OCc2cc(C(=O)N3CCCC3Cc3cccnc3)ccc2Cl)c2nn[nH]c2n1] | (3-((5-amino-3H-[1,2,3]triazolo[4,5-b]pyridin-7-yloxy)methyl)-4-chlorophenyl)(2-(pyridin-3-ylmethyl)pyrrolidin-1-yl)methanone | 464 |
| 175 | 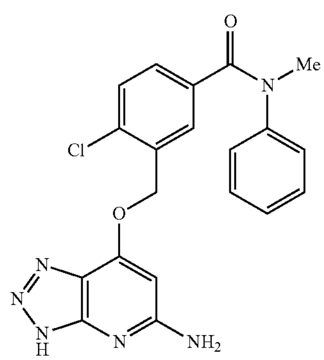 [SMILES: CN(C(=O)c1ccc(Cl)c(COc2cc(N)nc3[nH]nnc23)c1)c1ccccc1] | 3-((5-amino-3H-[1,2,3]triazolo[4,5-b]pyridin-7-yloxy)methyl)-4-chloro-N-methyl-N-phenylbenzamide | 409 |
| 176 | 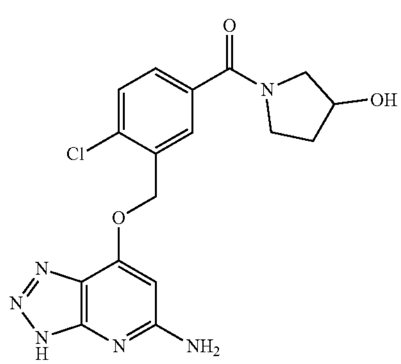 [SMILES: Nc1cc(OCc2cc(C(=O)N3CCC(O)C3)ccc2Cl)c2nn[nH]c2n1] | (3-((5-amino-3H-[1,2,3]triazolo[4,5-b]pyridin-7-yloxy)methyl)-4-chlorophenyl)(3-hydroxypyrrolidin-1-yl)methanone | 389 |

-continued

| Ex. No. | Structure | Name | MS(ESI) (M + H)+ |
|---|---|---|---|
| 177 | 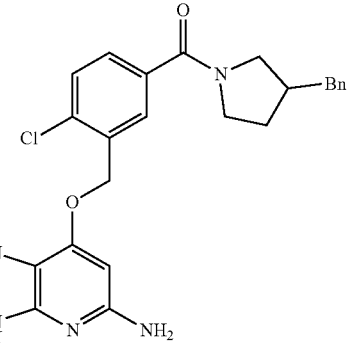 | (3-((5-amino-3H-[1,2,3]triazolo[4,5-b]pyridin-7-yloxy)methyl)-4-chlorophenyl)(3-benzylpyrrolidin-1-yl)methanone | 463 |
| 178 | 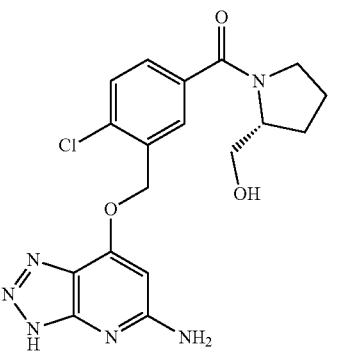 [SMILES: Nc1cc(OCc2cc(C(=O)N3CCC[C@@H]3CO)ccc2Cl)c2nn[nH]c2n1] | (R)-(3-((5-amino-3H-[1,2,3]triazolo[4,5-b]pyridin-7-yloxy)methyl)-4-chlorophenyl)(2-(hydroxymethyl)pyrrolidin-1-yl)methanone | 403 |
| 179 | 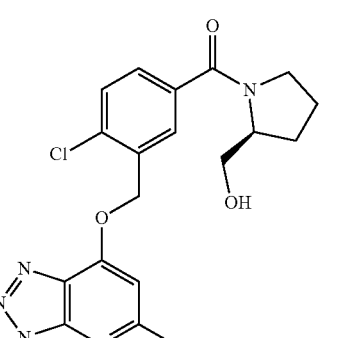 | (S)-(3-((5-amino-3H-[1,2,3]triazolo[4,5-b]pyridin-7-yloxy)methyl)-4-chlorophenyl)(2-(hydroxymethyl)pyrrolidin-1-yl)methanone | 403 |
| 182 | 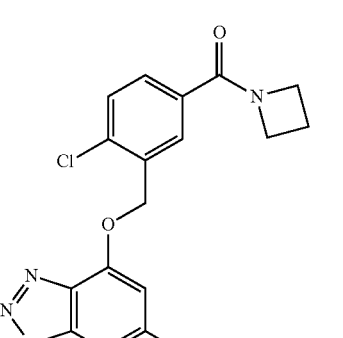 | (3-((5-amino-3H-[1,2,3]triazolo[4,5-b]pyridin-7-yloxy)methyl)-4-chlorophenyl)(azetidin-1-yl)methanone | 359 |

-continued

| Ex. No. | Structure | Name | MS(ESI) (M + H)+ |
|---|---|---|---|
| 183 | 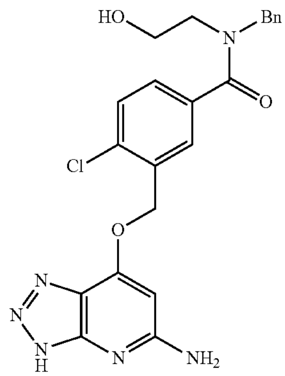 [SMILES: Nc1cc(OCc2cc(C(=O)N(CCO)Cc3ccccc3)ccc2Cl)c2nn[nH]c2n1] | 3-((5-amino-3H-[1,2,3]triazolo[4,5-b]pyridin-7-yloxy)methyl)-N-benzyl-4-chloro-N-(2-hydroxyethyl)benzamide | 453 |
| 184 | 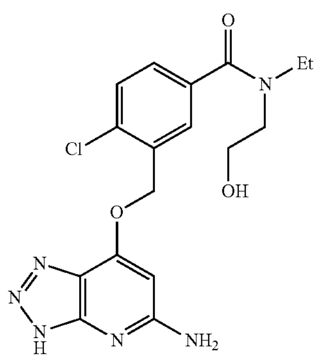 [SMILES: CCN(CCO)C(=O)c1ccc(Cl)c(COc2cc(N)nc3[nH]nnc23)c1] | 3-((5-amino-3H-[1,2,3]triazolo[4,5-b]pyridin-7-yloxy)methyl)-4-chloro-N-ethyl-N-(2-hydroxyethyl)benzamide | 391 |
| 185 | 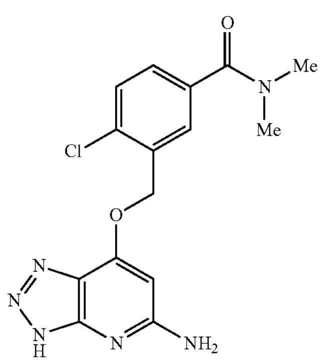 [SMILES: CN(C)C(=O)c1ccc(Cl)c(COc2cc(N)nc3[nH]nnc23)c1] | 3-((5-amino-3H-[1,2,3]triazolo[4,5-b]pyridin-7-yloxy)methyl)-4-chloro-N,N-dimethylbenzamide | 347 |
| 187 | 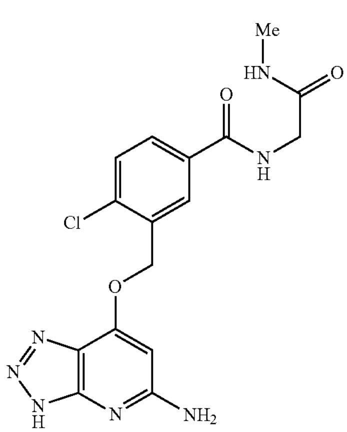 [SMILES: CNC(=O)CNC(=O)c1ccc(Cl)c(COc2cc(N)nc3[nH]nnc23)c1] | 3-((5-amino-3H-[1,2,3]triazolo[4,5-b]pyridin-7-yloxy)methyl)-4-chloro-N-(2-(methylamino)-2-oxoethyl)benzamide | 390 |

| Ex. No. | Structure | Name | MS(ESI) (M + H)+ |
|---|---|---|---|
| 188 | 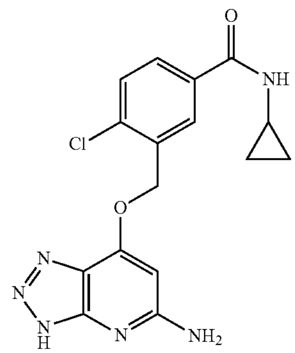 [SMILES: Nc1cc(OCc2cc(C(=O)NC3CC3)ccc2Cl)c2nn[nH]c2n1] | 3-((5-amino-3H-[1,2,3]triazolo[4,5-b]pyridin-7-yloxy)methyl)-4-chloro-N-cyclopropylbenzamide | 359 |
| 189 | 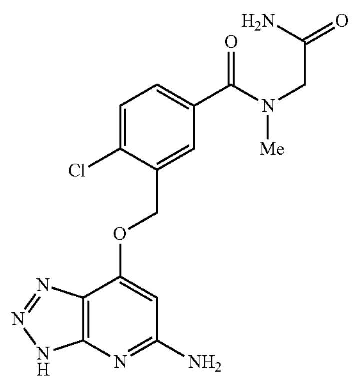 [SMILES: CN(CC(N)=O)C(=O)c1ccc(Cl)c(COc2cc(N)nc3[nH]nnc23)c1] | N-(2-amino-2-oxoethyl)-3-((5-amino-3H-[1,2,3]triazolo[4,5-b]pyridin-7-yloxy)methyl)-4-chloro-N-methylbenzamide | 390 |
| 190 | 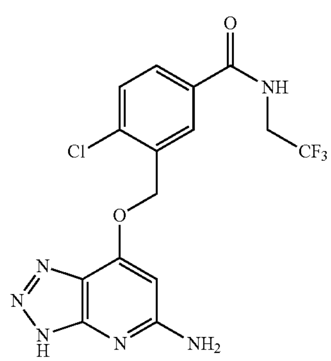 [SMILES: Nc1cc(OCc2cc(C(=O)NCC(F)(F)F)ccc2Cl)c2nn[nH]c2n1] | 3-((5-amino-3H-[1,2,3]triazolo[4,5-b]pyridin-7-yloxy)methyl)-4-chloro-N-(2,2,2-trifluoroethyl)benzamide | 401 |
| 191 | 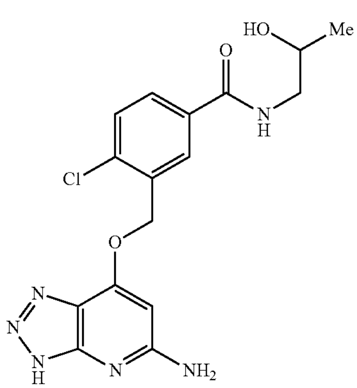 [SMILES: CC(O)CNC(=O)c1ccc(Cl)c(COc2cc(N)nc3[nH]nnc23)c1] | 3-((5-amino-3H-[1,2,3]triazolo[4,5-b]pyridin-7-yloxy)methyl)-4-chloro-N-(2-hydroxypropyl)benzamide | 377 |

-continued

| Ex. No. | Structure | Name | MS(ESI) (M + H)+ |
|---|---|---|---|
| 192 | 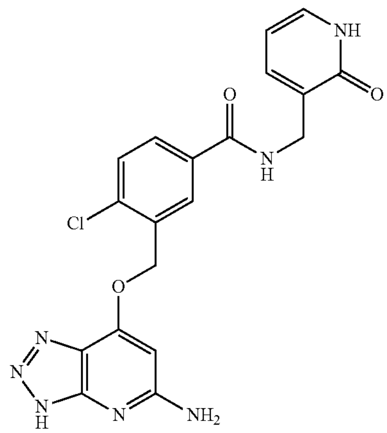 [SMILES: Nc1cc(OCc2cc(C(=O)NCc3ccc[nH]c3=O)ccc2Cl)c2nn[nH]c2n1] | 3-((5-amino-3H-[1,2,3]triazolo[4,5-b]pyridin-7-yloxy)methyl)-4-chloro-N-((2-oxo-1,2-dihydropyridin-3-yl)methyl)benzamide | 426 |
| 193 | 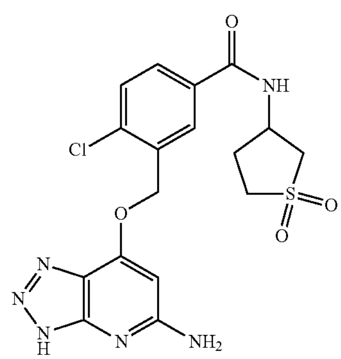 [SMILES: Nc1cc(OCc2cc(C(=O)NC3CCS(=O)(=O)C3)ccc2Cl)c2nn[nH]c2n1] | 3-((5-amino-3H-[1,2,3]triazolo[4,5-b]pyridin-7-yloxy)methyl)-4-chloro-N-(1,1-dioxidotetrahydrothien-3-yl)benzamide | 437 |

Example 194: Methyl 4-((5-amino-3H-[1,2,3]triazolo[4,5-b]pyridin-7-yloxy)methyl)-3-chlorobenzoate

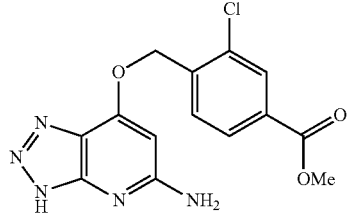

Example 194 was synthesized from Intermediate 4 and methyl 4-(bromomethyl)-3-chlorobenzoate using General Route 3. MS(ESI) m/z 334 (M+H). $^1$H NMR (500 MHz, CD$_3$OD) δ 8.09 (d, J=1.7 Hz, 1H), 8.02 (dd, J=8.1, 1.5 Hz, 1H), 7.82 (d, J=8.3 Hz, 1H), 6.35 (s, 1H), 5.60 (s, 2H), 3.94 (s, 3H). Analytical HPLC Method A: 4.43 min, 91%; Method B: 5.00 min, 93%. The compound was isolated as a TFA salt.

Intermediate 7: 4-((5-Amino-3H-[1,2,3]triazolo[4,5-b]pyridin-7-yloxy)methyl)-3-chlorobenzoic Acid

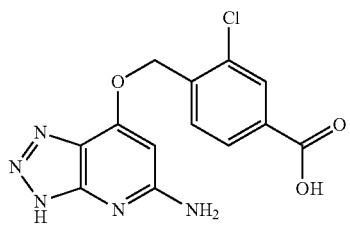 [SMILES: Nc1cc(OCc2ccc(C(=O)O)cc2Cl)c2nn[nH]c2n1]

Intermediate 7 was synthesized from Example 194 using an analogous procedure to 25A. MS(ESI) m/z 320 (M+H). $^1$H NMR (500 MHz, CD$_3$OD) δ 8.12 (s, 1H), 8.05 (d, J=8.3 Hz, 1H), 7.80 (d, J=8.0 Hz, 1H), 6.45 (s, 1H), 5.68 (s, 2H). Analytical HPLC Method A: 5.59 min, 98%; Method B: 7.62 min, 99%.

The following compounds were prepared in a manner similar to experimental procedures that are described in Example 25 using Intermediate 7 as starting material. Examples 196, 221, 223 and 224 were isolated as TFA salts.

| Ex. No. | Structure | Name | MS(ESI) (M + H)+ |
|---|---|---|---|
| 196 | 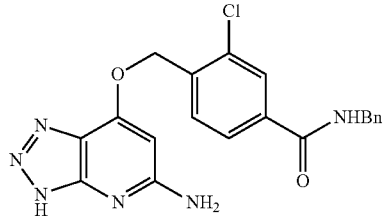 | 4-((5-amino-3H-[1,2,3]triazolo[4,5-b]pyridin-7-yloxy)methyl)-N-benzyl-3-chlorobenzamide | 409 |
| 197 | 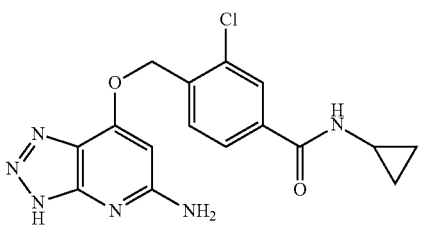 [SMILES: Nc1cc(OCc2ccc(C(=O)NC3CC3)cc2Cl)c2nn[nH]c2n1] | 4-((5-amino-3H-[1,2,3]triazolo[4,5-b]pyridin-7-yloxy)methyl)-3-chloro-N-cyclopropylbenzamide | 359 |
| 198 | 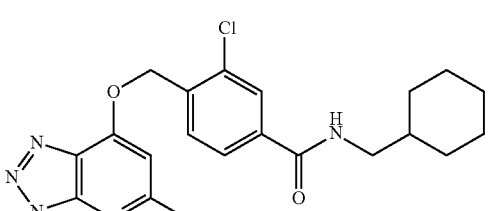 | 4-((5-amino-3H-[1,2,3]triazolo[4,5-b]pyridin-7-yloxy)methyl)-3-chloro-N-(cyclohexylmethyl)benzamide | 415 |
| 199 | 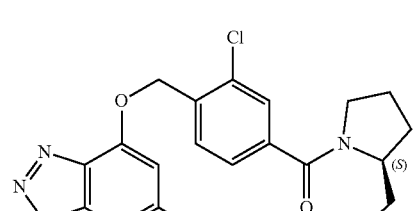 | (S)-(4-((5-amino-3H-[1,2,3]triazolo[4,5-b]pyridin-7-yloxy)methyl)-3-chlorophenyl)(2-(hydroxymethyl)pyrrolidin-1-yl)methanone | 403 |
| 201 | 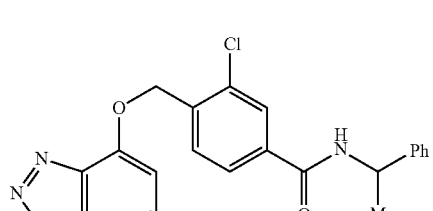 | 4-((5-amino-3H-[1,2,3]triazolo[4,5-b]pyridin-7-yloxy)methyl)-3-chloro-N-(1-phenylethyl)benzamide | 423 |
| 202 | 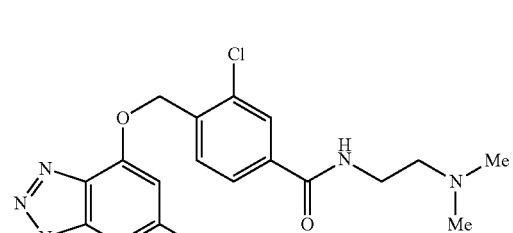 | 4-((5-amino-3H-[1,2,3]triazolo[4,5-b]pyridin-7-yloxy)methyl)-3-chloro-N-(2-(dimethylamino)ethyl)benzamide | 390 |

| Ex. No. | Structure | Name | MS(ESI) (M + H)+ |
|---|---|---|---|
| 203 | 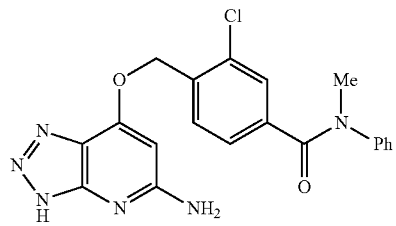 [SMILES: CN(C(=O)c1ccc(COc2cc(N)nc3[nH]nnc23)c(Cl)c1)c1ccccc1] | 4-((5-amino-3H-[1,2,3]triazolo[4,5-b]pyridin-7-yloxy)methyl)-3-chloro-N-methyl-N-phenylbenzamide | 409 |
| 204 | 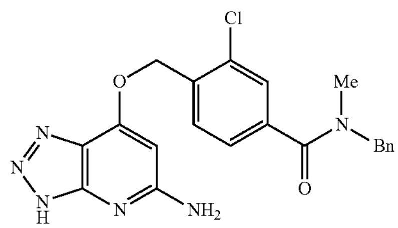 [SMILES: CN(Cc1ccccc1)C(=O)c1ccc(COc2cc(N)nc3[nH]nnc23)c(Cl)c1] | 4-((5-amino-3H-[1,2,3]triazolo[4,5-b]pyridin-7-yloxy)methyl)-N-benzyl-3-chloro-N-methylbenzamide | 423 |
| 205 | 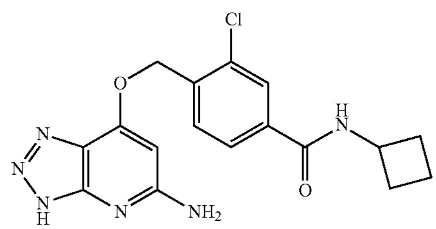 [SMILES: Nc1cc(OCc2ccc(C(=O)NC3CCC3)cc2Cl)c2nn[nH]c2n1] | 4-((5-amino-3H-[1,2,3]triazolo[4,5-b]pyridin-7-yloxy)methyl)-3-chloro-N-cyclobutylbenzamide | 373 |
| 206 | 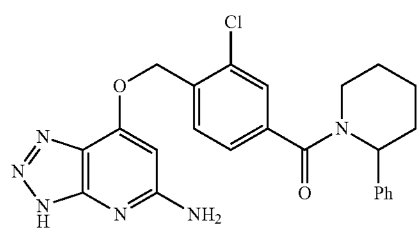 [SMILES: Nc1cc(OCc2ccc(C(=O)N3CCCCC3c3ccccc3)cc2Cl)c2nn[nH]c2n1] | 4-((5-amino-3H-[1,2,3]triazolo[4,5-b]pyridin-7-yloxy)methyl)-3-chlorophenyl)(2-phenylpiperidin-1-yl)methanone | 463 |
| 207 | 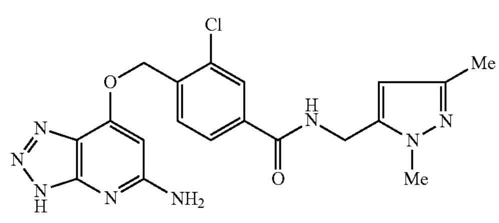 [SMILES: Cc1cc(CNC(=O)c2ccc(COc3cc(N)nc4[nH]nnc34)c(Cl)c2)n(C)n1] | 4-((5-amino-3H-[1,2,3]triazolo[4,5-b]pyridin-7-yloxy)methyl)-3-chloro-N-((1,3-dimethyl-1H-pyrazol-5-yl)methyl)benzamide | 427 |
| 209 | 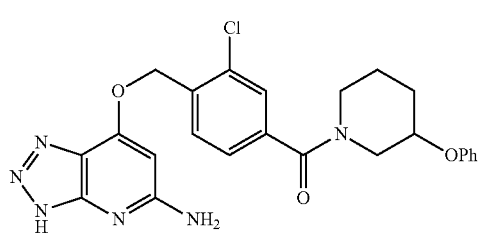 [SMILES: Nc1cc(OCc2ccc(C(=O)N3CCCC(Oc4ccccc4)C3)cc2Cl)c2nn[nH]c2n1] | 4-((5-amino-3H-[1,2,3]triazolo[4,5-b]pyridin-7-yloxy)methyl)-3-chlorophenyl)(3-phenoxypiperidin-1-yl)methanone | 479 |

-continued

| Ex. No. | Structure | Name | MS(ESI) (M + H)+ |
|---|---|---|---|
| 210 | 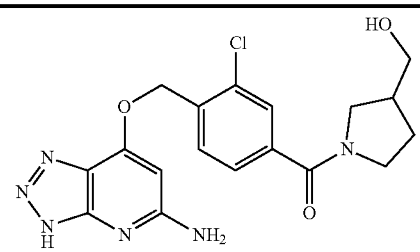 | 4-((5-amino-3H-[1,2,3]triazolo[4,5-b]pyridin-7-yloxy)methyl)-3-chlorophenyl)(3-(hydroxymethyl)pyrrolidin-1-yl)methanone | 403 |
| 212 | 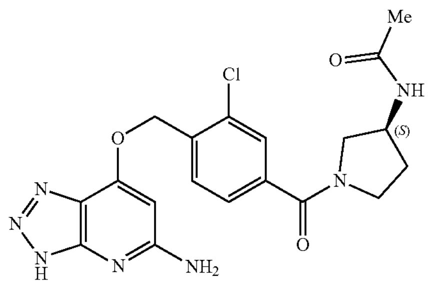 | (S)-N-(1-(4-((5-amino-3H-[1,2,3]triazolo[4,5-b]pyridin-7-yloxy)methyl)-3-chlorobenzoyl)pyrrolidin-3-yl)acetamide | 430 |
| 213 | 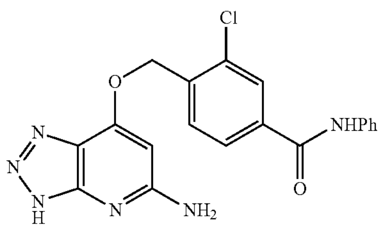 | 4-((5-amino-3H-[1,2,3]triazolo[4,5-b]pyridin-7-yloxy)methyl)-3-chloro-N-phenylbenzamide | 395 |
| 214 | 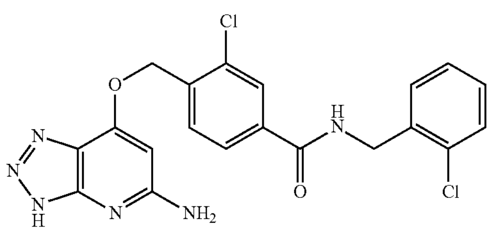 [SMILES: Nc1cc(OCc2ccc(C(=O)NCc3ccccc3Cl)cc2Cl)c2nn[nH]c2n1] | 4-((5-amino-3H-[1,2,3]triazolo[4,5-b]pyridin-7-yloxy)methyl)-3-chloro-N-(2-chlorobenzyl)benzamide | 443 |
| 215 | 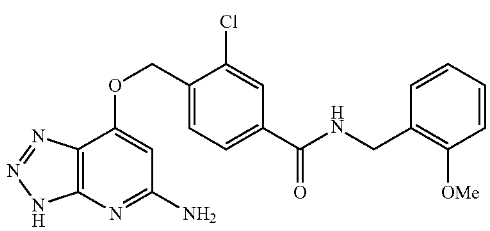 [SMILES: COc1ccccc1CNC(=O)c1ccc(COc2cc(N)nc3[nH]nnc23)c(Cl)c1] | 4-((5-amino-3H-[1,2,3]triazolo[4,5-b]pyridin-7-yloxy)methyl)-3-chloro-N-(2-methoxybenzyl)benzamide | 439 |
| 216 | 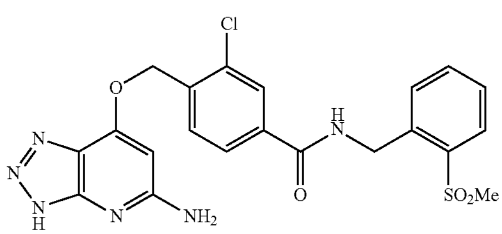 [SMILES: CS(=O)(=O)c1ccccc1CNC(=O)c1ccc(COc2cc(N)nc3[nH]nnc23)c(Cl)c1] | 4-((5-amino-3H-[1,2,3]triazolo[4,5-b]pyridin-7-yloxy)methyl)-3-chloro-N-(3-(methylsulfonyl)benzyl)benzamide | 487 |

| Ex. No. | Structure | Name | MS(ESI) (M + H)+ |
|---|---|---|---|
| 218 | 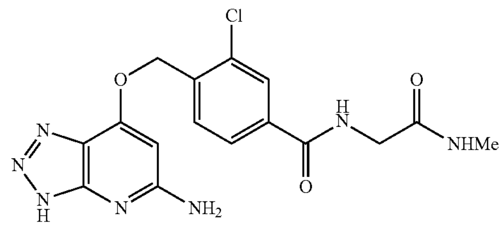 [SMILES: CNC(=O)CNC(=O)c1ccc(COc2cc(N)nc3[nH]nnc23)c(Cl)c1] | 4-((5-amino-3H-[1,2,3]triazolo[4,5-b]pyridin-7-yloxy)methyl)-3-chloro-N-(2-(methylamino)-2-oxoethyl)benzamide | 390 |
| 219 | 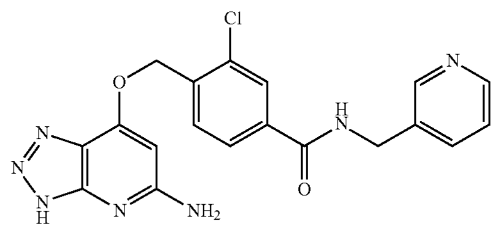 [SMILES: Nc1cc(OCc2ccc(C(=O)NCc3cccnc3)cc2Cl)c2nn[nH]c2n1] | 4-((5-amino-3H-[1,2,3]triazolo[4,5-b]pyridin-7-yloxy)methyl)-3-chloro-N-(pyridin-3-ylmethyl)benzamide | 410 |
| 220 | 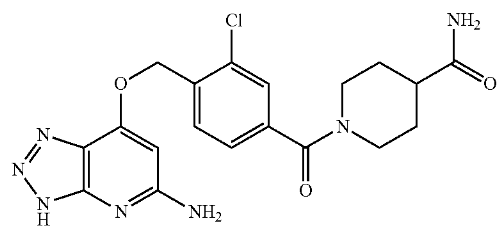 [SMILES: NC(=O)C1CCN(C(=O)c2ccc(COc3cc(N)nc4[nH]nnc34)c(Cl)c2)CC1] | 1-(4-((5-amino-3H-[1,2,3]triazolo[4,5-b]pyridin-7-yloxy)methyl)-3-chlorobenzoyl)piperidine-4-carboxamide | 430 |
| 221 | 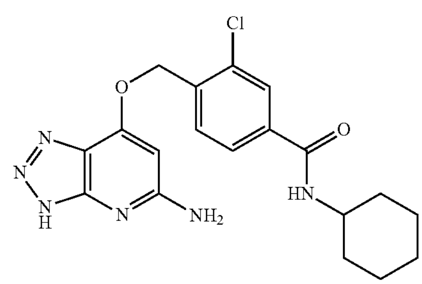 [SMILES: Nc1cc(OCc2ccc(C(=O)NC3CCCCC3)cc2Cl)c2nn[nH]c2n1] | 4-((5-amino-3H-[1,2,3]triazolo[4,5-b]pyridin-7-yloxy)methyl)-3-chloro-N-cyclohexylbenzamide | 401 |
| 222 | 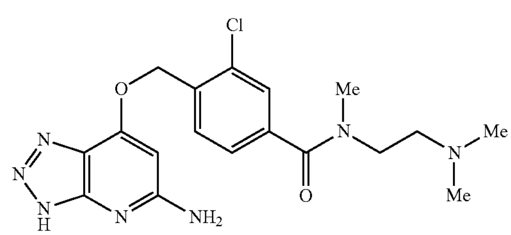 [SMILES: CN(C)CCN(C)C(=O)c1ccc(COc2cc(N)nc3[nH]nnc23)c(Cl)c1] | 4-((5-amino-3H-[1,2,3]triazolo[4,5-b]pyridin-7-yloxy)methyl)-3-chloro-N-(2-(dimethylamino)ethyl)-N-methylbenzamide | 404 |
| 223 | 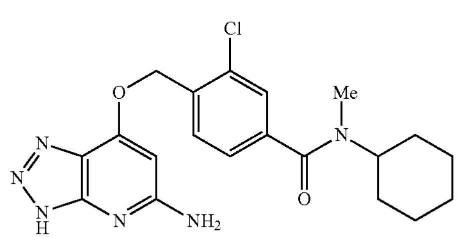 [SMILES: CN(C(=O)c1ccc(COc2cc(N)nc3[nH]nnc23)c(Cl)c1)C1CCCCC1] | 4-((5-amino-3H-[1,2,3]triazolo[4,5-b]pyridin-7-yloxy)methyl)-3-chloro-N-cyclohexyl-N-methylbenzamide | 415 |

| Ex. No. | Structure | Name | MS(ESI) (M + H)+ |
|---|---|---|---|
| 224 | 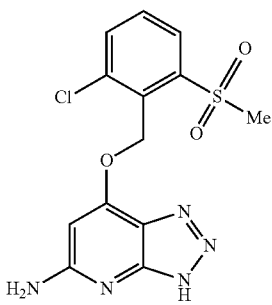 | N-(2-(1H-imidazol-4-yl)ethyl)-4-((5-amino-3H-[1,2,3]triazol[4,5-b]pyridin-7-yloxy)methyl)-3-chlorobenzamide | 413 |

Example 225: 7-(2-Chloro-6-(methylsulfonyl)benzyloxy)-3H-[1,2,3]triazolo[4,5-b]pyridin-5-amine

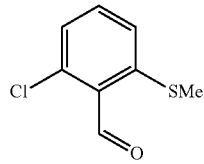 [SMILES: CSc1cccc(Cl)c1C=O]

225A: 2-Chloro-6-(methylthio)benzaldehyde

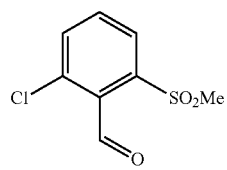 [SMILES: CS(=O)(=O)c1cccc(Cl)c1C=O]

Sodium thiomethoxide (0.53 g, 7.6 mmol) was added to a solution of 2-chloro-6-fluorobenzaldehyde (1 g, 6.31 mmol) in DMSO (30 mL), and the mixture was stirred over night. The reaction mixture was diluted with water and extracted with EtOAc (2×). The combined organics were washed with brine, dried over $Na_2SO_4$ and concentrated in vacuo. The crude product was purified by flash chromatography (loading in chloroform, 0% to 75% ethyl acetate in hexane over 15 min using a 40 g silica gel cartridge) to yield 225A (1.2 g) as a yellow solid. $^1$H NMR (500 MHz, $CD_3OD$) δ 10.60 (s, 1H), 7.54 (m, 1H), 7.41 (d, J=8.3 Hz, 1H), 7.30 (dd, J=8.0, 0.8 Hz, 1H), 2.48 (s, 3H).

225B: 2-Chloro-6-(methylsulfonyl)benzaldehyde

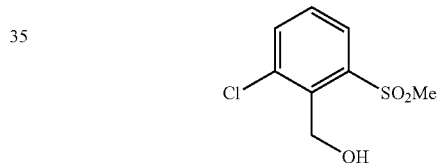

mCPBA (3.6 g, 21 mmol) was added to a solution of 225A (1.2 g, 6.3 mmol) in $CH_2Cl_2$ (35 mL) and the mixture was refluxed over night. The mixture was cooled to rt, diluted with 100 mL DCM and washed with $Na_2CO_3$ (2×50 mL). The organics were dried over $Na_2SO_4$ and concentrated in vacuo. The crude product was purified by flash chromatography (loading in chloroform, 0% to 100% ethyl acetate in hexane over 15 min using a 40 g silica gel cartridge) to yield 225B (0.93 g, 4.2 mmol, 61% yield) as a white solid. $^1$H NMR (400 MHz, $CD_3OD$) δ 10.48 (s, 1H), 8.04 (dd, J=7.8, 0.8 Hz, 1H), 7.85 (dd, J=8.1, 0.9 Hz, 1H), 7.74 (m, 1H), 3.30 (s, 3H).

225C: (2-Chloro-6-(methylsulfonyl)phenyl)methanol

Sodium borohydride (0.39 g, 10 mmol) was added to a solution of 225B (0.90 g, 4.1 mmol) in ethanol (20 mL) in 3 portions and the reaction mixture was stirred for 10 days. The mixture was quenched with water (1 mL), partially concentrated, diluted with water and extracted with EtOAc (2×). The combined organics were washed with brine, dried over $Na_2SO_4$ and concentrated in vacuo. The crude product was purified by flash chromatography (loading in chloroform, 0% to 75% EtOAc in hexane over 15 min using a 40 g silica gel cartridge to yield 225C (0.79 g, 3.6 mmol, 87% yield). $^1$H NMR (500 MHz, $CDCl_3$) δ 8.03 (dd, J=8.0, 1.1 Hz, 1H), 7.72 (dd, J=8.0, 1.4 Hz, 1H), 7.47 (m, 1H), 5.19 (s, 2H), 3.25 (s, 3H).

Example 225

Example 225 was synthesized from Intermediate 5 and 225C using General Route 5. MS(ESI) m/z 354 (M+H). $^1$H NMR (500 MHz, $CDCl_3$/$CD_3OD$, 1:1) δ 6.88 (d, J=8.0 Hz, 1H), 6.62 (d, J=8.0 Hz, 1H), 6.48-6.41 (m, 1H), 5.17 (s, 1H), 4.77 (s, 2H), 2.00 (s, 3H). The compound was isolated as a TFA salt.

Example 226: 7-(5-Pentafluorosulfanyl-2-fluorobenzyloxy)-3H-[1,2,3]triazolo[4,5-b]pyridin-5-amine

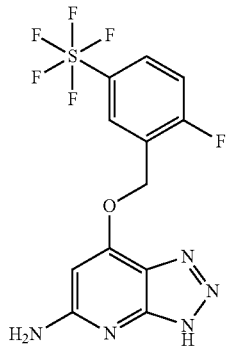 [SMILES: Nc1cc(OCc2cc(S(F)(F)(F)(F)F)ccc2F)c2nn[nH]c2n1]

226A: ((5-Pentafluorosulfanyl-2-fluoro)phenyl)methanol

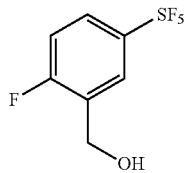

BH₃-THF (1.0 M in THF, 11 mL, 11 mmol) was added to a solution of 5-pentafluorosulfanyl-2-fluorophenyl) (1.0 g, 3.8 mmol) in THF (12 mL) and stirred over night at rt. The mixture was quenched slowly with MeOH and then concentrated. The crude product was purified by flash chromatography (loading in chloroform, 0% to 50% ethyl acetate in hexane over 15 min using a 40 g silica gel cartridge) to yield 226A (0.93 g, 3.69 mmol, 98% yield) as a clear oil. ¹H NMR (500 MHz, CDCl₃) δ 7.93 (dd, J=6.3, 2.8 Hz, 1H), 7.70 (ddd, J=8.9, 4.4, 2.9 Hz, 1H), 7.13 (t, J=9.1 Hz, 1H), 4.83 (d, J=6.1 Hz, 2H), 1.89 (t, J=6.1 Hz, 1H).

Example 226

Example 226 was synthesized from Intermediate 5 and 226A using General Route 5. MS(ESI) m/z 386 (M+H). ¹H NMR (500 MHz, DMSO-d₆) δ 8.27 (d, J=2.8 Hz, 1H), 8.16-8.04 (m, 1H), 7.60 (t, J=9.1 Hz, 1H), 6.54 (br. s., 2H), 6.12 (br. s., 1H), 5.52 (br. s., 2H). The compound was isolated as a formic acid salt.

Example 227: 7-((5-Chloro-2-(ethylsulfonyl)benzyl)oxy)-3H-[1,2,3]triazolo[4,5-b]pyridin-5-amine, TFA

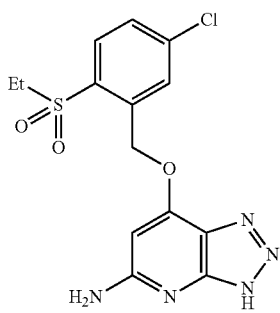 [SMILES: CCS(=O)(=O)c1ccc(Cl)cc1COc1cc(N)nc2[nH]nnc12]

227A: (4-Chloro-2-methylphenyl)(ethyl)sulfane

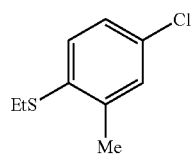

To a solution of 4-chloro-2-methylbenzenethiol (500 mg, 3.15 mmol) and TEA (0.439 mL, 3.15 mmol) in THF (10 mL) was added ethyl iodide (0.255 mL, 3.15 mmol). The reaction mixture was stirred at room temperature for 2 h and then acidified with 10 N HCl, extracted with EtOAc, washed with brine, dried over MgSO₄, and concentrated to obtain 227A as a colorless oil. ¹H NMR (500 MHz, CDCl₃) δ 7.20-7.14 (m, 2H), 7.14-7.10 (m, 1H), 2.89 (q, J=7.3 Hz, 2H), 2.34 (s, 3H), 1.31 (t, J=7.3 Hz, 3H).

227B: 4-Chloro-1-(ethylsulfonyl)-2-methylbenzene

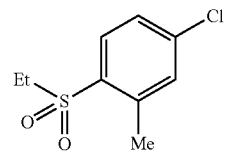 [SMILES: CCS(=O)(=O)c1ccc(Cl)cc1C]

To a solution of 227A (650 mg, 3.5 mmol) in DCM (20 mL) was added mCPBA (1800 mg, 10 mmol) and the resulting reaction mixture was heated at 80° C. overnight. The reaction mixture was diluted with EtOAc, washed with 1N KOH solution (3×) and brine, dried over MgSO₄ and concentrated to afford 227B as a white solid. ¹H NMR (500 MHz, CDCl₃) δ 7.93 (d, J=8.5 Hz, 1H), 7.41-7.31 (m, 2H), 7.26 (s, 1H), 3.14 (q, J=7.4 Hz, 2H), 2.67 (s, 3H), 1.27 (t, J=7.4 Hz, 3H).

227C: 2-(Bromomethyl)-4-chloro-1-(ethylsulfonyl)benzene

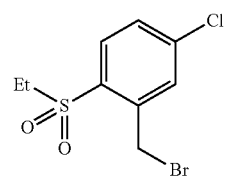 [SMILES: CCS(=O)(=O)c1ccc(Cl)cc1CBr]

A mixture of 227B (780 mg, 3.6 mmol), NBS (790 mg, 4.5 mmol) and AIBN (590 mg, 0.36 mmol) in CCl₄ (15 mL) was stirred at 80° C. for 2 days. The reaction mixture was partitioned between DCM and water, and the organic layer was separated. The aqueous phase was extracted with DCM, and the combined organic layers were dried (MgSO₄) and concentrated in vacuo to give a sticky oil. The material was used in the next reaction without further purification. MS(ESI) m/z 297/299 (M+H).

Example 227

Example 227 was synthesized from 227C and Intermediate 4 using General Route 3. MS(ESI) m/z 368 (M+H). ¹H NMR (500 MHz, CD$_3$OD) δ 8.06 (d, J=8.5 Hz, 1H), 7.96 (d, J=2.2 Hz, 1H), 7.81-7.66 (m, 1H), 6.40 (s, 1H), 5.84 (s, 2H), 3.41 (d, J=7.4 Hz, 2H), 1.24 (t, J=7.4 Hz, 3H). Analytical HPLC Method A: 5.17 min, 96%; Method B: 6.33 min, 100%. The compound was isolated as a TFA salt.

Example 228: 7-((2-(Benzylsulfonyl)-5-chlorobenzyl)oxy)-3H-[1,2,3]triazolo[4,5-b]pyridin-5-amine, TFA

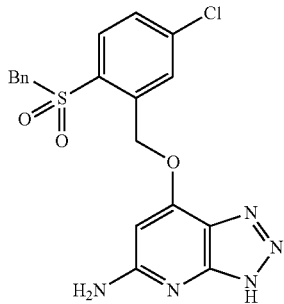 [SMILES: Nc1cc(OCc2cc(Cl)ccc2S(=O)(=O)Cc2ccccc2)c2nn[nH]c2n1]

228A: Benzyl(4-chloro-2-methylphenyl)sulfane

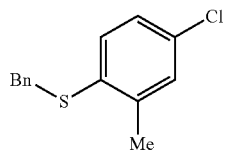

To a solution of 4-chloro-2-methylbenzenethiol (520 mg, 3.3 mmol) and TEA (0.46 mL, 3.3 mmol) in THF (10 mL) was added benzyl bromide (0.390 mL, 3.3 mmol). The reaction mixture was stirred at room temperature for 2 h. The reaction mixture was acidified with 1N HCl, extracted with EtOAc, washed with brine, dried over MgSO$_4$ and then concentrated to obtain a colorless oil. $^1$H NMR (500 MHz, CDCl$_3$) δ 7.34-7.04 (m, 8H), 4.03 (s, 2H), 2.28 (s, 3H).

228B: 1-(Benzylsulfonyl)-4-chloro-2-methylbenzene

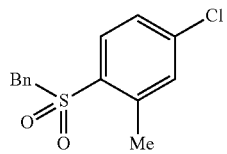

To a solution of 228A (800 mg, 3.2 mmol) in DCM (20 mL) was added mCPBA (1700 mg, 9.7 mmol), and the reaction mixture was heated at 80° C. for 18 h. The mixture was extracted with EtOAc (2×) and the combined organics were washed with 1 N KOH solution (2×), brine, dried over MgSO$_4$ and concentrated to obtain 228B as a white solid. $^1$H NMR (500 MHz, CDCl$_3$) δ 7.62 (d, J=8.5 Hz, 1H), 7.37-7.19 (m, 5H), 7.12-7.01 (m, 2H), 4.32 (s, 2H), 2.46 (s, 3H).

228C: 1-(Benzylsulfonyl)-2-(bromomethyl)-4-chlorobenzene

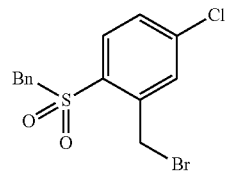

228C was synthesized using a method analogous to one used in 227C.

Example 228

Example 228 was synthesized from 228C and Intermediate 4 using General Route 3. MS(ESI) m/z 430 (M+H). $^1$H NMR (500 MHz, CD$_3$OD) δ 7.90 (d, J=1.9 Hz, 1H), 7.74 (d, J=8.5 Hz, 1H), 7.64-7.52 (m, 1H), 7.28-7.21 (m, 3H), 7.16 (dd, J=4.0, 3.4 Hz, 2H), 6.26 (s, 1H), 5.45 (s, 2H), 4.66 (s, 2H). Analytical HPLC Method A: 7.32 min, 93%; Method B: 7.32 min, 97%. The compound was isolated as a TFA salt.

Example 229: 2-(((5-Amino-3H-[1,2,3]triazolo[4,5-b]pyridin-7-yl)oxy)methyl)-N-methylbenzenesulfonamide, TFA

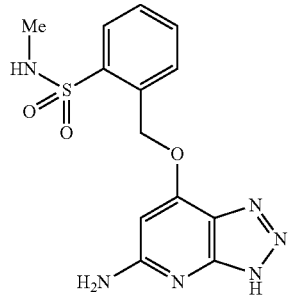 [SMILES: CNS(=O)(=O)c1ccccc1COc1cc(N)nc2[nH]nnc12]

229A: N,2-Dimethylbenzenesulfonamide

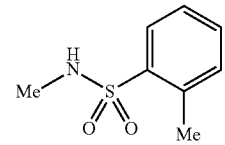

To a solution of 2-methylbenzene-1-sulfonyl chloride (1.0 g, 5.3 mmol) in acetone (10 mL) was added methylamine (2 M in methanol, 5.3 mL, 10 mmol). The reaction mixture was stirred at room temperature overnight. After concentration, the residue was dissolved in DCM, washed with saturated NaHCO$_3$ and brine (2×), dried over MgSO$_4$ and then concentrated to obtain 229A as a clear solid.

229B: 2-(Bromomethyl)-N-methylbenzenesulfonamide

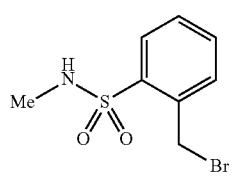

A mixture of 229A (0.92 g, 5.0 mmol), NBS (0.97 g, 5.5 mmol) and AIBN (0.25 g, 1.5 mmol) in CCl$_4$ (5 mL) was stirred at 65° C. overnight. The reaction mixture was diluted with DCM, washed with saturated NaHCO$_3$, brine, dried over MgSO$_4$ and concentrated to afford 229B. MS(ESI) m/z 264/266 (M+H).

Example 229

Example 229 was synthesized from 229B and Intermediate 4 using General Route 3. MS(ESI) m/z 335 (M+H). $^1$H NMR (500 MHz, CD$_3$OD) δ 8.00 (dd, J=7.8, 1.2 Hz, 1H), 7.92-7.84 (m, 1H), 7.72 (d, J=1.1 Hz, 1H), 7.63 (dd, J=7.7, 1.1 Hz, 1H), 6.41 (s, 1H), 5.86 (s, 2H), 2.61 (s, 3H). Analytical HPLC Method A: 4.3 min, 97%; Method B: 4.49 min, 91%. The compound was isolated as a TFA salt.

Example 230: 2-(((5-Amino-3H-[1,2,3]triazolo[4,5-b]pyridin-7-yl)oxy)methyl)benzenesulfonamide, TFA

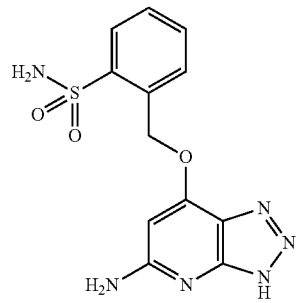 [SMILES: Nc1cc(OCc2ccccc2S(N)(=O)=O)c2nn[nH]c2n1]

230A: 2-Methylbenzenesulfonamide

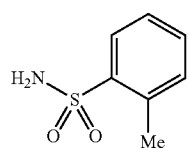

To a solution of 2-methylbenzene-1-sulfonyl chloride (1.0 g, 5.5 mmol) and in acetone (10 mL) was added ammonium hydroxide (2 mL). The reaction mixture was stirred at room temperature for 30 min. After concentration, the reddish residue was dissolved in DCM, washed with saturated NaHCO$_3$ and brine, dried over MgSO$_4$ and concentrated to obtain a reddish solid.

230B: 2-(Bromomethyl)benzenesulfonamide

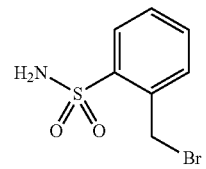 [SMILES: NS(=O)(=O)c1ccccc1CBr]

A mixture of 230A (780 mg, 4.6 mmol), NBS (940 mg, 5.3 mmol) and AIBN (230 mg, 1.4 mmol) in acetonitrile (5 mL) was stirred at 75° C. for 4 h. The reaction mixture was diluted with EtOAc, washed with saturated NaHCO$_3$ and brine, dried over MgSO$_4$ and then concentrated to obtain a brown solid. MS(ESI) m/z 250/252 (M+H).

Example 230

Example 230 was synthesized from 230B and Intermediate 4 using General Route 3. MS(ESI) m/z 321 (M+H). $^1$H NMR (500 MHz, CD$_3$OD) δ 8.14-8.05 (m, 1H), 7.88-7.80 (m, 1H), 7.74-7.65 (m, 1H), 7.64-7.55 (m, 1H), 6.43 (s, 1H), 5.90 (s, 2H). Analytical HPLC Method A: 3.46 min, 85%; Method B: 3.64 min, 78%. The compound was isolated as a TFA salt.

Example 231: 7-((4-Bromo-2-(methylsulfonyl)benzyl)oxy)-3H-[1,2,3]triazolo[4,5-b]pyridin-5-amine, TFA

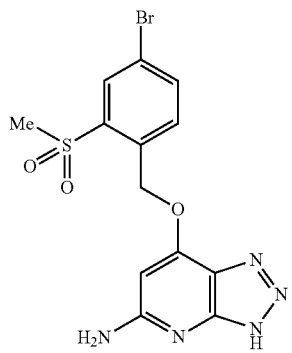 [SMILES: CS(=O)(=O)c1cc(Br)ccc1COc1cc(N)nc2[nH]nnc12]

231A: 4-Bromo-1-(bromomethyl)-2-(methylsulfonyl)benzene

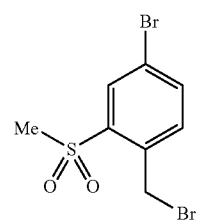

A mixture of 4-bromo-1-methyl-2-(methylsulfonyl)benzene (2.5 g, 10 mmol), NBS (2.1 g, 12 mmol) and AIBN (0.33 g, 2.0 mmol) in acetonitrile (30 mL) was stirred at 75° C. for 1 h. The reaction mixture was diluted with EtOAc, washed with saturated NaHCO$_3$ and brine, dried over MgSO$_4$ and then concentrated to obtain 231A as a white solid (3.3 g, 9.9 mmol, 99% yield).

Example 231

Example 231 was synthesized from 231A and Intermediate 4 using General Route 3. MS(ESI) m/z 399 (M+H). $^1$H NMR (500 MHz, CDCl$_3$/CD$_3$OD, 1:1) δ 8.29-8.18 (m, 1H), 7.92-7.86 (m, 1H), 7.80-7.69 (m, 1H), 6.19 (s, 1H), 5.76 (s, 2H), 3.34 (d, J=1.9 Hz, 3H).

Example 232: 7-((2-(Methylsulfonyl)benzyl)oxy)-3H-[1,2,3]triazolo[4,5-b]pyridin-5-amine

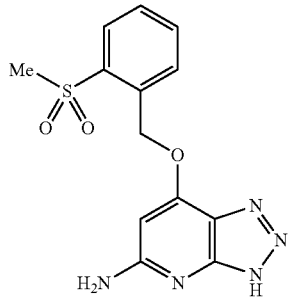 [SMILES: CS(=O)(=O)c1ccccc1COc1cc(N)nc2[nH]nnc12]

7-((4-Bromo-2-(methylsulfonyl)benzyl)oxy)-N,3-ditrityl-3H-[1,2,3]triazolo[4,5-b]pyridin-5-amine (45 mg, 0.051 mmol), pyridin-3-ylboronic acid (6.3 mg, 0.051 mmol), potassium carbonate (14 mg, 0.10 mmol), and tetrakis(triphenylphosphine)palladium(0) (5.9 mg, 5.1 µmol) were added to a vial, which was then evacuated and back-filled with argon three times. Degassed DMF (0.45 mL) and water (0.05 mL) were added. The reaction was stirred at 90° C. overnight. The above product was observed as a side product and purified by preparatory HPLC. MS(ESI) m/z 320 (M+H). $^1$H NMR (500 MHz, CDCl$_3$/CD$_3$OD, 1:1) δ 8.19-8.09 (m, 1H), 7.90-7.76 (m, 2H), 7.74-7.65 (m, 1H), 6.32 (s, 1H), 5.83 (s, 2H), 3.29 (s, 3H).

Example 233: 7-((4-Bromo-2,6-difluorobenzyl)oxy)-3H-[1,2,3]triazolo[4,5-b]pyridin-5-amine, TFA

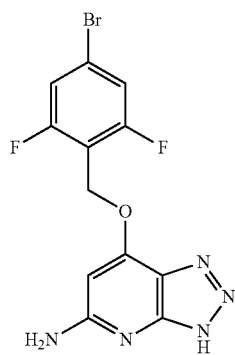 [SMILES: Nc1cc(OCc2c(F)cc(Br)cc2F)c2nn[nH]c2n1]

Example 233 was synthesized from 5-bromo-2-(bromomethyl)-1,3-difluorobenzene and Intermediate 4 using General Route 3. MS(ESI) m/z 357 (M+H). $^1$H NMR (500 MHz, DMSO-d$_6$) δ 7.64 (d, J=7.2 Hz, 2H), 6.53 (br. s., 2H), 6.11 (s, 1H).

Example 234: 7-((2,6-Dichlorobenzyl)oxy)-3H-[1,2,3]triazolo[4,5-b]pyridin-5-amine

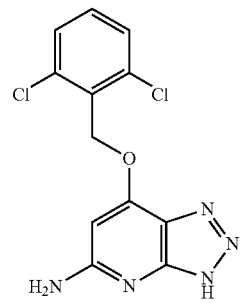 [SMILES: Nc1cc(OCc2c(Cl)cccc2Cl)c2nn[nH]c2n1]

Example 234 was synthesized from 1,3-dichloro-2-(chloromethyl)benzene and Intermediate 5 using General Route 5. MS(ESI) m/z 310 (M+H). $^1$H NMR (500 MHz, CDCl$_3$/CD$_3$OD, 1:1) δ 7.52-7.45 (m, 2H), 7.42 (s, 1H), 6.42 (s, 1H), 5.70 (s, 2H). The compound was isolated as a TFA salt.

Example 235: 7-((3-Bromo-2-chloro-6-fluorobenzyl)oxy)-3H-[1,2,3]triazolo[4,5-b]pyridin-5-amine

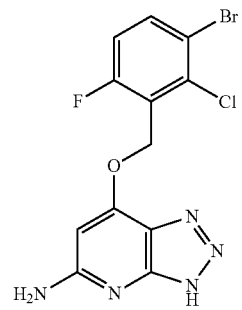 [SMILES: Nc1cc(OCc2c(F)ccc(Br)c2Cl)c2nn[nH]c2n1]

Example 235 was synthesized from (3-bromo-2-chloro-6-fluorophenyl)methanol and Intermediate 4 using General Route 3. MS(ESI) m/z 373 (M+H). $^1$H NMR (500 MHz, DMSO-d$_6$) δ 8.05-7.90 (m, 1H), 7.42 (t, J=8.9 Hz, 1H), 6.25 (br. s., 1H), 5.51 (s, 2H). The compound was isolated as a TFA salt.

Example 236: 7-((3-Bromo-2,6-difluorobenzyl)oxy)-3H-[1,2,3]triazolo[4,5-b]pyridin-5-amine

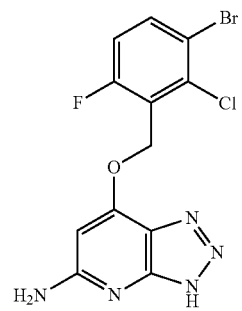 [SMILES: Nc1cc(OCc2c(F)ccc(Br)c2Cl)c2nn[nH]c2n1]

Example 236 was synthesized from (3-bromo-2,6-difluorophenyl)methanol and Intermediate 5 using General Route 5. MS(ESI) m/z 355 (M+H). $^1$H NMR (500 MHz, DMSO-$d_6$) δ 8.00-7.87 (m, 1H), 7.29 (s, 1H), 6.53 (br. s., 2H), 6.13 (s, 1H), 5.44 (s, 2H).

Example 237: 7-((2-Chloro-6-fluorobenzyl)oxy)-3H-[1,2,3]triazolo[4,5-b]pyridin-5-amine

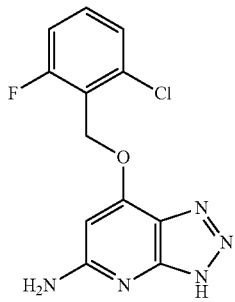 [SMILES: Nc1cc(OCc2c(F)cccc2Cl)c2nn[nH]c2n1]

Example 237 was synthesized from 1-chloro-2-(chloromethyl)-3-fluorobenzene and Intermediate 5 using General Route 5. MS(ESI) m/z 294 (M+H). $^1$H NMR (500 MHz, DMSO-$d_6$) δ 7.60 (d, J=6.3 Hz, 1H), 7.50 (d, J=8.0 Hz, 1H), 7.40 (t, J=8.9 Hz, 1H), 6.32-6.18 (m, 1H), 5.46 (s, 2H).

Example 238: 7-((2-(Difluoromethoxy)benzyl)oxy)-3H-[1,2,3]triazolo[4,5-b]pyridin-5-amine

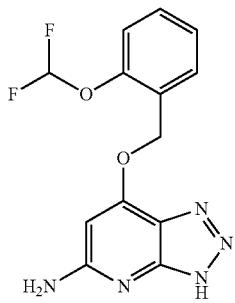 [SMILES: Nc1cc(OCc2ccccc2OC(F)F)c2nn[nH]c2n1]

Example 238 was synthesized from Intermediate 4 and (2-(difluoromethoxy)phenyl)methanol using General Route 3. MS(ESI) m/z 308 (M+H). The compound was isolated as a TFA salt.

Example 239: 7-((2-(Trifluoromethyl)benzyl)oxy)-3H-[1,2,3]triazolo[4,5-b]pyridin-5-amine

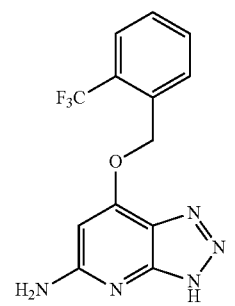 [SMILES: Nc1cc(OCc2ccccc2C(F)(F)F)c2nn[nH]c2n1]

Example 239 was synthesized from Intermediate 4 and (2-(trifluoromethyl)phenyl)methanol using General Route 3. MS(ESI) m/z 310 (M+H).

Example 240: 7-((4-Bromo-2-(trifluoromethoxy)benzyl)oxy)-3H-[1,2,3]triazolo[4,5-b]pyridin-5-amine

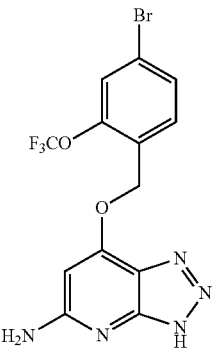 [SMILES: Nc1cc(OCc2ccc(Br)cc2OC(F)(F)F)c2nn[nH]c2n1]

Example 240 was synthesized from Intermediate 4 and (4-bromo-2-(trifluoromethoxy)phenyl)methanol using General Route 3. MS(ESI) m/z 405 (M+H). The compound was isolated as a TFA salt.

Example 241: 7-((5-Chloro-2-(trifluoromethyl)benzyl)oxy)-3H-[1,2,3]triazolo[4,5-b]pyridin-5-amine

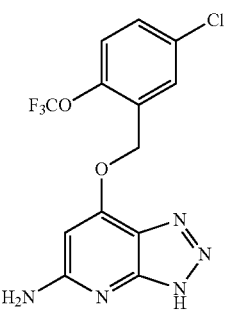 [SMILES: Nc1cc(OCc2cc(Cl)ccc2OC(F)(F)F)c2nn[nH]c2n1]

Example 241 was synthesized from Intermediate 4 and (5-chloro-2-(trifluoromethyl)phenyl)methanol using General Route 3. MS(ESI) m/z 344 (M+H).

Example 242: 7-((4-Bromo-2-methoxybenzyl)oxy)-3H-[1,2,3]triazolo[4,5-b]pyridin-5-amine

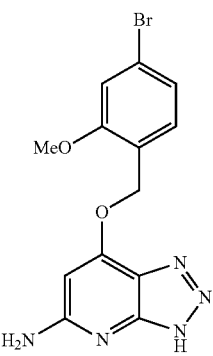 [SMILES: COc1cc(Br)ccc1COc1cc(N)nc2[nH]nnc12]

Example 242 was synthesized from Intermediate 4 and (4-bromo-2-methoxyphenyl)methanol using General Route 3. MS(ESI) m/z 350 (M+H).

Example 243: 7-((2-Methoxy-4-(1H-pyrazol-1-yl)benzyl)oxy)-3H-[1,2,3]triazolo[4,5-b]pyridin-5-amine

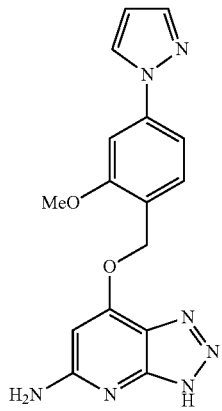 [SMILES: COc1cc(-n2cccn2)ccc1COc1cc(N)nc2[nH]nnc12]

243A: 7-((4-Bromo-2-methoxybenzyl)oxy)-N,3-ditrityl-3H-[1,2,3]triazolo[4,5-b]pyridin-5-amine

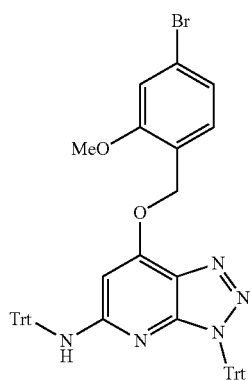

243A was synthesized by an analogous procedure to Intermediate 5D, starting from Example 242. MS(ESI) m/z 835 (M+H).

Example 243

243A (0.055 g, 0.066 mmol), 1H-pyrazole (4.5 mg, 0.066 mmol), $Cs_2CO_3$ (0.064 g, 0.20 mmol), and copper(I) iodide (0.22 µl, 6.6 µmol) were added to a vial, which was then evacuated and back-filled with argon three times. Degassed DMF (0.26 mL) was added, followed by N1,N2-dimethylethane-1,2-diamine (5.8 mg, 0.066 mmol). The reaction was stirred at 90° C. overnight. The reaction was diluted with $CH_2Cl_2$ (4 mL), filtered through a syringe filter and concentrated. TFA (0.07 mL) was added to a solution of 7-((2-methoxy-4-(1H-pyrazol-1-yl)benzyl)oxy)-N,3-ditrityl-3H-[1,2,3]triazolo[4,5-b]pyridin-5-amine (0.054 g, 0.066 mmol) in dichloromethane (0.6 mL) containing two drops of water and the subsequent solution was stirred at room temperature for 2 hours. The reaction was concentrated and purified by preparatory HPLC to yield Example 243 (21 mg, 60% yield). MS(ESI) m/z 338 (M+H). The compound was isolated as a TFA salt.

Example 244: 7-((4-(1H-Imidazol-1-yl)-2-(trifluoromethoxy)benzyl)oxy)-3H-[1,2,3]triazolo[4,5-b]pyridin-5-amine

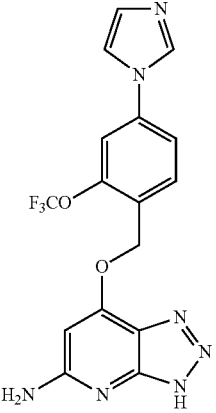 [SMILES: Nc1cc(OCc2ccc(-n3ccnc3)cc2OC(F)(F)F)c2nn[nH]c2n1]

244A: 7-((4-Bromo-2-(trifluoromethoxy)benzyl)oxy)-N,3-ditrityl-3H-[1,2,3]triazolo[4,5-b]pyridin-5-amine

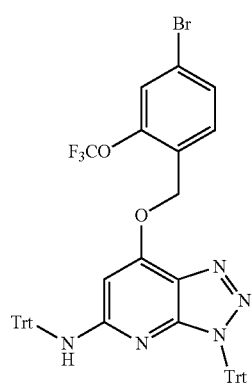

244A was synthesized by an analogous procedure to Intermediate 5D, starting from Example 240. MS(ESI) m/z 876 (M+H).

Example 244

244A (0.1 g, 0.1 mmol), 1H-imidazole (7 mg, 0.1 mmol), $Cs_2CO_3$ (0.11 g, 0.34 mmol), and copper(I) iodide (2 mg, 0.011 mmol) were added to a vial, which was then evacuated and back-filled with argon three times. Degassed DMF (0.45 mL) was added, followed by N1,N2-dimethylethane-1,2-diamine (10 mg, 0.113 mmol). The reaction was stirred at 90° C. overnight. Upon reaction completion, the reaction was diluted with $CH_2Cl_2$, filtered, and concentrated to dryness. The residue was dissolved in $CH_2Cl_2$ (4 mL) and TFA (1 mL) was added to produce a bright yellow solution. After 1 minute, LCMS showed reaction completion. Triethylsilane (0.03 mL, 0.2 mmol) was added until the bright yellow color dissipated. The reaction mixture was then concentrated in vacuo and purified by preparatory HPLC to yield Example 244 (18 mg, 44% yield). MS(ESI) m/z 392 (M+H). $^1$H NMR (500 MHz, DMSO-$d_6$) δ 8.41 (s, 1H), 7.94-7.78 (m, 4H), 7.16 (s, 1H), 6.49 (br. s., 2H), 6.10 (s, 1H), 5.49 (s, 2H).

Example 245: 2-(((5-Amino-3H-[1,2,3]triazolo[4,5-b]pyridin-7-yl)oxy)methyl)-5-bromobenzonitrile

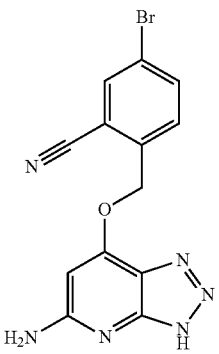 [SMILES: N#Cc1cc(Br)ccc1COc1cc(N)nc2[nH]nnc12]

245A: 5-Bromo-2-(((3-trityl-5-(tritylamino)-3H-[1,2,3]triazolo[4,5-b]pyridin-7-yl)oxy)methyl)benzonitrile

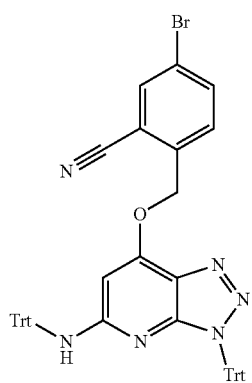

DMSO (0.5 mL) was added to a vial containing Intermediate 5 (0.05 g, 0.08 mmol), 5-bromo-2-(bromomethyl)benzonitrile (0.022 g, 0.079 mmol), and potassium carbonate (11 mg, 0.079 mmol) and the reaction mixture was stirred at rt for 1 h. Crude 245A was used in the next step to produce Example 245.

Example 245

The crude 245A was diluted with DCM (5 mL) and filtered. TFA (1 mL) was added to the solution to produce a bright yellow color. After 1 minute, $Et_3SiH$ (0.026 mL, 0.16 mmol) was added. The reaction was concentrated to dryness and purified by preparatory HPLC. MS(ESI) m/z 346 (M+H). $^1$H NMR (500 MHz, DMSO-$d_6$) δ 8.34-8.24 (m, 1H), 8.09-8.00 (m, 1H), 7.78-7.69 (m, 1H), 6.17-6.10 (m, 1H), 5.58-5.51 (m, 2H).

The following compounds were prepared in a manner similar to experimental procedures that are described in Example 245 using Intermediate 5 and the appropriate benzylic bromide as starting materials according to General Route 5. Examples 247, 249 and 250 were isolated as TFA salts.

| Ex. No. | Structure | Name | MS(ESI) (M + H)+ |
|---|---|---|---|
| 246 | (structure shown) | 7-((2-chloro-4-(methylsulfonyl)benzyl)oxy)-3H-[1,2,3]triazolo[4,5-b]pyridin-5-amine | 354 |
| 247 | (structure shown) | 2-(((5-amino-3H-[1,2,3]triazolo[4,5-b]pyridin-7-yl)oxy)methyl)benzonitrile | 267 |

-continued
| Ex. No. | Structure | Name | MS(ESI) (M + H)+ |
|---|---|---|---|
| 248 | 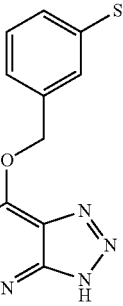 | 7-((3-((trifluoromethyl)thio)benzyl)oxy)-3H-[1,2,3]triazolo[4,5-b]pyridin-5-amine | 342 |
| 249 | 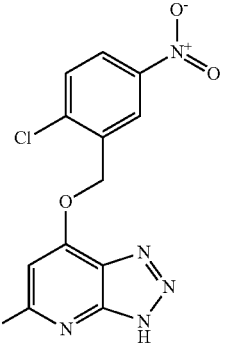 | 7-((2-chloro-5-nitrobenzyl)oxy)-3H-[1,2,3]triazolo[4,5-b]pyridin-5-amine | 321 |
| 250 | 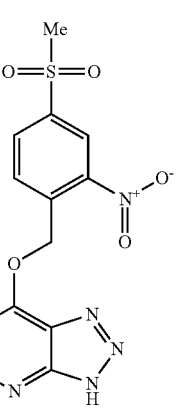 | 7-((4-(methylsulfonyl)-2-nitrobenzyl)oxy)-3H-[1,2,3]triazolo[4,5-b]pyridin-5-amine | 365 |
| 251 | 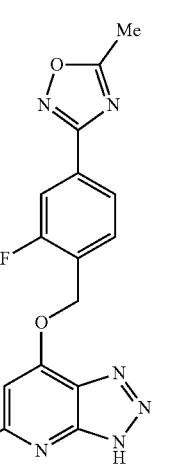 | 7-((2-fluoro-4-(5-methyl-1,2,4-oxadiazol-3-yl)benzyl)oxy)-3H-[1,2,3]triazolo[4,5-b]pyridin-5-amine | 342 |

Example 252: 7-((4,5-Dichloro-2-methoxybenzyl)oxy)-3H-[1,2,3]triazolo[4,5-b]pyridin-5-amine

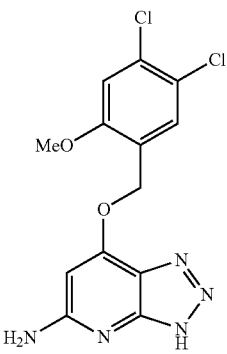 [SMILES: COc1cc(Cl)c(Cl)cc1COc1cc(N)nc2[nH]nnc12]

To a stirred solution of 3-trityl-5-(tritylamino)-3H-[1,2,3]triazolo[4,5-b]pyridin-7-ol (0.070 g, 0.11 mmol), (4,5-dichloro-2-methoxyphenyl)methanol (0.023 g, 0.11 mmol), and triphenylphosphine (0.043 g, 0.17 mmol) in THF (0.6 mL) was added DIAD (0.032 mL, 0.17 mmol) at rt and the solution was allowed to stir for 2 h. The solution was concentrated to dryness and purified by flash column chromatography, eluting with a linear gradient of 0% to 30% EtOAc in hexanes to yield 7-((4,5-dichloro-2-methoxybenzyl)oxy)-N,3-ditrityl-3H-[1,2,3]triazolo[4,5-b]pyridin-5-amine as a white solid. This intermediate was dissolved in DCM (4 mL). TFA (1 mL) was added, followed by triethylsilane (0.02 mL, 0.1 mmol). The reaction was concentrated to dryness and purified by preparatory HPLC to yield Example 252 (4 mg, 20% yield). MS(ESI) 341 (M+H)$^+$. $^1$H NMR (500 MHz, DMSO-d$_6$) δ 7.69 (s, 1H), 7.40 (s, 1H), 6.46 (br. s., 2H), 6.07 (s, 1H), 5.29 (s, 2H).

Example 253: 7-((2-(1H-1,2,4-Triazol-1-yl)benzyl)oxy)-3H-[1,2,3]triazolo[4,5-b]pyridin-5-amine

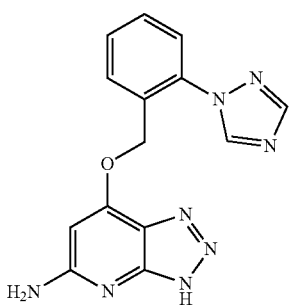 [SMILES: Nc1cc(OCc2ccccc2-n2cncn2)c2nn[nH]c2n1]

Example 253 was synthesized from Intermediate 5 and (2-(1H-1,2,4-triazol-1-yl)phenyl)methanol using General Route 5. MS(ESI) m/z 309 (M+H).

Example 254: 2-(((5-Amino-3H-[1,2,3]triazolo[4,5-b]pyridin-7-yl)oxy)methyl)benzamide

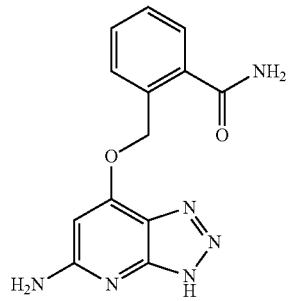 [SMILES: NC(=O)c1ccccc1COc1cc(N)nc2[nH]nnc12]

Example 254 was synthesized from Intermediate 5 and 2-(hydroxymethyl)benzamide using General Route 5. MS(ESI) m/z 285 (M+H).

Example 255: 7-((2-(1H-Pyrazol-1-yl)benzyl)oxy)-3H-[1,2,3]triazolo[4,5-b]pyridin-5-amine

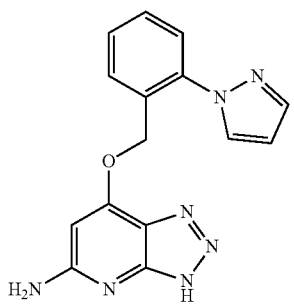 [SMILES: Nc1cc(OCc2ccccc2-n2cccn2)c2nn[nH]c2n1]

Example 255 was synthesized from Intermediate 5 and (2-(1H-pyrazol-1-yl)phenyl)methanol using General Route 5. MS(ESI) m/z 308 (M+H). The compound was isolated as a TFA salt.

The following compounds were prepared in a manner similar to experimental procedures that are described in Example 244 using Example 244A or 245A as starting material. Examples 257, 264, 273, 279 and 280 were isolated as TFA salts.

| Ex. No. | Structure | Name | MS(ESI) $^1$H NMR |
|---|---|---|---|
| 256 | 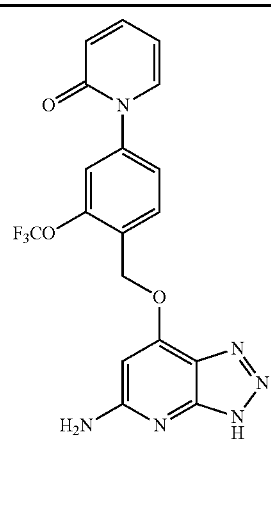 | 1-(4-(((5-amino-3H-[1,2,3]triazolo[4,5-b]pyridin-7-yl)oxy)methyl)-3-(trifluoromethoxy)phenyl)pyridin-2(1H)-one | 419 (M + H)$^+$. (500 MHz, CD$_3$OD/CDCl$_3$, 1:1) δ 7.91 (d, J = 8.0 Hz, 1H), 7.66-7.57 (m, 1H), 7.53 (dd, J = 6.9, 1.7 Hz, 1H), 7.51-7.44 (m, 2H), 6.69 (d, J = 9.1 Hz, 1H), 6.54-6.44 (m, 1H), 6.33 (s, 1H), 5.60 (s, 2H) |

| Ex. No. | Structure | Name | MS(ESI) ¹H NMR |
|---|---|---|---|
| 257 | 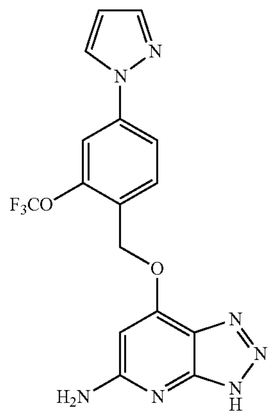 [SMILES: Nc1cc(OCc2ccc(-n3cccn3)cc2OC(F)(F)F)c2nn[nH]c2n1] | 7-((4-(1H-pyrazol-1-yl)-2-(trifluoromethoxy)benzoyl)oxy)-3H-[1,2,3]triazolo[4,5-b]pyridin-5-amine | 392 (M + H)⁺. (500 MHz, CD₃OD/CDCl₃, 1:1) δ 8.18 (d, J = 2.5 Hz, 1H), 7.87-7.80 (m, 2H), 7.80-7.73 (m, 2H), 7.63-7.57 (m, 1H), 6.57 (m, 1H), 6.37 (s, 1H), 5.56 (s, 2H). |
| 258 | 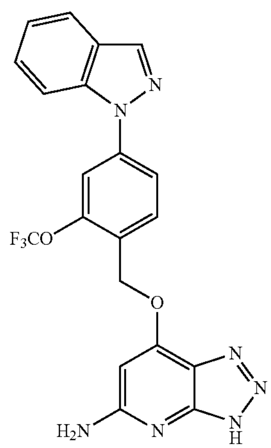 [SMILES: Nc1cc(OCc2ccc(-n3ncc4ccccc43)cc2OC(F)(F)F)c2nn[nH]c2n1] | 7-((4-(1H-indazol-1-yl)-2-(trifluoromethoxy)benzyl)oxy)-3H-[1,2,3]triazolo[4,5-b]pyridin-5-amine | 442 (M + H)⁺. (500 MHz, DMSO-d₆) δ 9.32-9.23 (m, 1H), 8.26 (m, 1H), 8.23 (s, 1H), 7.95 (m, 1H), 7.80 (d, J = 8.5 Hz, 1H), 7.75 (m, 1H), 7.36 (m, 1H), 7.18-7.09 (m, 1H), 6.53 (br. s., 2H), 6.13 (s, 1H), 5.53 (s, 2H) |
| 259 | 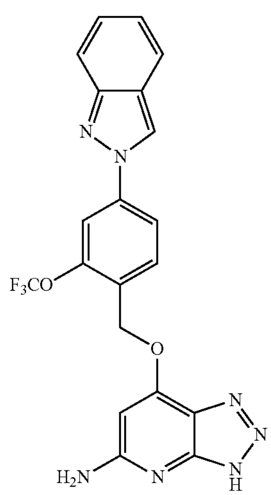 [SMILES: Nc1cc(OCc2ccc(-n3cc4ccccc4n3)cc2OC(F)(F)F)c2nn[nH]c2n1] | 7-((4-(2H-indazol-2-yl)-2-(trifluoromethoxy)benzyl)oxy)-3H-[1,2,3]triazolo[4,5-b]pyridin-5-amine | 442 (M + H)⁺. (500 MHz, DMSO-d₆) δ 8.49 (s, 1H), 8.04-7.91 (m, 4H), 7.87 (s, 1H), 7.61-7.52 (m, 1H), 7.38-7.30 (m, 1H), 6.52 (br. s., 2H), 6.14 (s, 1H), 5.54 (s, 2H). |

| Ex. No. | Structure | Name | MS(ESI) ¹H NMR |
|---|---|---|---|
| 260 | 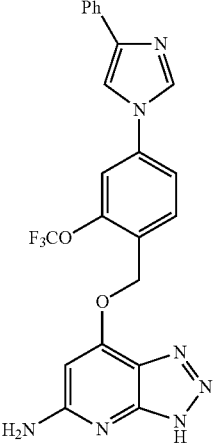 [SMILES: Nc1cc(OCc2ccc(-n3cnc(-c4ccccc4)c3)cc2OC(F)(F)F)c2nn[nH]c2n1] | 7-((4-(4-phenyl-1H-imidazol-1-yl)-2-(trifluoromethoxy)benzyl)oxy)-3H-[1,2,3]triazolo[4,5-b]pyridin-5-amine | 468 (M + H)⁺. (500 MHz, DMSO-$d_6$) δ 8.50 (d, J = 1.4 Hz, 1H), 8.44 (d, J = 1.4 Hz, 1H), 8.00-7.84 (m, 5H), 7.49-7.38 (m, 2H), 7.34-7.22 (m, 1H), 6.52 (br. s., 2H), 6.12 (s, 1H), 5.50 (s, 2H). |
| 261 | 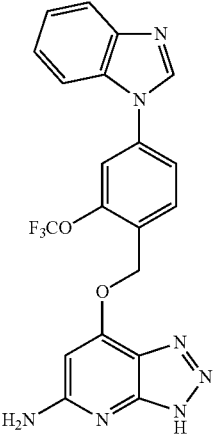 [SMILES: Nc1cc(OCc2ccc(-n3cnc4ccccc43)cc2OC(F)(F)F)c2nn[nH]c2n1] | 7-((4-(1H-benzo[d]imidazol-1-yl)-2-(trifluoromethoxy)benzyl)oxy)-3H-[1,2,3]triazolo[4,5-b]pyridin-5-amine | 442 (M + H)⁺. (500 MHz, DMSO-$d_6$) δ 8.66 (s, 1H), 7.99 (s, 1H), 7.92-7.87 (m, 2H), 7.82 (d, J = 7.4 Hz, 1H), 7.68 (d, J = 7.7 Hz, 1H), 7.36 (s, 2H), 6.53 (br. s., 2H), 6.15 (s, 1H), 5.56 (s, 2H). |
| 264 | 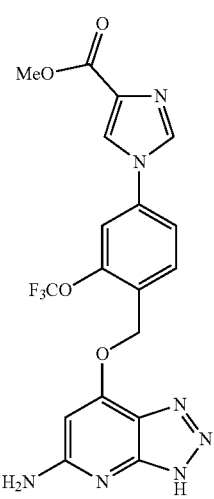 [SMILES: COC(=O)c1cn(-c2ccc(COc3cc(N)nc4[nH]nnc34)c(OC(F)(F)F)c2)cn1] | methyl 1-(4-(((5-amino-3H-[1,2,3]triazolo[4,5-b]pyridin-7-yl)oxy)methyl)-3-(trifluoromethoxy)phenyl)-1H-imidazole-4-carboxylate | 450 (M + H)⁺ |

| Ex. No. | Structure | Name | MS(ESI) ¹H NMR |
|---|---|---|---|
| 265 | 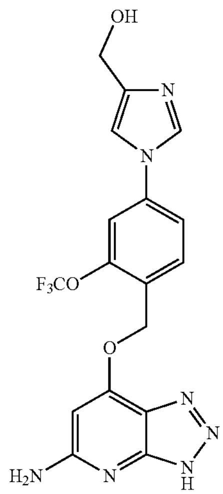 [SMILES: Nc1cc(OCc2ccc(-n3cnc(CO)c3)cc2OC(F)(F)F)c2nn[nH]c2n1] | (1-(4-(((5-amino-3H-[1,2,3]triazolo[4,5-b]pyridin-7-yl)oxy)methyl)-3-(trifluoromethoxy)phenyl)-1H-imidazol-4-yl)methanol | 422 (M + H)⁺. (500 MHz, DMSO-d₆) δ 8.34 (d, J = 0.8 Hz, 1H), 7.89-7.78 (m, 3H), 7.72 (s, 1H), 6.44 (br. s., 2H), 6.09 (s, 1H), 5.54-5.45 (m, 2H), 4.43 (s, 2H). |
| 266 | 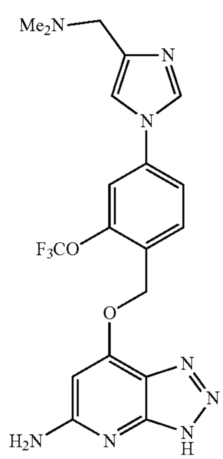 [SMILES: CN(C)Cc1cn(-c2ccc(COc3cc(N)nc4[nH]nnc34)c(OC(F)(F)F)c2)cn1] | 7-((4-(4-((dimethylamino)methyl)-1H-imidazol-1-yl)-2-(trifluoromethoxy)benzyl)oxy)-3H-[1,2,3]triazolo[4,5-b]pyridin-5-amine | 449 (M + H)⁺. (500 MHz, DMSO-d₆) δ 8.06 (s, 1H), 7.89 (d, J = 8.3 Hz, 1H), 7.75-7.68 (m, 1H), 7.55 (d, J = 1.1 Hz, 1H), 7.04 (d, J = 1.1 Hz, 1H), 6.50 (br. s., 2H), 6.12 (s, 1H), 5.51 (s, 2H), 3.41 (s, 2H), 2.15 (s, 6H). |
| 267 | 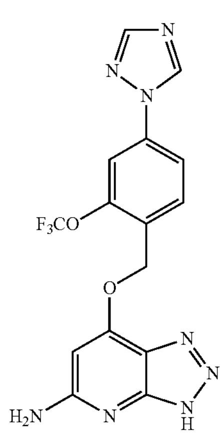 [SMILES: Nc1cc(OCc2ccc(-n3cncn3)cc2OC(F)(F)F)c2nn[nH]c2n1] | 7-((4-(1H-1,2,4-triazol-1-yl)-2-(trifluoromethoxy)benzyl)oxy)-3H-[1,2,3]triazolo[4,5-b]pyridin-5-amine | 393 (M + H)⁺. (500 MHz, DMSO-d₆) δ 9.50-9.40 (m, 1H), 8.39-8.27 (m, 1H), 8.11-7.90 (m, 3H), 6.59-6.45 (m, 2H), 6.17-6.06 (m, 1H), 5.59-5.48 (m, 2H). |

-continued

| Ex. No. | Structure | Name | MS(ESI) $^1$H NMR |
|---|---|---|---|
| 268 | 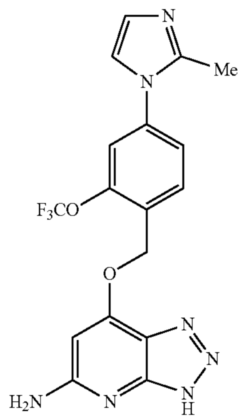 [SMILES: Cc1nccn1-c1ccc(COc2cc(N)nc3[nH]nnc23)c(OC(F)(F)F)c1] | 7-((4-(2-methyl-1H-imidazol-1-yl)-2-(trifluoromethoxy)benzyl)oxy)-3H-[1,2,3]triazolo[4,5-b]pyridin-5-amine | 406 (M + H)$^+$ |
| 270 | 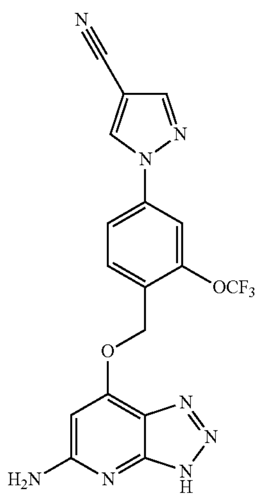 [SMILES: N#Cc1cnn(-c2ccc(COc3cc(N)nc4[nH]nnc34)c(OC(F)(F)F)c2)c1] | 1-(4-(((5-amino-3H-[1,2,3]triazolo[4,5-b]pyridin-7-yl)oxy)methyl)-3-(trifluoromethoxy)phenyl)-1H-pyrazole-4-carbonitrile | 417 (M + H)$^+$ |
| 271 | 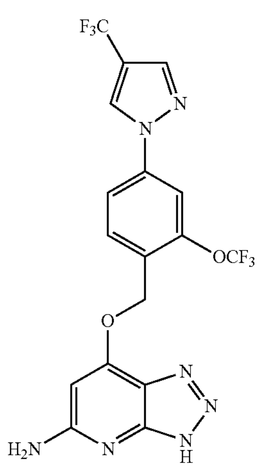 [SMILES: Nc1cc(OCc2ccc(-n3cc(C(F)(F)F)cn3)cc2OC(F)(F)F)c2nn[nH]c2n1] | 7-((2-(trifluoromethoxy)-4-(4-(trifluoromethyl)-1H-pyrazol-1-yl)benzyl)oxy)-3H-[1,2,3]triazolo[4,5-b]pyridin-5-amine | 460 (M + H)$^+$ |

| Ex. No. | Structure | Name | MS(ESI) $^1$H NMR |
|---|---|---|---|
| 272 | 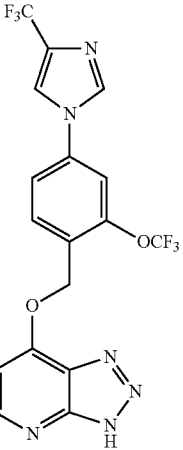 | 7-((2-(trifluoromethoxy)-4-(4-(trifluoromethyl)-1H-imidazol-1-yl)benzyl)oxy)-3H-[1,2,3]triazolo[4,5-b]pyridin-5-amine | 460 (M + H)$^+$ |
| 273 | 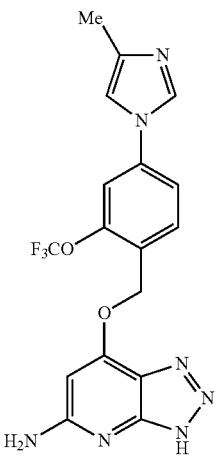 [SMILES: Cc1cn(-c2ccc(COc3cc(N)nc4[nH]nnc34)c(OC(F)(F)F)c2)cn1] | 7-((4-(4-methyl-1H-imidazol-1-yl)-2-(trifluoromethoxy)benzyl)oxy)-3H-[1,2,3]triazolo[4,5-b]pyridin-5-amine | 406 (M + H)$^+$ |
| 274 | 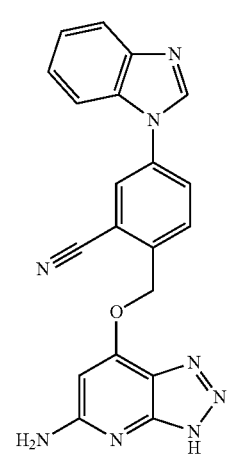 [SMILES: N#Cc1cc(-n2cnc3ccccc32)ccc1COc1cc(N)nc2[nH]nnc12] | 2-(((5-amino-3H-[1,2,3]triazolo[4,5-b]pyridin-7-yl)oxy)methyl)-5-(1H-benzo[d]imidazol-1-yl)benzonitrile | 383 (M + H)$^+$ |

-continued

| Ex. No. | Structure | Name | MS(ESI) ¹H NMR |
|---|---|---|---|
| 276 | 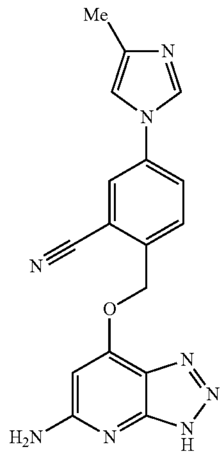 [SMILES: Cc1cn(-c2ccc(COc3cc(N)nc4[nH]nnc34)c(C#N)c2)cn1] | 2-(((5-amino-3H-[1,2,3]triazolo[4,5-b]pyridin-7-yl)oxy)methyl)-5-(4-methyl-1H-imidazol-1-yl)benzonitrile | 347 (M + H)+ |
| 277 | 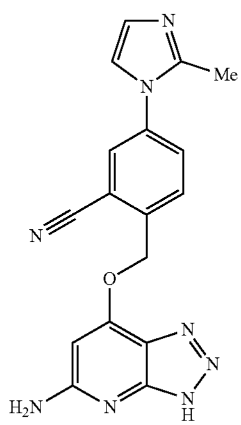 [SMILES: Cc1nccn1-c1ccc(COc2cc(N)nc3[nH]nnc23)c(C#N)c1] | 2-(((5-amino-3H-[1,2,3]triazolo[4,5-b]pyridin-7-yl)oxy)methyl)-5-(2-methyl-1H-imidazol-1-yl)benzonitrile | 347 (M + H)+ |
| 279 | 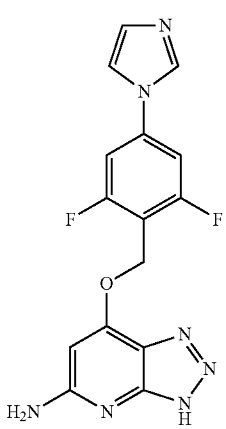 [SMILES: Nc1cc(OCc2c(F)cc(-n3ccnc3)cc2F)c2nn[nH]c2n1] | 7-((2,6-difluoro-4-(1H-imidazol-1-yl)benzyl)oxy)-3H-[1,2,3]triazolo[4,5-b]pyridin-5-amine | 344 (M + H)+ |

| Ex. No. | Structure | Name | MS(ESI) ¹H NMR |
|---|---|---|---|
| 280 | 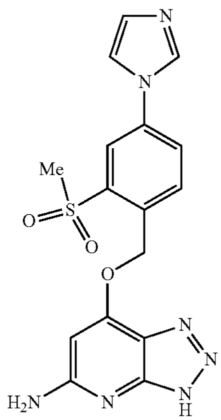 [SMILES: CS(=O)(=O)c1cc(-n2ccnc2)ccc1COc1cc(N)nc2[nH]nnc12] | 7-((4-(1H-imidazol-1-yl)-2-(methylsulfonyl)benzyl)oxy)-3H-[1,2,3]triazolo[4,5-b]pyridin-5-amine | 386 (M + H)⁺. (500 MHz, CD₃OD/CDCl₃, 1:1) δ 8.48 (s, 1H), 8.29 (s, 1H), 8.11-8.04 (m, 1H), 7.97 (d, J = 8.3 Hz, 1H), 7.72 (s, 1H), 7.34 (s, 1H), 6.36-6.27 (m, 1H), 5.89 (s, 2H), 3.40 (s, 3H). |
| 281 | 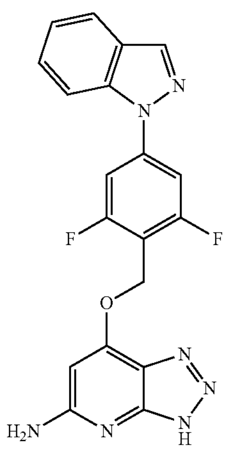 [SMILES: Nc1cc(OCc2c(F)cc(-n3ncc4ccccc43)cc2F)c2nn[nH]c2n1] | 7-((2,6-difluoro-4-(1H-indazol-1-yl)benzyl)oxy)-3H-[1,2,3]triazolo[4,5-b]pyridin-5-amine | 394 (M + H)⁺. (500 MHz, DMSO-d₆) δ 8.52 (s, 1H), 8.14-8.04 (m, 1H), 7.96 (d, J = 8.3 Hz, 1H), 7.79-7.71 (m, 2H), 7.60 (m, 1H), 7.42-7.32 (m, 1H), 6.22 (br. s., 1H), 5.48 (s, 2H). |
| 282 | 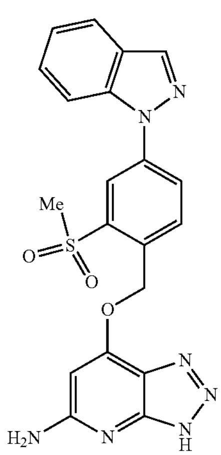 [SMILES: CS(=O)(=O)c1cc(-n2ncc3ccccc32)ccc1COc1cc(N)nc2[nH]nnc12] | 7-((4-(1H-indazol-1-yl)-2-(methylsulfonyl)benzyl)oxy)-3H-[1,2,3]triazol[4,5-b]pyridin-5-amine | 436 (M + H)⁺ |

Example 285: 7-((4-(Pyridin-3-yl)-2-(trifluoromethoxy)benzyl)oxy)-3H-[1,2,3]triazolo[4,5-b]pyridin-5-amine

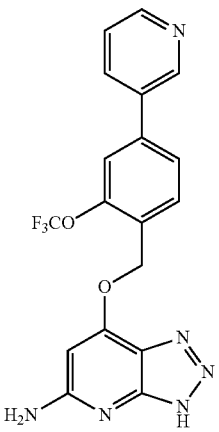 [SMILES: Nc1cc(OCc2ccc(-c3cccnc3)cc2OC(F)(F)F)c2nn[nH]c2n1]

245A (0.10 g, 0.11 mmol), pyridin-3-ylboronic acid (0.014 g, 0.11 mmol), (0.023 g, 0.11 mmol), potassium carbonate (0.031 g, 0.23 mmol), and tetrakis(triphenylphosphine)palladium(0) (0.013 g, 0.011 mmol) were added to a vial, which was then evacuated and back-filled with argon three times. Degassed DMF (0.45 mL) and water (0.05 mL) were added. The reaction mixture was stirred at 90° C. for 16 hours. The reaction mixture was cooled, diluted with $CH_2Cl_2$ (4 mL), filtered, and concentrated to dryness. The residue was redissolved in $CH_2Cl_2$ (4 mL). TFA (1 mL) was added to the solution to produce a bright yellow solution. After 1 minute, $Et_3SiH$ (0.032 mL, 0.21 mmol) was added until the bright yellow color had dissipated. The reaction mixture was concentrated in vacuo and purified by prep HPLC to yield Example 285 (39 mg, 60% yield). MS(ESI) m/z 403 (M+H). $^1$H NMR (500 MHz, DMSO-$d_6$) δ 8.94 (d, J=2.5 Hz, 1H), 8.62 (dd, J=4.8, 1.5 Hz, 1H), 8.20-8.12 (m, 1H), 7.90-7.82 (m, 2H), 7.78 (s, 1H), 7.54 (dd, J=8.0, 4.1 Hz, 1H), 6.58 (br. s., 1H), 5.55 (s, 2H).

The following compounds were prepared in a manner similar to experimental procedures that are described in Example 285 using 244A or 245A as starting material. Examples 286, 289, 290, 291, 292, 294, 311, 314, 315, 317, 319, 321, 322, 323, 324, 325, 329, 330, 33, 334, 337, 338, 339 and 340 were isolated as TFA salts. Example 328 was isolated as a formic acid salt.

| Ex. No. | Structure | Name | MS (ESI) $^1$H NMR |
|---|---|---|---|
| 286 | 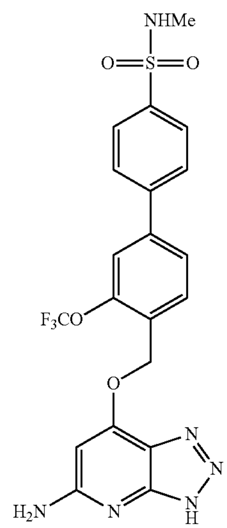 [SMILES: CNS(=O)(=O)c1ccc(-c2ccc(COc3cc(N)nc4[nH]nnc34)c(OC(F)(F)F)c2)cc1] | 4'-(((5-amino-3H-[1,2,3]triazolo[4,5-b]pyridin-7-yl)oxy)methyl)-N-methyl-3'-(trifluoromethoxy)-[1,1'-biphenyl]-4-sulfonamide | 495 (M + H)+ |
| 288 | 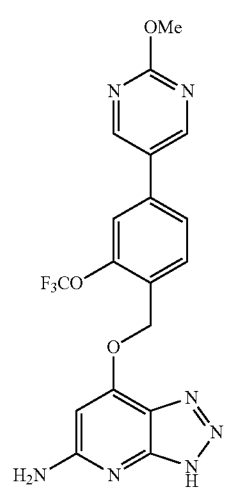 [SMILES: COc1ncc(-c2ccc(COc3cc(N)nc4[nH]nnc34)c(OC(F)(F)F)c2)cn1] | 7-((4-(2-methoxypyrimidin-5-yl)-2-(trifluoromethoxy)benzyl)oxy)-3H-[1,2,3]triazolo[4,5-b]pyridin-5-amine | 434 (M + H)+. (500 MHz, CD$_3$OD/CDCl$_3$, 1:1) δ 8.91 (s, 2H), 7.90 (d, J = 8.0 Hz, 1H), 7.79 (dd, J = 8.0, 1.7 Hz, 1H), 7.76-7.73 (m, 1H), 6.46 (s, 1H), 5.65 (s, 2H), 4.10 (s, 3H). |

| Ex. No. | Structure | Name | MS (ESI) $^1$H NMR |
|---|---|---|---|
| 289 | 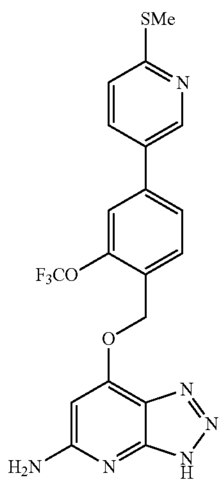 [SMILES: CSc1ccc(-c2ccc(COc3cc(N)nc4[nH]nnc34)c(OC(F)(F)F)c2)cn1] | 7-((4-(6-(methylthio) pyridin-3-yl)-2-(trifluoromethoxy) benzyl)oxy)-3H-[1,2,3] triazolo[4,5-b]pyridin-5-amine | 449 (M + H)$^+$ |
| 290 | 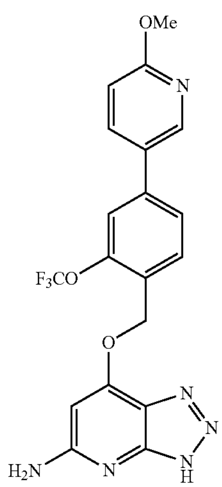 [SMILES: COc1ccc(-c2ccc(COc3cc(N)nc4[nH]nnc34)c(OC(F)(F)F)c2)cn1] | 7-((4-(6-methoxypyridin-3-yl)-2-(trifluoromethoxy) benzyl)oxy)-3H-[1,2,3] triazolo[4,5-b]pyridin-5-amine | 433 (M + H)$^+$. (500 MHz, DMSO-d$_6$) δ 8.61-8.60 (m, 1H), 8.59 (d, J = 2.5 Hz, 1H), 8.12 (dd, J = 8.7, 2.3 Hz, 1H), 7.83 (s, 2H), 7.75 (s, 1H), 6.97 (d, J = 8.8 Hz, 1H), 6.24 (br. s., 1H), 5.52 (s, 2H). |
| 291 | 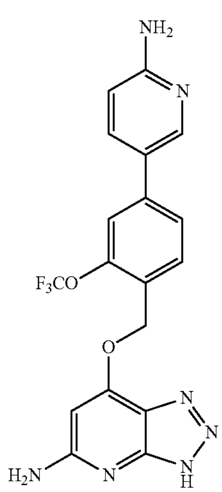 [SMILES: Nc1ccc(-c2ccc(COc3cc(N)nc4[nH]nnc34)c(OC(F)(F)F)c2)cn1] | 7-((4-(6-aminopyridin-3-yl)-2-(trifluoromethoxy) benzyl)oxy)-3H-[1,2,3]triazolo[4,5-b] pyridin-5-amine | 418 (M + H)$^+$ |

| Ex. No. | Structure | Name | MS (ESI) ¹H NMR |
|---|---|---|---|
| 292 | 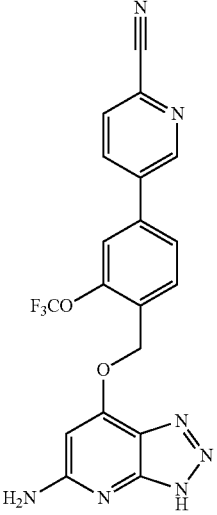 [SMILES: N#Cc1ccc(-c2ccc(COc3cc(N)nc4[nH]nnc34)c(OC(F)(F)F)c2)cn1] | 5-(4-(((5-amino-3H-[1,2,3]triazolo[4,5-b]pyridin-7-yl)oxy)methyl)-3-(trifluoromethoxy)phenyl)picolinonitrile | 428 (M + H)⁺. (500 MHz, DMSO-d₆) δ 9.19 (d, J = 2.2 Hz, 1H), 8.46 (dd, J = 8,1, 2.3 Hz, 1H), 8.19 (d, J = 8.3 Hz, 1H), 8.04-7.94 (m, 2H), 7.91 (d, J = 8.3 Hz, 1H), 6.20 (br. s., 1H), 5.56 (s, 2H). |
| 293 | 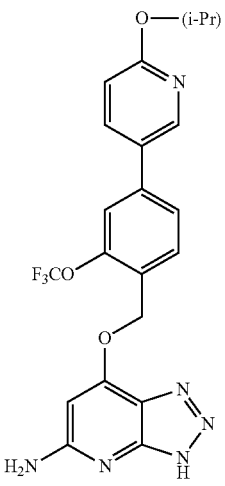 | 7-((4-(6-isopropoxypyridin-3-yl)-2-(trifluoromethoxy)benzyl)oxy)-3H-[1,2,3]triazolo[4,5-b]pyridin-5-amine | 461 (M + H)⁺ |
| 294 | 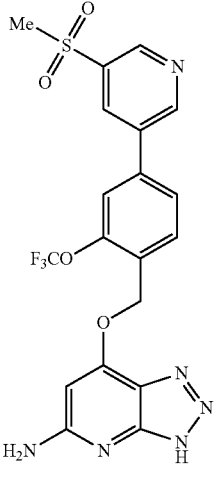 [SMILES: CS(=O)(=O)c1cncc(-c2ccc(COc3cc(N)nc4[nH]nnc34)c(OC(F)(F)F)c2)c1] | 7-((4-(5-(methylsulfonyl)pyridin-3-yl)-2-(trifluoromethoxy)benzyl)oxy)-3H-[1,2,3]triazolo[4,5-b]pyridin-5-amine | 481 (M + H)⁺ |

-continued

| Ex. No. | Structure | Name | MS (ESI) $^1$H NMR |
|---|---|---|---|
| 295 | 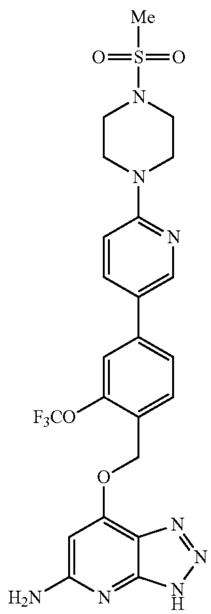 [SMILES: CS(=O)(=O)N1CCN(c2ccc(-c3ccc(COc4cc(N)nc5[nH]nnc45)c(OC(F)(F)F)c3)cn2)CC1] | 7-((4-(6-(4-(methylsulfonyl)piperazin-1-yl)pyridin-3-yl)-2-(trifluoromethoxy)benzyl)oxy)-3H-[1,2,3]triazolo[4,5-b]pyridin-5-amine | 565 (M + H)+. |
| 296 | 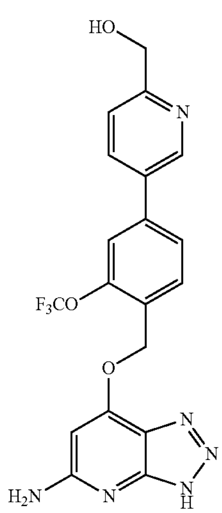 [SMILES: Nc1cc(OCc2ccc(-c3ccc(CO)nc3)cc2OC(F)(F)F)c2nn[nH]c2n1] | (5-(4-(((5-amino-3H-[1,2,3]triazolo[4,5-b]pyridin-7-yl)oxy)methyl)-3-(trifluoromethoxy)phenyl)pyridin-2-yl)methanol | 433 (M + H)+ |

| Ex. No. | Structure | Name | MS (ESI) $^1$H NMR |
|---|---|---|---|
| 297 | 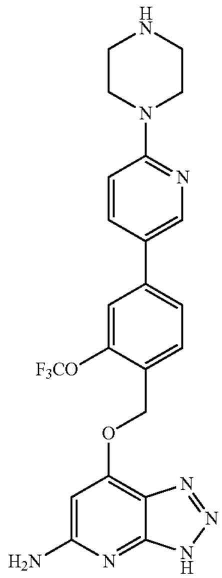 [SMILES: Nc1cc(OCc2ccc(-c3ccc(N4CCNCC4)nc3)cc2OC(F)(F)F)c2nn[nH]c2n1] | 7-((4-(6-(piperazin-1-yl)pyridin-3-yl)-2-(trifluoromethoxy)benzyl)oxy)-3H-[1,2,3]triazolo[4,5-b]pyridin-5-amine | 487 (M + H)$^+$. (500 MHz, DMSO-d$_6$) δ 8.53 (d, J = 2.5 Hz, 1H), 7.93 (dd, J = 8.9, 2.3 Hz, 1H), 7.76 (s, 2H), 7.67 (s, 1H), 6.92 (d, J = 8.8 Hz, 1H), 6.50 (s, 2H), 6.11 (s, 1H), 5.47 (s, 2H), 3.55-3.48 (m, 4H), 2.87-2.78 (m, 4H). |
| 299 | 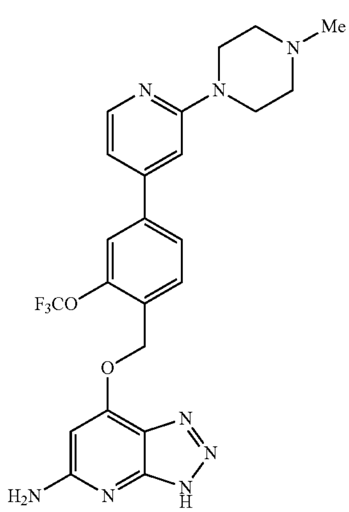 [SMILES: CN1CCN(c2cc(-c3ccc(COc4cc(N)nc5[nH]nnc45)c(OC(F)(F)F)c3)ccn2)CC1] | 7-((4-(2-(4-methylpiperazin-1-yl)pyridin-4-yl)-2-(trifluoromethoxy)benzyl)oxy)-3H-[1,2,3]triazolo[4,5-b]pyridin-5-amine | 501 (M + H)$^+$. (500 MHz, DMSO-d$_6$) δ 8.60-8.51 (m, 1H), 8.01-7.91 (m, 1H), 7.77 (s, 2H), 7.72-7.65 (m, 1H), 7.06-6.94 (m, 1H), 6.58-6.45 (m, 2H), 6.18-6.06 (m, 1H), 5.47 (s, 2H), 3.81-3.49 (m, 4H), 2.76-2.55 (m, 4H). |

-continued

| Ex. No. | Structure | Name | MS (ESI) ¹H NMR |
|---|---|---|---|
| 300 | 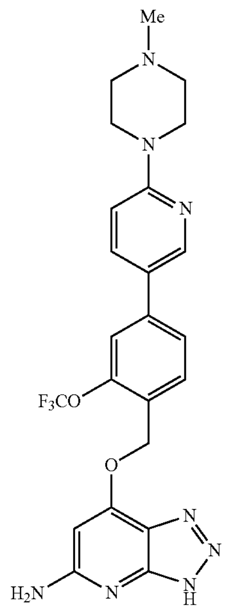 [SMILES: CN1CCN(c2ccc(-c3ccc(COc4cc(N)nc5[nH]nnc45)c(OC(F)(F)F)c3)cn2)CC1] | 7-((4-(6-(4-methylpiperazin-1-yl)pyridin-3-yl)-2-(trifluoromethoxy)benzyl)oxy)-3H-[1,2,3]triazolo[4,5-b]pyridin-5-amine | 501 (M + H)⁺ |
| 301 | 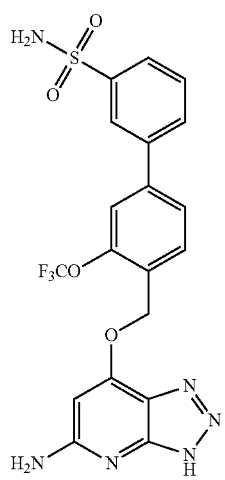 [SMILES: Nc1cc(OCc2ccc(-c3cccc(S(N)(=O)=O)c3)cc2OC(F)(F)F)c2nn[nH]c2n1] | 4'-(((5-amino-3H-[1,2,3]triazolo[4,5-b]pyridin-7-yl)oxy)methyl)-3'-(trifluoromethoxy)-[1,1'-biphenyl]-3-sulfonamide | 481 (M + H)⁺ |
| 302 | 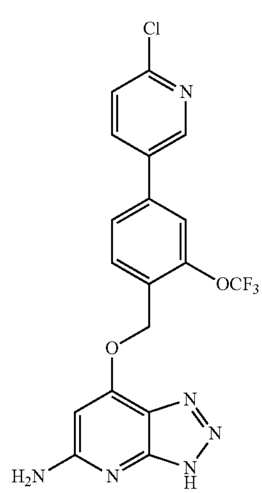 [SMILES: Nc1cc(OCc2ccc(-c3ccc(Cl)nc3)cc2OC(F)(F)F)c2nn[nH]c2n1] | 7-((4-(6-chloropyridin-3-yl)-2-(trifluoromethoxy)benzyl)oxy)-3H-[1,2,3]triazolo[4,5-b]pyridin-5-amine | 437 (M + H)⁺ |

-continued

| Ex. No. | Structure | Name | MS (ESI) ¹H NMR |
|---|---|---|---|
| 303 | 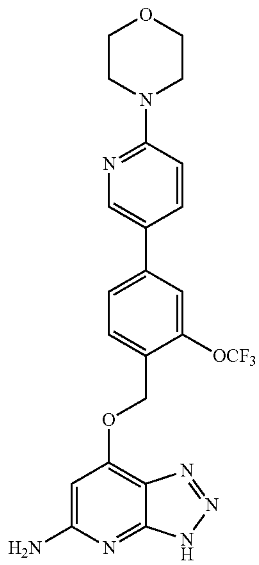 [SMILES: Nc1cc(OCc2ccc(-c3ccc(N4CCOCC4)nc3)cc2OC(F)(F)F)c2nn[nH]c2n1] | 7-((4-(6-morpholinopyridin-3-yl)-2-(trifluoromethoxy)benzyl)oxy)-3H-[1,2,3]triazolo[4,5-b]pyridin-5-amine | 488 (M + H)⁺ |
| 304 | 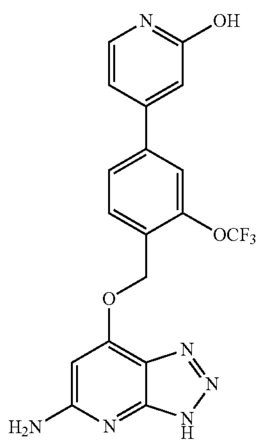 [SMILES: Nc1cc(OCc2ccc(-c3ccnc(O)c3)cc2OC(F)(F)F)c2nn[nH]c2n1] | 4-(4-(((5-amino-3H-[1,2,3]triazolo[4,5-b]pyridin-7-yl)oxy)methyl)-3-(trifluoromethoxy)phenyl)pyridin-2-ol | 419 (M + H)⁺ |
| 305 | 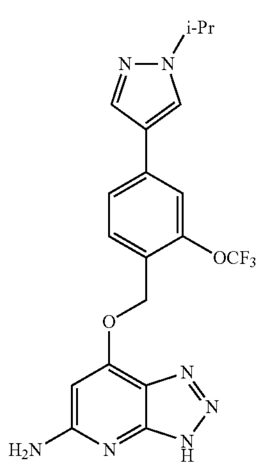 [SMILES: CC(C)n1cc(-c2ccc(COc3cc(N)nc4[nH]nnc34)c(OC(F)(F)F)c2)cn1] | 7-((4-(1-isopropyl-1H-pyrazol-4-yl)-2-(trifluoromethoxy)benzyl)oxy)-3H-[1,2,3]triazolo[4,5-b]pyridin-5-amine | 434 (M + H)⁺ |

| Ex. No. | Structure | Name | MS (ESI) ¹H NMR |
|---|---|---|---|
| 307 | 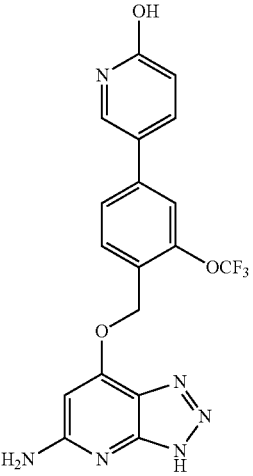 | 5-(4-(((5-amino-3H-[1,2,3]triazolo[4,5-b]pyridin-7-yl)oxy)methyl)-3-(trifluoromethoxy)phenyl)pyridin-2-ol | 419 (M + H)⁺ |
| 308 | 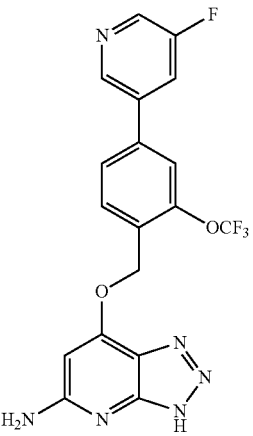 [SMILES: Nc1cc(OCc2ccc(-c3cncc(F)c3)cc2OC(F)(F)F)c2nn[nH]c2n1] | 7-((4-(5-fluoropyridin-3-yl)-2-(trifluoromethoxy)benzyl)oxy)-3H-[1,2,3]triazolo[4,5-b]pyridin-5-amine | 421 (M + H)⁺ |
| 309 | 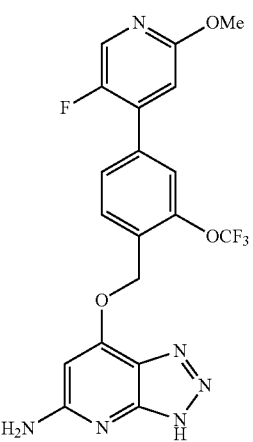 [SMILES: COc1cc(-c2ccc(COc3cc(N)nc4[nH]nnc34)c(OC(F)(F)F)c2)c(F)cn1] | 7-((4-(5-fluoro-2-methoxypyridin-4-yl)-2-(trifluoromethoxy)benzyl)oxy)-3H-[1,2,3]triazolo[4,5-b]pyridin-5-amine | 451 (M + H)⁺ |

-continued
| Ex. No. | Structure | Name | MS (ESI) <br> ¹H NMR |
|---|---|---|---|
| 310 | 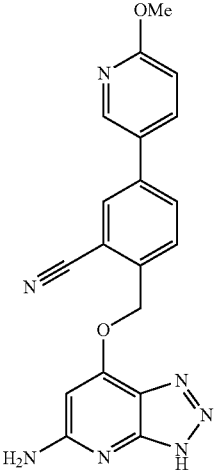 [SMILES: COc1ccc(-c2ccc(COc3cc(N)nc4[nH]nnc34)c(C#N)c2)cn1] | 2-(((5-amino-3H-[1,2,3]triazolo[4,5-b]pyridin-7-yl)oxy)methyl)-5-(6-methoxypyridin-3-yl)benzonitrile | 374 (M + H)⁺ |
| 311 | 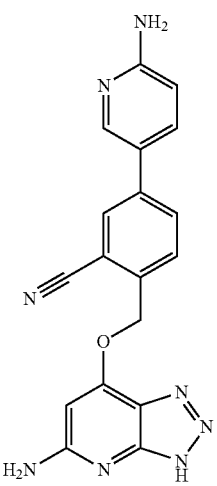 [SMILES: N#Cc1cc(-c2ccc(N)nc2)ccc1COc1cc(N)nc2[nH]nnc12] | 2-(((5-amino-3H-[1,2,3]triazolo[4,5-b]pyridin-7-yl)oxy)methyl)-5-(6-aminopyridin-3-yl)benzonitrile | 359 (M + H)⁺ |
| 312 | 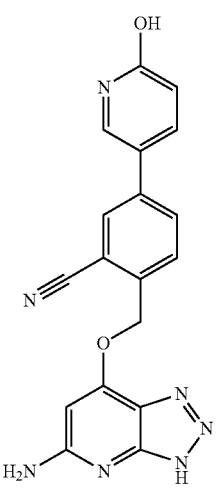 | 2-(((5-amino-3H-[1,2,3]triazolo[4,5-b]pyridin-7-yl)oxy)methyl)-5-(6-hydroxypyridin-3-yl)benzonitrile | 360 (M + H)⁺ |

| Ex. No. | Structure | Name | MS (ESI) ¹H NMR |
|---|---|---|---|
| 313 | 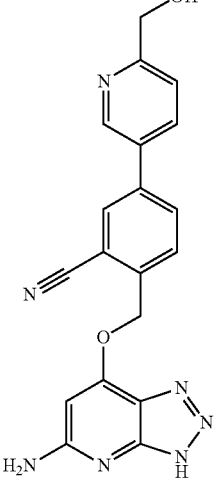 | 2-(((5-amino-3H-[1,2,3]triazolo[4,5-b]pyridin-7-yl)oxy)methyl)-5-(6-(hydroxymethyl)pyridin-3-yl)benzonitrile | 374 (M + H)⁺ |
| 314 | 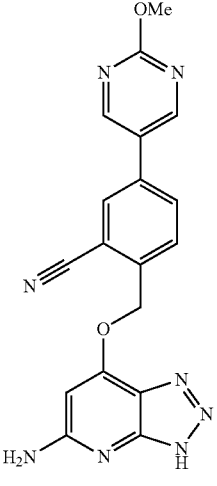 [SMILES: COc1ncc(-c2ccc(COc3cc(N)nc4[nH]nnc34)c(C#N)c2)cn1] | 2-(((5-amino-3H-[1,2,3]triazolo[4,5-b]pyridin-7-yl)oxy)methyl)-5-(2-methoxypyrimidin-5-yl)benzonitrile | 375 (M + H)⁺ |
| 315 | 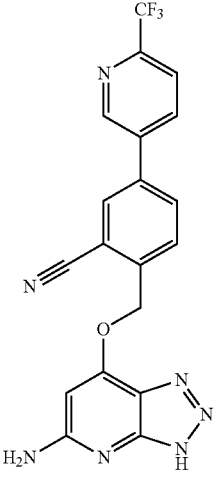 | 2-(((5-amino-3H-[1,2,3]triazolo[4,5-b]pyridin-7-yl)oxy)methyl)-5-(6-(trifluoromethyl)pyridin-3-yl)benzonitrile | 412 (M + H)⁺. 500 MHz, DMSO-d₆) δ 9.21 (d, J = 1.7 Hz, 1H), 8.55-8.48 (m, 2H), 8.26 (dd, J = 8.1, 1.8 Hz, 1H), 8.06 (d, J = 8.0 Hz, 1H), 7.99-7.92 (m, 2H), 6.23 (br. s., 1H), 5.66 (s, 2H) ppm. |

| Ex. No. | Structure | Name | MS (ESI) $^1$H NMR |
|---|---|---|---|
| 316 | 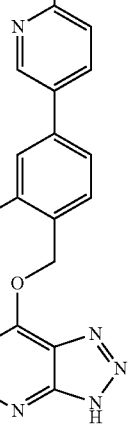 | 2-(((5-amino-3H-[1,2,3]triazolo[4,5-b]pyridin-7-yl)oxy)methyl)-5-(6-cyclopropylpyridin-3-yl)benzonitrile | 384 (M + H)$^+$ |
| 317 | 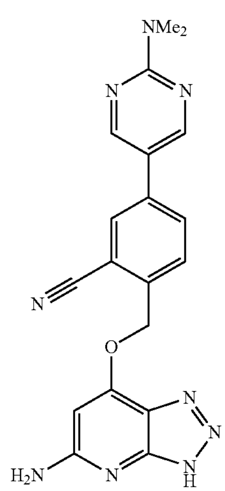 [SMILES: CN(C)c1ncc(-c2ccc(COc3cc(N)nc4[nH]nnc34)c(C#N)c2)cn1] | 2-(((5-amino-3H-[1,2,3]triazolo[4,5-b]pyridin-7-yl)oxy)methyl)-5-(2-(dimethylamino)pyrimidin-5-yl)benzonitrile | 388 (M + H)$^+$. (500 MHz, DMSO-d$_6$) δ 8.83-8.79 (s, 2H), 8.29 (d, J = 1.7 Hz, 1H), 8.07 (dd, J = 8.1, 1.8 Hz, 1H), 7.83 (d, J = 8.0 Hz, 1H), 6.20 (br. s., 1H), 5.58 (s, 2H), 3.19 (s, 6H) ppm. |

| Ex. No. | Structure | Name | MS (ESI) ¹H NMR |
|---|---|---|---|
| 318 | 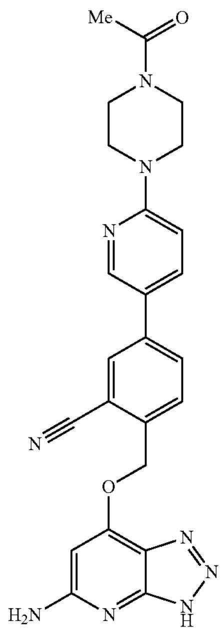 [SMILES: CC(=O)N1CCN(c2ccc(-c3ccc(COc4cc(N)nc5[nH]nnc45)c(C#N)c3)cn2)CC1] | 5-(6-(4-acetylpiperazin-1-yl)pyridin-3-yl)-2-(((5-amino-3H-[1,2,3]triazolo[4,5-b]pyridin-7-yl)oxy)methyl)benzonitrile | 470 (M + H)⁺ |
| 319 | 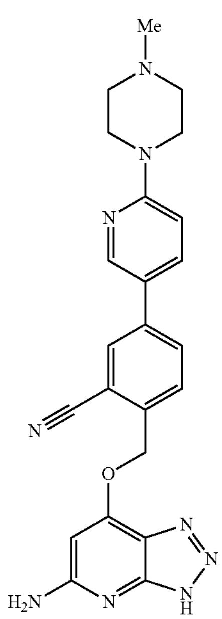 [SMILES: CN1CCN(c2ccc(-c3ccc(COc4cc(N)nc5[nH]nnc45)c(C#N)c3)cn2)CC1] | 2-(((5-amino-3H-[1,2,3]triazolo[4,5-b]pyridin-7-yl)oxy)methyl)-5-(6-(4-methylpiperazin-1-yl)pyridin-3-yl)benzonitrile | 442 (M + H)⁺ |

| Ex. No. | Structure | Name | MS (ESI) $^1$H NMR |
|---|---|---|---|
| 320 | 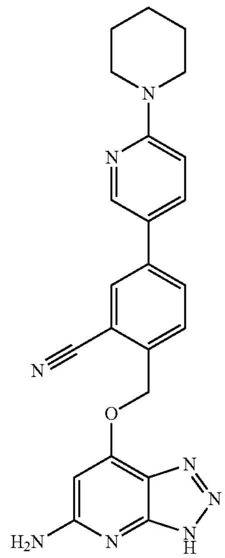 [SMILES: N#Cc1cc(-c2ccc(N3CCCCC3)nc2)ccc1COc1cc(N)nc2[nH]nnc12] | 2-(((5-amino-3H-[1,2,3]triazolo[4,5-b]pyridin-7-yl)oxy)methyl)-5-(6-(piperidin-1-yl)pyridin-3-yl)benzonitrile | 427 (M + H)$^+$. (500 MHz, DMSO-d$_6$) δ 8.55 (d, J = 2.2 Hz, 1H), 8.23 (s, 1H), 8.03 (d, J = 8.3 Hz, 1H), 7.95 (dd, J = 9.1, 2.5 Hz, 1H), 7.80 (d, J = 8.3 Hz, 1H), 6.92 (d, J = 9.1 Hz, 1H), 6.54 (br. s., 2H), 6.11 (s, 1H), 5.56 (br. s., 2H), 3.63-3.57 (m, 4H), 1.63 (m, 2H), 1.55 (m, 4H) ppm. |
| 321 | 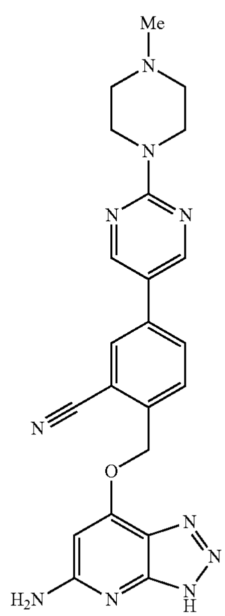 [SMILES: CN1CCN(c2ncc(-c3ccc(COc4cc(N)nc5[nH]nnc45)c(C#N)c3)cn2)CC1] | 2-(((5-amino-3H-[1,2,3]triazolo[4,5-b]pyridin-7-yl)oxy)methyl)-5-(2-(4-methylpiperazin-1-yl)pyrimidin-5-yl)benzonitrile | 443 (M + H)$^+$ |

-continued

| Ex. No. | Structure | Name | MS (ESI) ¹H NMR |
|---|---|---|---|
| 322 | 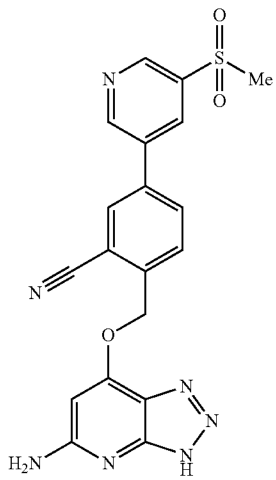 [SMILES: CS(=O)(=O)c1cncc(-c2ccc(COc3cc(N)nc4[nH]nnc34)c(C#N)c2)c1] | 2-(((5-amino-3H-[1,2,3]triazolo[4,5-b]pyridin-7-yl)oxy)methyl)-5-(5-(methylsulfonyl)pyridin-3-yl)benzonitrile | 422 (M + H)⁺ |
| 323 | 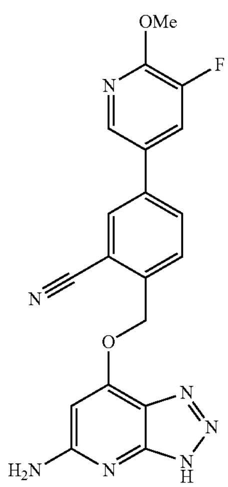 [SMILES: COc1ncc(-c2ccc(COc3cc(N)nc4[nH]nnc34)c(C#N)c2)cc1F] | 2-(((5-amino-3H-[1,2,3]triazolo[4,5-b]pyridin-7-yl)oxy)methyl)-5-(5-fluoro-6-methoxypyridin-3-yl)benzonitrile | 392 (M + H)⁺ |
| 324 | 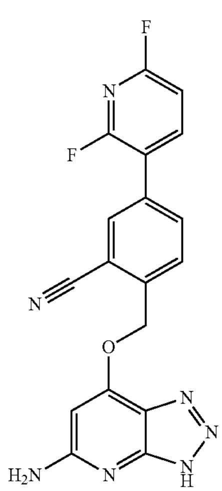 [SMILES: N#Cc1cc(-c2ccc(F)nc2F)ccc1COc1cc(N)nc2[nH]nnc12] | 2-(((5-amino-3H-[1,2,3]triazolo[4,5-b]pyridin-7-yl)oxy)methyl)-5-(2,6-difluoropyridin-3-yl)benzonitrile | 380 (M + H)⁺ |

| Ex. No. | Structure | Name | MS (ESI) ¹H NMR |
|---|---|---|---|
| | | -continued | |
| 325 | 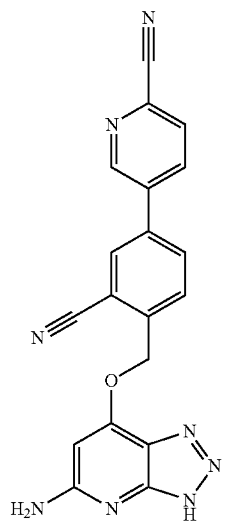 [SMILES: N#Cc1ccc(-c2ccc(COc3cc(N)nc4[nH]nnc34)c(C#N)c2)cn1] | 5-(4-(((5-amino-3H-[1,2,3]triazolo[4,5-b]pyridin-7-yl)oxy)methyl)-3-cyanophenyl)picolinonitrile | 369 (M + H)⁺ |
| 326 | 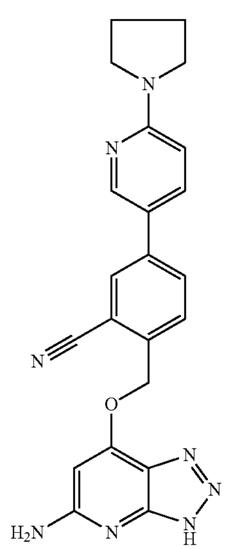 [SMILES: N#Cc1cc(-c2ccc(N3CCCC3)nc2)ccc1COc1cc(N)nc2[nH]nnc12] | 2-(((5-amino-3H-[1,2,3]triazolo[4,5-b]pyridin-7-yl)oxy)methyl)-5-(6-(pyrrolidin-1-yl)pyridin-3-yl)benzonitrile | 413 (M + H)⁺. (500 MHz, DMSO-d₆) δ 8.54 (d, J = 2.2 Hz, 1H), 8.21 (d, J = 1.9 Hz, 1H), 8.02 (dd, J = 8.3, 1.7 Hz, 1H), 7.97-7.91 (m, 1H), 7.79 (d, J = 8.3 Hz, 1H), 6.59-6.48 (m, 3H), 6.12 (br. s., 1H), 5.55 (br. s., 2H), 3.44 (t, J = 6.3 Hz, 4H), 1.96 (t, J = 6.5 Hz, 4H) ppm. |

| Ex. No. | Structure | Name | MS (ESI) ¹H NMR |
|---|---|---|---|
| 327 | 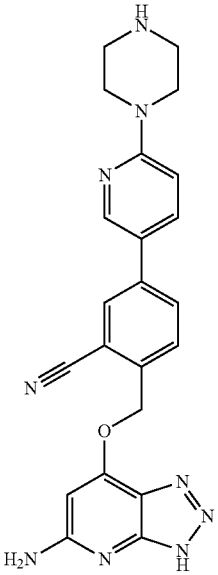 | 2-(((5-amino-3H-[1,2,3]triazolo[4,5-b]pyridin-7-yl)oxy)methyl)-5-(6-(piperazin-1-yl)pyridin-3-yl)benzonitrile | 428 (M + H)⁺ |
| 328 | 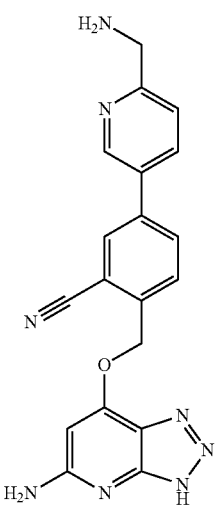 [SMILES: N#Cc1cc(-c2ccc(CN)nc2)ccc1COc1cc(N)nc2[nH]nnc12] | 2-(((5-amino-3H-[1,2,3]triazolo[4,5-b]pyridin-7-yl)oxy)methyl)-5-(6-(aminomethyl)pyridin-3-yl)benzonitrile | 373 (M + H)⁺ |

| Ex. No. | Structure | Name | MS (ESI) $^1$H NMR |
|---|---|---|---|
| 329 | 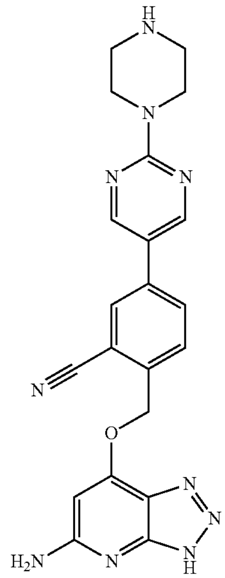 [SMILES: N#Cc1cc(-c2cnc(N3CCNCC3)nc2)ccc1COc1cc(N)nc2[nH]nnc12] | 2-(((5-amino-3H-[1,2,3]triazolo[4,5-b]pyridin-7-yl)oxy)methyl)-5-(2-(piperazin-1-yl)pyrimidin-5-yl)benzonitrile | 429 (M + H)$^+$ |
| 330 | 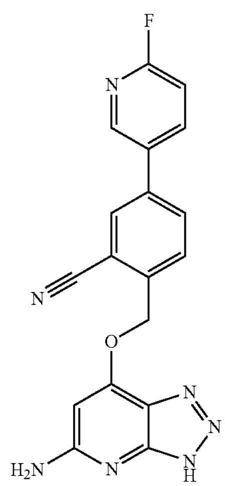 [SMILES: N#Cc1cc(-c2ccc(F)nc2)ccc1COc1cc(N)nc2[nH]nnc12] | 2-(((5-amino-3H-[1,2,3]triazolo[4,5-b]pyridin-7-yl)oxy)methyl)-5-(6-fluoropyridin-3-yl)benzonitrile | 362 (M + H)$^+$ |
| 331 | 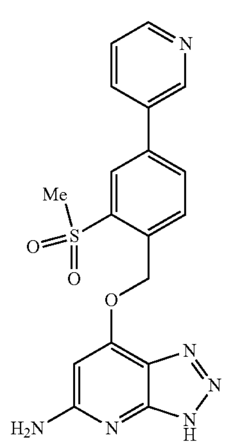 [SMILES: CS(=O)(=O)c1cc(-c2cccnc2)ccc1COc1cc(N)nc2[nH]nnc12] | 4-((5-amino-3H-[1,2,3]triazolo[4,5-b]pyridin-7-yloxy)methyl)-3-chloro-N-(2-methoxybenzyl)benzamide | 439 (M + H)$^+$ |

-continued
| Ex. No. | Structure | Name | MS (ESI) ¹H NMR |
|---|---|---|---|
| 332 | 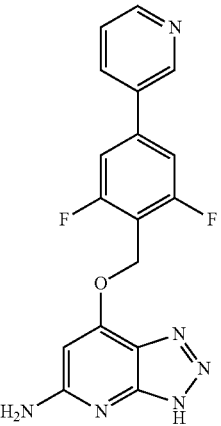 [SMILES: Nc1cc(OCc2c(F)cc(-c3cccnc3)cc2F)c2nn[nH]c2n1] | 7-((2,6-difluoro-4-(pyridin-3-yl)benzyl)oxy)-3H-[1,2,3]triazolo[4,5-b]pyridin-5-amine | 355 (M + H)⁺ |
| 333 | 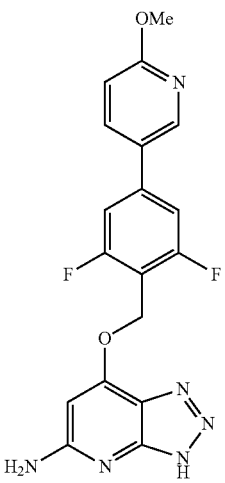 | 7-((2,6-difluoro-4-(6-methoxypyridin-3-yl)benzyl)oxy)-3H-[1,2,3]triazolo[4,5-b]pyridin-5-amine | 385 (M + H)⁺ |
| 334 | 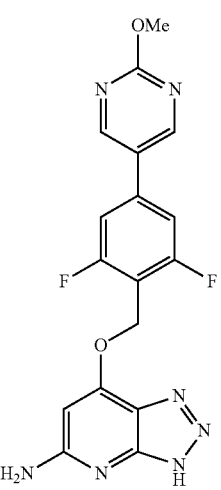 [SMILES: COc1ncc(-c2cc(F)c(COc3cc(N)nc4[nH]nnc34)c(F)c2)cn1] | 7-((2,6-difluoro-4-(2-methoxypyrimidin-5-yl)benzyl)oxy)-3H-[1,2,3]triazolo[4,5-b]pyridin-5-amine | 386 (M + H)⁺ |

| Ex. No. | Structure | Name | MS (ESI) <br> ¹H NMR |
|---|---|---|---|
| 335 | 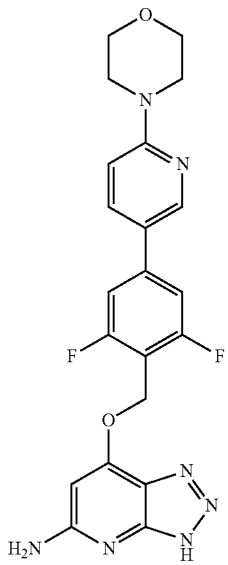 [SMILES: Nc1cc(OCc2c(F)cc(-c3ccc(N4CCOCC4)nc3)cc2F)c2nn[nH]c2n1] | 7-((2,6-difluoro-4-(6-morpholinopyridin-3-yl)benzyl)oxy)-3H-[1,2,3]triazolo[4,5-b]pyridin-5-amine | 440 (M + H)⁺ |
| 336 | 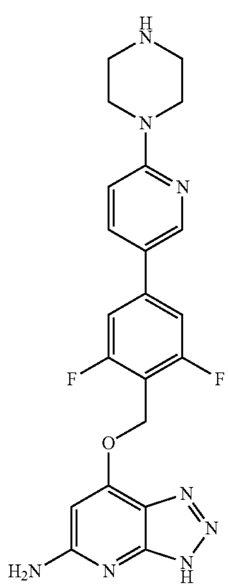 [SMILES: Nc1cc(OCc2c(F)cc(-c3ccc(N4CCNCC4)nc3)cc2F)c2nn[nH]c2n1] | 7-((2,6-difluoro-4-(6-(piperazin-1-yl)pyridin-3-yl)benzyl)oxy)-3H-[1,2,3]triazolo[4,5-b]pyridin-5-amine | 439 (M + H)⁺ |

| Ex. No. | Structure | Name | MS (ESI) $^1$H NMR |
|---|---|---|---|
| 337 | 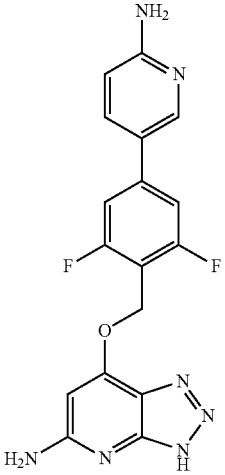 [SMILES: Nc1ccc(-c2cc(F)c(COc3cc(N)nc4[nH]nnc34)c(F)c2)cn1] | 7-((4-(6-aminopyridin-3-yl)-2,6-difluorobenzyl)oxy)-3H-[1,2,3]triazolo[4,5-b]pyridin-5-amine | 370 (M + H)$^+$ |
| 338 | 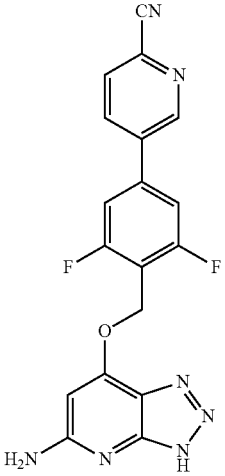 [SMILES: N#Cc1ccc(-c2cc(F)c(COc3cc(N)nc4[nH]nnc34)c(F)c2)cn1] | 5-(4-(((5-amino-3H-[1,2,3]triazolo[4,5-b]pyridin-7-yl)oxy)methyl)-3,5-difluorophenyl)picolinonitrile | 380 (M + H)$^+$ |
| 339 | 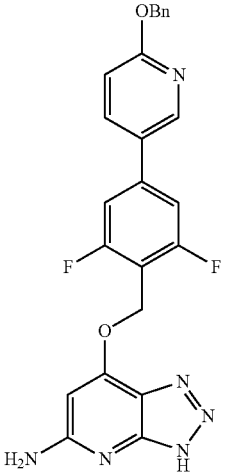 | 7-((4-(6-(benzyloxy)pyridin-3-yl)-2,6-difluorobenzyl)oxy)-3H-[1,2,3]triazolo[4,5-b]pyridin-5-amine | 461 (M + H)$^+$ |

| Ex. No. | Structure | Name | MS (ESI) $^1$H NMR |
|---|---|---|---|
| 340 | 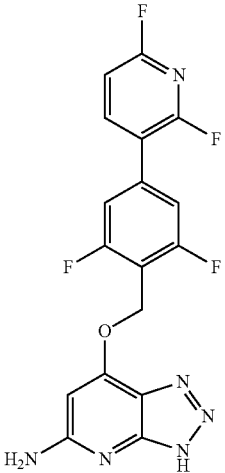 [SMILES: Nc1cc(OCc2c(F)cc(-c3ccc(F)nc3F)cc2F)c2nn[nH]c2n1] | 7-((4-(2,6-difluoropyridin-3-yl)-2,6-difluorobenzyl)oxy)-3H-[1,2,3]triazolo[4,5-b]pyridin-5-amine | 391 (M + H)$^+$ |
| 341 | 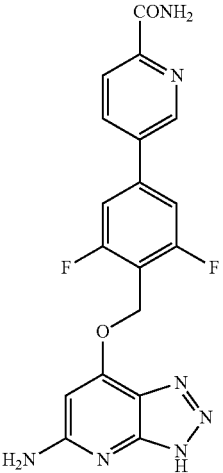 [SMILES: NC(=O)c1ccc(-c2cc(F)c(COc3cc(N)nc4[nH]nnc34)c(F)c2)cn1] | 5-(4-(((5-amino-3H-[1,2,3]triazolo[4,5-b]pyridin-7-yl)oxy)methyl)-3,5-difluorophenyl)picolinamide | 398 (M + H)$^+$ |
| 342 | 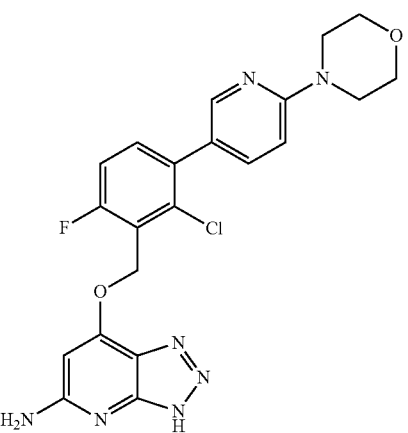 [SMILES: Nc1cc(OCc2c(F)ccc(-c3ccc(N4CCOCC4)nc3)c2Cl)c2nn[nH]c2n1] | 7-((2-chloro-6-fluoro-3-(6-morpholinopyridin-3-yl)benzyl)oxy)-3H-[1,2,3]triazolo[4,5-b]pyridin-5-amine | 456 (M + H)$^+$. (500 MHz, DMSO-d$_6$) δ 8.20 (d, J = 2.5 Hz, 1H), 7.69 (dd, J = 8.8, 2.2 Hz, 1H), 7.60 (dd, J = 8.7, 6.2 Hz, 1H), 7.47 (m, 1H), 6.94 (d, J = 8.8 Hz, 1H), 6.55 (br. s., 2H), 6.18 (br. s., 1H), 5.50 (br. s., 2H), 3.79-3.67 (m, 4H), 3.61-3.47 (m, 5H) |

| Ex. No. | Structure | Name | MS (ESI) $^1$H NMR |
|---|---|---|---|
| 343 | 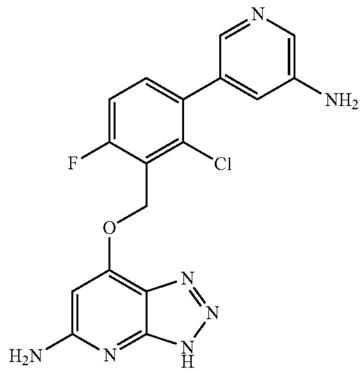 [SMILES: Nc1cncc(-c2ccc(F)c(COc3cc(N)nc4[nH]nnc34)c2Cl)c1] | 7-((3-(5-aminopyridin-3-yl)-2-chloro-6-fluorobenzyl)oxy)-3H-[1,2,3]triazolo[4,5-b]pyridin-5-amine | 386 (M + H)$^+$ |
| 344 | 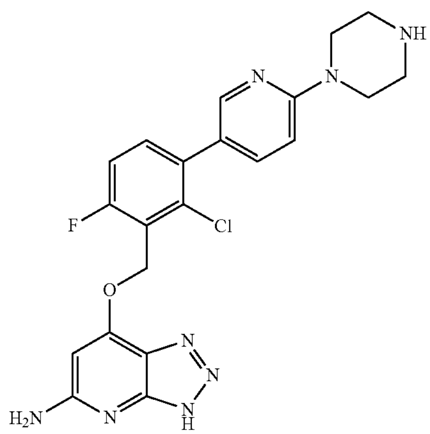 [SMILES: Nc1cc(OCc2c(F)ccc(-c3ccc(N4CCNCC4)nc3)c2Cl)c2nn[nH]c2n1] | 7-((2-chloro-6-fluoro-3-(6-(piperazin-1-yl)pyridin-3-yl)benzyl)oxy)-3H-[1,2,3]triazolo[4,5-b]pyridin-5-amine | 455 (M + H)$^+$ |
| 345 | 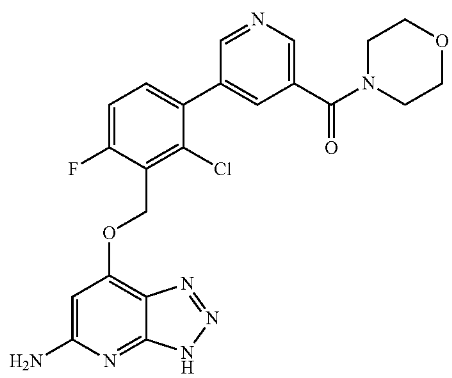 [SMILES: Nc1cc(OCc2c(F)ccc(-c3cncc(C(=O)N4CCOCC4)c3)c2Cl)c2nn[nH]c2n1] | (5-(3-(((5-amino-3H-[1,2,3]triazolo[4,5-b]pyridin-7-yl)oxy)methyl)-2-chloro-4-fluorophenyl)pyridin-3-yl)(morpholino)methanone | 484 (M + H)$^+$ |

| Ex. No. | Structure | Name | MS (ESI) $^1$H NMR |
|---|---|---|---|
| 346 | 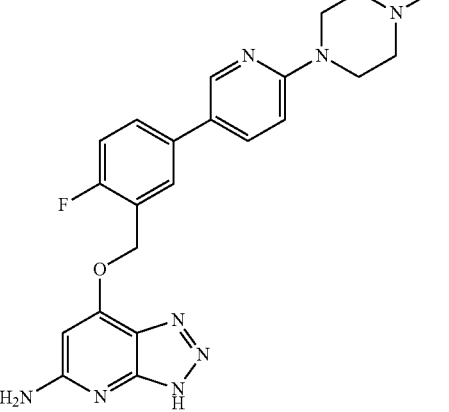 | 7-((2-fluoro-5-(6-(4-methylpiperazin-1-yl)pyridin-3-yl)benzyl)oxy)-3H-[1,2,3]triazolo[4,5-b]pyridin-5-amine | 435 (M + H)$^+$ |
| 347 | 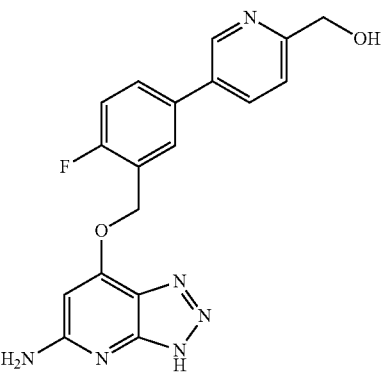 [SMILES: Nc1cc(OCc2cc(-c3ccc(CO)nc3)ccc2F)c2nn[nH]c2n1] | (5-(3-(((5-amino-3H-[1,2,3]triazolo[4,5-b]pyridin-7-yl)oxy)methyl)-4-fluorophenyl)pyridin-2-yl)methanol | 367 (M + H)$^+$ |
| 348 | 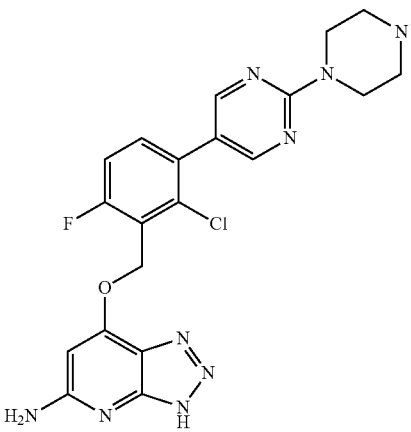 | 7-((2-chloro-6-fluoro-3-(2-(4-methylpiperazin-1-yl)pyrimidin-5-yl)benzyl)oxy)-3H-[1,2,3]triazolo[4,5-b]pyridin-5-amine | 470 (M + H)$^+$. (500 MHz, DMSO-d$_6$) δ 8.48 (s, 2H), 7.66 (m, 1H), 7.50 (m, 1H), 6.48 (br. s., 2H), 6.17 (s, 1H), 5.50 (s, 2H), 3.80 (m, 4H), 2.39 (m, 4H), 2.23 (s, 3H). |

Example 349: 2-(((5-Amino-3H-[1,2,3]triazolo[4,5-b]pyridin-7-yl)oxy)methyl)-5-(6-(3-oxopiperazin-1-yl)pyridin-3-yl)benzonitrile

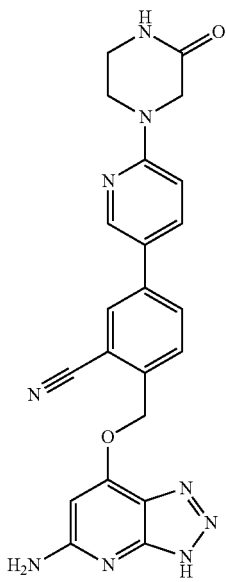 [SMILES: N#Cc1cc(-c2ccc(N3CCNC(=O)C3)nc2)ccc1COc1cc(N)nc2[nH]nnc12]

349A: 5-(6-Fluoropyridin-3-yl)-2-(((3-trityl-5-(tritylamino)-3H-[1,2,3]triazolo[4,5-b]pyridin-7-yl)oxy)methyl)benzonitrile

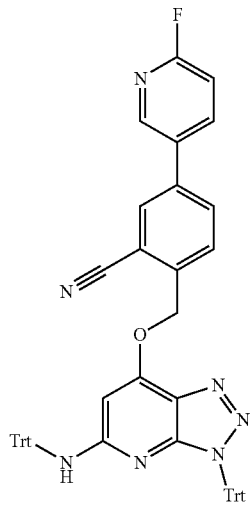

349A was synthesized in a manner analogous to Example 285 from Example 245A and (6-fluoropyridin-3-yl)boronic acid, wherein the deprotection step was omitted. MS(ESI) 846 [M+H].

Example 349

To a mixture of 349A (50 mg, 0.059 mmol), piperazin-2-one (6 mg, 0.06 mmol), potassium carbonate (9 mg, 0.065 mmol) and sodium iodide (5 mg, 0.03 mmol) in a microwave vial was added DMF (1 mL) and the reaction was stirred at 90° C. in an oil bath for 18 hours. The solution was diluted in DCM (5 mL) and filtered.

To the above solution was added TFA (1 mL) followed by triethylsilane (0.016 mL, 0.11 mmol) and stirred at rt. The reaction was concentrated to dryness and purified by preparatory HPLC to yield Example 349 (0.4 mg, 2% yield). MS(ESI) 442 [M+H]. $^1$H NMR (500 MHz, DMSO-$d_6$) δ 8.61 (s, 1H), 8.25 (s, 1H), 8.14-8.08 (m, 1H), 8.04 (s, 2H), 7.83-7.77 (m, 1H), 6.99-6.90 (m, 1H), 6.06-5.97 (m, 1H), 5.64 (s, 2H), 4.08 (s, 2H), 3.81 (br. s., 2H), 1.83-1.70 (m, 1H), 1.30-1.16 (m, 1H).

Example 350: 2-(((5-Amino-3H-[1,2,3]triazolo[4,5-b]pyridin-7-yl)oxy)methyl)-5-(6-(3,5-dimethylpiperazin-1-yl)pyridin-3-yl)benzonitrile

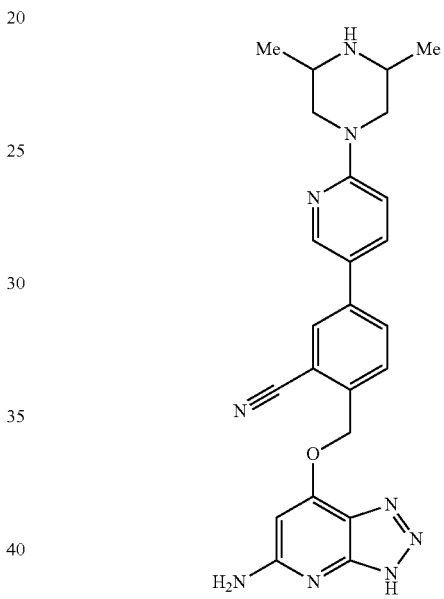

Example 350 was prepared in a manner analogous to Example 349 from 349A and 2,6-dimethylpiperazine. MS(ESI) 456 [M+H]. The compound was isolated as a TFA salt.

Example 351: 2-(((5-amino-3H-[1,2,3]triazolo[4,5-b]pyridin-7-yl)oxy)methyl)-4-(difluoromethoxy)benzonitrile

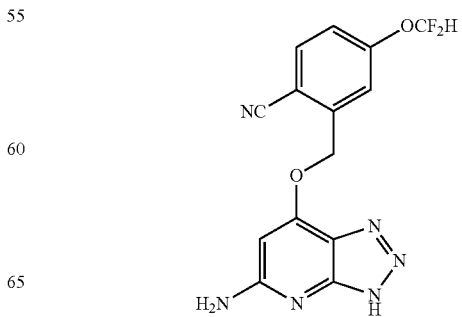

351A: 1-bromo-4-(difluoromethoxy)-2-methylbenzene

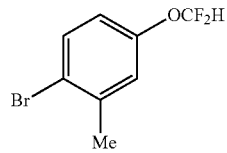

A mixture of 4-bromo-3-methylphenol (1.0 g, 5.4 mmol), K$_2$CO$_3$ (1.5 g, 11 mmol) in DMF (8 mL) was heated to 100° C. Sodium chlorodifluoroacetate (1.6 g, 11 mmol) was added and the mixture was stirred for 3 h at 100° C. Additional sodium chlorodifluoroacetate (800 mg) was added and the mixture was stirred for 2 h at 100° C. The reaction was diluted with ethyl acetate and washed with 10 N citric acid and brine and dried over sodium sulfate. The crude product was purified by flash chromatography (loading in chloroform, 0% to 20% gradient with ethyl acetate in hexane over 15 min using a 40 g silica gel cartridge) to yield Example 351A (200 mg, 0.84 mmol, 16% yield) as a clear oil. $^1$H NMR (500 MHz, CDCl$_3$) δ 7.49 (d, J=8.5 Hz, 1H), 7.01 (d, J=2.8 Hz, 1H), 6.88-6.79 (m, 1H), 6.46 (t, J=73.7 Hz, 1H), 2.39 (s, 3H).

351B: 4-(difluoromethoxy)-2-methylbenzonitrile

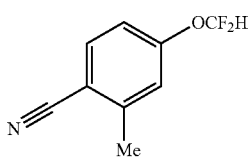

A mixture of Example 351A (200 mg, 0.84 mmol) and copper(I) cyanide (150 mg, 1.7 mmol) in DMF (1.1 mL) was heated at 160° C. for 5 h. Ammonium hydroxide (1 mL) and water (1 mL) were added to the mixture. The mixture was extracted with EtOAc (2×). The combined organics were washed with brine, dried over Na$_2$SO$_4$ and concentrated in vacuo. The crude product was purified by flash chromatography (loading in chloroform, 0% to 20% gradient with ethyl acetate in hexane over 10 min using a 4 g silica gel cartridge) to yield Example 351B (120 mg, 78% yield) as a white solid. $^1$H NMR (500 MHz, CDCl$_3$) δ 7.62 (d, J=8.5 Hz, 1H), 7.10-7.06 (m, 1H), 7.06-7.01 (m, 1H), 6.72 (t, J=72.6 Hz, 1H), 2.57 (s, 3H)

351C: 2-(bromomethyl)-4-(difluoromethoxy)benzonitrile

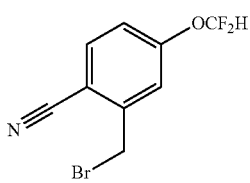

A solution of Example 351B (120 mg, 0.66 mmol), NBS (180 mg, 0.98 mmol) and AIBN (27 mg, 0.16 mmol) in CHCl$_3$ (8 mL) was heated over night at 100° C. The mixture was diluted with chloroform, washed with NaHCO$_3$ and brine, dried over Na$_2$SO$_4$ and concentrated in vacuo. The crude mixture was used in the next step without purification.

Example 351

Example 351 was synthesized from Example 351C and Intermediate 5 using General Route 5. MS (ESI) m/z: 333.1 (M+H)+. $^1$H NMR (500 MHz, DMSO-d$_6$) δ 8.08 (d, J=8.8 Hz, 1H), 7.62 (s, 1H), 7.55-7.38 (m, 2H), 6.58 (br. s., 2H), 6.12 (s, 1H), 5.56 (s, 2H).

Example 352: 2-(((5-amino-3H-[1,2,3]triazolo[4,5-b]pyridin-7-yl)oxy)methyl)-4-cyclopropoxybenzonitrile

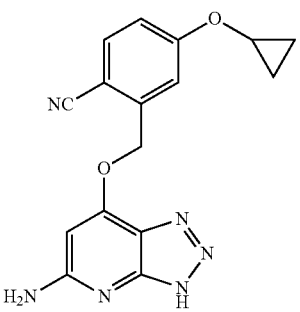 [SMILES: N#Cc1ccc(OC2CC2)cc1COc1cc(N)nc2[nH]nnc12]

352A: 1-bromo-4-cyclopropoxy-2-methylbenzene

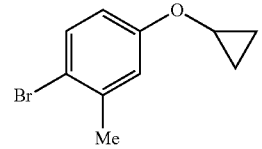

A mixture of 4-bromo-3-methylphenol (0.50 g, 2.7 mmol), cyclopropyl bromide (0.43 ml, 5.4 mmol), cesium carbonate (2.6 g, 8.2 mmol) and sodium iodide (0.040 g, 0.27 mmol) in DMF (11 mL) was stirred in a sealed vessel over night at 150° C. The mixture was diluted with EtOAc, washed with water and brine, dried over Na$_2$SO$_4$ and concentrated in vacuo. The crude product was purified by flash chromatography (loading neat, 0% to 20% gradient with ethyl acetate in hexane over 10 min using a 40 g silica gel cartridge) to yield Example 352A (0.42 g, 69% yield). $^1$H NMR (500 MHz, CDCl$_3$) δ 7.39 (d, J=8.5 Hz, 1H), 6.92 (d, J=2.5 Hz, 1H), 6.76 (dd, J=8.8, 2.8 Hz, 1H), 3.69 (tt, J=5.8, 3.2 Hz, 1H), 2.36 (s, 3H), 0.79-0.73 (m, 4H).

Example 352

Example 352 was synthesized from Example 352A and Intermediate 5 using procedures described in Example 351. MS (ESI) m/z: 323.1 (M+H)$^+$. 1H NMR (500 MHz, DMSO-d$_6$) δ 15.16 (s, 1H), 7.93 (d, J=8.5 Hz, 1H), 7.45 (m, 1H), 7.29 (d, J=8.5 Hz, 1H), 6.59 (br. s., 2H), 6.10 (s, 1H), 5.52 (s, 2H), 4.00 (m, 1H), 0.84 (m, 2H), 0.71 (m, 2H).

What is claimed is:

1. The compound of the formula (I)

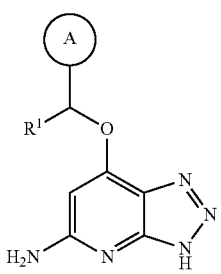

or a stereoisomer, a tautomer, a pharmaceutically acceptable salt, or a solvate thereof, wherein:

ring A is independently $C_{5-10}$ carbocycle substituted with 0-1 $R^2$ and 0-4 $R^3$;

$R^1$ is independently selected from: H, CN, $C_{1-6}$ alkyl, and $C_{1-6}$ haloalkyl;

$R^2$ is independently selected from: $SF_5$, —$(CH_2)_tOH$, —$(CH_2)_nR^4$, and —$(CH_2)_n(X_1)_n(CH_2)_nR^5$;

$X_1$ is independently selected from: O, S, CO and $SO_2$;

$R^3$ is, at each occurrence, independently selected from: halogen, CN, $C_{1-4}$ alkyl, $C_{1-4}$ alkoxy, $C_{1-4}$ haloalkyl, $C_{1-4}$ haloalkoxy, $NO_2$, $CONH_2$, and $SO_2(C_{1-4}$ alkyl);

$R^4$ is independently selected from: halogen, $C_{1-4}$ alkyl, $C_{1-4}$ alkoxy, $C_{1-4}$ alkylthio, $C_{1-4}$ haloalkyl, $C_{1-4}$ haloalkoxy, $C_{1-4}$ haloalkylthio, CN, $CO_2(C_{1-4}$ alkyl), $NO_2$, $NR^6R^7$, $CONR^6R^7$, $NHCOR^8$, $NHCO_2R^8$, $COR^{10}$, —$CONHCH_2CONR^9R^{10}$, $SO_2NR^9R^{10}$, and $S(O)_pR^8$;

$R^5$ is independently selected from: $C_{3-10}$ carbocycle substituted with 0-2 $R^{11}$, phenyl substituted with 0-3 $R^{11}$ and 0-1 $R^{12}$, and 5- to 10-membered heterocycle comprising carbon atoms and 1-4 heteroatoms selected from N, $NR^a$, O, and $S(O)_p$; wherein said heterocycle is substituted with 0-2 $R^{11}$ and 0-1 $R^{13}$;

$R^6$ is, at each occurrence, independently selected from: H, $C_{1-4}$ haloalkyl, $C_{1-6}$ alkyl substituted with 0-2 $R^{15}$, —$(CH_2)_t$—$(C_{3-6}$ cycloalkyl substituted with 0-1 $R^{14}$), —$(CHR^b)_n$-(phenyl substituted with 0-1 $R^{16}$), —$(CH_2)_t$-(phenyl substituted with 0-1 $R^{16}$), —$(CH_2)_t$-(a 5- to 10-membered heterocycle comprising carbon atoms and 1-4 heteroatoms selected from N, $NR^a$, O, and $S(O)_p$, wherein said heterocycle is substituted with 0-1 $R^{17}$);

$R^7$ is, at each occurrence, independently selected from: H and $C_{1-4}$ alkyl substituted with $R^{11}$;

alternatively, $R^6$ and $R^7$, together with the nitrogen atom to which they are attached, combine to form a 4- to 10-membered heterocyclic ring comprising carbon atoms and 1-4 heteroatoms selected from N, $NR^a$, O, and $S(O)_p$; wherein said heterocycle is substituted with 0-1 $R^{17}$;

$R^8$ is, at each occurrence, independently selected from: $C_{1-4}$ alkyl, —$(CH_2)_t$—$C_{3-6}$ cycloalkyl, and —$(CH_2)_t$-phenyl;

$R^9$ is, at each occurrence, independently selected from: H and $C_{1-4}$ alkyl; $R^{10}$ is, at each occurrence, independently selected from: $R^8$ and H;

$R^{11}$ is, at each occurrence, independently selected from: OH, halogen, $C_{1-4}$ alkoxy, $C_{1-4}$ haloalkyl, and $C_{1-4}$ haloalkoxy;

$R^{12}$ is independently selected from: halogen, CN, $C_{1-4}$ alkyl, $C_{1-4}$ alkoxy, $C_{1-4}$ haloalkyl, $C_{1-4}$ haloalkoxy, $C_{1-4}$ alkylthio, OH, $CH_2OH$, $CO_2H$, $CO_2(C_{1-4}$ alkyl), $NH_2$, $CH_2NH_2$, $N(C_{1-4}$ alkyl$)_2$, $CH_2N(C_{1-4}$ alkyl$)_2$, $CONH_2$, $CON(C_{1-4}$ alkyl$)_2$, $SO_2NH_2$, $SO_2NH(C_{1-4}$ alkyl), $SO_2N(C_{1-4}$ alkyl$)_2$, CONHPh, NHCOPh, —$(CH_2)_n$—$(C_{3-6}$ carbocycle substituted with 0-2 $R^c$), and a 5- to 6-membered heterocycle comprising carbon atoms and 1-4 heteroatoms selected from N, $NR^a$, O, and $S(O)_p$, wherein said heterocycle is substituted with 0-2 $R^c$);

$R^{13}$ is independently selected from: $R^{12}$ and =O;

$R^{14}$ and $R^{16}$ are, at each occurrence, independently selected from: halogen, $C_{1-4}$ alkyl, $C_{1-4}$ alkoxy, $C_{1-4}$ haloalkyl, $C_{1-4}$ haloalkoxy, OH, $CH_2OH$, $N(C_{1-4}$ alkyl$)_2$, $CONH_2$, $CONH(C_{1-4}$ alkyl), $CON(C_{1-4}$ alkyl$)_2$, $OCH_2CONH_2$, $NHCO(C_{1-4}$ alkyl), $NHCO_2(C_{1-4}$ alkyl), $SO_2(C_{1-4}$ alkyl), —$(CH_2)_n$-phenyl, —O—$(CH_2)_n$-phenyl, and pyridylmethyl;

$R^{15}$ is, at each occurrence, independently selected from: OH, $C_{1-4}$ alkoxy, $C_{1-4}$ haloalkyl, $C_{1-4}$ haloalkoxy, $N(C_{1-4}$ alkyl$)_2$, $CONH_2$, $CONH(C_{1-4}$ alkyl), and $CON(C_{1-4}$ alkyl$)_2$;

$R^{17}$ is independently selected from: $R^{14}$ and =O;

$R^a$ is, at each occurrence, independently selected from the group consisting of H, $C_{1-4}$ alkyl, $CO(C_{1-4}$ alkyl), $CO_2(C_{1-4}$ alkyl), $SO_2(C_{1-4}$ alkyl), —$(CH_2)_n$-phenyl, and —CO(—$(CH_2)_n$-phenyl);

$R^b$ is, at each occurrence, independently selected from: H and $C_{1-4}$ alkyl;

$R^c$ is, at each occurrence, independently selected from: OH, $C_{1-4}$ alkyl, halogen, $C_{1-4}$ alkoxy, $C_{1-4}$ haloalkyl, and $C_{1-4}$ haloalkoxy;

n is, at each occurrence, independently selected from: 0 and 1;

p is, at each occurrence, independently selected from: 0, 1 and 2;

s is, at each occurrence, independently selected from: 1 and 2; and t is, at each occurrence, independently selected from: 0, 1, 2, 3 and 4;

provided that

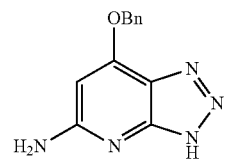 [SMILES: Nc1cc(OCc2ccccc2)c2nn[nH]c2n1]

is excluded.

2. A compound according to claim 1 or a stereoisomer, a tautomer, a pharmaceutically acceptable salt, or a solvate thereof, wherein:

ring A is substituted with 0-1 $R^2$ and 0-3 $R^3$ and selected from: cyclohexyl, bicyclo[2.2.1]heptanyl, phenyl, 1,2,3,4-tetrahydronaphthalenyl, and naphthalenyl;

provided that

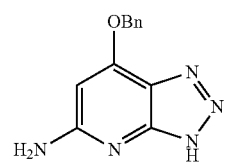 [SMILES: Nc1cc(OCc2ccccc2)c2nn[nH]c2n1]

is excluded.

3. A compound according to claim 2 or a stereoisomer, a tautomer, a pharmaceutically acceptable salt, or a solvate thereof, wherein:

ring A is phenyl substituted with 1 $R^2$ and 0-3 $R^3$.

4. A compound according to claim 3 or a stereoisomer, a tautomer, a pharmaceutically acceptable salt, or a solvate thereof, wherein:

$R^2$ is independently selected from: halogen, CN, $CH_2OH$, $C_{1-4}$ alkyl, —$CH_2$—$C_{1-4}$ alkoxy, $C_{1-4}$ alkoxy, $C_{1-4}$ haloalkyl, $C_{1-4}$ haloalkoxy, $C_{1-4}$ haloalkylthio, $SF_5$, $CO_2(C_{1-4}$ alkyl), $NR^6R^7$, $CONR^6R^7$, —$NHCO(C_{1-4}$ alkyl), $NO_2$, $SO_2NR^8R^9$, $SO_2R^8$, $C_{3-6}$ cycloalkyl, —O—$C_{3-6}$ cycloalkyl, phenoxy, benzoxy, —$(CH_2)_{0-1}$-(phenyl substituted with 0-2 $R^{11}$ and 0-1 $R^{12}$), (a heterocycle substituted with 0-1 $R^{11}$ and 0-1 $R^{13}$, wherein said heterocycle is a 5- to 10-membered heterocycle comprising carbon atoms and 1-4 heteroatoms selected from N, $NR^a$, O, and S),

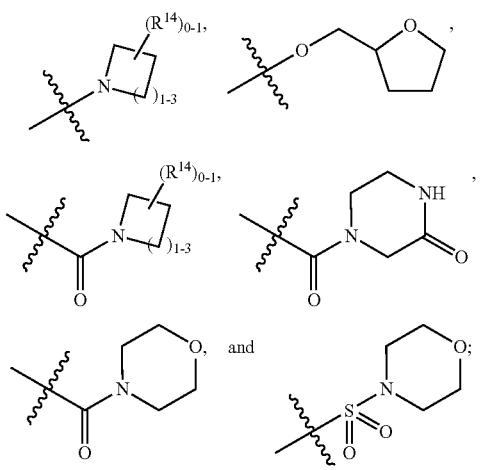

$R^6$ is independently selected from: H, $C_{1-4}$ haloalkyl, $C_{1-6}$ alkyl substituted with 0-2 $R^{15}$, —$(CH_2)_n$—($C_{3-6}$ cycloalkyl substituted with 0-1 $R^{14}$), —$(CHR^b)_n$-(phenyl substituted with 0-1 $R^{16}$), —$(CH_2)_r$-(a 5- to 10-membered heterocycle comprising carbon atoms and 1-4 heteroatoms selected from N, $NR^a$, O, and $S(O)_p$, wherein said heterocycle is substituted with 0-1 $R^{17}$);

$R^{12}$ is, at each occurrence, independently selected from: halogen, CN, $C_{1-4}$ alkoxy, $C_{1-4}$ haloalkyl, $C_{1-4}$ haloalkoxy, $CON(C_{1-4}$ alkyl$)_2$, $SO_2NH_2$, $SO_2NH(C_{1-4}$ alkyl), $SO_2N(C_{1-4}$ alkyl$)_2$, Ph, CONHPh, NHCOPh, pyrazolyl, and

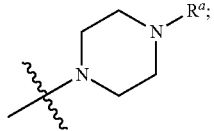

$R^{13}$ is, at each occurrence, independently selected from: =O, halogen, $C_{1-4}$ alkyl, $C_{1-4}$ alkoxy, $C_{1-4}$ haloalkyl, $C_{1-4}$ alkylthio, OH, $CH_2OH$, $CO_2(C_{1-4}$ alkyl), CN, $NH_2$, $CH_2NH_2$, $N(C_{1-4}$ alkyl$)_2$, $CH_2N(C_{1-4}$ alkyl$)_2$, $CONH_2$, $C_{3-6}$ cycloalkyl, Ph, Bn, pyrrolidinyl, piperidinyl, morpholinyl, piperazinyl,

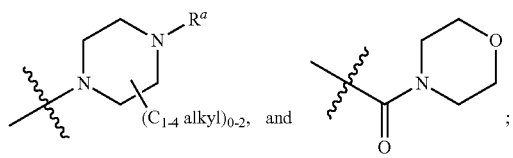

$R^{15}$ is, at each occurrence, independently selected from: OH, $C_{1-4}$ alkyl, $C_{1-4}$ alkoxy, $C_{1-4}$ haloalkyl, $N(C_{1-4}$ alkyl$)_2$, $CONH_2$, $CONH(C_{1-4}$ alkyl), and $CON(C_{1-4}$ alkyl$)_2$; and $R^{16}$ is independently selected from: halogen, $C_{1-4}$ alkoxy, and $SO_2(C_{1-4}$ alkyl).

5. A compound according to claim 1 of formula (II)

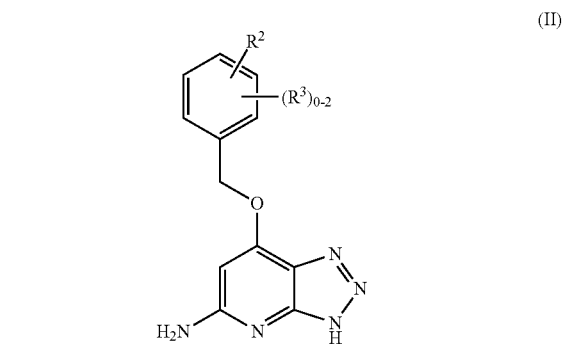

(II)

or a stereoisomer, a tautomer, a pharmaceutically acceptable salt, or a solvate thereof, wherein:

$R^2$ is independently selected from: halogen, CN, $CH_2OH$, $C_{1-4}$ alkoxy, $C_{1-4}$ haloalkyl, $C_{1-4}$ haloalkoxy, $C_{1-4}$ haloalkylthio, $SF_5$, $CO_2(C_{1-4}$ alkyl), NHBn, $CONR^6R^7$, —$NHCO(C_{1-4}$ alkyl), $NO_2$, $SO_2(C_{1-4}$ alkyl), $SO_2Bn$, $SO_2NH_2$, $SO_2NH(C_{1-4}$ alkyl), $C_{3-6}$ cycloalkyl, —O—$C_{3-6}$ cycloalkyl, phenoxy, benzoxy, —$(CH_2)_{0-1}$-(phenyl substituted with 0-2 $R^{11}$ and 0-1 $R^{12}$), (a heterocycle substituted with 0-1 $R^{11}$ and 0-1 $R^{13}$, wherein said heterocycle is selected from: pyrazolyl, 1-$C_{1-4}$ alkyl-pyrazolyl, 1-(4-halo-Ph)-pyrazolyl 1-Bn-pyrazolyl, imidazolyl, oxadiazolyl, triazolyl, pyridyl, pyrimidinyl,

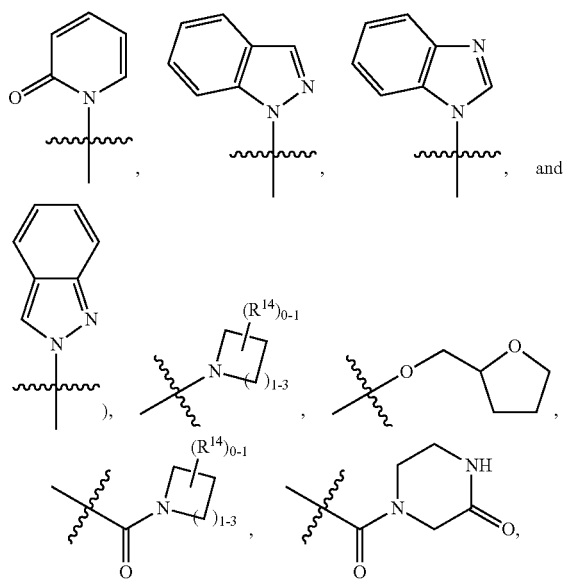

-continued

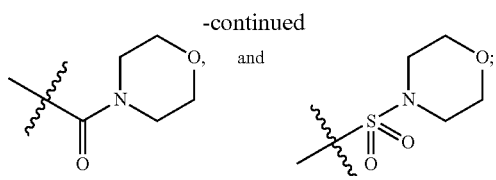

$R^3$ is, at each occurrence, independently selected from: halogen, CN, $C_{1-4}$ alkyl, $C_{1-4}$ alkoxy, $C_{1-4}$ haloalkyl, $C_{1-4}$ haloalkoxy, $NO_2$, $CONH_2$, and $SO_2(C_{1-4}$ alkyl);

$R^6$ is independently selected from: H, $C_{1-4}$ haloalkyl, $C_{1-6}$ alkyl substituted with 0-2 $R^{15}$, —$(CH_2)_{0-1}$—$C_{3-6}$ cycloalkyl, —$CH(C_{1-4}$ alkyl)(Ph), —$(CH_2)_{0-1}$-(phenyl substituted with 0-1 $R^{16}$);

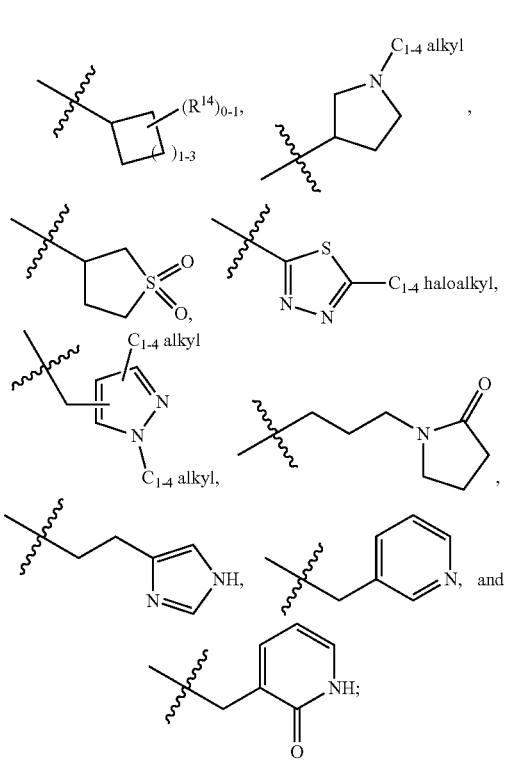

$R^7$ is independently selected from: H and $C_{1-4}$ alkyl substituted with 0-1 OH;

$R^{11}$ is, at each occurrence, independently selected from: halogen, $C_{1-4}$ alkoxy, $C_{1-4}$ haloalkyl, and $C_{1-4}$ haloalkoxy;

$R^{12}$ is independently selected from: halogen, CN, $C_{1-4}$ alkoxy, $C_{1-4}$ haloalkyl, $C_{1-4}$ haloalkoxy, $CO_2(C_{1-4}$ alkyl), $CON(C_{1-4}$ alkyl)$_2$, $SO_2NH_2$, $SO_2NH(C_{1-4}$ alkyl), $SO_2N(C_{1-4}$ alkyl)$_2$, Ph, CONHPh, NHCOPh, pyrazolyl, and

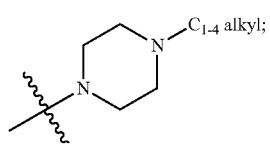

$R^{13}$ is independently selected from: halogen, $C_{1-4}$ alkyl, $C_{1-4}$ alkoxy, $C_{1-4}$ haloalkyl, $C_{1-4}$ alkylthio, OH, $CH_2OH$, $CO_2(C_{1-4}$ alkyl), CN, $NH_2$, $CH_2NH_2$, $N(C_{1-4}$ alkyl)$_2$, $CH_2N(C_{1-4}$ alkyl)$_2$, $CONH_2$, $C_{3-6}$ cycloalkyl, Ph, Bn, pyrrolidinyl, piperidinyl, morpholinyl, piperazinyl,

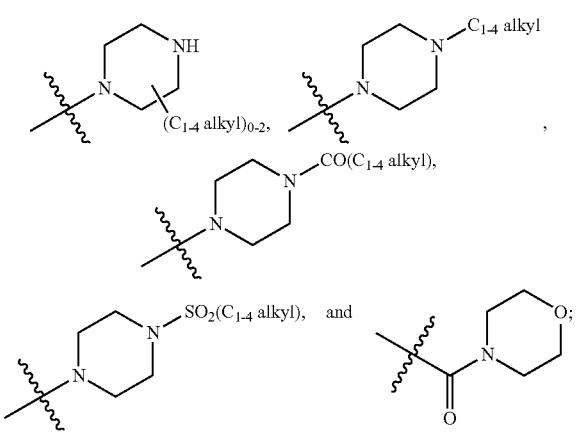

$R^{14}$ is independently selected from: $C_{1-4}$ alkyl, $C_{1-4}$ alkoxy, OH, $CH_2OH$, $CONH_2$, $NHCO(C_{1-4}$ alkyl), Ph, Bn, phenoxy, benzoxy, and pyridylmethyl;

$R^{15}$ is, at each occurrence, independently selected from: OH, $C_{1-4}$ alkyl, $C_{1-4}$ alkoxy, $C_{1-4}$ haloalkyl, $N(C_{1-4}$ alkyl)$_2$, $CONH_2$, $CONH(C_{1-4}$ alkyl), and $CON(C_{1-4}$ alkyl)$_2$; and $R^{16}$ is independently selected from: halogen, $C_{1-4}$ alkoxy, and $SO_2(C_{1-4}$ alkyl).

6. A compound according to claim 5 of the formula

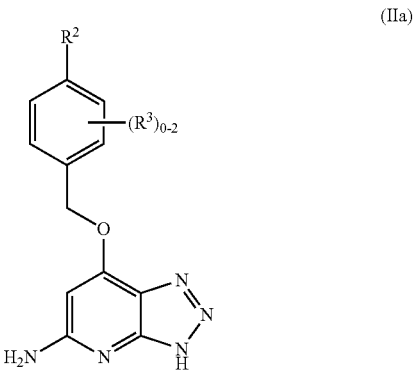

or a stereoisomer, a tautomer, a pharmaceutically acceptable salt, or a solvate thereof.

7. A compound according to claim 6 or a stereoisomer, a tautomer, a pharmaceutically acceptable salt, or a solvate thereof, wherein:

$R^2$ is independently selected from: halogen, CN, $CH_2OH$, $C_{1-4}$ alkoxy, $C_{1-4}$ haloalkyl, $C_{1-4}$ haloalkoxy, $C_{1-4}$ haloalkylthio, SF$_5$, CO$_2$(C$_{1-4}$ alkyl), NHBn, CONH$_2$, —CONH(CH$_2$)$_{1-2}$O(C$_{1-4}$ alkyl), —CONHCH$_2$CH(OH)(C$_{1-4}$ alkyl), —CONH(CH$_2$)$_2$N(C$_{1-4}$ alkyl)$_2$, —CONH(CH$_2$)$_{1-2}$CONH$_2$, —CONHCH(C$_{1-4}$ alkyl)CONH$_2$, —CONH(CH$_2$)$_{1-2}$CONH(C$_{1-4}$ alkyl), —CONH(C$_{1-4}$ haloalkyl), —CON(C$_{1-4}$ alkyl)CH$_2$CONH$_2$, CON(C$_{1-4}$ alkyl)$_2$, —CON(C$_{1-4}$ alkyl)(CH$_2$)$_2$OH, —CON(C$_{1-4}$ alkyl)(CH$_2$)$_2$N(C$_{1-4}$ alkyl)$_2$, —CONH(C$_{3-6}$ cycloalkyl), —CONHPh, —CONH(3-halo-Ph), —CONHBn, —CONH(2-C$_{1-4}$ alkoxy-Bn), —CONH(2-halo-Bn), —CONH(3-SO$_2$(C$_{1-4}$ alkyl)-Bn), —CONHCH(C$_{1-4}$ alkyl)(Ph), —CON(C$_{1-4}$ alkyl)(C$_{3-6}$ cycloalkyl), —CON(C$_{1-4}$ alkyl)Ph, —CON(C$_{1-4}$ alkyl)Bn, —CON(Bn)(CH$_2$)$_2$OH, —NHCO(C$_{1-4}$ alkyl), NO$_2$, SO$_2$(C$_{1-4}$ alkyl), SO$_2$Bn, SO$_2$NH$_2$, SO$_2$NH(C$_{1-4}$ alkyl), Ph, Bn, 2-C$_{1-4}$ alkoxy-Ph, 3-C$_{1-4}$ alkoxy-Ph, 4-C$_{1-4}$ alkoxy-Ph, 2-halo-Ph, 3-halo-Ph, 4-halo-Ph, 3-CN-Ph, 4-CN-Ph, 3-C$_{1-4}$ haloalkyl-Ph, 4-C$_{1-4}$ haloalkoxy-Ph, 3-SO$_2$NH$_2$-Ph, 4-SO$_2$NH(C$_{1-4}$ alkyl)-Ph, 2-SO$_2$N(C$_{1-4}$ alkyl)$_2$-Ph, 4-(CONHPh)-Ph, 4-(NHCOPh)-Ph, 4-(1H-pyrazol-5-yl)-Ph, 2-C$_{1-4}$ alkoxy-3-halo-Ph, 2-halo-4-C$_{1-4}$ alkoxy-Ph, 3-halo-4-C$_{1-4}$ alkoxy-Ph, 2-C$_{1-4}$ alkoxy-6-halo-Ph, 3-halo-4-(CON(C$_{1-4}$ alkyl)$_2$)-Ph, 2-C$_{1-4}$ alkoxy-3-halo-5-halo-Ph, —O—C$_{3-6}$ cycloalkyl, phenoxy, benzoxy, 4-biphenyl, pyrazolyl, 3-C$_{1-4}$ alkyl-pyrazol-1-yl, 1-C$_{1-4}$ alkyl-pyrazolyl, 4-CN-pyrazol-1-yl, 4-C$_{1-4}$ haloalkyl-pyrazol-1-yl, 1-(4-halo-Ph)-pyrazolyl, 1-Bn-pyrazolyl, 1-C$_{1-4}$ alkyl-3-C$_{1-4}$ alkyl-pyrazol-5-yl, 1-C$_{1-4}$ alkyl-3-C$_{1-4}$ haloalkyl-pyrazol-5-yl, 1-C$_{1-4}$ alkyl-5-C$_{1-4}$ haloalkyl-pyrazol-3-yl, 1-C$_{1-4}$ alkyl-5-C$_{3-6}$ cycloalkyl-pyrazol-3-yl, imidazolyl, 2-C$_{1-4}$ alkyl-imidazol-1-yl, 3-C$_{1-4}$ alkyl-imidazol-1-yl, 4-C$_{1-4}$ alkyl-imidazol-1-yl, 4-CH$_2$OH-imidazol-1-yl, 4-C$_{1-4}$ haloalkyl-imidazol-1-yl, 4-CO$_2$(C$_{1-4}$ alkyl)-imidazol-1-yl, 4-CH$_2$N(C$_{1-4}$ alkyl)$_2$-imidazol-1-yl, 4-Ph-imidazol-1-yl, 5-C$_{1-4}$ alkyl-1,2,4-oxadiazol-3-yl, 1,2,4-triazol-1-yl, 3-C$_{1-4}$ alkyl-1,2,4-triazol-1-yl, 3-C$_{1-4}$ haloalkyl-1,2,4-triazol-1-yl, pyridyl, 5-halo-pyrid-3-yl, 6-halo-pyrid-3-yl, 6-OH-pyrid-3-yl, 2-OH-pyrid-4-yl, 6-CH$_2$OH-pyrid-3-yl, 6-C$_{1-4}$ alkoxy-pyrid-3-yl, 6-C$_{1-4}$ alkylthio-pyrid-3-yl, 5-SO$_2$(C$_{1-4}$ alkyl)-pyrid-3-yl, 6-CN-pyrid-3-yl, 6-C$_{1-4}$ haloalkyl-pyrid-2-yl, 6-C$_{1-4}$ haloalkyl-pyrid-3-yl, 5-NH$_2$-pyrid-3-yl, 6-NH$_2$-pyrid-3-yl, 6-CH$_2$NH$_2$-pyrid-3-yl, 6-CONH$_2$-pyrid-3-yl, 6-OBn-pyrid-3-yl, 2-halo-6-halo-pyrid-3-yl, 2-C$_{1-4}$ alkoxy-5-halo-pyrid-4-yl, 5-halo-6-C$_{1-4}$ alkoxy-pyrid-3-yl, pyrimidinyl, 2-C$_{1-4}$ alkoxy-pyrimidin-5-yl, 2-N(C$_{1-4}$ alkyl)$_2$-pyrimidin-5-yl,

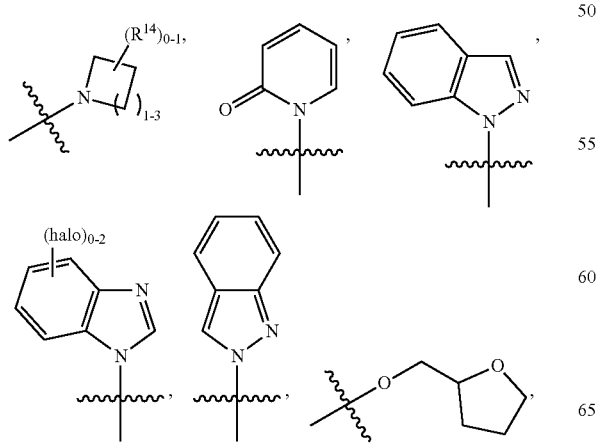

-continued

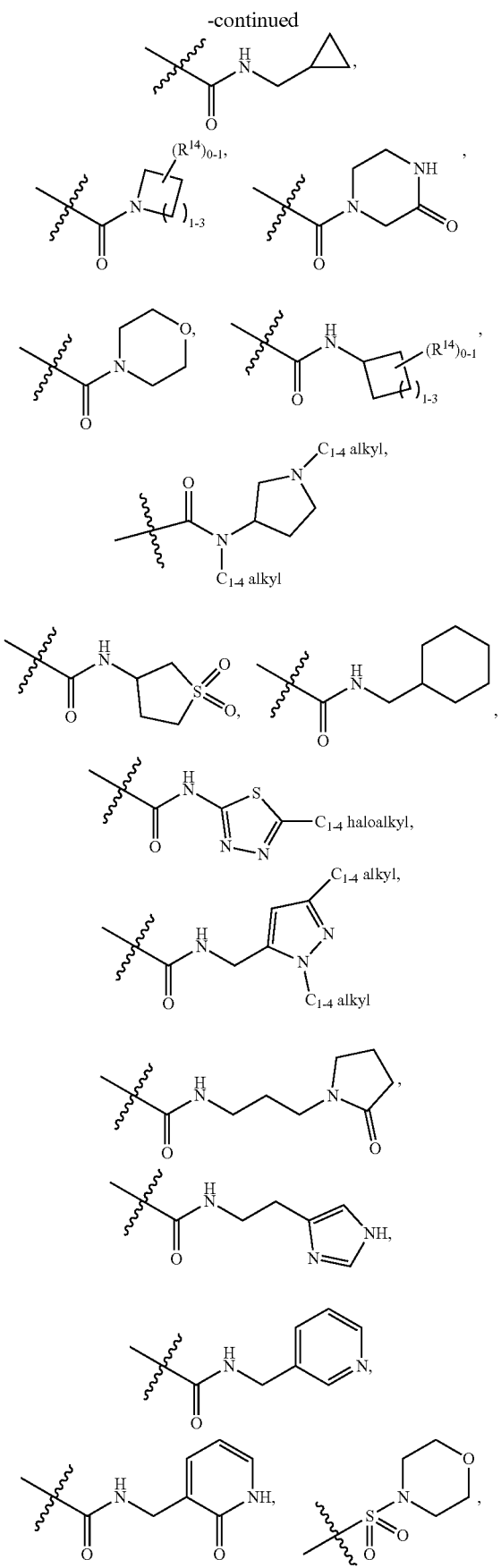

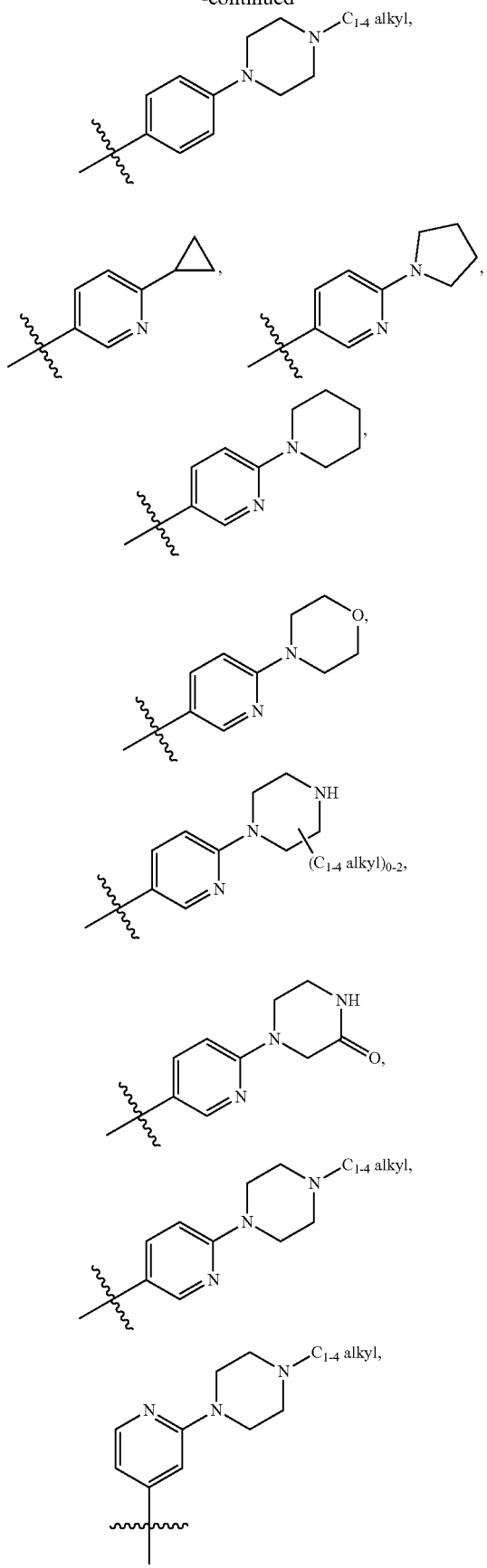
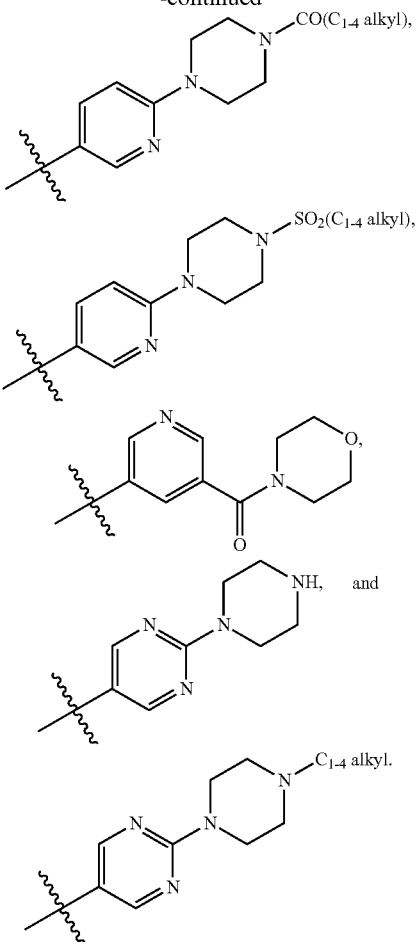

8. A compound according to claim 7 or a stereoisomer, a tautomer, a pharmaceutically acceptable salt, or a solvate thereof, wherein:

$R^2$ is independently selected from: F, Cl, Br, OMe, OEt, CN, $CH_2OH$, $CF_3$, $OCHF_2$, $OCF_3$, $SCF_3$, $SF_5$, $CO_2Me$, NHBn, $CONH_2$, —$CONH(CH_2)_2OMe$, —$CONHCH_2CH(OH)Me$, —$CONH(CH_2)_2N(Me)_2$, —$CONH(CH_2)_{1-2}CONH_2$, —$CONHCH_2CONHMe$, —$CONHCH_2CF_3$, —$CON(Me)CH_2CONH_2$, $CON(Me)_2$, —$CON(Me)(CH_2)_2OH$, —$CON(Me)(CH_2)_2N(Me)_2$, —$CON(Et)(CH_2)_2OH$, —$CONH(cyclopropyl)$, —$CONH(cyclobutyl)$, —$CONH(cyclohexyl)$, —CONHPh, —CONH(3-Cl-Ph), —CONHBn, —CONH(2-OMe-Bn), —CONH(2-Cl-Bn), —CONH(3-$SO_2Me$-Bn), —CO NHCH(Me)(Ph), —CON(Me)(cyclohexyl), —CON(Me)Ph, —CON(Me)Bn, —CON(Bn)$(CH_2)_2OH$, —NH COMe, $NO_2$, $SO_2Me$, $SO_2Et$, $SO_2Bn$, $SO_2NH_2$, $SO_2NHMe$, Ph, Bn, 2-OMe-Ph, 3-OMe-Ph, 4-OMe-Ph, 2-F-Ph, 3-F-Ph, 4-F-Ph, 2-Cl-Ph, 3-Cl-Ph, 4-Cl-Ph, 3-$CF_3$-Ph, 4-$OCF_3$-Ph, 3-CN-Ph, 4-CN-Ph, 3-$SO_2NH_2$-Ph, 4-$SO_2NHMe$-Ph, 2-$SO_2N(Me)_2$-Ph, 4-(CONHPh)-Ph, 4-(NHCOPh)-Ph, 4-(1H-pyrazol-5-yl)-Ph, 2-OMe-3-F-Ph, 2-F-4-OMe-Ph, 3-F-4-OMe-Ph, 2-OMe-6-Cl-Ph, 3-F-4-(CON(Me)(Et))-Ph, 2-OMe-3,5-diF-Ph, phenoxy, benzoxy, 4-biphenyl, pyrazol-1-yl, 3-Me-pyrazol-1-yl, 1-Me-pyrazol-3-yl, 1-Me-pyrazol-4-yl, 1-(i-Pr)-pyrazol-4-yl, 1-(i-Bu)-pyrazol-4-yl, 1-Me-pyrazol-5-yl, 4-CN-pyrazol-1-yl, 4-$CF_3$-pyrazol-1-yl, 1-Bn-pyrazol-3-yl, 1-Bn-pyrazol- 4-yl, 1-Me-3-CF$_3$-pyrazol-5-yl, imidazol-1-yl, 2-Me-imidazol-1-yl, 4-Me-imidazol-1-yl, 4-CH$_2$OH-imidazol-1-yl, 4-CF$_3$-imidazol-1-yl, 4-CO$_2$Me-imidazol-1-yl, 4-CH$_2$N(Me)$_2$-imidazol-1-yl, 4-Ph-imidazol-1-yl, 5-Me-1,2,4-oxadiazol-3-yl, 1,2,4-triazol-1-yl, 3-Me-1,2,4-triazol-1-yl, 3-CHF$_2$-1,2,4-triazol-1-yl, pyrid-3-yl, 5-F-pyrid-3-yl, 6-F-pyrid-3-yl, 6-Cl-pyrid-3-yl, 6-OH-pyrid-3-yl, 2-OH-pyrid-4-yl, 6-CH$_2$OH-pyrid-3-yl, 6-OMe-pyrid-3-yl, 6-(O-i-Pr)-pyrid-3-yl, 6-SMe-pyrid-3-yl, 5-SO$_2$Me-pyrid-3-yl, 6-CN-pyrid-3-yl, 6-CF$_3$-pyrid-3-yl, 5-NH$_2$-pyrid-3-yl, 6-NH$_2$-pyrid-3-yl, 6-CH$_2$NH$_2$-pyrid-3-yl, 6-CONH$_2$-pyrid-3-yl, 6-OBn-pyrid-3-yl, 2,6-diF-pyrid-3-yl, 2-OMe-5-F-pyrid-4-yl, 5-F-6-OMe-pyrid-3-yl, pyrimidin-2-yl, 2-OMe-pyrimidin-5-yl, 2-N(Me)$_2$-pyrimidin-5-yl,

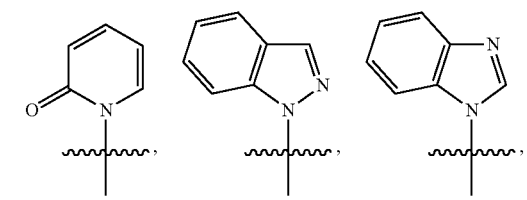

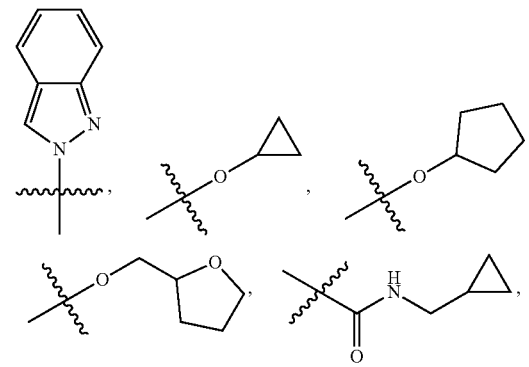

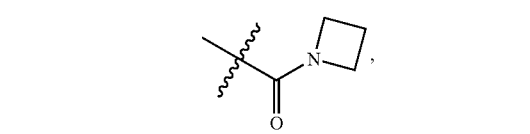

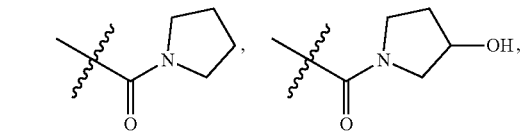

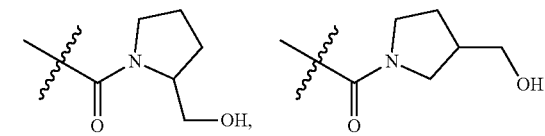

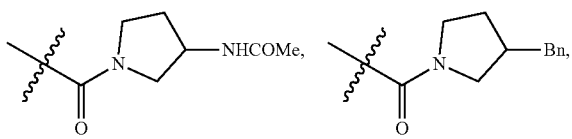

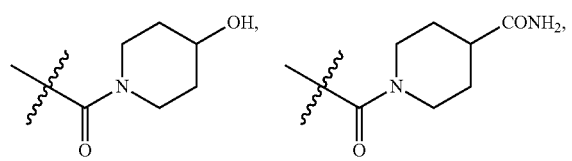

-continued

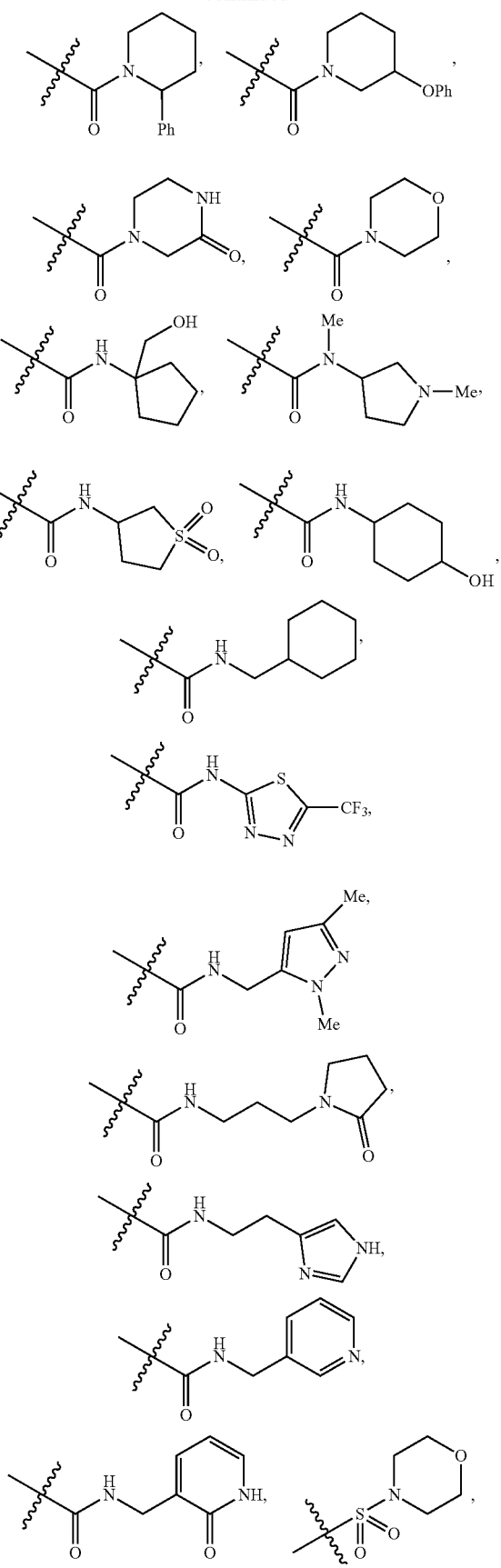

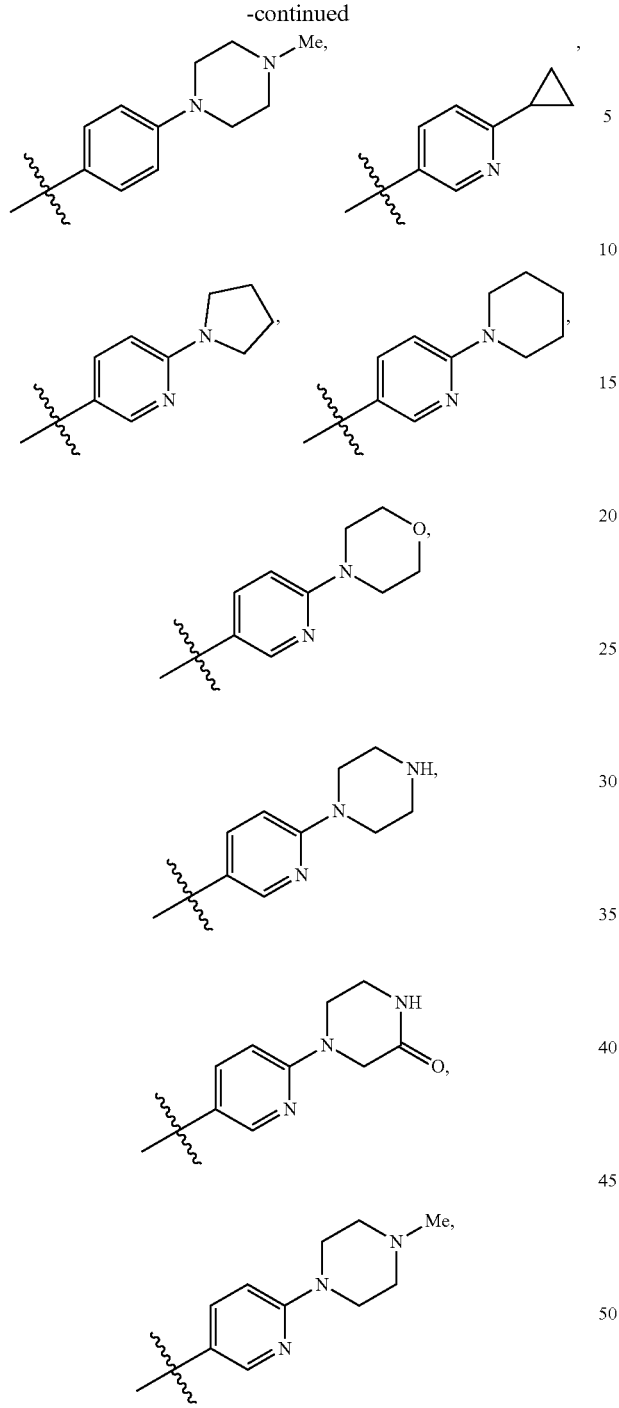
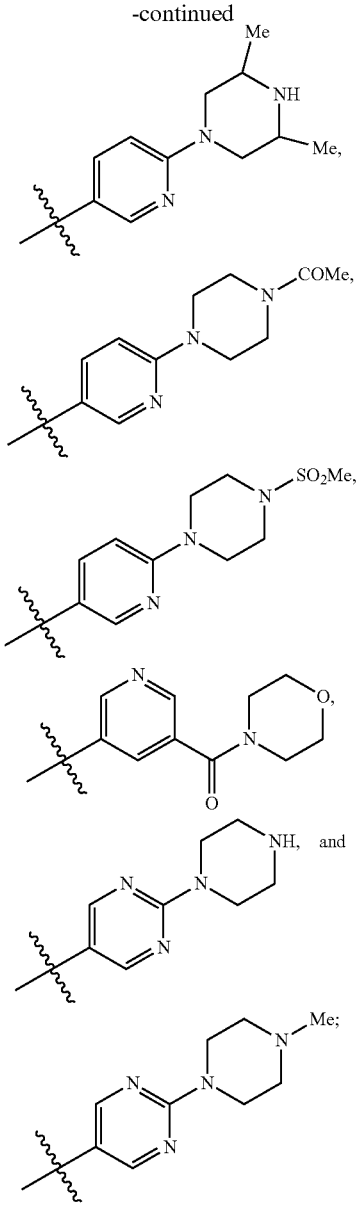
R³ is, at each occurrence, independently selected from: F, Cl, Me, OMe, OEt, CN, CF₃, OCHF₂, OCF₃, NO₂, CONH₂, SO₂Me, and SO₂Et.
9. A pharmaceutical composition, comprising: a pharmaceutically acceptable carrier and a compound of claim 1, or a stereoisomer, a tautomer, or a pharmaceutically acceptable salt thereof.
* * * * *